US012319739B2

(12) United States Patent
Munoz-Olaya et al.

(10) Patent No.: US 12,319,739 B2
(45) Date of Patent: Jun. 3, 2025

(54) MESOTHELIN AND CD137 BINDING MOLECULES

(71) Applicant: F-star Delta Limited, Cambridge (GB)

(72) Inventors: Jose Munoz-Olaya, Cambridge (GB); Mihriban Tuna, Cambridge (GB); Remi Fertin, Cambridge (GB); Claire Reader, Cambridge (GB); Francisca Wollerton, Cambridge (GB); Neil Brewis, Cambridge (GB)

(73) Assignee: INVOX PHARMA LIMITED, London (GB)

( * ) Notice: Subject to any disclaimer, the term of this patent is extended or adjusted under 35 U.S.C. 154(b) by 1018 days.

(21) Appl. No.: 17/259,634

(22) PCT Filed: Jul. 12, 2019

(86) PCT No.: PCT/EP2019/068817

§ 371 (c)(1),
(2) Date: Jan. 12, 2021

(87) PCT Pub. No.: WO2020/011976

PCT Pub. Date: Jan. 16, 2020

(65) Prior Publication Data

US 2021/0309753 A1 Oct. 7, 2021

(30) Foreign Application Priority Data

Jul. 12, 2018 (GB) ..................................... 1811450

(51) Int. Cl.
*C07K 16/28* (2006.01)
*A61K 39/00* (2006.01)

(52) U.S. Cl.
CPC .... *C07K 16/2878* (2013.01); *A61K 2039/505* (2013.01); *C07K 2317/31* (2013.01); *C07K 2317/33* (2013.01); *C07K 2317/35* (2013.01); *C07K 2317/40* (2013.01); *C07K 2317/72* (2013.01); *C07K 2317/75* (2013.01); *C07K 2317/92* (2013.01)

(58) Field of Classification Search
CPC ............ C07K 16/2878; C07K 2317/31; C07K 2317/33; C07K 2317/35; C07K 2317/40; C07K 2317/72; C07K 2317/75; C07K 2317/92; A61K 2039/505; A61P 35/00
See application file for complete search history.

(56) References Cited

U.S. PATENT DOCUMENTS

| | | | |
|---|---|---|---|
| 3,909,459 | A | 9/1975 | Friese et al. |
| 3,967,230 | A | 6/1976 | Kamigaito et al. |
| 4,004,183 | A | 1/1977 | Oki et al. |
| 5,595,756 | A | 1/1997 | Bally et al. |
| 6,380,664 | B1 | 4/2002 | Pollner |
| 7,288,638 | B2 | 10/2007 | Jure-Kunkel et al. |
| 7,592,426 | B2 | 9/2009 | Ebel et al. |
| 8,217,149 | B2 | 7/2012 | Irving et al. |
| 8,383,796 | B2 | 2/2013 | Korman et al. |
| 8,911,732 | B2 | 12/2014 | Dennis et al. |
| 9,567,399 | B1 | 2/2017 | Campbell et al. |
| 9,617,338 | B1 | 4/2017 | Campbell et al. |
| 10,090,646 | B2 | 10/2018 | Takaoka et al. |
| 10,205,305 | B2 | 2/2019 | Uegaki et al. |
| 10,233,258 | B2 | 3/2019 | Akamatsu et al. |
| 10,604,576 | B2 | 3/2020 | Campbell et al. |
| 11,214,618 | B2 | 1/2022 | Tuna et al. |
| 11,214,620 | B2 | 1/2022 | Campbell et al. |
| 11,548,948 | B2 | 1/2023 | Tuna et al. |
| 11,629,193 | B2 | 4/2023 | Tuna et al. |
| 12,103,976 | B2 | 10/2024 | Lakins et al. |
| 2003/0030355 | A1 | 2/2003 | Honda |
| 2007/0071675 | A1 | 3/2007 | Wu et al. |
| 2009/0055944 | A1 | 2/2009 | Korman et al. |
| 2012/0237498 | A1 | 9/2012 | Ahrens et al. |
| 2012/0276104 | A1 | 11/2012 | Woisetschlager |
| 2013/0034559 | A1 | 2/2013 | Queva et al. |
| 2014/0004121 | A1 | 1/2014 | Fanslow, III et al. |
| 2014/0341917 | A1 | 11/2014 | Nastri et al. |
| 2015/0214697 | A1 | 7/2015 | Yoshida et al. |
| 2015/0259420 | A1 | 9/2015 | Triebel et al. |
| 2015/0307620 | A1 | 10/2015 | Vella et al. |
| 2016/0043531 | A1 | 2/2016 | Firstenberg et al. |

(Continued)

FOREIGN PATENT DOCUMENTS

| | | | |
|---|---|---|---|
| CN | 101802006 | A | 8/2010 |
| CN | 104955845 | A | 9/2015 |

(Continued)

OTHER PUBLICATIONS

Kaas, Q et. al. "IG, TR and IgSF, MHC and MhcSF: what do we learn fromthe IMGT Colliers de Perles?", 2008, Briefings in Functional Genomics and Proteomics, 6(4), 253-264. (Year: 2008).*
U.S. Appl. No. 16/955,450, filed Jun. 18, 2020, Tuna et al.
U.S. Appl. No. 17/259,680, filed Jan. 12, 2021, Pechouckova et al.
U.S. Appl. No. 17/259,677, filed Jan. 12, 2021, Munoz-Olaya et al.
U.S. Appl. No. 17/259,754, filed Jan. 12, 2021, Lakins et al.

(Continued)

*Primary Examiner* — Nelson B Moseley, II
*Assistant Examiner* — Alyssa Rae Stonebraker
(74) *Attorney, Agent, or Firm* — Wolf, Greenfield & Sacks, P.C.

(57) ABSTRACT

The present invention relates to antibody molecules that bind both mesothelin (MSLN) and CD137. The antibody molecules comprise a CDR-based binding site for MSLN, and a CD137 antigen-binding site located in a constant domain of the antibody molecule. The antibody molecules find application in the treatment of cancer, for example.

22 Claims, 15 Drawing Sheets

Specification includes a Sequence Listing.

(56) References Cited

U.S. PATENT DOCUMENTS

| | | | |
|---|---|---|---|
| 2016/0137740 | A1 | 5/2016 | Hammond et al. |
| 2016/0244528 | A1 | 8/2016 | Gray et al. |
| 2017/0198050 | A1 | 7/2017 | Eckelman et al. |
| 2017/0355756 | A1 | 12/2017 | Julien et al. |
| 2017/0362321 | A1 | 12/2017 | Campbell et al. |
| 2018/0118841 | A1 | 5/2018 | Ellmark et al. |
| 2018/0175592 | A1 | 6/2018 | Uegaki et al. |
| 2018/0194862 | A1 | 7/2018 | Akamatsu et al. |
| 2018/0339031 | A1 | 11/2018 | Masternak et al. |
| 2019/0106494 | A1 | 4/2019 | Wang et al. |
| 2019/0202920 | A1 | 7/2019 | Tuna et al. |
| 2019/0256602 | A1 | 8/2019 | Campbell et al. |
| 2019/0330344 | A1 | 10/2019 | Tuna et al. |
| 2019/0330351 | A1 | 10/2019 | Campbell et al. |
| 2019/0338032 | A1 | 11/2019 | Campbell et al. |
| 2019/0338049 | A1 | 11/2019 | Tuna et al. |
| 2020/0407446 | A1 | 12/2020 | McCourt et al. |
| 2021/0139590 | A1 | 5/2021 | Tuna et al. |
| 2021/0237498 | A1 | 8/2021 | Yoda et al. |
| 2021/0238299 | A1 | 8/2021 | Pechouckova et al. |
| 2021/0277134 | A1 | 9/2021 | Lakins et al. |
| 2021/0301022 | A1 | 9/2021 | Wollerton et al. |
| 2021/0355228 | A1 | 11/2021 | Lakins et al. |
| 2022/0048996 | A1 | 2/2022 | Tuna et al. |
| 2022/0049007 | A1 | 2/2022 | Lakins et al. |
| 2022/0185890 | A1 | 6/2022 | Tuna et al. |
| 2022/0185894 | A1 | 6/2022 | Campbell et al. |
| 2022/0267421 | A1 | 8/2022 | Munoz-Olaya et al. |
| 2022/0275092 | A1 | 9/2022 | Morrow et al. |
| 2023/0357413 | A1 | 11/2023 | Tuna et al. |
| 2023/0406935 | A1 | 12/2023 | Tuna et al. |

FOREIGN PATENT DOCUMENTS

| | | | | |
|---|---|---|---|---|
| CN | 104968364 | A | 10/2015 | |
| CN | 107523546 | A | 12/2017 | |
| CN | 109563171 | A | 4/2019 | |
| EP | 1025230 | B1 | 2/2006 | |
| EP | 1180123 | B1 | 7/2008 | |
| EP | 2407487 | A1 | 1/2012 | |
| EP | 2546268 | A1 | 1/2013 | |
| EP | 2242771 | B1 | 7/2013 | |
| EP | 2905030 | A1 | 8/2015 | |
| EP | 2215121 | B1 | 2/2016 | |
| EP | 3354661 | A1 | 8/2018 | |
| EP | 3470426 | A1 | 4/2019 | |
| JP | S51-046628 | A | 4/1976 | |
| JP | 2003-0228556 | A | 1/2003 | |
| JP | 2011-521905 | A | 7/2011 | |
| JP | 2012-500006 | A | 1/2012 | |
| JP | 2016-513467 | A | 5/2016 | |
| JP | 2016-533395 | A | 10/2016 | |
| JP | 2017-010741 | A | 1/2017 | |
| JP | 2018-508475 | A | 3/2018 | |
| RU | 2017112379 | A | 10/2018 | |
| TW | 201642897 | A | 12/2016 | |
| WO | WO 2001/077342 | A1 | 10/2001 | |
| WO | WO 2005/035584 | A1 | 4/2005 | |
| WO | WO 2006/072620 | A1 | 7/2006 | |
| WO | WO 2006/088447 | A1 | 8/2006 | |
| WO | WO 2006/099141 | A2 | 9/2006 | |
| WO | WO 2008/003103 | A2 | 1/2008 | |
| WO | WO 2008/068048 | A2 | 6/2008 | |
| WO | WO 2009/000006 | A1 | 12/2008 | |
| WO | WO 2009/068204 | A1 | 6/2009 | |
| WO | WO 2009/126944 | A1 | 10/2009 | |
| WO | WO 2009/132876 | A1 | 11/2009 | |
| WO | WO 2010/019570 | A2 | 2/2010 | |
| WO | WO 2010/057047 | A1 | 5/2010 | |
| WO | WO 2010/111282 | A1 | 9/2010 | |
| WO | WO 2010/124797 | A1 | 11/2010 | |
| WO | WO 2012/130831 | A1 | 10/2012 | |
| WO | WO 2013/181634 | A2 | 12/2013 | |
| WO | WO 2014/004549 | A2 | 1/2014 | |
| WO | WO 2014/008218 | A1 | 1/2014 | |
| WO | WO 2014/052064 | A1 | 4/2014 | |
| WO | WO 2014/089113 | A1 | 6/2014 | |
| WO | WO 2014/140180 | A1 | 9/2014 | |
| WO | WO 2014/151910 | A1 | 9/2014 | |
| WO | WO 2015/048312 | A1 | 4/2015 | |
| WO | WO 2015/049537 | A1 | 4/2015 | |
| WO | WO 2015/119923 | A1 | 8/2015 | |
| WO | WO 2015/138920 | A1 | 9/2015 | |
| WO | WO 2015/198312 | A1 | 12/2015 | |
| WO | WO 2015/200119 | A1 | 12/2015 | |
| WO | WO 2016/028672 | A1 | 2/2016 | |
| WO | WO 2016/040880 | A1 | 3/2016 | |
| WO | WO 2016/110584 | A1 | 7/2016 | |
| WO | WO 2016/111645 | A1 | 7/2016 | |
| WO | WO 2016/162505 | A1 | 10/2016 | |
| WO | WO 2016/177802 | A1 | 11/2016 | |
| WO | WO 2016/185016 | A1 | 11/2016 | |
| WO | WO 2016/200782 | A1 | 12/2016 | |
| WO | WO 2017/009456 | A1 | 1/2017 | |
| WO | WO 2017/015560 | A2 | 1/2017 | |
| WO | WO 2017/019846 | A8 | 2/2017 | |
| WO | WO 2017/025498 | A1 | 2/2017 | |
| WO | WO 2017/049452 | A1 | 3/2017 | |
| WO | WO 2017/052241 | A1 | 3/2017 | |
| WO | WO 2017/055398 | A2 | 4/2017 | |
| WO | WO 2017/062888 | A1 | 4/2017 | |
| WO | WO 2017/077085 | A2 | 5/2017 | |
| WO | WO 2017/087589 | A2 | 5/2017 | |
| WO | WO 2017/087901 | A2 | 5/2017 | |
| WO | WO 2017/123650 | A2 | 7/2017 | |
| WO | WO-2017182672 | A1 * | 10/2017 | ......... A61K 39/3955 |
| WO | WO 2017/193032 | A2 | 11/2017 | |
| WO | WO 2017/205738 | A1 | 11/2017 | |
| WO | WO 2017/220555 | A1 | 12/2017 | |
| WO | WO 2017/220569 | A1 | 12/2017 | |
| WO | WO 2017/220990 | A9 | 12/2017 | |
| WO | WO 2018/017673 | A1 | 1/2018 | |
| WO | WO 2018/056821 | A1 | 3/2018 | |
| WO | WO 2018/060480 | A1 | 4/2018 | |
| WO | WO 2018/091740 | A2 | 5/2018 | |
| WO | WO 2018/115859 | A1 | 6/2018 | |
| WO | WO 2018/127610 | A1 | 7/2018 | |
| WO | WO 2018/222711 | A2 | 12/2018 | |
| WO | WO 2019/025545 | A1 | 2/2019 | |

OTHER PUBLICATIONS

U.S. Appl. No. 17/259,642, filed Jan. 12, 2021, Wollerton et al.

U.S. Appl. No. 17/259,714, filed Jan. 12, 2021, Tuna et al.

U.S. Appl. No. 17/259,791, filed Jan. 12, 2021, Lakins et al.

U.S. Appl. No. 17/259,796, filed Jan. 12, 2021, Tuna et al.

PCT/EP2019/068817, Oct. 23, 2019, International Search Report and Written Opinion.

PCT/EP2019/068817, Jan. 21, 2021, International Preliminary Report on Patentability.

[No Author Listed], Molecular biological basis of immunotherapy. New and Orphan Drugs for Leukemia Therapeutics. Sep. 30, 2016. 387-390. Retrieved on Dec. 18, 2023. 7 pages.

Chen et al., Enhancement and destruction of antibody function by somatic mutation: unequal occurrence is controlled by V gene combinatorial associations. EMBO J. Jun. 15, 1995;14(12):2784-94. doi: 10.1002/j.1460-2075.1995.tb07278.x.

Cooper, The Development and Causes of Cancer. From the Cell: Molecular Approach. 2nd Ed. Sunderland, MA. Sinauer Associates. 2000. 9 pages.

Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.

Heppner et al., Tumor heterogeneity: biological implications and therapeutic consequences. Cancer Metastasis Rev. 1983;2(1):5-23. doi: 10.1007/BF00046903.

Koenig et al., Mutational landscape of antibody variable domains reveals a switch modulating the interdomain conformational dynamics and antigen binding. Proc Natl Acad Sci U S A. Jan. 24, 2017;114(4):E486-E495. doi: 10.1073/pnas.1613231114. Epub Jan. 5, 2017.

(56) References Cited

OTHER PUBLICATIONS

Kussie et al., A single engineered amino acid substitution changes antibody fine specificity. J Immunol. Jan. 1, 1994;152(1):146-52.
Lo et al., Effector-attenuating Substitutions That Maintain Antibody Stability and Reduce Toxicity in Mice. J Biol Chem. Mar. 3, 2017;292(9):3900-3908. doi: 10.1074/jbc.M116.767749. Epub Jan. 11, 2017.
Seckinger et al., Development and characterization of NILK-2301, a novel CEACAM5xCD3 κλ bispecific antibody for immunotherapy of CEACAM5-expressing cancers. J Hematol Oncol. Dec. 12, 2023;16(1):117. doi: 10.1186/s13045-023-01516-3.
Yap et al., Abstract TPS2652: A first-in-human phase I study of FS118, an anti-LAG-3/PD-L1 bispecific antibody in patients with solid tumors that have progressed on prior PD-1/PD-L1 therapy. Journal of Clinical Oncology. May 15, 2019;37(15_suppl). 2019 ASCO Annual Meeting Proceedings. 4 pages.
[No Author Listed], Abstract for CHI Immuno-Oncology Summit Europe. Mar. 18-22, 2019. 1 page. PDR303.
[No Author Listed], First-in-Class bispecific antibodies for cancer immunotherapy. Presentation at Takeda. Dec. 31, 2016. 24 pages. PDR160.
[No Author Listed] F-Star Modular Bispecific Antibodies. Summary for Atlas deck. Presented at JP Morgan. Jan. 2017. 1 page. PDR159.
[No Author Listed], FS118 First in Human Study in Patients With Advanced Malignancies. Sponsored by F-star Therapeutics Limited. Clinical Trial. Retrieved from https://clinicaltrials.gov/ct2/show/NCT03440437. Feb. 22, 2018. 7 pages.
[No Author Listed], Pipeline Overview: F-star is developing a pipeline of bispecific antibodies focused on oncology and immuno-oncology. F-Start website update. Sep. 2016. 2 pages. PDR126.
Ascierto et al., Initial efficacy of anti-lymphocyte activation gene-3 (anti-LAG-3:BMS-986016) in combination with nivolumab (nivo) in pts with melanoma (MEL) previously treated with anti-PD-1/PD-L1 therapy. J Clin Oncology. May 20, 2017;35(15):9520-9520. Abstract only. doi: 10.1200/JCO.2017.35.15_suppl.9520. EPub May 30, 2017.
Asgarov et al., A new anti-mesothelin antibody targets selectively the membrane-associated form. MAbs. Apr. 2017;9(3):Supplementary Data. doi: 10.1080/19420862.2017.1288770. 6 pages.
Awuah et al., Reduced Shedding of Surface Mesothelin Improves Efficacy of Mesothelin-Targeting Recombinant Immunotoxins. Mol Cancer Ther. Jul. 2016;15(7):1648-55. doi: 10.1158/1535-7163.MCT-15-0863. Epub May 18, 2016.
Berg et al., Biochemistry. 5th ed. New York. 2002. Accessible at https://www.ncbi.nlm.nih.gov/books/NBK22358/section5.5. Accessed Jun. 9, 2021. 4 pages.
Bernett et al., Abstract P122: Multiple bispecific checkpoint combinations enhance T cell activity. J Immunother Cancer. 2016;4(Suppl 1):P122. 2 pages.
Bernett et al., Multiple bispecific checkpoint combinations enhance T cell activity. Xencor Poster Presentation. 2016. 1 page.
Bodhankar et al., PD-L1 Monoclonal Antibody Treats Ischemic Stroke by Controlling Central Nervous System Inflammation. Stroke. Oct. 2015;46(10):2926-34. doi: 10.1161/STROKEAHA.115.010592. Epub Aug. 25, 2015.
Borlak et al., Immune-mediated liver injury of the cancer therapeutic antibody catumaxomab targeting EpCAM, CD3 and Fcγ receptors. Oncotarget. May 10, 2016;7(19):28059-74. doi: 10.18632/oncotarget.8574.
Brewis, Development of an anti-PD-L1 Fcab. Presentation. Human Antibodies and Hybrodomas Conference. Oct. 22, 2018. PDR 312.
Brewis, Identification of a PD-L1 binding Fcab: a potent inhibitor of immunosuppressive signals. Abstract. Human Antibodies and Hybridomas 2018. Jun. 11, 2018. 1 page. PDR282.
Brewis, The use of bispecific antibodies to modulate anti-tumour immune responses. Oral Presentation at ELRIG—Research and Innovation. Mar. 29, 2017. 33 pages. PDR177.
Brewis, The use of bispecific antibodies to modulate anti-tumour immune responses. Oral Presentation at Peptalk. Jan. 12, 2017. 26 pages. PDR163.
Burova et al., Abstract 1484: Combined treatment with anti-LAG-3 and anti-PD-1 fully human monoclonal antibodies inhibits tumor growth in immunocompetent double-humanized LAG-3/PD-1 mice. Proceedings: AACR 107th Annual Meeting 2016. Apr. 16-20, 2016. New Orleans, LA. doi: 10.1158/1538-7445.AM2016-1484. Published Jul. 2016. 8 pages.
Burova et al., Abstract P195: A novel anti-human LAG-3 antibody in combination with anti-human PD-1 (REGN2810) shows enhanced anti-tumor activity in PD-1 x LAG-3 dual-humanized mice and favorable pharmacokinetic and safety profiles in cynomolgus monkey. J Immunother Cancer. 2016;4(Suppl 1):P195. 2 pages.
Callahan et al., Targeting T Cell Co-receptors for Cancer Therapy. Immunity. May 17, 2016;44(5):1069-78. doi: 10.1016/j.immuni.2016.04.023.
Camisaschi et al., LAG-3 expression defines a subset of CD4(+)CD25(high)Foxp3(+) regulatory T cells that are expanded at tumor sites. J Immunol. Jun. 1, 2010;184(11):6545-51. doi: 10.4049/jimmunol.0903879. Epub Apr. 26, 2010.
Cemerski et al., T cell activation and anti-tumor efficacy of anti-LAG-3 antibodies is independent of LAG-3-MHCII blocking capacity. Poster Presentation. 30th Annual Meeting and Associated Programs of the Society for Immunotherapy of Cancer (SITC 2015). National Harbor, MD. Nov. 4-8, 2015. 1 page.
Chatterjee et al., Noninvasive Imaging of Immune Checkpoint Ligand PD-L1 in Tumors and Metastases for Guiding Immunotherapy. Mol Imaging. Jan.-Dec. 2017;16:1536012117718459. doi: 10.1177/1536012117718459. 5 pages.
Chen et al., Molecular mechanisms of T cell co-stimulation and co-inhibition. Nat Rev Immunol. Apr. 2013;13(4):227-42. doi: 10.1038/nri3405. Epub Mar. 8, 2013. Erratum in: Nat Rev Immunol. Jul. 2013;13(7):542.
Chiu et al., Antibody Structure and Function: The Basis for Engineering Therapeutics. Antibodies (Basel). Dec. 3, 2019;8(4):55. doi: 10.3390/antib8040055.
Chu et al., An Update on Anti-CD137 Antibodies in Immunotherapies for Cancer. Int J Mol Sci. Apr. 12, 2019;20(8):1822. doi: 10.3390/ijms20081822. 17 pages.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80. doi: 10.1073/pnas.0915174107. Epub Feb. 16, 2010.
Dahlén et al., Bispecific antibodies in cancer immunotherapy. Ther Adv Vaccines Immunother. Feb. 2018;6(1):3-17. doi: 10.1177/2515135518763280. Epub Mar. 28, 2018.
Davies, Analytical challenges for next generation biologics. Oral Presentation at Waters Biopharma Mini-Seminar. May 24, 2017. 20 pages. PDR191.
Davies, Bispecific Antibodies: New Opportunities for Novel Therapies. Oral Presentation at Bioprocess UK 2016. Nov. 26, 2016. 14 pages. PDR 135.
Davies, Overcoming the Manufacturing Challenges for Bisepcific mAbs. Oral Presentation at 5th Annual Cell Culture and Bioprocessing Congress. Nov. 6, 2016. 16 pages. PDR142.
Davies, Overcoming the Manufacturing Challenges for Bisepcific mAbs. Oral Presentation at Biopronet 3rd Annual Scientific Symposium. Oct. 20, 2016. 15 pages. PDR136.
Daxini et al., Vasculitis associated with immune checkpoint inhibitors—a systematic review. Clin Rheumatol. Sep. 2018;37(9):2579-2584. doi: 10.1007/s10067-018-4177-0. Epub Jun. 19, 2018.
Del Bano et al., A Bispecific Antibody-Based Approach for Targeting Mesothelin in Triple Negative Breast Cancer. Front Immunol. Jul. 10, 2019;10:1593. doi: 10.3389/fimmu.2019.01593.
Demeure et al., T Lymphocytes infiltrating various tumour types express the MHC class II ligand lymphocyte activation gene-3 (LAG-3): role of LAG-3/MHC class II interactions in cell-cell contacts. Eur J Cancer. Sep. 2001;37(13):1709-18. doi: 10.1016/s0959-8049(01)00184-8.
Deng et al., LAG-3 confers poor prognosis and its blockade reshapes antitumor response in head and neck squamous cell carcinoma. Oncoimmunology. Oct. 7, 2016;5(11):e1239005. doi: 10.1080/2162402X.2016.1239005.

(56) References Cited

OTHER PUBLICATIONS

Doody et al., Abstract B091: A LAG-3/PD-L1 bispecific antibody inhibits tumor growth in two syngeneic colon carcinoma models. Second CRI-CIMT-EATI-AACR International Cancer Immunotherapy Conference: Translating Science into Survival. Sep. 25-28, 2016. New York, NY. doi: 10.1158/23/26-6066.IMM2016-B091. Published Nov. 2016. 8 pages.

Doody, An anti-murine LAG-3/PD-L1 bispecific antibody which modulates T cell activity and inhibits tumour growth. Oral Presentation at 2nd Annual Advances in Immuno-Oncology Congress. May 16, 2017. 17 pages. PDR188.

Doody, In vivo Efficacy of bispecific antibodies targeting two immmune-modulatory receptors. Oral Presentation at PEGS Europe. Nov. 4, 2016. 16 pages. PDR144.

El-Khoueiry et al., The relationship of pharmacodynamics (PD) and pharmacokinetics (PK) to clinical outcomes in a phase I study of OX40 agonistic monoclonal antibody (mAb) PF-04518600 (PF-8600). J Clin Oncol. May 20, 2017. 35(15_suppl):3027-3027. Meeting Abstract. 2017 ASCO Annual Meeting I. doi: 10.1200/JCO.2017.35.15_suppl.3027. 4 pages.

Everett et al., A LAG-3/PD-L1 bispecific antibody inhibits tumour growth in two syngeneic colon carcinoma models. Poster Presentation. AACR Tumor Immunology and Immunotherapy. Oct. 21, 2016. 1 page. PDR137.

Everett et al., Abstract PR06: A LAG-3/PD-L1 bispecific antibody inhibits tumour growth in two syngeneic colon carcinoma models. AACR Special Conference on Tumor Immunology and Immunotherapy. Oct. 20-23, 2016. Boston, MA. Doi: 10.1158/2326-6074.TUMIMM16-PR06. Published Mar. 2017. 8 pages.

Everett, A LAG-3/PD-L1 Bispecific Antibody Inhibits Tumour Growth in Two Syngeneic Colon Carcinoma Models. Oral Presentation at AACR Tumor Immunology and Immunotherapy. Boston, MA. Oct. 20-23, 2016. 5 pages. PDR141.

Faroudi et al., Abstract 2399: LAG-3/PD-L1 mAb2 can overcome PD-L1-mediated compensatory upregulation of LAG-3 induced by single-agent checkpoint blockade. Proceedings: AACR Annual Meeting 2019; Mar. 29-Apr. 3, 2019. Atlanta, GA. Doi: 10.1158/1538-7445.AM2019-2399. Published Jul. 2019. 2 pages.

Faroudi et al., Abstract B009: FS118, a LAG-3/PD-L1 bispecific antibody, capable of driving potent anti-tumour immune responses and overcome PD-(L)1-mediated compensatory. Sep. 25-28, 2019. Fifth CRI-CIMT-EATI-AACR International Cancer Immunotherapy Conference (2019): Translating Science into Survival. Paris. 1 page.

Faroudi et al., FS118, a LAG-3/PD-L1 bispecific antibody, capable of driving potent anti-tumour immune responses and overcome PD-(L)1-mediated compensatory. Sep. 25-28, 2019. Poster. Fifth CRI-CIMT-EATI-AACR International Cancer Immunotherapy Conference (2019): Translating Science into Survival. Paris. 1 page.

Fiehler, Development of an anti-PD-L1 Fcab. Presentation. European Antibody Congress. Oct. 29, 2018. 26 pages. PDR312.

Foy et al., Poxvirus-Based Active Immunotherapy with PD-1 and LAG-3 Dual Immune Checkpoint Inhibition Overcomes Compensatory Immune Regulation, Yielding Complete Tumor Regression in Mice. PLoS One. Feb. 24, 2016;11(2):e0150084. doi: 10.1371/journal.pone.0150084.

Frenzel et al., Phage display-derived human antibodies in clinical development and therapy. MAbs. Oct. 2016;8(7):1177-1194. doi: 10.1080/19420862.2016.1212149. Epub Jul. 14, 2016.

F-Star, First-in-Class Bispecific Antibodies for Cance Immunotherapy. Jul. 2016. Presentation. 14 pages. PDR119.

F-Star, Next-Generation Bispecifics for Cancer Immunotherapy. Feb. 2020. Presented on Mar. 11, 2020 at Immuno-Oncology Summit Europe 2020. London. 46 pages.

F-Star, Redirecting T Cells. Overcoming Cancer. Improving Lives. Oct. 2019 Presentation in Investor Meeting. 36 pages.

F-Star, Redirecting T Cells. Overcoming Cancer. Improving Lives. Apr. 2020 Presentation in Investor Meeting. 43 pages.

F-Star, Redirecting T Cells. Overcoming Cancer. Improving Lives. Jan. 2020 Presentation in Investor Meeting. 41 pages.

Gandhi et al., Expression of LAG-3 by tumor-infiltrating lymphocytes is coincident with the suppression of latent membrane antigen-specific CD8+ T-cell function in Hodgkin lymphoma patients. Blood. Oct. 1, 2006;108(7):2280-9. doi: 10.1182/blood-2006-04-015164. Epub Jun. 6, 2006.

Gaspar et al., FS120 mAb2, a dual agonist bispecific antibody targeting OX40 and CD137, activates T cells in vitro and induces FcyR-independent anti-tumour activity. SITC 2018. Nov. 7, 2018. Poster. 10 pages.

Gaspar, FS120 mAb2, a dual agonist bispecific antibody targeting OX40 and CD137. SITC 2018. Nov. 11, 2018. Presentation. 12 pages.

Geuijen et al., Abstract 541: An unbiased screen identifies a CD137xPD-L1 bispecific IgG1 antibody with unique T cell activation and binding properties. Cancer Res. 2019;79(13_Supplement):541. Poster Presentation AACR Conference 2019. Jul. 1, 2019. doi: 10.1158/1538-7445.AM2019-541. 4 pages.

Gliddon, Pushing all the buttons: innovating in immuno-oncology with mAb. Oral Presentation at Phacilitate Immunotherapy World 2017. Jan. 18, 2017. 11 pages. PDR165.

Glisson et al., Phase 1 study of MEDI0562, a humanized OX40 agonist monoclonal antibody (mAb), in adult patients (pts) with advanced solid tumors. Annals Onocol. Oct. 1, 2016;27(6):vi361. doi: 10.1093/annonc/mdw378.07.

Golfier et al., Anetumab ravtansine: a novel mesothelin-targeting antibody-drug conjugate cures tumors with heterogeneous target expression favored by bystander effect. Mol Cancer Ther. Jun. 2014;13(6):1537-48. doi: 10.1158/1535-7163.MCT-13-0926. Epub Apr. 8, 2014.

Grosso et al., Programmed death-ligand 1 (PD-L1) expression in various tumor types. J Immunother Cancer. 2013;1(Suppl 1):P53. http://www.immunotherapyofcancer.org/content/1/S1/P53. 1 page.

Gunde et al., Abstract 1532: A novel, monovalent tri-specific antibody-based molecule that simultaneously modulates PD-L1 and 4-1BB exhibits potent anti-tumoral activity in vivo. Cancer Res. 2019;79(13_Supplement):1532. AACR Conference 2019. Jul. 1, 2019. doi: 10.1158/1538-7445.AM2019-1532. 4 pages.

Haines et al., Abstract 4714: Blockade of LAG-3 amplifies immune activation signatures and augments curative antitumor responses to anti-PD-1 therapy in immune competent mouse models of cancer. Proceedings: AACR Annual Meeting 2017. Apr. 1-5, 2017. Washington, DC. doi: 10.1158/1538-7445.AM2017-4714. Published Jul. 2017. 8 pages.

Han et al., Bispecific anti-CD3 x anti-HER2 antibody mediates T cell cytolytic activity to HER2-positive colorectal cancer in vitro and in vivo. Int J Oncol. Dec. 2014;45(6):2446-54. doi: 10.3892/ijo.2014.2663. Epub Sep. 18, 2014.

Hassan et al., Mesothelin Immunotherapy for Cancer: Ready for Prime Time? J Clin Oncol. Dec. 2016;34(34):4171-4179. doi: 10.1200/JCO.2016.68.3672. Epub Oct. 31, 2016.

Hassan et al., Phase II clinical trial of amatuximab, a chimeric antimesothelin antibody with pemetrexed and cisplatin in advanced unresectable pleural mesothelioma. Clin Cancer Res. Dec. 1, 2014;20(23):5927-36. doi: 10.1158/1078-0432.CCR-14-0804. Epub Sep. 17, 2014.

Hebb et al., Administration of low-dose combination anti-CTLA4, anti-CD137, and anti-OX40 into murine tumor or proximal to the tumor draining lymph node induces systemic tumor regression. Cancer Immunol Immunother. Jan. 2018;67(1):47-60. doi: 10.1007/s00262-017-2059-y. Epub Sep. 13, 2017. Author Manuscript. 20 pages.

Herbst et al., Predictive correlates of response to the anti-PD-L1 antibody MPDL3280A in cancer patients. Nature. Nov. 27, 2014;515(7528):563-7. doi: 10.1038/nature14011. Author Manuscript.

Hid Cadena et al., Checks and Balances in Autoimmune Vasculitis. Front Immunol. Feb. 22, 2018;9:315. doi: 10.3389/fimmu.2018.00315.

Ho et al., A novel high-affinity human monoclonal antibody to mesothelin. Int J Cancer. May 1, 2011;128(9):2020-30. doi: 10.1002/ijc.25557.

Horn et al., CD3xPDL1 bi-specific T cell engager (BiTE) simultaneously activates T cells and NKT cells, kills PDL1+ tumor cells,

(56) References Cited

OTHER PUBLICATIONS and extends the survival of tumor-bearing humanized mice. Oncotarget. Aug. 3, 2017;8(35):57964-57980. doi: 10.18632/oncotarget.19865.
Huang et al., Abstract PR03: Combinatorial blockade of PD-1, CTLA-4, and LAG-3 pathways inhibits murine ovarian tumor growth. Abstracts: AACR Special Conference: Advances in Ovarian Cancer Research: Exploiting Vulnerabilities. Oct. 17-20, 2015. Orlando, FL. doi: 10.1158/1557-3265.OVCA15-PR03. Published Jan. 2016. 8 pages.
Iwai et al., Involvement of PD-L1 on tumor cells in the escape from host immune system and tumor immunotherapy by PD-L1 blockade. Proc Natl Acad Sci U S A. Sep. 17, 2002;99(19):12293-7. doi: 10.1073/pnas.192461099. Epub Sep. 6, 2002.
Jochems et al., Analyses of functions of an anti-PD-L1/TGFBR2 bispecific fusion protein (M7824). Oncotarget. Sep. 8, 2017;8(43):75217-75231. doi: 10.18632/oncotarget.20680.
Kehry et al., Abstract 271: Targeting PD-1, TIM-3 and LAG-3 in combination for improved immunotherapy combinations. AACR 106th Annual Meeting. Apr. 18-22, 2015. Philadelphia, PA. doi: 10.1158/1538-7445.AM2015-271. 8 pages.
Klooster et al., Abstract B088: Generation of immuno-modulatory receptor binding bispecific antibodies to modulate tumor immunity. Second CRI-CIMT-EATI-AACR International Cancer Immunotherapy Conference: Translating Science into Survival. Sep. 25-28, 2016. New York, NY. doi: 10.1158/2326-6066.IMM2016-B088. 4 pages.
Koopmans et al., A novel bispecific antibody for EGFR-directed blockade of the PD-1/PD-L1 immune checkpoint. Oncoimmunology. May 31, 2018;7(8):e1466016. doi: 10.1080/2162402X.2018.1466016.
Kraman et al., A LAG-3/PD-L1 bispecific antibody inhibits tmour growth in two syngeneic colon carcinoma models. Poster Presentation. BSI/NVVI Congress. Dec. 6, 2016. 1 page. PDR153.
Kraman et al., A LAG-3/PD-L1 bispecific antibody inhibits tumour growth in two syngeneic colon carcinoma models. Abstract B091. Poster Presentation. CRI-CIMT-EATI-AACR Cancer Immunotherapy Conference. Sep. 26, 2016. 1 page. PDR129.
Kraman et al., A LAG-3/PD-L1 bispecific antibody inhibits tumour growth in two syngeneic colon carcinoma models. Poster 003. Poster Presentation. 2nd Annual Advances in Immuno-Oncology Congress. May 15, 2017. 1 page. PDR185.
Kraman et al., A LAG-3/PD-L1 bispecific antibody inhibits tumour growth in two syngeneic colon carcinoma models. Poster 1103. Poster Presentation. Keystone Symposium—Cancer Immunology and Immunotherapy. Mar. 19, 2017. 1 page. PDR174.
Kraman et al., A LAG-3/PD-L1 bispecific antibody inhibits tumour growth in two syngeneic colon carcinoma models. Poster 128. Poster Presentation at SITC. Nov. 9, 2016. 1 page. PDR143.
Kraman et al., A LAG-3/PD-L1 bispecific antibody inhibits tumour growth in two syngeneic colon carcinoma models. Poster 5651. Poster Presentation. AACR Annual Meeting. Apr. 1, 2017. 1 page. PDR176.
Kraman et al., A Lag-3/PD-L1 bispecific antibody inhibits tumour growth in two syngeneic colon carcinoma models. Poster Presentation. International Conference on Human & Translational Immunology. Sep. 16, 2016. 1 page. PDR123.
Kraman et al., A LAG-3/PD-L1 bispecific antibody inhibits tumour growth in two syngeneic coon carcinoma models. Poster 3005. Poster Presentation. Keystome Symposium—Biobetters and Next-Generation Biologics. Jan. 22-26, 2017. 1 page. PDR164.
Kraman et al., Abstract 5651:A LAG-3/PD/L1 bispecific antibody inhibits tumor growth in two syngeneic colon carcinoma models. AACR Annual Meeting 2017. Apr. 1-5, 2017. Washington, DC. Doi: 10.1158/1538-7445.AM2017-5651. 8 pages.
Kraman et al., Dual blockade of PD-L1 and LAG-3 with FS118, a unique bispecific antibody, induces CD8+ T-cell activation and modulates the tumour microenvironment to promote anti-tumour immune responses. Apr. 14-18, 2018. Poster 2719. Proceedings of the American Association for Cancer Research Annual Meeting 2018. Chicago, IL. 2 pages.
Kraman et al., Dual blockade of PD-L1 and LAG-3 with FS118, a unique bispecific antibody, induces T-cell activation with the potential to drive potent anti-tumour immune responses. Nov. 7, 2017;5 Suppl 2 (87):Abstract P348. 32nd Annual Meeting and Pre-Conference Programs of the Society for Immunotherapy of Cancer (SITC). Part II. Nov. 8-12, 2017. National Harbor, MD. 2 pages.
Kraman et al., Dual blockade of PD-L1 and LAG-3 with FS118, a unique bispecific antibody, induces T-cell activation with the potential to drive potent anti-tumour immune responses. Apr. 14-18, 2018;78(13 Suppl);Abstract 2719. Proceedings of the American Association for Cancer Research Annual Meeting 2018. Chicago, IL. 5 pages.
Kraman et al., Dual blockade of PD-L1 and LAG-3 with FS118, a unique bispecific antibody, induces T-cell activation with the potential to drive potent anti-tumour immune responses. Poster P348. 32nd Annual Meeting and Pre-Conference Programs of the Society for Immunotherapy of Cancer (SITC). Part II. Nov. 8-12, 2017. National Harbor, MD. 1 page.
Kraman et al., FS118, a Bispecific Antibody Targeting LAG-3 and PD-L1, Enhances T-Cell Activation Resulting in Potent Antitumor Activity. Clin Cancer Res. Jul. 1, 2020;26(13):3333-3344. doi: 10.1158/1078-0432.CCR-19-3548. Epub Apr. 16, 2020.
Kunik et al., Structural consensus among antibodies defines the antigen binding site. PLoS Comput Biol. 2012;8(2):e1002388. doi: 10.1371/journal.pcbi.1002388. Epub Feb. 23, 2012. 12 pages.
Kvarnhammar et al., The CTLA-4 x OX40 bispecific antibody ATOR-1015 induces anti-tumor effects through tumor-directed immune activation. J Immunother Cancer. Apr. 11, 2019;7(1):103. doi: 10.1186/s40425-019-0570-8.
La Motte-Mohs et al., Abstract 3217: MGD013, a bispecific PD-1 x LAG-3 Dual-Affinity Re-Targeting (DART®) protein with T-cell immunomodulatory activity for cancer treatment. AACR 107th Annual Meeting. Apr. 16-20, 2016. New Orleans, LA. Doi: 10.1158/1538-7445.AM2016-3217. 8 pages.
La Motte-Mohs et al., MGD013, a bispecific PD-1 x LAG-3 Dual-Affinity Re-Targeting (DART®) protein with T-cell immunomodulatory activity for cancer treatment. Poster Presentation. 2016. http://ir.macrogenics.com/events.cfm. 1 page.
Lakins et al., FS222 mAb2, a bispecific conditional agonist antibody targeting CD137 and PD-L1, induces potent lymphocyte activation and has a favourable safety profile. F-star, Cambridge, UK. Poster Presentation. AACR Annual Meeting Mar. 29-Apr 3, 2019. Atlanta, GA. Poster No. 1540. 1 page.
Lakins et al., Optimising TNFRSF agonism and checkpoint blockade with a novel CD137/PD-L1 bispecific antibody. Abstracts Therapeutic Development. Dec. 1, 2018;29(Supplement 10):X30. doi: 10.1093/annonc/mdy487.014. 1 page.
Lamberts et al., ImmunoPET with Anti-Mesothelin Antibody in Patients with Pancreatic and Ovarian Cancer before Anti-Mesothelin Antibody-Drug Conjugate Treatment. Clin Cancer Res. Apr. 1, 2016;22(7):1642-52. doi: 10.1158/1078-0432.CCR-15-1272. Epub Nov. 20, 2015.
Larkin et al., Combined Nivolumab and Ipilimumab or Monotherapy in Untreated Melanoma. N Engl J Med. Jul. 2, 2015;373(1):23-34. doi: 10.1056/NEJMoa1504030. Epub May 31, 2015. Erratum in: N Engl J Med. Nov. 29, 2018;379(22):2185.
Levitan, Amgen Halts Rilotumumab Development Due to Increased Death Signal. Cancer Network. Nov. 26, 2014. Retrieved from www.cancernetwork.com/view/amgen-halts-rilotumumab-development-due-increased-death-signal. 3 pages.
Li et al., Discovery and preclinical characterization of the antagonist anti-PD-L1 monoclonal antibody LY3300054. J Immunother Cancer. Apr. 30, 2018;6(1):31. doi: 10.1186/s40425-018-0329-7. Erratum in: J Immunother Cancer. Jun. 4, 2018;6(1):45.
Lin et al., Fc-dependent expression of CD137 on human NK cells: insights into "agonistic" effects of anti-CD137 monoclonal antibodies. Blood. Aug. 1, 2008;112(3):699-707. doi: 10.1182/blood-2007-11-122465. Epub Jun. 2, 2008.
Link et al., Abstract 3752: Preclinical pharmacology of MP0310: A 4-1BB/FAP bispecific DARPin drug candidate promoting tumor-restricted T-cell costimulation. Cancer Res. Jul. 1, 2018;78(13_Supplement):3752.

(56) References Cited

OTHER PUBLICATIONS

Liu et al., Abstract 3642: Tumor-antigen expression-dependent activation of the CD137 costimulatory pathway by bispecific DART® proteins. Cancer Res. Jul. 1, 2017;77(13_Supplement):3642.
Liu et al., Dual Targeting of Innate and Adaptive Checkpoints on Tumor Cells Limits Immune Evasion. Cell Rep. Aug. 21, 2018;24(8):2101-2111. doi: 10.1016/j.celrep.2018.07.062.
Ma et al., Recognition of mesothelin by the therapeutic antibody MORAb-009: structural and mechanistic insights. J Biol Chem. Sep. 28, 2012;287(40):33123-31. doi: 10.1074/jbc.M112.381756. Epub Jul. 11, 2012.
Mayes et al., Abstract 539: A bispecific Fc-silenced IgG1 antibody (MCLA-145) requires PD-L1 binding to activate CD137. Cancer Res. 2019;79(13_Supplement):539. AACR Presentation 2019. Jul. 1, 2019. doi: 10.1158/1538-7445.AM2019-539. 4 pages.
McCourt et al., KY1055; a novel ICOS/PD-L1 bispecific antibody, enhance T cell activation and delivers potent monotherapy anti-tumour response in vivo. Abstract. CIMT 2018. Feb. 28, 2018. 1 page. PDR245.
McCourt et al., KY1055; a novel ICOS/PD-L1 bispecific antibody, enhance T cell activation and delivers potent monotherapy anti-tumour response in vivo. Poster Presentation. CIMT Conference. May 9, 2018. 1 page. PDR 264.
McCourt et al., KY1055; a novel ICOS/PD-L1 bispecific antibody, enhance T cell activation and delivers potent monotherapy anti-tumour response in vivo. Presentation. CIMT Conference. May 9, 2018. 13 pages. PDR265.
McCourt, Development of an ICOS/PD-L1 Bispecific, Mar. 18-22, 2019. Abstract. Cambridge Healthtech Institute's 4th Annual Immuno-Oncology Summit Europe 2019 (London).
Melero et al., Clinical development of immunostimulatory monoclonal antibodies and opportunities for combination. Clin Cancer Res. Mar. 1, 2013;19(5):997-1008. doi: 10.1158/1078-0432.CCR-12-2214.
Michaelson et al., Anti-tumor activity of stability-engineered IgG-like bispecific antibodies targeting Trail-R2 and LTbetaR. MAbs. Mar.-Apr. 2009;1(2):128-41. doi: 10.4161/mabs.1.2.7631. Epub Mar. 11, 2009.
Munoz-Olaya, Development of an anti-PD-L1Fcab. Presentation. PEGS Lisbon. Nov. 16, 2018. 24 pages. PDR321.
Nalivaiko et al., A Recombinant Bispecific CD20xCD95 Antibody With Superior Activity Against Normal and Malignant B-cells. Mol Ther. Feb. 2016;24(2):298-305. doi: 10.1038/mt.2015.209. Epub Nov. 19, 2015.
Pavlidou et al., Simultaneous costimulatory T-cell engagement and checkpoint inhibition by PRS-344/ONC0055, a 4-1BB/PD-L1 bispecific compound for tumor localized activation of the immune system. SITC 2018. Poster Presentation. 2018. 1 page.
Perez-Ruiz et al., Anti-CD137 and PD-1/PD-L1 Antibodies En Route toward Clinical Synergy. Clin Cancer Res. Sep. 15, 2017;23(18):5326-5328. doi: 10.1158/1078-0432.CCR-17-1799. Epub Aug. 8, 2017.
Poon et al., Dual agonist bispecific antibody targeting OX40 and DC137 mediates anti-tumour immunity and synergises with PD-1/PD-L1 blockade to improve survival in a syngeneic mouse model. AACR 2019. Mar. 29, 2019. Poster. 9 pages.
Powles et al., MPDL3280A (anti-PD-L1) treatment leads to clinical activity in metastatic bladder cancer. Nature. Nov. 27, 2014;515(7528):558-62. doi: 10.1038/nature13904.
Reichen et al., Abstract 3029: FAP-mediated tumor accumulation of a T-cell agonistic FAP/4-1BB DARPin drug candidate analyzed by Spect/CT and quantitative biodistribution. Cancer Res. Jul. 1, 2018;78(13_Supplement):3029.
Ryan et al., A novel biologic platform elicits profound T cell costimulatory activity and antitumor immunity in mice. Cancer Immunol Immunother. Apr. 2018;67(4):605-613. doi: 10.1007/s00262-018-2116-1. Epub Jan. 11, 2018.
Sainson et al., KY1055, a novel ICOS/PD-L1 bispecific antibody, efficiently enhances T cell activation and delivers a potent anti-tumour response in vivo. Abstract. AACR. Jan. 22, 2018. 1 page. PDR236.
Sainson et al., KY1055, a novel ICOS/PD-L1 bispecific antibody, efficiently enhances T cell activation and delivers a potent anti-tumour response in vivo. Poster Presentation. AACR 2018. Apr. 4, 2018. 1 page. PDR254.
Schroeder, Chapter 13: Immunoglobulins and Their Genes. From Arthritis and Allied Conditions: A Textbook of Rheumatology. 15th Ed. vol. 1. Eds Koopman et al.Lippincot Williams & Wilkins. pp. 289-304. Supplied by the British Library Jul. 31, 2023.
Segal et al., Results from an Integrated Safety Analysis of Urelumab, an Agonist Anti-CD137 Monoclonal Antibody. Clin Cancer Res. Apr. 15, 2017;23(8):1929-1936. doi: 10.1158/1078-0432.CCR-16-1272. Epub Oct. 18, 2016.
Strauss et al., Phase I Trial of M7824 (MSB0011359C), a Bifunctional Fusion Protein Targeting PD-L1 and TGFβ, in Advanced Solid Tumors. Clin Cancer Res. Mar. 15, 2018;24(6): 1287-1295. doi: 10.1158/1078-0432.CCR-17-2653. Epub Jan. 3, 2018.
Tang et al., A human single-domain antibody elicits potent antitumor activity by targeting an epitope in mesothelin close to the cancer cell surface. Mol Cancer Ther. Apr. 2013;12(4):416-26. doi: 10.1158/1535-7163.MCT-12-0731. Epub Jan. 31, 2013.
Tuna, Delivering the next immuno-oncology breakthrough. PEGS Europe 2018. Nov. 11, 2018. Presentation. 24 pages.
Tuna, Identification of a PD-L1 binding FCAB: a potent inhibitor of immunosuppressive signals. Abstract. European Antibody Congress. May 3, 2018. 1 page. PDR270.
Tuna, The use of bispecific antibodies to modulate anti-tumour immune responses. Oral Presentation at 10th Annual Proteins and Antibodies Congress. Apr. 24, 2017. 26 pages. PDR183.
Vanamee et al., Structural principles of tumor necrosis factor superfamily signaling. Sci Signal. Jan. 2, 2018;11(511):eaao4910. doi: 10.1126/scisignal.aao4910. 12 pages.
Wang et al., Retargeting T cells for HER2-positive tumor killing by a bispecific Fv-Fc antibody. PLoS One. Sep. 23, 2013;8(9):e75589. doi: 10.1371/journal.pone.0075589. eCollection 2013.
Weismann, A LAG-3/PD-L1 Bispecific Antibody Inhibits Tumour Growth in Two Syngeneic Colon Carcinoma Models. International Conference on Human and Translational Immunology. Rhodes, Greece. Sep. 16-21, 2016. Presentation. 6 pages. PDR128.
Wherry, T cell exhaustion. Nat Immunol. Jun. 2011;12(6):492-9. doi: 10.1038/ni.2035.
Wilton, KY1055, a bispecific mAb2 targeting ICOS and PD-L1. Presentation. Feb. 21, 2018. 17 pages. PDR238.
Wolchok et al., Nivolumab plus ipilimumab in advanced melanoma. N Engl J Med. Jul. 11, 2013;369(2):122-33. doi: 10.1056/NEJMoa1302369. Epub Jun. 2, 2013. Erratum in: N Engl J Med. Nov. 29, 2018;379(22):2185. Author Manuscript.
Woo et al., Immune inhibitory molecules LAG-3 and PD-1 synergistically regulate T-cell function to promote tumoral immune escape. Cancer Res. Feb. 15, 2012;72(4):917-27. doi: 10.1158/0008-5472.CAN-11-1620. Epub Dec. 20, 2011.
Workman et al., Negative regulation of T cell homeostasis by lymphocyte activation gene-3 (CD223). J Immunol. Jan. 15, 2005;174(2):688-95. doi: 10.4049/jimmunol.174.2.688.
Workman et al., The CD4-related molecule, LAG-3 (CD223), regulates the expansion of activated T cells. Eur J Immunol. Apr. 2003;33(4):970-9. doi: 10.1002/eji.200323382.
Wydro, Bispecific antibodies: new opportunities for novel therapies. Oral Presentation at 7th Annual Biologics Symposium. Mar. 1, 2017. 24 pages. PDR172.
Wykes et al., Immune checkpoint blockade in infectious diseases. Nat Rev Immunol. Feb. 2018;18(2):91-104. doi: 10.1038/nri.2017.112. Epub Oct. 9, 2017.
Yap et al., A first-in-human phase I study of FS118, an anti-LAG-3/PD-L1 bispecific antibody in patients with solid tumors that have progressed on prior PD-1/PD-L1 therapy. Journal of Clinical Oncology. Jun. 1, 2019. Poster TPS2652. 2019 ASCO Annual Meeting Proceedings. 20 pages.
Yap et al., A first-in-human phase I study of FS118, an anti-LAG-3/PD-L1 bispecific antibody in patients with solid tumors that have

(56) References Cited

OTHER PUBLICATIONS progressed on prior PD-1/PD-L1 therapy. Journal of Clinical Oncology. May 26, 2019;37(15_suppl). 3 pages.
Yonezawa et al., Boosting Cancer Immunotherapy with Anti-CD137 Antibody Therapy. Clin Cancer Res. Jul. 15, 2015;21(14):3113-20. doi: 10.1158/1078-0432.CCR-15-0263. Epub Apr. 23, 2015.
Zhang et al., Structural basis of a novel PD-L1 nanobody for immune checkpoint blockade. Cell Discov. Mar. 7, 2017;3:17004. doi: 10.1038/celldisc.2017.4.
Zhao et al., Novel Antibody Therapeutics Targeting Mesothelin in Solid Tumors. Clin Cancer Drugs. Oct. 2016;3(2):76-86. doi: 10.2174/2212697X03666160218215744.
International Search Report and Written Opinion for Application No. PCT/EP2019/068817, mailed Oct. 23, 2019.
International Preliminary Report on Patentability for Application No. PCT/EP2019/068817, mailed Jan. 21, 2021.
[No Author Listed] F-star Alpha: A new asset centric company. Retrieved from http://www.onenucleus.com/media/Events/LSLS/11%20feb%202014/Jane%20Dancer.pdf on Jan. 8, 2015. 15 pages.
Asgarov et al., A new anti-mesothelin antibody targets selectively the membrane-associated form. MAbs. Apr. 2017;9(3):567-577. doi: 10.1080/19420862.2017.1288770.
Bacac et al., Abstract 1494: CEA TCB: A novel head-to-tail 2:1 T cell bispecific antibody for treatment of CEA-positive solid tumors. Oncoimmunology. Aug. 2016; 5(Abstract): e1203498. Epub Jun. 24, 2016. doi: 10.1080/2162402X.2016.1203498.
Chester et al., 4-1BB agonism: adding the accelerator to cancer immunotherapy. Cancer Immunol Immunother. Oct. 2016;65(10):1243-8. doi: 10.1007/s00262-016-1829-2. Epub Mar. 31, 2016.
Chester et al., Dual antibody therapy to harness the innate anti-tumor immune response to enhance antibody targeting of tumors. Curr Opin Immunol. Apr. 2015;33:1-8. doi: 10.1016/j.coi.2014.12.010. Epub Jan. 7, 2015.
Goding et al., Combination of adoptive cell transfer, anti-PD-L1 and anti-LAG-3 antibodies for the treatment of recurrent tumors: better with more. OncoImmunology. Oct. 22, 2013;2(8):e25050-1-e25050-3.
Hasenhindl et al., Creating stable stem regions for loop elongation in Fcabs—insights from combining yeast surface display, in silico loop reconstruction and molecular dynamics simulations. Biochim Biophys Acta. 2014;1844(9):1530-1540. doi:10.1016/j.bbapap.2014.04.020.
Hasenhindl et al., Stability assessment on a library scale: a rapid method for the evaluation of the commutability and insertion of residues in C-terminal loops of the CH3 domains of IgG1-Fc. Protein Eng Des Sel. 2013;26(10):675-682.
Jing et al., Combined immune checkpoint protein blockade and low dose whole body irradiation as immunotherapy for myeloma. Journal of Immunotherapy of Cancer. doi: 10.1186/S40425-014-0043-Z. Jan. 20, 2015. 15 pages.
Kraman et al., A LAG-3/PD-L1 bispecific antibody inhibits tumor growth in two syngeneic colon carcinoma models. Journal of ImmunoTherapy of Cancer. 2016;4(Suppl 1):82(abstract P124).
Kraman et al., A LAG-3/PD-L1 bispecific antibody inhibits tumor growth in two syngeneic colon carcinoma models. Retrieved from http://www.f-star.com/media/73722/A-LAG-3-PD-L1-bispecific-antibody-inhibits-tumour-growth-in-two-syngeneic-colon-carcinoma-models.pdf. Nov. 9-13, 2016. 1 page.
Lakins et al., A Novel CD137/PD-L1 Bispecific Antibody Modulates the Tumour Microenvironmentby Activating CD8+ T cells and Results in Tumour Growth Inhibition. F-Star Poster. Nov. 7, 2018. 1 page. Retrieved from https://www.f-star.com/media/87488/201811-SITC-2018-F-star-FS222-Poster-ONLINE.pdf.
Lee et al., 4-1BB and OX40 dual costimulation synergistically stimulate primary specific CD8 T cells for robust effector function. J Immunol. Sep. 1, 2004;173(5):3002-12. doi: 10.4049/jimmunol.173.5.3002.
Leung et al., A HER2-specific Modified Fc Fragment (Fcab) Induces Antitumor Effects Through Degradation of HER2 and Apoptosis. Mol Ther. Nov. 2015;23(11):1722-1733. doi: 10.1038/mt.2015.127. Epub Aug. 3, 2015. Erratum in: Mol Ther. Nov. 2015;23(11):1794.
Lobner et al., Engineered IgG1-Fc—one fragment to bind them all. Immunol Rev. Mar. 2016;270(1):113-31. doi: 10.1111/imr.12385.
Lobner et al., Two-faced Fcab prevents polymerization with VEGF and reveals thermodynamics and the 2.15 Å crystal structure of the complex. MAbs. Oct. 2017;9(7):1088-1104. doi: 10.1080/19420862.2017.1364825. Epub Aug. 17, 2017.
Lundqvist et al., 31st Annual Meeting and Associated Programs of the Society for Immunotherapy of Cancer (SITC 2016): Part One. Journal for Immunotherapy of Cancer. Nov. 16, 2016;4(1):74(abstract p. 124).
Qui et al., CD134 plus CD137 dual costimulation induces Eomesodermin in CD4 T cells to program cytotoxic Th1 differentiation. J Immunol. Oct. 1, 2011;187(7):3555-64. doi: 10.4049/jimmunol.1101244. Epub Aug. 31, 2011.
Ramelet et al., Beneficial outcome of combination therapy with 4-1BB targeting antibody. Eur J Cancer. Nov. 29, 2016;69(Suppl 1):S96-S97.
Sallin et al., The anti-lymphoma activities of anti-CD137 monoclonal antibodies are enhanced in FcγRIII(-/-) mice. Cancer Immunol Immunother. Sep. 2014;63(9):947-58. doi: 10.1007/s00262-014-1567-2. Epub Jun. 14, 2014.
Schlothauer et al., Novel human IgG1 and IgG4 Fc-engineered antibodies with completely abolished immune effector functions. Protein Eng Des Sel. Oct. 2016;29(10):457-466. doi: 10.1093/protein/gzw040. Epub Aug. 29, 2016.
Shindo et al., Combination immunotherapy with 4-1BB activation and PD-1 blockade enhances antitumor efficacy in a mouse model of subcutaneous tumor. Anticancer Res. Jan. 2015;35(1):129-36.
Vilgelm et al., Combinatorial approach to cancer immunotherapy: strength in numbers. Journal of Leukocyte Biology. 2016;100(2):275-90. Epub Jun. 2, 2016.
Wozniak-Knopp et al., Designing Fcabs: well-expressed and stable high affinity antigen-binding Fc fragments. Protein Eng Des Sel. Sep. 1, 2017;30(9):657-671. doi: 10.1093/protein/gzx042.
Wozniak-Knopp et al., Introducing antigen-binding sites in structural loops of immunoglobulin constant domains: Fc fragments with engineered HER2/neu-binding sites and antibody properties. Protein Eng Des Sel. 2010;23(4):289-297. doi:10.1093/protein/gzq005.
Xu et al, In vitro characterization of five humanized OKT3 effector function variant antibodies. Cell Immunol. Feb. 25, 2000;200(1):16-26.
[No Author Listed], mesothelin isoform 1 preproprotein [*Homo sapiens*]. NCBI Reference Sequence: NP_001170826.1. May 2, 2024. Retrieved from https://www.ncbi.nlm.nih.gov/protein/NP_001170826.1/. 4 pages.
[No Author Listed], mesothelin isoform 1 preproprotein [Mus musculus]. NCBI Reference Sequence: NP_001343215.1. Jun. 18, 2024. Retrieved from https://www.ncbi.nlm.nih.gov/protein/NP_001343215.1. 3 pages.
[No Author Listed], Predicted: mesothelin isoform X4 [Macaca fascicularis]. NCBI Reference Sequence: XP_005590874.2. Jan. 25, 2016. Retrieved from https://www.ncbi.nlm.nih.gov/protein/XP_005590874.2. 2 pages.
[No Author Listed], tumor necrosis factor receptor superfamily member 9 precursor [*Homo sapiens*]. NCBI Reference Sequence: NP_001552.2. Jun. 9, 2024. Retrieved from https://www.ncbi.nlm.nih.gov/protein/NP_001552.2. 4 pages.
Badri et al., Optimization of radiation dosing schedules for proneural glioblastoma. J Math Biol. Apr. 2016;72(5):1301-36. doi: 10.1007/s00285-015-0908-x.
Baylot et al., TCTP Has a Crucial Role in the Different Stages of Prostate Cancer Malignant Progression. Results Probl Cell Differ. 2017;64:255-261. doi: 10.1007/978-3-319-67591-6_13.
Brinkmann et al., The making of bispecific antibodies. MAbs. Feb./Mar. 2017;9(2):182-212. doi: 10.1080/19420862.2016.1268307.
Durham et al., Lymphocyte Activation Gene 3 (LAG-3) modulates the ability of CD4 T-cells to be suppressed in vivo. PLoS One. Nov. 5, 2014;9(11):e109080. doi: 10.1371/journal.pone.0109080. 13 pages.

(56) References Cited

OTHER PUBLICATIONS

Gide et al., Distinct Immune Cell Populations Define Response to Anti-PD-1 Monotherapy and Anti-PD-1/Anti-CTLA-4 Combined Therapy. Cancer Cell. Feb. 11, 2019;35(2):238-255.e6. doi: 10.1016/j.ccell.2019.01.003.

Gough et al., OX40 agonist therapy enhances CD8 infiltration and decreases immune suppression in the tumor. Cancer Res. Jul. 1, 2008;68(13):5206-15. doi: 10.1158/0008-5472.CAN-07-6484.

Hong et al., An Agonistic Anti-CD137 Antibody Disrupts Lymphoid Follicle Structure and T-Cell-Dependent Antibody Responses. Cell Rep Med. Jun. 23, 2020;1(3):100035. doi: 10.1016/j.xcrm.2020.100035.

Koyama et al., Adaptive resistance to therapeutic PD-1 blockade is associated with upregulation of alternative immune checkpoints. Nat Commun. Feb. 17, 2016;7:10501. doi: 10.1038/ncomms10501. 9 pages.

Matsuzaki et al., Tumor-infiltrating NY-ESO-1-specific CD8+ T cells are negatively regulated by LAG-3 and PD-1 in human ovarian cancer. Proc Natl Acad Sci U S A. Apr. 27, 2010;107(17):7875-80. doi: 10.1073/pnas.1003345107. Epub Apr. 12, 2010.

Muller et al., Spliceosomal peptide P140 for immunotherapy of systemic lupus erythematosus: results of an early phase II clinical trial. Arthritis Rheum. Dec. 2008;58(12):3873-83. doi: 10.1002/art.24027.

Otano et al., CD137 (4-1BB) costimulation of CD8+ T cells is more potent when provided in cis than in trans with respect to CD3-TCR stimulation. Nat Commun. Dec. 15, 2021;12(1):7296. doi: 10.1038/s41467-021-27613-w.

Shen, et al. Single variable domain-IgG fusion. A novel recombinant approach to Fc domain-containing bispecific antibodies. J Biol Chem. Apr. 21, 2006;281(16):10706-14. doi: 10.1074/jbc.M513415200. Epub Feb. 15, 2006.

Shepherd et al., T Cell Immunity to Bacterial Pathogens: Mechanisms of Immune Control and Bacterial Evasion. Int J Mol Sci. Aug. 26, 2020;21(17):6144. doi: 10.3390/ijms21176144.

Torres et al., The immunoglobulin constant region contributes to affinity and specificity. Trends Immunol. Feb. 2008;29(2):91-7. doi: 10.1016/j.it.2007.11.004. Epub Jan. 10, 2008.

Turaj et al., Augmentation of CD134 (OX40)-dependent NK anti-tumour activity is dependent on antibody cross-linking. Sci Rep. Feb. 2, 2018;8(1):2278. doi: 10.1038/s41598-018-20656-y.

Ye et al., CD137, an attractive candidate for the immunotherapy of lung cancer. Cancer Sci. May 2020;111(5):1461-1467. doi: 10.1111/cas.14354. Epub Apr. 3, 2020.

Yuan et al., Contributions of Costimulatory Molecule CD137 in Endothelial Cells. J Am Heart Assoc. Jun. 2021;10(11):e020721. doi: 10.1161/JAHA.120.020721. Epub May 22, 2021.

* cited by examiner

A

B

C

D

E

F

A

B

MESOTHELIN AND CD137 BINDING MOLECULES

RELATED APPLICATION

This application is a national stage filing under 35 U.S.C. 371 of International Patent Application Serial No. PCT/EP2019/068817, filed Jul. 12, 2019, the entire contents of which is incorporated herein by reference in its entirety.

REFERENCE TO AN ELECTRONIC SEQUENCE LISTING

The contents of the electronic sequence listing (F083170005US00-SUBSEQ-ZJG.xml; Size: 308,520 bytes; and Date of Creation: Nov. 20, 2024) is herein incorporated by reference in its entirety.

FIELD OF THE INVENTION

The present invention relates to antibody molecules that bind both mesothelin (MSLN) and CD137. The antibody molecules comprise a CDR-based binding site for MSLN, and a CD137 antigen-binding site located in a constant domain of the antibody molecule. The antibody molecules find application in the treatment of cancer, for example.

BACKGROUND TO THE INVENTION

Cell signalling is an essential part of the life of all organisms and normally involves cell surface receptors that interact with soluble or surface expressed ligands. This interaction results in changes to the receptor, the ligand or both. For example, ligand binding can induce conformational changes in the receptors causing them to cluster together into dimers or oligomers. This clustering effect then results in activation of intracellular signalling pathways.

There are numerous receptors that are activated in this way, including members of the tumour necrosis factor receptor superfamily (TNFRSF), such as CD137.

CD137 (4-1 BB; TNFRSF9) is a co-stimulatory molecule of the tumour necrosis factor receptor superfamily (TNFRSF). CD137 is widely known to be upregulated on $CD8^+$ T cells following activation, and can also be expressed on activated $CD4^+$ helper T cells, B cells, regulatory T cells, natural killer (NK) cells, natural killer T (NKT) cells and dendritic cells (DCs) (Bartkowiak & Curran, 2015). The primary functional role of CD137 in enhancing T cell cytotoxicity was first described in 1997 (Shuford et al., 1997), and soon thereafter anti-CD137 mAbs were proposed as anti-cancer therapeutics.

CD137 is a transmembrane protein with four extracellular cysteine-rich domains, referred to as CRD1-4, and a cytoplasmic region responsible for CD137 signalling. The ligand for CD137 is CD137L. Although no crystal structure exists for the CD137/CD137L complex, it is predicted that CD137 forms a trimer/trimer complex with CD137L (Won et al., 2010).

Engagement of CD137L results in receptor trimer formation and subsequent clustering of multiple receptor trimers, and leads to the activation of the CD137 signalling cascade. This signalling cascade provides a survival signal to T cells against activation-induced cell death (Hurtado et al., 1997) thereby playing a critical role in sustaining effective T cell immune responses and generating immunological memory (Bartkowiak & Curran, 2015).

The role of CD137 in leukocyte biology is generally well understood with a clear biological rationale behind its role in tumour immunology. CD137 is expressed by activated T cells and has been used as a marker to identify antigen-specific $CD4^+$ and $CD8^+$ T cells. Typically, expression of CD137 is higher on $CD8^+$ T cells than $CD4^+$ T cells (Wen et al., 2002). In the case of $CD8^+$ T cells, proliferation, survival and cytotoxic effector function via the production of interferon gamma and interleukin 2 have been attributed to CD137 crosslinking. CD137 crosslinking also contributes to the differentiation and maintenance of memory $CD8^+$ T cells. In some subsets of $CD4^+$ T cells, CD137 crosslinking similarly leads to proliferation and activation and results in the release of cytokines such as interleukin 2 (Makkouk et al., 2016).

Natural killer (NK)-mediated antibody-dependent cellular cytotoxicity (ADCC) via tumour-targeting mAbs has been demonstrated to be enhanced as a consequence of CD137 stimulation via agonistic anti-CD137 monoclonal antibodies in vitro and in vivo (Bartkowiak & Curran, 2015). NK cells bind antibodies via their Fc receptor and, depending on the antibody isotype, this can lead to NK cell activation, eliciting cytotoxic granule release and the lysis of target cells (Kohrt et al., 2012). Kohrt and colleagues demonstrated that an anti-CD137 agonistic antibody enhanced the antitumor activity of therapeutic antibodies rituximab, trastuzumab, and cetuximab by enhancing ADCC when dosed in combination therewith (Kohrt et al., 2014; Kohrt et al., 2011). In addition, human NK cells upregulate expression of CD137 after encountering cell-bound antibodies via their FcγR. Subsequent stimulation of these NK cells with an anti-CD137 antibody has been shown to enhance their ADCC against tumour cells (Chester et al., 2015; Chester et al., 2016).

B lymphocytes also express CD137 upon activation. Binding of CD137 ligand to CD137 enhances B cell proliferation, survival and cytokine production. CD137 expression is also induced on normal and malignant human B cells following binding of CD40 to its ligand CD154 (CD40 ligand), resulting in enhanced B cell survival if CD137 is subsequently activated.

CD137 has also been demonstrated to be expressed on tumour-reactive subsets of tumour-infiltrating lymphocytes (TILs). CD137 monotherapy has been shown to be efficacious in several preclinical immunogenic tumour models such as MC38, CT26 and B cell lymphomas. Combination of CD137 engagement with other anti-cancer agents such as chemotherapy, cytokines and other checkpoint regulators has been demonstrated to result in enhanced growth reduction of established tumours. Specifically, combination of anti-CD137 antibodies with anti-CD20, anti-EGFR, and anti-HER-2 antibodies has been shown to result in a synergistic effect on tumour growth reduction in various preclinical xenograft models (Kohrt et al., 2014; Kohrt et al., 2012; Kohrt et al., 2011).

Coupling a tumour-targeted monoclonal antibody therapy with treatment with an anti-CD137 agonist antibody has shown promising results in preclinical models for lymphoma (Kohrt et al., 2011), head and neck cancer, colorectal cancer (Kohrt et al., 2014) and breast cancer (Kohrt et al., 2012). However, clinical development has been slowed due to dose-limiting high-grade liver inflammation associated with CD137 agonist antibody treatment. Urelumab (BMS-663513), a non-ligand blocking human IgG4 isotype antibody (Chester et al., 2018), was the first anti-CD137 antibody to enter clinical trials but these were halted after significant, on target, dose-dependent liver toxicity was observed (Chester et al., 2018). More recently, clinical trials of urelumab in the treatment of solid cancers was recommenced in which urelumab treatment was combined with radiotherapy (NCT03431948) or with other therapeutic antibodies, such as rituximab (NCT01775631), cetuximab (NCT02110082), anti-PD-1 antibody nivolumab (NCT02253992, NCT02534506, NCT02845323), and a combination of nivolumab and the anti-LAG-3 antibody BMS986016 (NCT02658981). However, to reduce liver toxicity associated with urelumab treatment, dosing of urelumab in these trials had to be limited and efficacy results were disappointing (Chester et al., 2018).

No dose-limiting toxicity (DLT) has been observed with Pfizer's anti-CD137 antibody utomilumab (PF-05082566), a human IgG2 isotype antibody, in the dose range 0.03 mg/kg up to 10 mg/kg in Phase I clinical trials of advanced cancer (Chester et al. 2016; Segal et al., 2018). However, the overall objective response rate with this antibody was only 3.8% in patients with solid tumours, potentially indicating that utomilumab has a weaker potency and clinical efficacy than urelumab, whilst having a more favourable safety profile (Chester et al., 2018; Segal et al., 2018). Utomilumab has been tested in combination with radiotherapy (NCT03217747) or chemotherapy, as well as in combination with other antibody therapies, including anti-PD-L1 antibody avelumab (NCT02554812), and anti-PD-1 antibody pembrolizumab (NCT02179918), to assess the safety, tolerability, dose-limiting toxicities (DLTs), maximum tolerated dose (MTD) and efficacy of the different treatment combinations. These trials are ongoing with early results showing no DLTs for doses up to 5 mg/kg and a 26% patient response rate for the combination of utomilumab and pembrolizumab. Triple combinations of utomilumab with avelumab and other immunooncology therapies are also being tested (NCT02554812, NCT03217747).

MSLN is expressed at relatively low levels on mesothelial cells lining the pleura, peritoneum, and pericardium (Hassan et al., 2005) of healthy individuals, but is highly expressed in several different cancers, including mesotheliomas, squamous cell carcinomas, pancreatic cancer, lung, gastric, breast, endometrial and ovarian cancer. The normal biological function of mesothelin is not known. In the context of cancer, high expression levels of MSLN have been correlated with poor prognosis in ovarian cancer, cholangiocarcinoma, lung adenocarcinoma and triple-negative breast cancer. The limited expression of MSLN on normal cells versus the high expression on tumour cells makes it an attractive therapeutic target using monoclonal antibodies (Hassan et al., 2016).

MSLN is expressed as a 69-kDa precursor protein (628 amino acids). The precursor protein is then cleaved by the endoprotease furin to release the secreted N-terminal region called megakaryocyte-potentiating factor (MPF), whereas the 40-kDa protein mature MSLN remains attached to the cell membrane via a glycosylphosphatidylinositol (GPI) linker. Human MSLN shares 60% and 87% amino acid identity with the murine and cynomolgus orthologs of MSLN, respectively.

Membrane bound, mature MSLN is shed from cells as a result of alternative splicing, by creating variants lacking the membrane-anchor sequence, or protease cleavage by tumour necrosis factor α-converting enzyme (TACE) (Sapede et al., 2008; Zhang et al., 2011). Soluble shed MSLN is found in patient's sera and in stroma of tumours including malignant mesothelioma, ovarian cancers or highly metastatic cancers. Measuring soluble MSLN levels in the blood and effusions of mesothelioma patients has been approved by the US FDA for monitoring patient response to treatment and progression (Hollevoet et al., 2012, Creany et al., 2015).

Several antibody-based therapies targeting MSLN have been developed and tested in clinical trials, predominantly in mesothelioma, pancreatic and non-small cell lung cancer (Hassan et al., 2016). The strategies employed include direct tumour cell killing through the use of anti-MSLN antibodies, such as amatuximab, with antibody-dependent cell-mediated cytotoxicity (ADCC) activity, as well as the use of antibody drug conjugates (ADCs), such as SS1P-PE38 and anetumab-ravtansine, comprising an antibody or antibody fragment conjugated to a toxin.

Unconjugated antibodies targeting MSLN have shown favourable safety profiles but their therapeutic efficacy has been limited, whereas ADCs have shown more potent in anti-tumour activity but were associated with dose limiting toxicities. Several bispecific molecules intended to engage the immune system are also in development, including ABBV-428, which targets MSLN as well as the costimulatory protein CD40, the MSLN-CD3 bispecific T cell engager (BITE), and a MSLN-CD47 bispecific molecule.

STATEMENTS OF INVENTION

As explained in the background section above, clinical development of CD137 agonist molecules has been held back due to treatment being either associated with dose-limiting high-grade liver inflammation (urelumab) or low clinical efficacy (utomilumab).

The present inventors recognised that there is a need in the art for CD137 agonist molecules which exhibit high activity but are not associated with dose-limiting liver inflammation. Such molecules could be administered to individuals at doses which optimize the potency and therefore efficacy of the molecule, and could be employed in the treatment of cancer as immunotherapeutic agents, for example.

Without wishing to be bound by theory, it is thought that T cells present in the liver may have the potential to be activated by anti-CD137 agonist molecules, leading to liver inflammation. $CD8^+$ T cells have been shown to promote liver inflammation and apoptosis after sepsis/viral infection (Wesche-Soldato et al., 2007). However, this effect was not CD137 specific. Anti-CD137 agonist antibody therapy in mice has been shown to result in CD137-dependent T cell infiltration into the liver (Dubrot J et al., 2010). The results from these studies, when taken together, indicate that anti-CD137 agonist antibodies with high activity, such as urelumab, may cause infiltration of activated $CD8^+$ T cells into the liver, thereby leading to liver inflammation.

Initial ligation of CD137 ligand to CD137 is thought to initiate a chain of events that leads to receptor trimerisation, followed by receptor clustering, activation and subsequent initiation of potent anti-tumour immune cell activity. For a therapeutic agent to efficiently achieve activation of CD137, it is therefore expected that several receptor monomers need to be bridged together in a way that mimics bridging by the trimeric ligand.

The present inventors have isolated antibody molecules which comprise a complementarity determining region (CDR)-based antigen-binding site for MSLN and a CD137 antigen-binding site located in a constant domain of the antibody molecule. The inventors have shown that such antibody molecules are capable of inducing clustering and signalling of CD137 when bound to both CD137 and MSLN in vitro.

Without wishing to be bound by theory, it is thought that the antibody molecules bind to MSLN via their CDR-based antigen-binding sites, resulting in crosslinking of several antibody molecules on a tumour cell surface, followed by binding of the CD137 antigen-binding site of the antibody molecules to CD137 on the surface of an immune cell, such as a tumour infiltrating lymphocyte (TIL), leading to clustering and activation of CD137, and thereby immune activation. The activated immune cells can then act on the tumour, resulting in tumour immunotherapy.

It is thought that the concentration of MSLN present at the tumour cell surface affects the level of CD137 agonism. Specifically, it is thought that a higher concentration of MSLN results in increased binding and crosslinking of the antibody molecules across the cell surfaces and consequently increased CD137 agonism.

The CD137 agonist activity of the antibody molecule of the invention is dependent on the simultaneous binding of the antibody molecule to MSLN. Activation of CD137 by the antibody molecules is therefore expected to be limited to the tumour microenvironment. The antibody molecules of the invention are therefore also referred to as "conditional agonists" herein. In this context, it should be noted that the conditional agonist activity of the antibody molecules is not an intrinsic feature of antibodies which comprise a CD137 antigen-binding site in their constant domain. Rather, many of the molecules isolated during the screening program conducted by the present inventors bound to CD137 but did not require crosslinking for CD137 clustering and activation or induced limited CD137 clustering and activation in the absence of crosslinking. Due to the conditional agonist activity of the antibody molecules of the invention, localised in the tumour microenvironment, these molecules are not expected to cause liver inflammation.

Conventional antibodies specific for TNF receptors such as CD137 typically have no or only very moderate intrinsic agonistic activity and require secondary crosslinking of antibody-TNFRSF member complexes using external crosslinking agents, such as protein A or G or secondary antibodies, or binding of the antibody to plasma membrane localised Fcγ receptors, in order to induce higher levels of TNF receptor member clustering and activation (Wajant, 2015). The low levels or lack of agonist activity of TNF receptor-specific antibodies in the absence of crosslinking can be explained by the fact that a normal bivalent antibody can maximally crosslink two monomeric TNF receptors which is insufficient for TNF receptor activation. Therefore, for in vivo efficacy, a monospecific antibody targeting CD137 requires the presence of Fcγ receptor-expressing cells in close proximity to CD137-expressing T cells to achieve crosslinking of the CD137-specific antibodies and subsequent clustering and activation of the CD137 receptor. Fcγ receptor-mediated crosslinking, however, is thought to be inefficient. In addition, cells expressing Fcγ receptors are present throughout the body and thus antibody crosslinking and activation of immune cells expressing CD137 is not restricted to a particular site such as the tumour microenvironment, for example. Furthermore, the isotype of such CD137 antibodies needs to be selected to mediate effective binding to Fcγ receptors for crosslinking. However, this can result in the antibodies eliciting effector functions mediated by Fcγ receptors, such as ADCC, thereby eliminating the immune cells intended to be activated by the antibody.

In contrast, the antibody molecules of the invention are capable of activating CD137 conditionally in the presence of MSLN without the need for e.g. Fcγ receptor crosslinking as required by conventional antibody molecules. Furthermore, crosslinking of the antibody molecules of the invention through binding to MSLN is expected to be more efficient than Fcγ receptor-mediated crosslinking. Mutations for abrogating Fcγ receptor binding are known in the art and are preferably included in the antibody molecules of the invention. Thus, in the absence of MSLN, the antibody molecules of the invention do not exhibit CD137 agonist activity and thus are not expected to induce liver inflammation.

The present inventors have further shown that antibody molecules comprising MSLN and CD137 antigen-binding sites as detailed above which had been modified to reduce or abrogate binding to one or more Fcγ receptors were capable of suppressing tumour growth in mouse tumour models in vivo. As these antibody molecules have abrogated or reduced ADCC activity, it is expected that the antibody molecules suppressed tumour growth by activating T cells expressing CD137.

The antibody molecules have been shown to bind to dimeric CD137 with a higher affinity than to monomeric CD137.

'Affinity' as referred to herein may refer to the strength of the binding interaction between an antibody molecule and its cognate antigen as measured by $K_D$. As would be readily apparent to the skilled person, where the antibody molecule is capable of forming multiple binding interactions with an antigen (e.g. where the antibody molecule is capable of binding the antigen bivalently and, optionally, the antigen is dimeric) the affinity, as measured by $K_D$, may also be influenced by avidity, whereby avidity refers to the overall strength of an antibody-antigen complex.

Expression of CD137 by T cells is upregulated on activation. Without wishing to be bound by theory, it is thought that due to the high expression of CD137 on activated T cells, CD137 will be in the form of dimers, trimers and higher-order multimers on the surface of such cells. In contrast, naïve immune cells, such as naïve T cells, express low or negligible levels of CD137 on their cell surface and any CD137 present is therefore likely to be in monomeric form. It is therefore expected that antibody molecules which bind to CD137 with high affinity, but do not bind to monomeric CD137 with high affinity, will preferentially bind to activated immune cells, such as activated T cells, as opposed to naïve immune cells present in the liver, for example.

In addition, the antibody molecules of the invention have been shown to bind with higher affinity to immobilised MSLN than to MSLN in solution. Specifically, it is thought that the antibody molecules of the invention bind to MSLN with high avidity and thus bind MSLN more strongly where the antibody is able to bind to two MSLN molecules, as is the case where multiple copies of the antigen are immobilised at a surface, than where the MSLN is in monomeric form, as is expected to be the case with MSLN in solution. Without wishing to be bound by theory, it is therefore thought that the antibody molecules of the invention will not remain bound to shed MSLN in solution in vivo due to the low affinity of the antibodies for monomeric MSLN, and thus will not be cleared from the tumour site as quickly, and hence will have longer to exert their therapeutic effect by binding MSLN on the surface of tumour cells.

The antibody molecules of the invention bind different epitopes/regions on MSLN. This evident from the fact that some of the antibody molecules are capable of blocking binding of the ligand MUC16 to MSLN while others are not.

Some of the antibody molecules of the invention have been shown to have a similar or higher affinity for MSLN than for CD137. This is thought to be beneficial for localising the antibody molecule to tumours expressing MSLN. Binding of the antibody molecule to MSLN is expected to result in antibody crosslinking, binding to CD137 expressed at the surface of an immune cell, followed by CD137 clustering and activation, ultimately resulting in activation of the immune cell.

The antibody molecules of the invention have also been shown to be capable of binding with high affinity both to human and cynomolgus MSLN and to human and cynomolgus CD137. This cross-reactivity is advantageous, as it allows dosing and safety testing of the antibody molecules to be performed in cynomolgus monkeys during preclinical development.

In vivo studies in mouse syngeneic tumour models have shown that antibody molecules containing a Fab binding site for human MSLN and a mouse CD137 binding site in the CH3 domain have greater anti-tumour efficacy compared to isotype control antibodies or the component parts of the bispecific antibody molecules delivered as monotherapy or combination therapies (see Example 13). The antibody molecules showed advantageous features by demonstrating a significant reduction in tumour growth and survival benefit and were able to stimulate an anti-tumour response in tumours expressing different levels of MSLN. A dose dependent anti-tumour response was also observed following treatment with these molecules. Overall, the antibodies showed advantageous features in vivo compared to control molecules in reducing tumour growth and increasing survival of the animals.

Further, no liver hepatotoxicity was observed was observed following treatment with the antibody molecules. This is advantageous as treatment with other anti-CD137 agonistic antibodies has been shown in the literature to result in liver toxicity. Mechanistic studies showed that the antibody molecules stimulated activation of T cells in the tumour microenvironment, while a control CD137 agonist stimulated greater T cell activation outside of the tumour microenvironment, further supporting this advantageous feature.

A further advantageous feature of the antibody molecules identified by the inventors is that the antigen-binding sites for MSLN and CD137 are both contained within the antibody structure itself. In particular, the antibody molecules do not require other proteins to be fused to the antibody molecule via linkers or other means to result in molecule which can bind bivalently to both of its targets. This has a number of advantages. Specifically, the antibody molecules identified by the inventors can be produced using methods similar to those employed for the production of standard antibodies, as they do not comprise any additional fused portions. The structure is also expected to result in improved antibody stability, as linkers may degrade over time, resulting in a heterogeneous population of antibody molecules. Those antibodies in the population having only one protein fused may not be able to preferentially bind to cell-bound MSLN or cluster and signal via CD137 as a result of crosslinking by binding to both CD137 and MSLN. Cleavage/degradation of the linker could take place prior to administration or after administration of the therapeutic to the individual (e.g. through enzymatic cleavage or the in vivo pH of the individual), thereby resulting in a reduction of its effectiveness whilst circulating in the individual. As there are no linkers in the antibody molecules identified by the inventors, the antibody molecules are expected to retain the same number of binding sites both before and after administration. Furthermore, the structure of the antibody molecules identified by the inventors is also preferred from the perspective of immunogenicity of the molecules, as the introduction of fused proteins or linkers or both may induce immunogenicity when the molecules are administered to an individual, resulting in reduced effectiveness of the therapeutic.

Thus, the present invention provides:

[1] An antibody molecule that binds to mesothelin (MSLN) and CD137, comprising (a) a complementarity determining region (CDR)-based antigen-binding site for MSLN; and (b) a CD137 antigen-binding site located in a CH3 domain of the antibody molecule;

wherein the CDR-based antigen-binding site comprises CDRs 1-6 set forth in:

(i) SEQ ID NOs 42, 33, 44, 20, 22, and 80, respectively [FS28-256-271];

(ii) SEQ ID NOs 14, 16, 27, 20, 22 and 24, respectively [FS28-024-052];

(iii) SEQ ID NOs 42, 33, 44, 20, 22, and 40, respectively [FS28-256-021];

(iv) SEQ ID NOs 42, 33, 44, 20, 22, and 37, respectively [FS28-256-012];

(v) SEQ ID NOs 50, 33, 52, 20, 22 and 40, respectively [FS28-256-023];

(vi) SEQ ID NOs 42, 33, 44, 20, 22 and 41, respectively [FS28-256-024];

(vii) SEQ ID NOs 50, 33, 52, 20, 22 and 41, respectively [FS28-256-026];

(viii) SEQ ID NOs 42, 33, 44, 20, 22, and 80, respectively [FS28-256-027];

(ix) SEQ ID NOs 38, 33, 35, 20, 22, and 40, respectively [FS28-256-001];

(x) SEQ ID NOs 38, 33, 35, 20, 22, and 41 respectively [FS28-256-005];

(xi) SEQ ID NOs 46, 33, 48, 20, 22 and 37, respectively [FS28-256-014];

(xii) SEQ ID NOs 50, 33, 52, 20, 22 and 37, respectively [FS28-256-018];

(xiii) SEQ ID NOs 31, 33, 35, 20, 22 and 37, respectively [FS28-256];

(xiv) SEQ ID NOs 14, 16, 25, 20, 22 and 24, respectively [FS28-024-051];

(xv) SEQ ID NOs 14, 16, 29, 20, 22 and 24, respectively [FS28-024-053]; or (xvi) SEQ ID NOs 14, 16, 18, 20, 22 and 24, respectively [FS28-024];

wherein the CDR sequences are defined according to the ImMunoGeneTics (IMGT) numbering scheme; and wherein the CD137 antigen-binding site comprises a first sequence and a second sequence located in the AB and EF structural loops of the CH3 domain, respectively, wherein the first and second sequence have the sequence set forth in SEQ ID NOs 10 and 11 [FS22-172-003], respectively.

[2] An antibody molecule that binds to mesothelin (MSLN) and CD137, comprising (a) a complementarity determining region (CDR)-based antigen-binding site for MSLN; and (b) a CD137 antigen-binding site located in a CH3 domain of the antibody molecule;

wherein the CDR-based antigen-binding site comprises CDRs 1-6 set forth in:

(i) SEQ ID NOs 43, 5, 45, 21, 23, and 80, respectively [FS28-256-271];

(ii) SEQ ID NOs 15, 17, 28, 21, 23 and 24, respectively [FS28-024-052];

(iii) SEQ ID NOs 43, 34, 45, 21, 23 and 40, respectively [FS28-256-021];

(iv) SEQ ID NOs 43, 34, 45, 21, 23 and 37, respectively [FS28-256-012];

(v) SEQ ID NOs 51, 34, 53, 21, 23 and 40, respectively [FS28-256-023];

(vi) SEQ ID NOs 43, 34, 45, 21, 23 and 41, respectively [FS28-256-024];

(vii) SEQ ID NOs 51, 34, 53, 21, 23 and 41, respectively [FS28-256-026];

(viii) SEQ ID NOs 43, 34, 45, 21, 23 and 80, respectively [FS28-256-027];

(ix) SEQ ID NOs 39, 34, 36, 21, 23 and 40, respectively [FS28-256-001];

(x) SEQ ID NOs 39, 34, 36, 21, 23 and 41, respectively [FS28-256-005];

(xi) SEQ ID NOs 47, 34, 49, 21, 23 and 37, respectively [FS28-256-014];

(xii) SEQ ID NOs 51, 34, 53, 21, 23 and 37, respectively [FS28-256-018];

(xiii) SEQ ID NOs 32, 34, 36, 21, 23 and 37, respectively [FS28-256];

(xiv) SEQ ID NOs 15, 17, 26, 21, 23 and 24, respectively [FS28-024-051];

(xv) SEQ ID NOs 15, 17, 30, 21, 23 and 24, respectively [FS28-024-053]; or (xvi) SEQ ID NOs 15, 17, 19, 21, 23 and 24, respectively [FS28-024];

wherein the CDR sequences are defined according to Kabat; and wherein the CD137 antigen-binding site comprises a first sequence and a second sequence located in the AB and EF structural loops of the CH3 domain, respectively, wherein the first and second sequence have the sequence set forth in SEQ ID NOs 10 and 11 [FS22-172-003], respectively.

[3] The antibody molecule according to [1] or [2], wherein the antibody molecule comprises CDRs 1-6 set out in (i) of [1] or [2].

[4] The antibody molecule according to [1] or [2], wherein the antibody molecule comprises CDRs 1-6 set out in (ii) of [1] or [2].

[5] The antibody molecule according to any one of [1] to [4], wherein the antibody molecule comprises a heavy chain variable (VH) domain and/or light chain variable (VL) domain, preferably a VH domain and a VL domain.

[6] The antibody molecule according to any one of [1] to [5], wherein the antibody molecule comprises an immunoglobulin heavy chain and/or an immunoglobulin light chain, preferably an immunoglobulin heavy chain and an immunoglobulin light chain.

[7] The antibody molecule according to any one of [5] to [6], wherein the antibody molecule comprises the VH domain and/or VL domain, preferably the VH domain and the VL domain set forth in:

(i) SEQ ID NOs 177 and 76, respectively [FS28-256-271];

(ii) SEQ ID NOs 58 and 54, respectively [FS28-024-052];

(iii) SEQ ID NOs 70 and 68, respectively [FS28-256-021];

(iv) SEQ ID NOs 70 and 64, respectively [FS28-256-012];

(v) SEQ ID NOs 74 and 68, respectively [FS28-256-023];

(vi) SEQ ID NOs 70 and 78, respectively [FS28-256-024];

(vii) SEQ ID NOs 74 and 78, respectively [FS28-256-026];

(viii) SEQ ID NOs 70 and 76, respectively [FS28-256-027];

(ix) SEQ ID NOs 66 and 68, respectively [FS28-256-001];

(x) SEQ ID NOs 66 and 78, respectively [FS28-256-005];

(xi) SEQ ID NOs 72 and 64, respectively [FS28-256-014];

(xii) SEQ ID NOs 74 and 64, respectively [FS28-256-018];

(xiii) SEQ ID NOs 62 and 64, respectively [FS28-256];

(xiv) SEQ ID NOs 56 and 54, respectively [FS28-024-051];

(xv) SEQ ID NOs 60 and 54, respectively [FS28-024-053]; or (xvi) SEQ ID NOs 12 and 54, respectively [FS28-024].

[8] The antibody molecule according to [7], wherein the antibody molecule comprises the VH domain and VL domain set forth in SEQ ID NOs 177 and 76, respectively [FS28-256-271].

[9] The antibody molecule according to [7], wherein the antibody molecule comprises the VH domain and VL domain set forth in SEQ ID NOs 58 and 54, respectively [FS28-024-052].

[10] The antibody molecule according to any one of [1] to [9], wherein the first sequence is located between positions 14 and 17 of the CH3 domain of the antibody molecule, wherein the amino acid residue numbering is according to the IMGT numbering scheme.

[11] The antibody molecule according to [10], wherein the first sequence is located at positions 15, 16, 16.5, 16.4, 16.3, 16.2, and 16.1 of the CH3 domain of the antibody molecule, wherein the amino acid residue numbering is according to the IMGT numbering scheme.

[12] The antibody molecule according to any one of [1] to [11], wherein the second sequence is located at positions 92 to 98 of the CH3 domain of the antibody molecule, wherein the amino acid residue numbering is according to the IMGT numbering scheme.

[13] The antibody molecule according to any one of [1] to [12], wherein the antibody molecule further comprises a third sequence located in the CD structural loop of the CH3 domain.

[14] The antibody molecule according to [13], wherein the third sequence is located at positions 43 to 78 of the CH3 domain of the antibody molecule, wherein the amino acid residue numbering is according to the IMGT numbering scheme.

[15] The antibody molecule according to any one of [13] to [14], wherein the third sequence has the sequence set forth in SEQ ID NO: 157. [16] The antibody molecule according to any one of [1] to [15], wherein the antibody molecule comprises the CH3 domain sequence set forth in SEQ ID NO: 8 [FS22-172-003]. [17] An antibody molecule according to any one of [1] to [16], wherein the antibody molecule is a human IgG1 molecule.

[18] The antibody molecule according to any one of [1] to [17], wherein the antibody molecule comprises the heavy chain and light chain of antibody:

(i) FS22-172-003-AA/FS28-256-271 set forth in SEQ ID NOs 3 and 84, respectively;

(ii) FS22-172-003-AA/FS28-024-052 set forth in SEQ ID NOs 102 and 85, respectively;

(iii) FS22-172-003-AA/FS28-256-021 set forth in SEQ ID NOs 125 and 82, respectively;
(iv) FS22-172-003-AA/FS28-256-012 set forth in SEQ ID NOs 125 and 116, respectively;
(v) FS22-172-003-AA/FS28-256-023 set forth in SEQ ID NOs 133 and 82, respectively;
(vi) FS22-172-003-AA/FS28-256-024 set forth in SEQ ID NOs 125 and 83, respectively;
(vii) FS22-172-003-AA/FS28-256-026 set forth in SEQ ID NOs 133 and 83, respectively;
(viii) FS22-172-003-AA/FS28-256-027 set forth in SEQ ID NOs 125 and 84, respectively;
(ix) FS22-172-003-AA/FS28-256-001 set forth in SEQ ID NOs 120 and 82, respectively;
(x) FS22-172-003-AA/FS28-256-005 set forth in SEQ ID NOs 120 and 83, respectively;
(xi) FS22-172-003-AA/FS28-256-014 set forth in SEQ ID NOs 129 and 116, respectively;
(xii) FS22-172-003-AA/FS28-256-018 set forth in SEQ ID NOs 133 and 116, respectively;
(xiii) FS22-172-003-AA/FS28-256 set forth in SEQ ID NOs 114 and 116, respectively;
(xiv) FS22-172-003-AA/FS28-024-051 set forth in SEQ ID NOs 98 and 85, respectively;
(xv) FS22-172-003-AA/FS28-024-053 set forth in SEQ ID NOs 106 and 85, respectively; or
(xvi) FS22-172-003-AA/FS28-024 set forth in SEQ ID NOs 94 and 85, respectively.

[19] The antibody molecule according to [18], wherein the antibody molecule comprises light chain and heavy chain of FS22-172-003-AA/FS28-256-271 set forth in SEQ ID NOs 84 and 3, respectively.

[20] The antibody molecule according to [18], wherein the antibody molecule comprises light chain and heavy chain of FS22-172-003-AA/FS28-024-052 set forth in SEQ ID NOs 85 and 102, respectively.

[21] The antibody molecule according to any one of [18] to [20], wherein the proline (P) at position 114 of the CH2 domain of the antibody is substituted with alanine (A), and wherein the amino acid residue numbering is according to the IMGT numbering scheme.

[22] The antibody molecule according to any one of [1] to [21], wherein the MSLN is cell-surface bound MSLN.

[23] The antibody molecule according to [22], wherein the antibody molecule binds to immobilised MSLN with a higher affinity than to soluble MSLN.

[24] The antibody molecule according to [23], wherein
(i) the antibody molecule binds to immobilised MSLN with a kD of 8 nM or with a higher affinity; and/or
(ii) the antibody molecule binds to soluble MSLN with a kD of 15 nM or with a lower affinity.

[25] The antibody molecule according to any one of [1] to [24], wherein the antibody molecule binds human MSLN and human CD137.

[26] The antibody molecule according to [25], wherein the MSLN consists of or comprises the sequence set forth in SEQ ID NO: 375.

[27] The antibody molecule according to [25] or [26], wherein the human CD137 consists of or comprises the sequence set forth in SEQ ID NO: 373.

[28] The antibody molecule according to any one of [1] to [27], wherein the antibody molecule comprises CDRs 1-6 set forth in any one of (ii) or (xiv) to (xvi) of [1] or [2], and wherein the antibody blocks binding of MUC16 to MSLN.

[29] The antibody molecule according to any one of [1] to [27], wherein the antibody molecule comprises CDRs 1-6 set forth in any one of (i) or (iii) to (xiii) of [1] or [2], and wherein the antibody does not block binding of MUC16 to MSLN.

[30] The antibody molecule according to [28] or [29], wherein the MUC16 is human MUC16.

[31] The antibody molecule according to any one of [1] to [30], wherein the antibody molecule is capable of activating CD137 on an immune cell in the presence of tumour cell-surface bound MSLN.

[32] The antibody molecule according to any one of [1] to [31], wherein binding of the antibody molecule to CD137 on an immune cell and to tumour cell-surface bound MSLN, causes clustering of CD137 on the immune cell.

[33] The antibody molecule according to [31] or [32], wherein the immune cell is a T cell, B cell, natural killer (NK) cell, natural killer T (NKT) cell, or dendritic cell (DC).

[34] The antibody molecule according to [33], wherein the immune cell is a T cell.

[35] The antibody molecule according to any one of [1] to [34], wherein the antibody molecule has been modified to reduce or abrogate binding of the CH2 domain of the antibody molecule or antibody molecule to one or more Fcγ receptors.

[36] The antibody molecule according to any one of [1] to [35], wherein the antibody molecule does not bind to Fcγ receptors.

[37] The antibody molecule according to [35] or [36], wherein the Fcγ receptor is selected from the group consisting of: FcγRI, FcγRIIa, FcγRIIb and FcγRIII.

[38] A conjugate comprising the antibody molecule according to any one of [1] to [37] and a bioactive molecule.

[39] A conjugate comprising the antibody molecule according to any one of [1] to [37] and a detectable label.

[40] A nucleic acid molecule or molecules encoding the antibody molecule according to any one of [1] to [37].

[41] A nucleic acid molecule or molecules encoding the antibody molecule according to any one of [1] to [37], wherein the nucleic acid molecule(s) comprise(s) the heavy chain nucleic acid sequence and/or light chain nucleic acid sequence of:
(i) FS22-172-003-AA/FS28-256-271 set forth in SEQ ID NOs 4 and 91, respectively;
(ii) FS22-172-003-AA/FS28-024-052 set forth in SEQ ID NOs 103 and 86, respectively;
(iii) FS22-172-003-AA/FS28-256-021 set forth in SEQ ID NOs 126 and 122, respectively;
(iv) FS22-172-003-AA/FS28-256-012 set forth in SEQ ID NOs 126 and 117, respectively;
(v) FS22-172-003-AA/FS28-256-023 set forth in SEQ ID NOs 134 and 122, respectively;
(vi) FS22-172-003-AA/FS28-256-024 set forth in SEQ ID NOs 126 and 90, respectively;
(vii) FS22-172-003-AA/FS28-256-026 set forth in SEQ ID NOs 134 and 90, respectively;
(viii) FS22-172-003-AA/FS28-256-027 set forth in SEQ ID NOs 126 and 91, respectively;
(ix) FS22-172-003-AA/FS28-256-001 set forth in SEQ ID NOs 121 and 122, respectively;
(x) FS22-172-003-AA/FS28-256-005 set forth in SEQ ID NOs 121 and 90, respectively;
(xi) FS22-172-003-AA/FS28-256-014 set forth in SEQ ID NOs 130 and 117, respectively;

(xii) FS22-172-003-AA/FS28-256-018 set forth in SEQ ID NOs 134 and 117, respectively;

(xiii) FS22-172-003-AA/FS28-256 set forth in SEQ ID NOs 115 and 117, respectively;

(xiv) FS22-172-003-AA/FS28-024-051 set forth in SEQ ID NOs 99 and 86, respectively;

(xv) FS22-172-003-AA/FS28-024-053 set forth in SEQ ID NOs 107 and 86, respectively; or (xvi) FS22-172-003-AA/FS28-024 set forth in SEQ ID NOs 95 and 86, respectively.

[42] A vector or vectors comprising the nucleic acid molecule or molecules according to any one of [40] or [41].

[43] A recombinant host cell comprising the nucleic acid molecule(s) according to any one of [40] to [41], or the vector(s) according to [42].

[44] A method of producing the antibody molecule according to any one of [1] to [37] comprising culturing the recombinant host cell of [43] under conditions for production of the antibody molecule.

[45] The method according to [44] further comprising isolating and/or purifying the antibody molecule.

[46] A pharmaceutical composition comprising the antibody molecule or conjugate according to any one of [1] to [39] and a pharmaceutically acceptable excipient.

[47] The antibody molecule or conjugate according to any one of [1] to [39] for use in a method of treating cancer in an individual.

[48] A method of treating cancer in an individual comprising administering to the individual a therapeutically effective amount of the antibody molecule or conjugate according to any one of [1] to [39].

[49] The use of the antibody molecule or conjugate according to any one of [1] to [39] in the preparation of a medicament for the treatment of cancer.

[50] The antibody molecule or conjugate for use, the method, or the use according to any one of [47] to [49], wherein the cancer is ovarian cancer, pancreatic cancer, lung cancer, or a mesothelioma.

[51] The antibody molecule or conjugate for use according to [47], wherein the treatment comprises administering the antibody molecule or conjugate to the individual in combination with a second therapeutic.

[52] The method according to [48], wherein the method further comprises administering a therapeutically effective amount of a second therapeutic to the individual.

DETAILED DESCRIPTION

Figure 1:
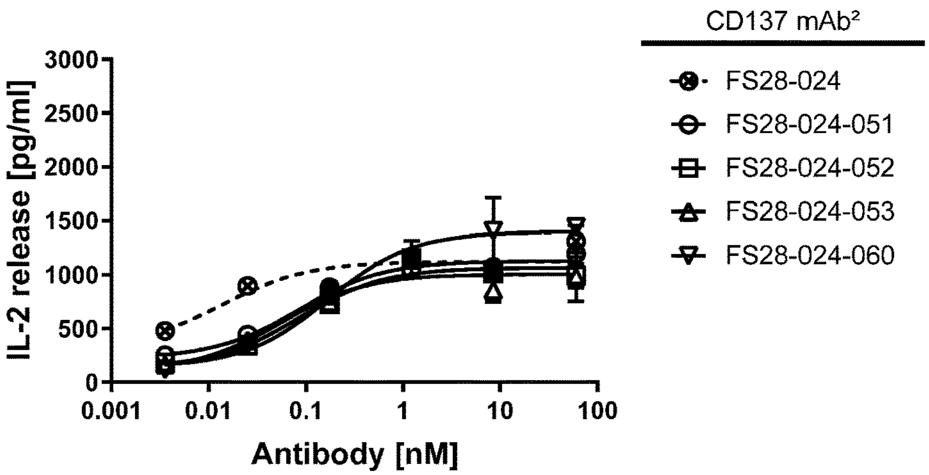
FIG. 1 shows the results of a T cell activation assay where $mAb^2$ comprising Fabs that bind different regions of human MSLN drive CD137-mediated activation of $CD8^+$ T cells when the $mAb^2$ are crosslinked by MSLN positive NCI-H226 cells, leading to the release of human IL-2. These results show that $mAb^2$ comprising Fabs from the FS28-185 lineage (B) do not have functional activity in this assay. $mAb^2$ comprising Fabs from lineages FS28-024 (A) and FS28-256 (C) all show an increase of hIL-2 release in the presence of subnamolar to 1.5 nM concentrations of $mAb^2$.
Figure 1:
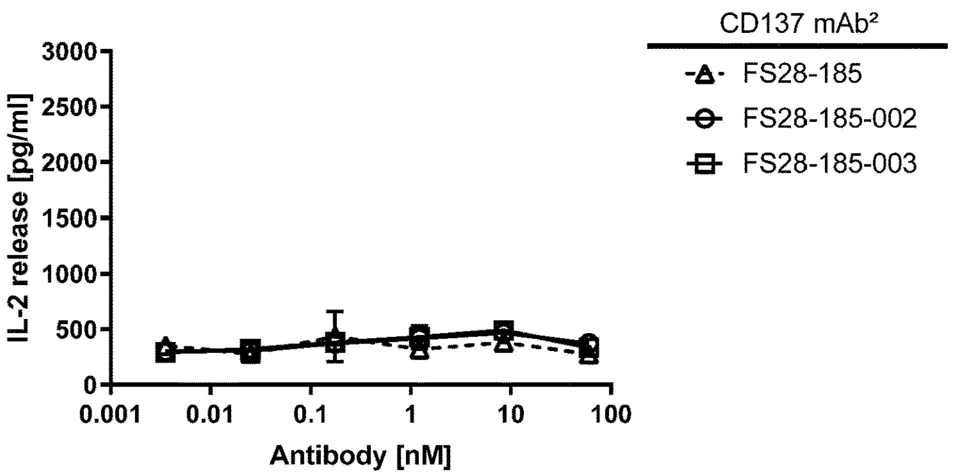
Figure 1:
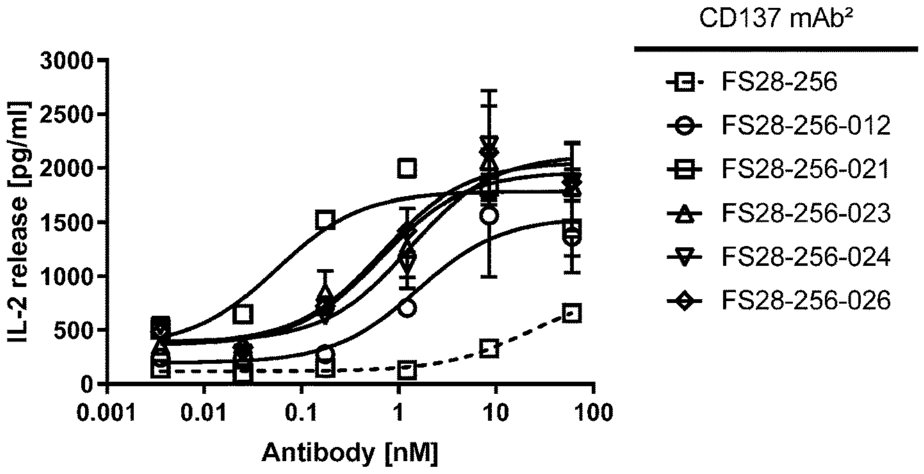

The present invention relates to antibody molecules which bind both to MSLN and CD137. Specifically, the antibody molecules of the present invention comprise a CDR-based antigen binding site for MSLN and a CD137 antigen binding site located in a constant domain of the antibody molecule.

The antibody molecule preferably binds MSLN and CD137 specifically. The term "specific" may refer to the situation in which the antibody molecule will not show any significant binding to molecules other than its specific binding partner(s), here MSLN and CD137. The term "specific" is also applicable where the antibody molecule is specific for particular epitopes, such as epitopes on MSLN and CD137 that are carried by a number of antigens in which case the antibody molecule will be able to bind to the various antigens carrying the epitope. In a preferred embodiment, the antibody molecule of the present invention does not bind, or does not show any significant binding to OX40, GITR, CD40, CEACAM-5, E-Cadherin, Thrombomodulin, or EpCAM.

The term "antibody molecule" describes an immunoglobulin whether natural or partly or wholly synthetically produced. The antibody molecule may be human or humanised, preferably human. The antibody molecule is preferably a monoclonal antibody molecule. Examples of antibodies are the immunoglobulin isotypes, such as immunoglobulin G, and their isotypic subclasses, such as IgG1, IgG2, IgG3 and IgG4, as well as fragments thereof. The antibody molecule may be isolated, in the sense of being free from contaminants, such as antibodies able to bind other polypeptides and/or serum components.

The term "antibody molecule", as used herein, thus includes antibody fragments, provided said fragments comprise a CDR-based antigen binding site for MSLN and a CD137 antigen binding site located in a constant domain.

The antibody molecule may be natural or partly or wholly synthetically produced. For example, the antibody molecule may be a recombinant antibody molecule.

The antibody molecule comprises one or more CDR-based antigen-binding sites for MSLN and one or more antigen-binding sites for CD137 in one or more constant domains, preferably one or more CH3 domains, of the antibody molecule.

The antibody molecule may be an immunoglobulin or an antigen-binding fragment thereof. For example, the antibody molecule may be an IgG, IgA, IgE or IgM molecule, preferably an IgG molecule, such as an IgG1, IgG2, IgG3 or IgG4 molecule, more preferably an IgG1 or IgG2 molecule, most preferably an IgG1 molecule, or a fragment thereof. In a preferred embodiment, the antibody molecule is a complete immunoglobulin molecule.

In other embodiments, the antibody molecule may be an antigen-binding fragment comprising a CDR-based antigen-binding site for MSLN and an antigen-binding sites for CD137 located in a constant domain. For example, the antigen-binding fragment may be a scFv-Fc fusion where the scFv binds to MSLN and the Fc binds to OX40 or a minibody, which comprises an scFv joined to a CH3 domain (Hu et al. (1996), Cancer Res., 56(13):3055-61).

Antibodies and methods for their construction and use are well-known in the art and are described in, for example, Holliger and Hudson, 2005. It is possible to take monoclonal and other antibodies and use techniques of recombinant DNA technology to produce other antibodies or chimeric molecules which retain the specificity of the original antibody. Such techniques may involve introducing CDRs or variable regions of one antibody molecule into a different antibody molecule (EP-A-184187, GB 2188638A and EP-A-239400).

In a preferred embodiment, the antibody molecule is a $mAb^2$ (TM) bispecific antibody. A $mAb^2$ bispecific antibody, as referred to herein, is an IgG immunoglobulin which includes a CDR-based antigen binding site in each of its variable regions and at least one antigen binding site in a constant domain of the antibody molecule.

In a preferred embodiment, the antibody is an antibody molecule that binds MSLN and CD137, the antibody molecule comprising:

(i) two CDR-based antigen-binding sites for MSLN, each formed by an immunoglobulin VH domain and an immunoglobulin VL domain; and (ii) two antigen-binding sites that bind CD137 located in the two CH3 domains of the antibody molecule.

In a more preferred embodiment, the antibody is a complete immunoglobulin molecule, e.g. a complete IgG1 molecule, that binds MSLN and CD137, the antibody molecule comprising:

(i) two CDR-based antigen-binding sites for MSLN, each formed by an immunoglobulin VH domain and an immunoglobulin VL domain; and (ii) two antigen-binding sites that bind CD137 located in the two CH3 domains of the antibody molecule; and wherein the immunoglobulin molecule further comprises CH1, CH2 and CL domains.

A CDR-based antigen-binding site is an antigen-binding site in an antibody variable region. A CDR-based antigen-binding site, may be formed by three CDRs, such as the three light chain variable domain (VL) CDRs or three heavy chain variable domain (VH) CDRs. Preferably the CDR-based antigen-binding site is formed by six CDRs, three VL CDRs and three VH CDRs. The contributions of the different CDRs to the binding of the antigen may vary in different antigen binding sites.

The three VH domain CDRs of the antigen-binding site may be located within an immunoglobulin VH domain and the three VL domain CDRs may be located within an immunoglobulin VL domain. For example, the CDR-based antigen-binding site may be located in an antibody variable region.

The antibody molecule has one or preferably more than one, for example two, CDR-based antigen binding sites for MSLN. The antibody molecule thus may comprise one VH and one VL domain but preferably comprises two VH and two VL domains, i.e. two VH/VL domain pairs, as is the case in naturally-occurring IgG molecules, for example.

The CDR-based antigen-binding site may comprise the three VH CDRs or three VL CDRs, preferably the three VH CDRs and the three VL CDRs, of antibody FS22-172-003-AA/FS28-256-271, FS22-172-003-AA/FS28-024-052, FS22-172-003-AA/FS28-256-021, FS22-172-003-AA/FS28-256-012, FS22-172-003-AA/FS28-256-023, FS22-172-003-AA/FS28-256-024, FS22-172-003-AA/FS28-256-026, FS22-172-003-AA/FS28-256-027, FS22-172-003-AA/FS28-256-001, FS22-172-003-AA/FS28-256-005, FS22-172-003-AA/FS28-256-014, FS22-172-003-AA/FS28-256-018, FS22-172-003-AA/FS28-256, FS22-172-003-AA/FS28-024-051, FS22-172-003-AA/FS28-024-053, or FS22-172-003-AA/FS28-024, preferably antibody FS22-172-003-AA/FS28-256-271 or FS22-172-003-AA/FS28-024-052, most preferably antibody FS22-172-003-AA/FS28-256-271.

The sequences of the CDRs may be readily determined from the VH and VL domain sequences of an antibody molecule using routine techniques. The VH and VL domain sequences of antibodies FS22-172-003-AA/FS28-256-271, FS22-172-003-AA/FS28-024-052, FS22-172-003-AA/FS28-256-021, FS22-172-003-AA/FS28-256-012, FS22-172-003-AA/FS28-256-023, FS22-172-003-AA/FS28-256-024, FS22-172-003-AA/FS28-256-026, FS22-172-003-AA/FS28-256-027, FS22-172-003-AA/FS28-256-001, FS22-172-003-AA/FS28-256-005, FS22-172-003-AA/FS28-256-014, FS22-172-003-AA/FS28-256-018, FS22-172-003-AA/FS28-256, FS22-172-003-AA/FS28-024-051, FS22-172-003-AA/FS28-024-053, and FS22-172-003-AA/FS28-024 are described herein, and the three VH and three VL domain CDRs of said antibodies may thus be determined from said sequences. The CDR sequences may, for example, be determined according to Kabat et al., 1991 or the international ImMunoGeneTics information system (IMGT) (Lefranc et al., 2015).

The sequences of the VH domain and VL domain of an antibody containing the LALA mutation in the CH2 domain are the same as an antibody which does not contain the LALA mutation. For example, the VH and VL sequences of antibody FS22-172-003-AA/FS28-256-271 are the same as the VH and VL sequences of antibody FS22-172-003/FS28-256-271. Likewise, the VH domain CDR1, CDR2 and CDR3 and the VL domain CDR1, CDR2 and CDR3 of an antibody containing the LALA mutation in the CH2 domain are the same as an antibody which does not contain the LALA mutation. For example, the VH domain CDR1, CDR2 and CDR3 and VL domain CDR1, CDR2 and CDR3 sequences of antibody FS22-172-003-AA/FS28-256-271 are the same as the VH domain CDR1, CDR2 and CDR3 and VL domain CDR1, CDR2 and CDR3 sequences of antibody FS22-172-003/FS28-256-271.

The VH domain CDR1, CDR2 and CDR3 sequences of the antibody molecule according to IMGT numbering may be the sequences located at positions 27-38, 56-65, and 105-117, of the VH domain of the antibody molecule, respectively.

The VH domain CDR1, CDR2 and CDR3 sequences of the antibody molecule according to Kabat numbering may be the sequences at located positions 31-35, 50-65, and 95-102 of the VH domain, respectively.

The VL domain CDR1, CDR2 and CDR3 sequences of the antibody molecule according to IMGT numbering may be the sequences located at positions 27-38, 56-65, and 105-117, of the VL domain, respectively.

The VL domain CDR1, CDR2 and CDR3 sequences of the antibody molecule according to Kabat numbering may be the sequences at located positions 24-34, 50-56, and 89-97 of the VL domain, respectively.

For example, the sequence of the VH domain CDR1, CDR2 and CDR3 of:

(i) FS22-172-003-AA/FS28-256-271 may be as set forth in SEQ ID NOs 42, 33, and 44, respectively;
(ii) FS22-172-003-AA/FS28-024-052 may be as set forth in SEQ ID NOs 14, 16, and 27, respectively;
(iii) FS22-172-003-AA/FS28-256-021 may be as set forth in SEQ ID NOs 42, 33, and 44, respectively;
(iv) FS22-172-003-AA/FS28-256-012 may be as set forth in SEQ ID NOs 42, 33, and 44, respectively;
(v) FS22-172-003-AA/FS28-256-023 may be as set forth in SEQ ID NOs 50, 33, and 52, respectively;
(vi) FS22-172-003-AA/FS28-256-024 may be as set forth in SEQ ID NOs 42, 33, and 44, respectively;
(vii) FS22-172-003-AA/FS28-256-026 may be as set forth in SEQ ID NOs 50, 33, and 52, respectively;
(viii) FS22-172-003-AA/FS28-256-027 may be as set forth in SEQ ID NOs 42, 33, and 44, respectively;
(ix) FS22-172-003-AA/FS28-256-001 may be as set forth in SEQ ID NOs 38, 33, and 35, respectively;
(x) FS22-172-003-AA/FS28-256-005 may be as set forth in SEQ ID NOs 38, 33, and 35, respectively;
(xi) FS22-172-003-AA/FS28-256-014 may be as set forth in SEQ ID NOs 46, 33, and 48, respectively;
(xii) FS22-172-003-AA/FS28-256-018 may be as set forth in SEQ ID NOs 50, 33, and 52, respectively;
(xiii) FS22-172-003-AA/FS28-256 may be as set forth in SEQ ID NOs 31, 33, and 35, respectively;
(xiv) FS22-172-003-AA/FS28-024-051 may be as set forth in SEQ ID NOs 14, 16, and 25, respectively;
(xv) FS22-172-003-AA/FS28-024-053 may be as set forth in SEQ ID NOs 14, 16, and 29, respectively; and
(xvi) FS22-172-003-AA/FS28-024 may be as set forth in SEQ ID NOs 14, 16, and 18, respectively;

wherein the CDR sequences are defined according to the IMGT numbering scheme.

The sequence of the VL domain CDR1, CDR2 and CDR3 of:

(i) FS22-172-003-AA/FS28-256-271 may be as set forth in SEQ ID NOs 20, 22, and 80, respectively;
(ii) FS22-172-003-AA/FS28-024-052 may be as set forth in SEQ ID NOs 20, 22, 24, respectively;
(iii) FS22-172-003-AA/FS28-256-021 may be as set forth in SEQ ID NOs 20, 22, 40, respectively;
(iv) FS22-172-003-AA/FS28-256-012 may be as set forth in SEQ ID NOs 20, 22, 37, respectively;
(v) FS22-172-003-AA/FS28-256-023 may be as set forth in SEQ ID NOs 20, 22, 40, respectively;
(vi) FS22-172-003-AA/FS28-256-024 may be as set forth in SEQ ID NOs 20, 22, 41, respectively;
(vii) FS22-172-003-AA/FS28-256-026 may be as set forth in SEQ ID NOs 20, 22, 41, respectively;
(viii) FS22-172-003-AA/FS28-256-027 may be as set forth in SEQ ID NOs 20, 22, 80, respectively;
(ix) FS22-172-003-AA/FS28-256-001 may be as set forth in SEQ ID NOs 20, 22, 40, respectively;
(x) FS22-172-003-AA/FS28-256-005 may be as set forth in SEQ ID NOs 20, 22, 41, respectively;
(xi) FS22-172-003-AA/FS28-256-014 may be as set forth in SEQ ID NOs 20, 22, 37, respectively;
(xii) FS22-172-003-AA/FS28-256-018 may be as set forth in SEQ ID NOs 20, 22, 37, respectively;
(xiii) FS22-172-003-AA/FS28-256 may be as set forth in SEQ ID NOs 20, 22, 37, respectively;
(xiv) FS22-172-003-AA/FS28-024-051 may be as set forth in SEQ ID NOs 20, 22, 24, respectively;
(xv) FS22-172-003-AA/FS28-024-053 may be as set forth in SEQ ID NOs 20, 22, 24, respectively; and
(xvi) FS22-172-003-AA/FS28-024 may be as set forth in SEQ ID NOs 20, 22, 24, respectively;

wherein the CDR sequences are defined according to the IMGT numbering scheme.

For example, the sequence of the VH domain CDR1, CDR2 and CDR3 of:

(i) FS22-172-003-AA/FS28-256-271 may be as set forth in SEQ ID NOs 43, 5, and 45, respectively;
(ii) FS22-172-003-AA/FS28-024-052 may be as set forth in SEQ ID NOs 15, 17 and 28, respectively;
(iii) FS22-172-003-AA/FS28-256-021 may be as set forth in SEQ ID NOs 43, 34, 45, respectively;
(iv) FS22-172-003-AA/FS28-256-012 may be as set forth in SEQ ID NOs 43, 34 and 45, respectively;
(v) FS22-172-003-AA/FS28-256-023 may be as set forth in SEQ ID NOs 51, 34 and 53, respectively;
(vi) FS22-172-003-AA/FS28-256-024 may be as set forth in SEQ ID NOs 43, 34 and 45, respectively;
(vii) FS22-172-003-AA/FS28-256-026 may be as set forth in SEQ ID NOs 51, 34 and 53, respectively;
(viii) FS22-172-003-AA/FS28-256-027 may be as set forth in SEQ ID NOs 43, 34 and 45, respectively;
(ix) FS22-172-003-AA/FS28-256-001 may be as set forth in SEQ ID NOs 39, 34 and 36, respectively;
(x) FS22-172-003-AA/FS28-256-005 may be as set forth in SEQ ID NOs 39, 34 and 36, respectively;
(xi) FS22-172-003-AA/FS28-256-014 may be as set forth in SEQ ID NOs 47, 34 and 49, respectively;
(xii) FS22-172-003-AA/FS28-256-018 may be as set forth in SEQ ID NOs 51, 34 and 53, respectively;
(xiii) FS22-172-003-AA/FS28-256 may be as set forth in SEQ ID NOs 32, 34 and 36, respectively;
(xiv) FS22-172-003-AA/FS28-024-051 may be as set forth in SEQ ID NOs 15, 17 and 26, respectively;
(xv) FS22-172-003-AA/FS28-024-053 may be as set forth in SEQ ID NOs 15, 17 and 30, respectively; and
(xvi) FS22-172-003-AA/FS28-024 may be as set forth in SEQ ID NOs 15, 17 and 19, respectively;

wherein the CDR sequences are defined according to the Kabat numbering scheme.

The sequence of the VL domain CDR1, CDR2 and CDR3 of:

(i) FS22-172-003-AA/FS28-256-271 may be as set forth in SEQ ID NOs 21, 23, and 80, respectively;
(ii) FS22-172-003-AA/FS28-024-052 may be as set forth in SEQ ID NOs 21, 23 and 24, respectively;
(iii) FS22-172-003-AA/FS28-256-021 may be as set forth in SEQ ID NOs 21, 23 and 40, respectively;
(iv) FS22-172-003-AA/FS28-256-012 may be as set forth in SEQ ID NOs 21, 23 and 37, respectively;
(v) FS22-172-003-AA/FS28-256-023 may be as set forth in SEQ ID NOs 21, 23 and 40, respectively;
(vi) FS22-172-003-AA/FS28-256-024 may be as set forth in SEQ ID NOs 21, 23 and 41, respectively;
(vii) FS22-172-003-AA/FS28-256-026 may be as set forth in SEQ ID NOs 21, 23 and 41, respectively;
(viii) FS22-172-003-AA/FS28-256-027 may be as set forth in SEQ ID NOs 21, 23 and 80, respectively;
(ix) FS22-172-003-AA/FS28-256-001 may be as set forth in SEQ ID NOs 21, 23 and 40, respectively;

(x) FS22-172-003-AA/FS28-256-005 may be as set forth in SEQ ID NOs 21, 23 and 41, respectively;
(xi) FS22-172-003-AA/FS28-256-014 may be as set forth in SEQ ID NOs 21, 23 and 37, respectively;
(xii) FS22-172-003-AA/FS28-256-018 may be as set forth in SEQ ID NOs 21, 23 and 37, respectively;
(xiii) FS22-172-003-AA/FS28-256 may be as set forth in SEQ ID NOs 21, 23 and 37, respectively;
(xiv) FS22-172-003-AA/FS28-024-051 may be as set forth in SEQ ID NOs 21, 23 and 24, respectively;
(xv) FS22-172-003-AA/FS28-024-053 may be as set forth in SEQ ID NOs 21, 23 and 24, respectively; and
(xvi) FS22-172-003-AA/FS28-024 may be as set forth in SEQ ID NOs 21, 23 and 24, respectively;

wherein the CDR sequences are defined according to the Kabat numbering scheme.

The CDR-based antigen-binding site may comprise the VH or VL domains, preferably the VH and VL domains, of antibody of antibody antibody FS22-172-003-AA/FS28-256-271, FS22-172-003-AA/FS28-024-052, FS22-172-003-AA/FS28-256-021, FS22-172-003-AA/FS28-256-012, FS22-172-003-AA/FS28-256-023, FS22-172-003-AA/FS28-256-024, FS22-172-003-AA/FS28-256-026, FS22-172-003-AA/FS28-256-027, FS22-172-003-AA/FS28-256-001, FS22-172-003-AA/FS28-256-005, FS22-172-003-AA/FS28-256-014, FS22-172-003-AA/FS28-256-018, FS22-172-003-AA/FS28-256, FS22-172-003-AA/FS28-024-051, FS22-172-003-AA/FS28-024-053, or FS22-172-003-AA/FS28-024, preferably antibody FS22-172-003-AA/FS28-256-271 or FS22-172-003-AA/FS28-024-052, most preferably antibody FS22-172-003-AA/FS28-256-271.

The VH domain of antibodies FS22-172-003-AA/FS28-256-271, FS22-172-003-AA/FS28-024-052, FS22-172-003-AA/FS28-256-021, FS22-172-003-AA/FS28-256-012, FS22-172-003-AA/FS28-256-023, FS22-172-003-AA/FS28-256-024, FS22-172-003-AA/FS28-256-026, FS22-172-003-AA/FS28-256-027, FS22-172-003-AA/FS28-256-001, FS22-172-003-AA/FS28-256-005, FS22-172-003-AA/FS28-256-014, FS22-172-003-AA/FS28-256-018, FS22-172-003-AA/FS28-256, FS22-172-003-AA/FS28-024-051, FS22-172-003-AA/FS28-024-053, and FS22-172-003-AA/FS28-024 may have the sequence set forth in SEQ ID NOs 177, 58, 70, 70, 74, 70, 74, 70, 66, 66, 72, 74, 62, 56, 60, and 12, respectively.

The VL domain of antibodies FS22-172-003-AA/FS28-256-271, FS22-172-003-AA/FS28-024-052, FS22-172-003-AA/FS28-256-021, FS22-172-003-AA/FS28-256-012, FS22-172-003-AA/FS28-256-023, FS22-172-003-AA/FS28-256-024, FS22-172-003-AA/FS28-256-026, FS22-172-003-AA/FS28-256-027, FS22-172-003-AA/FS28-256-001, FS22-172-003-AA/FS28-256-005, FS22-172-003-AA/FS28-256-014, FS22-172-003-AA/FS28-256-018, FS22-172-003-AA/FS28-256, FS22-172-003-AA/FS28-024-051, FS22-172-003-AA/FS28-024-053, and FS22-172-003-AA/FS28-024 may have the sequence set forth in SEQ ID NOs 76, 54, 68, 64, 68, 78, 78, 76, 68, 78, 64, 64, 64, 54, 54 and, 54, respectively.

The antibody molecule preferably binds human MSLN, more preferably human and cynomolgus MSLN. The antibody molecule of the present invention is preferably capable of binding to MSLN expressed on the surface of a cell. The cell is preferably a tumour cell.

As explained in the background section above, mature MSLN is shed from tumour cells and is cleared from the tumour site. This shed MSLN can act as a sink for anti-MSLN binding molecules which after binding to the shed MSLN are also cleared from the tumour site. In order to select for molecules which preferentially bind to MSLN present on the surface of tumour cells, the present inventors selected for antibody molecules with high avidity for MSLN. Specifically, the present inventors selected antibody molecules which bound to immobilised MSLN with higher affinity than to MSLN in solution. Antibody molecules which bind to MSLN with high avidity are thought to preferentially bind to MSLN present on tumour cells where multiple copies of MSLN are expected to be present and available for bivalent binding by the antibody molecule, as opposed to MSLN shed from tumour cells which is expected to be in monomeric form. Without wishing to be bound by theory, the antibody molecules of the invention are therefore expected to be cleared from the tumour site less quickly, and hence to have longer time window in which to exert their therapeutic effect.

The antibody molecule preferably binds to immobilised MSLN with a higher affinity than to MSLN in solution. Immobilised MSLN may be MSLN immobilised at a surface, such as chip for use in surface plasmon resonance. MSLN in solution is also referred to as soluble MSLN herein and is not immobilised. The soluble MSLN is preferably in monomeric form, i.e. monomeric mesothelin.

The affinity of an antibody for its cognate antigen can be expressed as the equilibrium dissociation constant ($K_D$) with which the antibody interacts with said antigen. The higher the $K_D$ value, the lower the affinity of the antibody molecule for the antigen.

The antibody molecule preferably binds to immobilised MSLN with an affinity ($K_D$) of 9 nM, 8 nM, 7 nM, or 6 nM or with a higher affinity. Preferably, the antibody molecule binds to immobilised MSLN with a $K_D$ of 7 nM, or 6 nM or a lower $K_D$ value.

The antibody molecule preferably binds to MSLN in solution with an affinity ($K_D$) of 15 nM, or with an affinity that is lower. More preferably, the antibody molecule binds to immobilised MSLN with an affinity ($K_D$) of 16 nM, 17 nM, or 18 nM, or with an affinity that is lower.

In a preferred embodiment, the antibody molecule binds immobilised MSLN with an affinity ($K_D$) of 6 nM or with a higher affinity, and binds MSLN in solution with an affinity ($K_D$) of 18 nM or with a lower affinity.

The binding affinity of an antibody molecule for cells comprising surface-bound MSLN may be measured by determining the concentration of the antibody molecule needed to achieve half-maximal binding ($EC_{50}$) of the antibody molecule to the cells. Suitable methods for determining the concentration of an antibody molecule needed to achieve half-maximal binding of an antibody molecule to cells are known in the art and disclosed in the present Examples (see e.g. Example 7). As explained above, antibody molecules whose binding to tumour cells comprising surface-bound MSLN is not affected or less affected by the presence of soluble MSLN are preferred in view of the presence of shed MSLN in the tumour environment. Thus, in a preferred embodiment, the concentration of the antibody molecule needed to achieve half-maximal binding ($EC_{50}$) of the antibody to cells (e.g. tumour cells) comprising surface-bound MSLN in the presence of 20 nM soluble MSLN is less than 20-fold, less than 15-fold, less than 10-fold, less than 9-fold, less than 8-fold, less than 7-fold, less than 6-fold, less than 5-fold, less than 4-fold, or less than 3-fold higher than the concentration of the antibody molecule needed to achieve half-maximal binding ($EC_{50}$) of the antibody to the cells in the absence of soluble MSLN.

The binding of antibody molecules, which do not block binding of MUC16 to MSLN, to cells comprising cell-bound MSLN has been shown to be less affected by the presence of soluble MSLN. Thus, an antibody molecule which is not capable of, or does not block, binding of MUC16 to MSLN may be preferred.

The immobilised MSLN may have the sequence set forth in SEQ ID NO: 142. The MSLN in solution may have the sequence set forth in SEQ ID NO: 142.

The antibody molecules of the invention have also been shown to bind cynomolgus MSLN. This is thought to be beneficial for carrying out efficacy and toxicity studies with the antibody molecule in cynomolgus monkeys, which may be predictive of the efficacy and toxicity of the antibody molecule in humans.

The antibody molecule may bind to immobilised human MSLN and immobilised cynomolgus MSLN with similar affinity. In addition, the antibody molecule may bind to human MSLN in solution and cynomolgus MSLN in solution with similar affinity. This is thought to be beneficial for ensuring that efficacy and toxicity studies carried out with the antibody molecule in cynomolgus monkeys are predictive of the efficacy and toxicity of the antibody molecule in humans.

Thus, in a preferred embodiment, the antibody molecule binds to immobilised cynomolgus MSLN with an affinity which is no more than 10-fold, preferably no more than 5-fold, more preferably no more than 3-fold lower or higher than the affinity with which the antibody molecule binds immobilised human MSLN. In addition, the antibody molecule preferably binds to cynomolgus MSLN in solution with an affinity which is no more than 10-fold, preferably no more than 5-fold, more preferably no more than 2-fold lower or higher than the affinity with which the antibody molecule binds human MSLN in solution.

The antibody molecules have been shown to have range of activities on ligand binding. For example, the antibody molecule may be capable of blocking, or may not be capable of blocking binding of MUC16 to MSLN.

The antibody molecule may comprise CDRs 1-6, the VH domain and/or VL domain of antibody FS22-172-003-AA/FS28-024-051, FS22-172-003-AA/FS28-024-052, FS22-172-003-AA/FS28-024-053, or FS22-172-003-AA/FS28-024, or a variant thereof, wherein the antibody molecule blocks binding of MUC16 to MSLN.

Alternatively, the antibody molecule may comprise CDRs 1-6, the VH domain and/or VL domain of antibody FS22-172-003-AA/FS28-256-271, FS22-172-003-AA/FS28-256-021, FS22-172-003-AA/FS28-256-012, FS22-172-003-AA/FS28-256-023, FS22-172-003-AA/FS28-256-024, FS22-172-003-AA/FS28-256-026, FS22-172-003-AA/FS28-256-027, FS22-172-003-AA/FS28-256-001, FS22-172-003-AA/FS28-256-005, FS22-172-003-AA/FS28-256-014, FS22-172-003-AA/FS28-256-018, or FS22-172-003-AA/FS28-256, or a variant thereof, wherein the antibody molecule does not block binding of MUC16 to MSLN.

Methods which are suitable for determining the ability of an antibody molecule to block the binding of MUC16 to MSLN are known in the art and include ELISAs and cell-based assays, for example an assay where the antibody competes for binding with MUC16 for binding to cells expressing MSLN, such as NCI-H226 cells.

The antibody molecule of the invention comprises a CD137 antigen-binding site. The CD137 antigen-binding site is located in a constant domain of the antibody molecule, preferably a CH3 domain. The CD137 antigen-binding site comprises one or more modified structural loops in a constant domain of the antibody molecule. Engineering antibody constant domain structural loops to create antigen-binding sites for target antigens is known in the art and is described, for example, Wozniak-Knopp G et al. (2010) Protein Eng Des. 23 (4): 289-297; WO2006/072620 and WO2009/132876. The CD137 constant domain antigen-binding site comprised in the antibody molecules of the invention was identified following an extensive selection and affinity maturation program, and preferentially binds to dimeric rather than monomeric human CD137.

The CD137 antigen-binding site of the antibody molecule comprises a first and second sequence, wherein the first and second sequences are located in the AB and EF structural loops of the constant domain, preferably the CH3 domain, of the antibody molecule, respectively. The first sequence and second sequence are preferably the first and second sequence of FS22-172-003 set forth in SEQ ID NOs 10 and 11, respectively. The first and second sequences are preferably located between positions 14 and 17, and positions 91 and 99, of the CH3 domain of antibody molecule, respectively, wherein the residue numbering is according to IMGT numbering.

The CD loop sequence of the antibody molecule is preferably unmodified, i.e. wild-type. The CD loop sequence therefore preferably has the sequence set forth in SEQ ID NO: 157. The CD loop sequence is preferably located at positions 43 to 78 of the CH3 domain of the antibody molecule, wherein the residue numbering is according to IMGT numbering.

In a preferred embodiment, the antibody molecule comprises a CH3 domain which comprises, has, or consists of the CH3 domain sequence of FS22-172-003 set forth in SEQ ID NO: 8.

The CH3 domain of the antibody molecule may optionally comprise an additional lysine residue (K) at the immediate C-terminus of the CH3 domain sequence.

It is possible to take monoclonal and other antibodies and use techniques of recombinant DNA technology to produce other antibodies or chimeric molecules which retain the specificity of the original antibody. Such techniques may involve introducing the CDRs, or variable regions, into a different immunoglobulin. Introduction of the CDRs of one immunoglobulin into another immunoglobulin is described, for example, in EP-A-184187, GB 2188638A and EP-A-239400. Similar techniques could be employed to introduce the constant domain sequences making up the CD137 antigen-binding site of an antibody molecule according to the invention into a constant domain, e.g. a CH3 domain, of another antibody molecule, thereby resulting in an antibody molecule comprising a CD137 antigen-binding site in its constant domain. Alternatively, an entire constant domain sequence of an antibody molecule could be replaced with the constant domain sequence of an antibody molecule according to the invention to prepare an antibody molecule comprising a CD137 antigen-binding site in its constant domain. Similarly a fragment of the constant domain sequence of an antibody molecule could be replaced with a corresponding fragment of a constant domain sequence of an antibody molecule according to the invention comprising the CD137 antigen-binding site.

The antibody molecule preferably binds human CD137, more preferably human and cynomolgus CD137, yet more preferably dimeric human and cynomolgus CD137. The portion of CD137 bound by the antibody molecule is preferably the CD137 extracellular domain. The extracellular domain of human and cynomolgus CD137 may comprise or consist of the sequence set forth in SEQ ID NOs 149 and 153, respectively. The antibody molecule is preferably capable of binding to CD137 expressed on the surface of a cell. The cell is preferably an immune cell, such as a $CD8^+$ or $CD4^+$ T cell or regulatory T (Treg) cell, preferably a $CD8^+$ T cell, or a B cell, natural killer (NK) cell, natural killer T (NKT) cell, dendritic cell (DC), or a tumour-infiltrating lymphocyte (TIL).

As explained in the background section above, treatment of patients with the anti-CD137 antibody urelumab was associated with dose-limiting high-grade liver inflammation. Without wishing to be bound by theory, it is thought that the liver inflammation seen with urelumab treatment may have been due to activation of T cells present in the liver, or infiltration and accumulation of activated T cells in the liver of the patients. In order to select for molecules with reduced or no liver inflammation, the present inventors selected for Fcabs with high avidity for CD137. Specifically, the present inventors selected Fcabs which bound to dimeric CD137 with higher affinity than monomeric CD137. Expression of CD137 by T cells is upregulated on priming and activation. It is thought that due to the higher expression of CD137 on activated T cells, CD137 will be in the form of dimers, trimers and higher-order multimers on the surface of such cells. In contrast, CD137 expression by inactive T cells express low or even undetectable. It is therefore thought that CD137, in so far as this is expressed at all on the surface of such T cells, is likely to be in monomeric form. CD137/MSLN $mAb^2$ which bind to CD137 with high avidity are therefore thought to preferentially bind to activated T cells, as opposed to inactive T cells, such as inactive T cells present in the liver, and therefore exhibit reduced or no liver inflammation. This expectation was confirmed by determining the liver pharmacology of mice treated with an anti-mouse CD137/MSLN $mAb^2$, which showed that the treatment did not result in hepatotoxicity (Example 13).

The antibody molecule preferably binds to dimeric human CD137 with an affinity ($K_D$) of 60 nM, 50 nM, 40 nM, 30 nM, 20 nM, 10 nM, 5 nM, 4 nM, 3 nM, or 2 nM, or an affinity which is greater.

In a preferred embodiment, the antibody molecule binds to dimeric CD137 with a higher affinity than monomeric CD137. In a preferred embodiment, the antibody molecule binds to dimeric CD137 with an affinity which is at least 50-fold, 60-fold, 70-fold, 80-fold, 90-fold, 100-fold, 110-fold, 120-fold, 130-fold, 140-fold, 150-fold, 160-fold, 170-fold or 200-fold higher than the affinity of the antibody molecule for monomeric CD137.

The monomeric human CD137 may, for example, have the sequence set forth in SEQ ID NO: 149.

Antibody molecules from the FS22-172 lineage have also been shown to bind dimeric cynomolgus CD137. Binding to cynomolgus CD137 as well as human CD137 is beneficial as it permits testing of the antibody molecule in cynomolgus monkeys for efficacy and toxicity prior to administration to humans.

In a preferred embodiment, the antibody molecule may bind to dimeric cynomolgus CD137 with an affinity ($K_D$) of 250 nM, 200 nM, 150 nM, 140 nM, 120 nM, 100 nM, 90 nM, 80 nM, 70 nM, 60 nM, 50 nM, 40 nM, 30 nM, 20 nM, 10 nM, 5 nM, 4 nM, 3 nM, or 2 nM or an affinity which is greater. Preferably, the antibody molecule binds to cynomolgus CD137, with an affinity ($K_D$) of 2 nM, or an affinity which is greater.

The antibody molecule may bind to dimeric human CD137 and dimeric cynomolgus CD137 with similar affinity. This is thought to be beneficial for ensuring that efficacy and toxicity studies carried out with the antibody molecule in cynomolgus monkeys are predictive of the efficacy and toxicity of the antibody molecule in humans.

Thus, in a preferred embodiment, the antibody molecule binds to dimeric cynomolgus CD137 with an affinity which is no more than 10-fold, preferably no more than 5-fold lower or higher than the affinity with which the antibody molecule binds dimeric human CD137.

The binding affinity of an antibody molecule to a cognate antigen, such as human or cynomolgus CD137 can be determined by surface plasmon resonance (SPR), such as Biacore, for example.

The antibody molecule may be capable of blocking the interaction between CD137 and its ligand, CD137L, preferably human CD137 and human CD137L. The ability of antibody molecule to block the binding of CD137L to CD137 may be determined using an ELISA.

In addition, the antibody molecule may comprise a CH2 domain of an immunoglobulin G molecule, such as a CH2 domain of an IgG1, IgG2, IgG3, or IgG4 molecule. Preferably the antibody molecule comprises a CH2 domain of an IgG1 molecule. The CH2 domain may have the sequence set forth in SEQ ID NO:154. The CH2 domain is known bind to Fcγ receptors and complement. Binding of the CH2 domain to Fcγ receptors is required antibody-dependent cell-mediated cytotoxicity (ADCC), while binding to complement is required complement-dependent cytotoxicity (CDC).

The CH2 domain of the antibody molecule preferably comprises one or more mutations that reduce or abrogate binding of the CH2 domain to one or more Fcγ receptors, such as FcγRI, FcγRIIa, FcγRIIb, FcγRIII, and/or to complement. The inventors postulate that reducing or abrogating binding to Fcγ receptors will decrease or eliminate ADCC mediated by the antibody molecule. Similarly, reducing or abrogating binding to complement is expected to reduce or eliminate CDC mediated by the antibody molecule. Without wishing to be bound by theory, this is expected to reduce or avoid liver inflammation when the antibody molecule is administered to a patient. Mutations to decrease or abrogate binding of the CH2 domain to one or more Fcγ receptors and/or complement are known in the art (Wang et al., 2018). These mutations include the "LALA mutation" described in Bruhns et al., 2009 and Hezareh et al., 2001, which involves substitution of the leucine residues at positions 1.3 and 1.2 of the CH2 domain with alanine (L1.3A and L1.2A). Alternatively, the generation of a-glycosyl antibodies through mutation of the conserved N-linked glycosylation site by mutating the asparagine (N) at position 84.4 of the CH2 domain to alanine, glycine or glutamine (N84.4A, N84.4G or N84.4Q) is also known to decrease IgG1 effector function (Wang et al., 2018). As a further alternative, complement activation (C1q binding) and ADCC are known to be reduced through mutation of the proline at position 114 of the CH2 domain to alanine or glycine (P114A or P114G) (Idusogie et al., 2000; Klein et al., 2016). These mutations may also be combined in order to generate antibody molecules with further reduced or no ADCC or CDC activity.

Thus, the antibody molecule may comprise a CH2 domain, wherein the CH2 domain comprises:

(i) alanine residues at positions 1.3 and 1.2; and/or
(ii) an alanine or glycine at position 114; and/or
(iii) an alanine, glutamine or glycine at position 84.4;
wherein the amino acid residue numbering is according to the IMGT numbering scheme.

In a preferred embodiment, the antibody molecule comprises a CH2 domain, wherein the CH2 domain comprises:

(i) an alanine residue at position 1.3; and
(ii) an alanine residue at position 1.2;

wherein the amino acid residue numbering is according to the IMGT numbering scheme.

For example, the CH2 domain may have the sequence set forth in SEQ ID NO: 155.

In an alternative preferred embodiment, the antibody molecule comprises a CH2 domain, wherein the CH2 domain comprises:

(i) an alanine residue at position 1.3;

(ii) an alanine residue at position 1.2; and (iii) an alanine at position 114;

wherein the amino acid residue numbering is according to the IMGT numbering scheme.

For example, the CH2 domain may have the sequence set forth in SEQ ID NO: 156.

In an alternative preferred embodiment, the antibody molecule comprises the heavy chain and/or light chain, preferably the heavy chain and light chain, of antibody:

(i) FS22-172-003-AA/FS28-256-271 set forth in SEQ ID NOs 3 and 84, respectively;

(ii) FS22-172-003-AA/FS28-024-052 set forth in SEQ ID NOs 102 and 85, respectively;

(iii) FS22-172-003-AA/FS28-256-021 set forth in SEQ ID NOs 125 and 82, respectively;

(iv) FS22-172-003-AA/FS28-256-012 set forth in SEQ ID NOs 125 and 116, respectively;

(v) FS22-172-003-AA/FS28-256-023 set forth in SEQ ID NOs 133 and 82, respectively;

(vi) FS22-172-003-AA/FS28-256-024 set forth in SEQ ID NOs 125 and 83, respectively;

(vii) FS22-172-003-AA/FS28-256-026 set forth in SEQ ID NOs 133 and 83, respectively;

(viii) FS22-172-003-AA/FS28-256-027 set forth in SEQ ID NOs 125 and 84, respectively;

(ix) FS22-172-003-AA/FS28-256-001 set forth in SEQ ID NOs 120 and 82, respectively;

(x) FS22-172-003-AA/FS28-256-005 set forth in SEQ ID NOs 120 and 78, respectively;

(xi) FS22-172-003-AA/FS28-256-014 set forth in SEQ ID NOs 129 and 116, respectively;

(xii) FS22-172-003-AA/FS28-256-018 set forth in SEQ ID NOs 133 and 116, respectively;

(xiii) FS22-172-003-AA/FS28-256 set forth in SEQ ID NOs 114 and 116, respectively;

(xiv) FS22-172-003-AA/FS28-024-051 set forth in SEQ ID NOs 98 and 85, respectively;

(xv) FS22-172-003-AA/FS28-024-053 set forth in SEQ ID NOs 106 and 85, respectively; or (xvi) FS22-172-003-AA/FS28-024 set forth in SEQ ID NOs 94 and 85, respectively.

In a more preferred embodiment, the antibody molecule comprises the heavy chain and/or light chain, preferably the heavy chain and light chain, of: antibody FS22-172-003-AA/FS28-256-271 or FS22-172-003-AA/FS28-024-052, most preferably antibody FS22-172-003-AA/FS28-256-, wherein the heavy and light chain sequences of these antibodies are as set out above.

The antibody molecules of the present invention may also comprise variants of a first, second or third sequence, AB, CD or EF structural loop sequence, CH3 domain, CH2 domain, CDR, VH domain, VL domain, light chain and/or heavy chain sequences disclosed herein. Suitable variants can be obtained by means of methods of sequence alteration, or mutation, and screening. In a preferred embodiment, an antibody molecule comprising one or more variant sequences retains one or more of the functional characteristics of the parent antibody molecule, such as binding specificity and/or binding affinity for MSLN and CD137. For example, an antibody molecule comprising one or more variant sequences preferably binds to MSLN and/or CD137 with the same affinity, or a higher affinity, than the (parent) antibody molecule. The parent antibody molecule is an antibody molecule which does not comprise the amino acid substitution(s), deletion(s), and/or insertion(s) which have been incorporated into the variant antibody molecule.

An antibody molecule which comprises CDRs 1-6, the VH domain, and/or the heavy chain of antibody FS22-172-003-AA/FS28-256-021, FS22-172-003-AA/FS28-256-012, FS22-172-003-AA/FS28-256-023, FS22-172-003-AA/FS28-256-024, FS22-172-003-AA/FS28-256-026, FS22-172-003-AA/FS28-256-027, FS22-172-003-AA/FS28-256-001, FS22-172-003-AA/FS28-256-005, FS22-172-003-AA/FS28-256-014, FS22-172-003-AA/FS28-256-018, or FS22-172-003-AA/FS28-256 may comprise an amino acid substitution at position 55 or 57 of the VH domain, wherein the amino acid residue numbering is according to the IMGT numbering scheme.

For example, the antibody molecule may comprise CDRs 1-6, the VH domain, and/or the heavy chain of antibody FS22-172-003-AA/FS28-256-027, wherein the antibody molecule comprises an amino acid substitution at position 55 of the VH domain, and wherein the amino acid residue numbering is according to the IMGT numbering scheme.

For example, an antibody molecule of the invention may comprise a first, second or third sequence, AB, CD or EF structural loop sequence, CH3 domain, CH2 domain, CDR, VH domain, VL domain, light chain and/or heavy chain sequence which has at least 70%, at least 75%, at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to a structural loop, CH3 domain, CH2 domain, CDR, VH domain, VL domain, light chain or heavy chain sequence disclosed herein.

In a preferred embodiment, the antibody molecule of the invention comprises a CH3 domain sequence which has at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to a CH3 domain as disclosed herein.

In a further preferred embodiment, the antibody molecule has or comprises a CH2 domain sequence, which has at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to a CH2 domain as disclosed herein.

Sequence identity is commonly defined with reference to the algorithm GAP (Wisconsin GCG package, Accelerys Inc, San Diego USA). GAP uses the Needleman and Wunsch algorithm to align two complete sequences, maximising the number of matches and minimising the number of gaps. Generally, default parameters are used, with a gap creation penalty equaling 12 and a gap extension penalty equaling 4. Use of GAP may be preferred but other algorithms may be used, e.g. BLAST (which uses the method of Altschul et al., 1990), FASTA (which uses the method of Pearson and Lipman, 1988), or the Smith-Waterman algorithm (Smith and Waterman, 1981), or the TBLASTN program, of Altschul et al., 1990 supra, generally employing default parameters. In particular, the psi-Blast algorithm (Altschul et al., 1997) may be used.

An antibody molecule of the invention may also comprise a first, second or third sequence, AB, CD or EF structural loop sequence, CH3 domain, CH2 domain, VH domain, VL domain, light chain and/or heavy chain which has one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with a first, second or third sequence, AB, CD or EF structural loop sequence, CH3 domain, CH2 domain, Fcab, CDR, VH domain, VL domain, light chain or heavy chain sequence disclosed herein. In particular, alterations may be made in one or more framework regions of the antibody molecule outside the VH and VL domain sequences and/or in one or more framework regions of the CH3 domain. For example, the alterations may be in the CH3 domain outside of the sequences described herein as a first, second and third sequences, or as AB, CD or EF structural loop sequences.

The antibody molecule may comprise a VH CDR1, VH CDR2, VH CDR3, VL CDR1, VL CDR2, and/or VL CDR3 which has one or more amino acid sequence alterations (addition, deletion, substitution and/or insertion of an amino acid residue), preferably 3 alterations or fewer, 2 alterations or fewer, or 1 alteration compared with the VH CDR1, VH CDR2, VH CDR3, VL CDR1, VL CDR2, and/or VL CDR3 as disclosed herein.

In a preferred embodiment, the antibody molecule of the invention may comprise a CH3 domain sequence with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH3 domain as disclosed herein.

In preferred embodiments in which one or more amino acids are substituted with another amino acid, the substitutions may conservative substitutions, for example according to the following Table. In some embodiments, amino acids in the same category in the middle column are substituted for one another, i.e. a non-polar amino acid is substituted with another non-polar amino acid, for example. In some embodiments, amino acids in the same line in the rightmost column are substituted for one another.

| | | |
|---|---|---|
| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

In some embodiments, substitution(s) may be functionally conservative. That is, in some embodiments the substitution may not affect (or may not substantially affect) one or more functional properties (e.g. binding affinity) of the antibody molecule comprising the substitution as compared to the equivalent unsubstituted antibody molecule.

The antibody molecule of the invention preferably induces increased T cell activation when the antibody molecule is crosslinked, e.g. through binding to MSLN, than when the antibody molecule is not crosslinked.

The ability of an antibody molecule to activate T cells may be measured using a T cell activation assay. T cells release IL-2 on activation. A T cell activation assay may therefore measure IL-2 release to determine the level of T cell activation induced by the antibody molecule or antibody molecule.

For example, the ability of the antibody molecule to activate T cells may be determined by measuring the concentration of the antibody molecule required to achieve half-maximal release of IL-2 by the T cells in a T cells activation assay when the antibody molecule is crosslinked. This is referred to as the $EC_{50}$ of the antibody molecule below. A lower $EC_{50}$ indicates that a lower concentration of the antibody molecule is needed to achieve half-maximal release of IL-2 by the T cells in the T cells activation assay, and thus that the antibody molecule has a higher T cell activation activity. The antibody molecule may be crosslinked using an anti-CH2 antibody, for example.

In a preferred embodiment, the antibody molecule has an $EC_{50}$ in a T cell activation assay which is within 10-fold, 5-fold, 4-fold, 3-fold, or 2-fold of the $EC_{50}$ FS22-172-003-AA/FS28-256-271 or FS22-172-003-AA/FS28-024-052 in the same assay.

In an alternative preferred embodiment, the antibody molecule has an $EC_{50}$ in a T cell activation assay which is within 10-fold, 5-fold, 4-fold, 3-fold, or 2-fold of the $EC_{50}$ FS22-172-003-AA/FS28-256-271 or FS22-172-003-AA/FS28-024-052 in the same assay.

For example, the antibody molecule may have an $EC_{50}$ in a T cell activation assay of 5 nM or less, 4 nM or less, 3 nM or less, 2 nM or less, 1 nM or less, or 0.5 nM or less.

In addition, or alternatively, the ability of an antibody molecule to activate T cells may be determined by measuring the maximum concentration of IL-2 released by the T cells in a T cell activation assay in the presence of the antibody molecule, wherein the antibody molecule is crosslinked.

In a preferred embodiment, the maximum concentration of IL-2 released by the T cells in a T cell activation assay in the presence of the antibody molecule in the presence of crosslinking is within 3-fold, 2-fold, or 1.5-fold of the maximum concentration of IL-2 released by the T cells in the presence of FS22-172-003-AA/FS28-256-271 or FS22-172-003-AA/FS28-024-052 in the same assay.

The T cell activation assay may be a T cell assay as described herein, such as a $CD8^+$ T cell assay, as described in the present Examples, see e.g. Example 8.

For example, a T cell activation assay may be an IL-2 release assay based on $CD8^+$ T cells isolated from human Peripheral Blood Mononuclear Cells (PBMCs). For example, the T cell activation assay may comprise isolating human PBMCs from leucocyte depletion cones. Methods for isolating PBMCs are known in the art and described in the present examples. The $CD8^+$ T cells may then be isolated from the PBMCs. Methods for isolating $CD8^+$ T cells from PBMCs are known in the art and described in the present examples.

The $CD8^+$ T cells may then be added to multiwall plates coated with an anti-human CD3 antibody. A suitable dilution of each test antibody molecule may be prepared and added to the wells. The T cells may then be incubated at 37° C., 5% $CO_2$ for 24 hours with the test antibody. Supernatants may be collected and assayed to determine the concentration of IL-2 in the supernatant. Methods for determining the concentration of IL-2 in a solution are known in the art and described in the present examples. The concentration of human IL-2 may be plotted versus the log concentration of the antibody molecule. The resulting curves may be fitted using the log (agonist) versus response equation.

The antibody molecule may be conjugated to a bioactive molecule or a detectable label. In this case, the antibody molecule may be referred to as a conjugate. Such conjugates find application in the treatment and/or diagnosis of diseases as described herein.

For example, the bioactive molecule may be an immune system modulator, such as a cytokine, preferably a human cytokine. For example, the cytokine may be a cytokine which stimulates T cell activation and/or proliferation. Examples of cytokines for conjugation to the antibody molecule include IL-2, IL-10, IL-12, IL-15, IL-21, GM-CSF and IFN-gamma.

Alternatively, the bioactive molecule may be a ligand trap, such as a ligand trap of a cytokine, e.g. of TGF-beta or IL-6.

As a further alternative, the bioactive molecule may be a ligand such as CD137L, OX40L, TRAIL, CD40L, CD27L, or GITRL.

As a further alternative, the bioactive molecule may be a drug such as an inhibitor of tubulin polymerisation (e.g. an auristatin), a tubulin depolymerisation agent (e.g. a maytansine), a DNA strand scission inducing agent (e.g. calicheamicin), a DNA alkylating agent (e.g. duocarmycin), or an RNA polymerase inhibitor (such as alpha-amanitin).

Suitable detectable labels which may be conjugated to antibody molecules are known in the art and include radioisotopes such as iodine-125, iodine-131, yttrium-90, indium-111 and technetium-99; fluorochromes, such as fluorescein, rhodamine, phycoerythrin, Texas Red and cyanine dye derivatives for example, Cy7 and Alexa750; chromogenic dyes, such as diaminobenzidine; latex beads; enzyme labels such as horseradish peroxidase; phosphor or laser dyes with spectrally isolated absorption or emission characteristics; and chemical moieties, such as biotin, which may be detected via binding to a specific cognate detectable moiety, e.g. labelled avidin.

The antibody molecule may be conjugated to the bioactive molecule or detectable label by means of any suitable covalent or non-covalent linkage, such as a disulphide or peptide bond. Where the bioactive molecule is a cytokine, the cytokine may be joined to the antibody molecule by means of a peptide linker. Suitable peptide linkers are known in the art and may be 5 to 25, 5 to 20, 5 to 15, 10 to 25, 10 to 20, or 10 to 15 amino acids in length.

In some embodiments, the bioactive molecule may be conjugated to the antibody molecule by a cleavable linker. The linker may allow release of the bioactive molecule from the antibody molecule at a site of therapy. Linkers may include amide bonds (e.g. peptidic linkers), disulphide bonds or hydrazones. Peptide linkers for example may be cleaved by site specific proteases, disulphide bonds may be cleaved by the reducing environment of the cytosol and hydrazones may be cleaved by acid-mediated hydrolysis.

The conjugate may be a fusion protein comprising the antibody molecule and the bioactive molecule. In this case the bioactive molecule may be conjugated to the antibody molecule by means of a peptide linker or peptide bond. Where the antibody molecule is a multichain molecule, such as where the antibody molecule is or comprises an Fcab or is a $mAb^2$, the bioactive molecule may be conjugated to one or more chains of the antibody molecule. For example, the bioactive molecule may be conjugated to one or both of the heavy chains of the $mAb^2$ molecule. Fusion proteins have the advantage of being easier to produce and purify, facilitating the production of clinical-grade material.

The invention also provides an isolated nucleic acid molecule or molecules encoding an antibody molecule of the invention. The skilled person would have no difficulty in preparing such nucleic acid molecules using methods well-known in the art.

In an alternative preferred embodiment, the nucleic acid molecule(s) encode(s) the heavy chain and/or light chain, preferably the heavy chain and light chain, of: antibody FS22-172-003-AA/FS28-256-271, FS22-172-003-AA/FS28-024-052, FS22-172-003-AA/FS28-256-021, FS22-172-003-AA/FS28-256-012, FS22-172-003-AA/FS28-256-023, FS22-172-003-AA/FS28-256-024, FS22-172-003-AA/FS28-256-026, FS22-172-003-AA/FS28-256-027, FS22-172-003-AA/FS28-256-001, FS22-172-003-AA/FS28-256-005, FS22-172-003-AA/FS28-256-014, FS22-172-003-AA/FS28-256-018, FS22-172-003-AA/FS28-256, FS22-172-003-AA/FS28-024-051, FS22-172-003-AA/FS28-024-053, or FS22-172-003-AA/FS28-024, preferably antibody FS22-172-003-AA/FS28-256-271 or FS22-172-003-AA/FS28-024-052, most preferably antibody FS22-172-003-AA/FS28-256-271.

A nucleic acid molecule which encodes the heavy chain of antibody FS22-172-003-AA/FS28-256-271, FS22-172-003-AA/FS28-024-052, FS22-172-003-AA/FS28-256-021, FS22-172-003-AA/FS28-256-012, FS22-172-003-AA/FS28-256-023, FS22-172-003-AA/FS28-256-024, FS22-172-003-AA/FS28-256-026, FS22-172-003-AA/FS28-256-027, FS22-172-003-AA/FS28-256-001, FS22-172-003-AA/FS28-256-005, FS22-172-003-AA/FS28-256-014, FS22-172-003-AA/FS28-256-018, FS22-172-003-AA/FS28-256, FS22-172-003-AA/FS28-024-051, FS22-172-003-AA/FS28-024-053, and FS22-172-003-AA/FS28-024, is set forth in SEQ ID NOs: 4, 103, 126, 126, 134, 126, 134, 126, 121, 121, 130, 134, 115, 99, 107, and 95, respectively.

A nucleic acid molecule which encodes the light chain of antibody FS22-172-003-AA/FS28-256-271, FS22-172-003-AA/FS28-024-052, FS22-172-003-AA/FS28-256-021, FS22-172-003-AA/FS28-256-012, FS22-172-003-AA/FS28-256-023, FS22-172-003-AA/FS28-256-024, FS22-172-003-AA/FS28-256-026, FS22-172-003-AA/FS28-256-027, FS22-172-003-AA/FS28-256-001, FS22-172-003-AA/FS28-256-005, FS22-172-003-AA/FS28-256-014, FS22-172-003-AA/FS28-256-018, FS22-172-003-AA/FS28-256, FS22-172-003-AA/FS28-024-051, FS22-172-003-AA/FS28-024-053, and FS22-172-003-AA/FS28-024, is set forth in SEQ ID NOs: 91, 86, 122, 117, 122, 90, 90, 91, 122, 90, 117, 117, 117, 86, 86 and 86, respectively.

Where the nucleic acid encodes the heavy and light chain, of an antibody molecule of the invention, the two domains or chains may be encoded on two separate nucleic acid molecules.

An isolated nucleic acid molecule may be used to express an antibody molecule of the invention. The nucleic acid will generally be provided in the form of a recombinant vector for expression. Another aspect of the invention thus provides a vector comprising a nucleic acid as described above. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in a host cell. Vectors may be plasmids, viral e.g. phage, or phagemid, as appropriate.

A nucleic acid molecule or vector as described herein may be introduced into a host cell. Techniques for the introduction of nucleic acid or vectors into host cells are well established in the art and any suitable technique may be employed. A range of host cells suitable for the production of recombinant antibody molecules are known in the art, and include bacterial, yeast, insect or mammalian host cells. A preferred host cell is a mammalian cell, such as a CHO, NS0, or HEK cell, for example a HEK293 cell.

Another aspect of the invention provides a method of producing an antibody molecule of the invention comprising expressing a nucleic acid encoding the antibody molecule in a host cell and optionally isolating and/or purifying the antibody molecule thus produced. Methods for culturing host cells are well-known in the art. The method may further comprise isolating and/or purifying the antibody molecule. Techniques for the purification of recombinant antibody molecules are well-known in the art and include, for example HPLC, FPLC or affinity chromatography, e.g. using Protein A or Protein L. In some embodiments, purification may be performed using an affinity tag on antibody molecule. The method may also comprise formulating the antibody molecule into a pharmaceutical composition, optionally with a pharmaceutically acceptable excipient or other substance as described below.

As explained above, MSLN is expressed on the surface of tumour cells and high expression levels of soluble MSLN have been correlated with poor prognosis in several cancers. Anti-MSLN antibodies have been investigated as anti-cancer therapeutics. These anti-MSLN antibodies either induce direct cell killing through their ADCC activity or are used in the form of ADCs.

The antibody molecules described herein are therefore expected to find application in the treatment of cancer. Related aspects of the invention thus provide:

(i) an antibody molecule described herein for use in a method of treating cancer in an individual, (ii) the use of an antibody molecule described herein in the manufacture of a medicament for use in the treatment of cancer in an individual; and, (iv) a method of treating cancer in an individual, wherein the method comprises administering to the individual a therapeutically effective amount of an antibody molecule as described herein.

The individual may be a patient, preferably a human patient.

The antibody molecules of the invention have been shown to preferentially bind to MSLN present on the surface of a cancer cell as compared to soluble MSLN. The cancer to be treated using an antibody molecule of the invention therefore preferably expresses, or has been determined to express, MSLN. More preferably, cells of the cancer to be treated comprise, or have been determined to comprise, MSLN at their cell surface, i.e. to comprise cell-surface bound MSLN.

The cancer preferably comprises, or has been determined to comprise, tumour infiltrating lymphocytes (TILs) that express CD137. Specifically, the TILs preferably comprise, or have been determined to comprise, CD137 on their cell surface.

Methods for determining the presence of an antigen on a cell surface are known in the art and include, for example, flow cytometry.

The cancer may be a primary or a secondary cancer. Thus, an antibody molecule as described herein may be for use in a method of treating cancer in an individual, wherein the cancer is a primary tumour and/or a tumour metastasis.

The cancer to be treated using an antibody molecule of the invention may be a solid cancer.

The cancer may be selected from the group consisting of: mesothelioma, pancreatic cancer, ovarian cancer, lung cancer (such as small-cell lung cancer and non-small cell lung cancer), oesophageal cancer, breast cancer, gastric cancer, cholangiocarcinoma, colon cancer, thymic carcinoma, endometrial cancer, head and neck cancer, sarcoma (such as biphasic synovial sarcoma, Kaposi's sarcoma, osteogenic sarcoma, rhabdomyosarcoma, or soft-tissue sarcoma), desmoplastic small round cell tumours, leukaemia (such as acute lymphocytic leukaemia, chronic lymphocytic leukaemia, acute granulocytic leukaemia, chronic granulocytic leukaemia, hairy cell leukaemia, or myeloid leukaemia), adrenal cortex cancer, bladder cancer, brain cancer, cervical cancer, cervical hyperplasia, testicular choriocarcinoma, essential thrombocytosis, genitourinary carcinoma, glioma, glioblastoma, lymphoma (such as Hodgkin's disease or non-Hodgkin's lymphoma), malignant carcinoid carcinoma, malignant hypercalcemia, melanoma (also referred to as malignant melanoma), malignant pancreatic insulinoma, medullary thyroid carcinoma, multiple myeloma, mycosis fungoides, neuroblastoma, polycythemia vera, primary brain carcinoma, primary macroglobulinemia, prostate cancer, renal cell cancer, skin cancer, squamous cell cancer, stomach cancer, testicular cancer, thyroid cancer, and Wilms' tumor.

Preferably, the cancer is selected from the group consisting of: mesothelioma, pancreatic cancer, ovarian cancer, lung cancer, oesophageal cancer, breast cancer, gastric cancer, cholangiocarcinoma, colon cancer, thymic carcinoma, endometrial cancer, head and neck cancer, biphasic synovial sarcomas, and desmoplastic small round cell tumours.

More preferably, the cancer is selected from the group consisting of: mesothelioma, pancreatic cancer, ovarian cancer, and lung cancer.

Cancer is characterised by the abnormal proliferation of malignant cancer cells. Where a particular type of cancer, such as breast cancer, is referred to, this refers to an abnormal proliferation of malignant cells of the relevant tissue, such as breast tissue. A secondary cancer which is located in the breast but is the result of abnormal proliferation of malignant cells of another tissue, such as ovarian tissue, is not a breast cancer as referred to herein but an ovarian cancer.

In the context of cancer, treatment may include inhibiting cancer growth, including complete cancer remission, and/or inhibiting cancer metastasis, as well as inhibiting cancer recurrence. Cancer growth generally refers to any one of a number of indices that indicate change within the cancer to a more developed form. Thus, indices for measuring an inhibition of cancer growth include a decrease in cancer cell survival, a decrease in tumour volume or morphology (for example, as determined using computed tomographic (CT), sonography, or other imaging method), a delayed tumour growth, a destruction of tumour vasculature, improved performance in delayed hypersensitivity skin test, an increase in the activity of anti-cancer immune cells or other anti-cancer immune responses, and a decrease in levels of tumour-specific antigens. Activating or enhancing immune responses to cancerous tumours in an individual may improve the capacity of the individual to resist cancer growth, in particular growth of a cancer already present in the subject and/or decrease the propensity for cancer growth in the individual.

Whilst an antibody molecule may be administered alone, antibody molecules will usually be administered in the form of a pharmaceutical composition, which may comprise at least one component in addition to the antibody molecule. Another aspect of the invention therefore provides a pharmaceutical composition comprising an antibody molecule as described herein. A method comprising formulating an antibody molecule into a pharmaceutical composition is also provided.

Pharmaceutical compositions may comprise, in addition to the antibody molecule, a pharmaceutically acceptable excipient, carrier, buffer, stabilizer or other materials well known to those skilled in the art. The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. The precise nature of the carrier or other material will depend on the route of administration, which may be by infusion, injection or any other suitable route, as discussed below.

For parenteral, for example subcutaneous or intravenous administration, e.g. by injection, the pharmaceutical composition comprising the antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

In some embodiments, antibody molecules may be provided in a lyophilised form for reconstitution prior to administration. For example, lyophilised antibody molecules may be re-constituted in sterile water and mixed with saline prior to administration to an individual.

Administration may be in a "therapeutically effective amount", this being sufficient to show benefit to an individual. The actual amount administered, and rate and time-course of administration, will depend on the nature and severity of what is being treated, the particular individual being treated, the clinical condition of the individual, the cause of the disorder, the site of delivery of the composition, the type of antibody molecule, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. Appropriate doses of antibody molecules are well known in the art (Ledermann et al., 1991; Bagshawe et al., 1991). Specific dosages indicated herein, or in the Physician's Desk Reference (2003) as appropriate for an antibody molecule being administered, may be used. A therapeutically effective amount or suitable dose of an antibody molecule can be determined by comparing in vitro activity and in vivo activity in an animal model. Methods for extrapolation of effective dosages in mice and other test animals to humans are known. The precise dose will depend upon a number of factors, including whether the size and location of the area to be treated, and the precise nature of the antibody molecule.

A typical antibody dose is in the range 100 μg to 1 g for systemic applications, and 1 μg to 1 mg for topical applications. An initial higher loading dose, followed by one or more lower doses, may be administered. This is a dose for a single treatment of an adult individual, which may be proportionally adjusted for children and infants, and also adjusted for other antibody formats in proportion to molecular weight.

Treatments may be repeated at daily, twice-weekly, weekly or monthly intervals, at the discretion of the physician. The treatment schedule for an individual may be dependent on the pharmocokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Suitable formulations and routes of administration are described above.

In the context of cancer treatment, an antibody molecule as described herein may be administered to an individual in combination with another anti-cancer therapy or therapeutic agent, such as an anti-cancer therapy or therapeutic agent which has been shown to be suitable, or is expected to be suitable, for the treatment of the cancer in question. For example, the antibody molecule may be administered to the individual in combination with a chemotherapeutic agent, radiotherapy, an immunotherapeutic agent, an anti-tumour vaccine, an oncolytic virus, an adoptive cell transfer (ACT) therapy (such as adoptive NK cell therapy or therapy with chimeric antigen receptor (CAR) T-cells, autologous tumour infiltrating lymphocytes (TILs), or gamma/delta T cells, or an agent for hormone therapy.

Without wishing to be bound by theory, it is thought that the antibody molecule as described herein, wherein the antibody molecules comprises a second antigen-binding site for an immune cell antigen, such as a TNFRSF receptor, may act as an adjuvant in anti-cancer therapy. Specifically, it is thought that administration of the antibody molecule to an in individual in combination with chemotherapy and/or radiotherapy, or in combination with an anti-tumour vaccine, for example, will trigger a greater immune response against the cancer than is achieved with chemotherapy and/or radiotherapy, or with an anti-tumour vaccine, alone.

One or more chemotherapeutic agents for administration in combination with an antibody molecule as described herein may be selected from the group consisting of: taxanes, cytotoxic antibiotics, tyrosine kinase inhibitors, PARP inhibitors, B-Raf enzyme inhibitors, MEK inhibitors, c-MET inhibitors, VEGFR inhibitors, PDGFR inhibitors, alkylating agents, platinum analogues, nucleoside analogues, antifolates, thalidomide derivatives, antineoplastic chemotherapeutic agents and others. Taxanes include docetaxel, paclitaxel and nab-paclitaxel; cytotoxic antibiotics include actinomycin, bleomycin, and anthracyclines such as doxorubicin, mitoxantrone and valrubicin; tyrosine kinase inhibitors include erlotinib, gefitinib, axitinib, PLX3397, imatinib, cobemitinib and trametinib; PARP inhibitors include piraparib; B-Raf enzyme inhibitors include vemurafenib and dabrafenib; alkylating agents include dacarbazine, cyclophosphamide and temozolomide; platinum analogues include carboplatin, cisplatin and oxaliplatin; nucleoside analogues include azacitidine, capecitabine, fludarabine, fluorouracil and gemcitabine; antifolates include methotrexate and pemetrexed. Other chemotherapeutic agents suitable for use in the present invention include defactinib, entinostat, eribulin, irinotecan and vinblastine.

Preferred therapeutic agents for administration with an antibody molecule as described herein are pentostatin, cyclophosphamide, cis-platin, pemetrexed, paclitaxel, carboplatin, gemcitabine, doxorubicin, vinorelbine, docetaxel, or etoposide A radiotherapy for administration in combination with an antibody molecule as described herein may be external beam radiotherapy (such as intensity-modulated radiotherapy (IMRT), stereotactic body radiotherapy (SBRT), image-guided radiotherapy (IGRT), intra-operative radiotherapy (IORT), electron therapy or electron beam therapy (EBT), superficial radiotherapy (SRT)), or internal radiotherapy (such as brachytherapy, radioisotope or radionuclide therapy, SIRT. Preferably, the radiotherapy is conventional external beam radiotherapy, external beam radiation therapy (EBRT), stereotactic radiotherapy, or brachytherapy An immunotherapeutic agent for administration in combination with an antibody molecule as described herein may be a therapeutic antibody molecule, nucleic acid, cytokine, or cytokine-based therapy. For example, the therapeutic antibody molecule may bind to an immune regulatory molecule, e.g. an inhibitory checkpoint molecule or an immune costimulatory molecule, a receptor of the innate immune system, or a tumour antigen, e.g. a cell surface tumour antigen or a soluble tumour antigen. Examples of immune regulatory molecules to which the therapeutic antibody molecule may bind include inhibitory checkpoint molecules, such as CTLA-4, LAG-3, TIGIT, TIM-3, VISTA, PD-L1, PD-1, or KIR, immune costimulatory molecules, such as OX40, CD40, GITR, CD27, or ICOS, other immune regulatory molecules such as CD47, CD73, CSF-1R, HVEM, TGFB, or CSF-1. Examples of receptors of the innate immune system to which the therapeutic antibody molecule may bind include TLR1, TLR2, TLR4, TLR5, TLR7, TLR9, RIG-1-like receptors (e.g. RIG-1 and MDA-5), and STING.

The nucleic acid for administration in combination with an antibody molecule as described herein may be an siRNA.

The cytokines or cytokine-based therapy may be selected from the group consisting of: IL-2, prodrug of conjugated IL-2, GM-CSF, IL-7, IL-12, IL-9, IL-15, IL-18, IL-21, and type I interferon.

Anti-tumour vaccines for the treatment of cancer have both been implemented in the clinic and discussed in detail within scientific literature (such as Rosenberg, S. 2000). This mainly involves strategies to prompt the immune system to respond to various cellular markers expressed by autologous or allogenic cancer cells by using those cells as a vaccination method, both with or without granulocyte-macrophage colony-stimulating factor (GM-CSF). GM-CSF provokes a strong response in antigen presentation and works particularly well when employed with said strategies.

The chemotherapeutic agent, radiotherapy, immunotherapeutic agent, anti-tumour vaccine, oncolytic virus, ACT therapy, or agent for hormone therapy is preferably a chemotherapeutic agent, radiotherapy, immunotherapeutic agent, anti-tumour vaccine, oncolytic virus, ACT therapy, or agent for hormone therapy for the cancer in question, i.e. a chemotherapeutic agent, radiotherapy, immunotherapeutic agent, anti-tumour vaccine, oncolytic virus, ACT therapy, or agent for hormone therapy which has been shown to be effective in the treatment of the cancer in question. The selection of a suitable chemotherapeutic agent, radiotherapy, immunotherapeutic agent, anti-tumour vaccine, oncolytic virus, ACT therapy, or agent for hormone therapy which has been shown to be effective for the cancer in question is well within the capabilities of the skilled practitioner.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Other aspects and embodiments of the invention provide the aspects and embodiments described above with the term "comprising" replaced by the term "consisting of" or "consisting essentially of", unless the context dictates otherwise.

Certain aspects and embodiments of the invention will now be illustrated by way of example and with reference to the figures described above.

EXAMPLES

Example 1: Antigen Selection and Characterisation

The selection and screening methods used to identify $mAb^2$ that are capable of binding MSLN and CD137 and result in CD137 agonism required the use of various MSLN and CD137 antigens. The production of these antigens is described in more detail below.

1.1 Recombinant CD137 Antigens

Tumour necrosis factor receptor superfamily (TNFRSF) members, such as CD137, are known for their tendency to form multimers which cluster together when bound to their cognate ligands (Croft, M. 2003). This propensity to aggregate for their functionality makes it challenging to produce soluble recombinant proteins that do not aggregate in solution for use in in vitro selections such as phage and yeast display and for characterisation of selected proteins.

As the majority of commercially available antigens were deemed unsuitable, the following recombinant dimeric and monomeric CD137 antigens (see Table 1), were produced in-house for use in selections:

TABLE 1

CD137 Antigens

| Type | Designation | Species | Soluble or cell | Bio-tinylated | Antigen Format |
|---|---|---|---|---|---|
| Recombinant | mCD137-mFc-Avi | Mouse | Soluble | Yes | Dimer |
| Recombinant | mCD137-Avi-His | Mouse | Soluble | Yes | Monomer |
| Recombinant | hCD137-mFc-Avi | Human | Soluble | Yes | Dimer |
| Recombinant | hCD137-Avi-His | Human | Soluble | Yes | Monomer |
| Recombinant | cCD137-mFc-Avi | Cyno | Soluble | Yes | Dimer |

Monomeric antigens were produced by cloning DNA encoding the extracellular domain of the human (as indicated in SEQ ID NO: 149) or mouse CD137 (as indicated in SEQ ID NO:150) along with an Avi tag sequence and six C-terminal histidine residues into modified pFUSE vectors (InvivoGen, pfuse-mIgG2A-Fc2) using EcoRI-HF and BamHI-HF restriction enzymes. The vectors were transfected into HEK293-6E cells (National Research Council of Canada), and expressed CD137 was purified using HisTrap™ excel nickel column (GE Healthcare Life Sciences 29048586) and size-exclusion chromatography (SEC) to ensure antigen was a single species and did not contain aggregates.

To produce the dimeric antigens, DNA constructs encoding the extracellular domain of the human, mouse or cynomolgus CD137 fused with the mIgG2a Fc domain along with an Avi tag sequence were cloned into modified pFUSE vectors and transfected into HEK293-6E cells. Recombinant CD137 was purified using MabSelect SuRe™ protein A column (GE Healthcare Life Sciences, 11003494 and size-exclusion chromatography (SEC) to ensure antigen was a single species and did not contain aggregates.

Each of the dimeric and monomeric antigens were biotinylated using a BirA biotin-protein ligase reaction kit (Avidity LLC, BirA500) to produce monomeric CD137 antigens labelled with a single biotin molecule and dimeric CD137 antigens labelled with two biotin molecules, one per each of the two monomers. 3 mg of antigen was mixed with 7.8 µl BirA enzyme mix to a molar ratio of enzyme to substrate of 1:50. Additives were then added in accordance with the manufacturer's recommendations (142 µl Biomix A, 142 µl Biomix B, 142 µl Biotin) and the reaction mix was incubated for two hours at room temperature. To maintain the integrity of the biotinylated protein, the reaction mix was immediately buffer exchanged to DPBS (ThermoFisher Scientific 14190-169) using Amicon 30 µm filters (Merck, UFC503096).

Proteins were further purified by SEC to ensure removal of the BirA enzyme and production of a final high-quality monodispersed protein preparation with no high molecular weight aggregates. Materials were analysed for stability and purity by size-exclusion high-performance liquid chromatography (SE-HPLC), SDS polyacrylamide gel electrophoresis (SDS-PAGE), and size-exclusion chromatography with multi-angle light scattering (SEC-MALS). Complete biotinylation of the proteins was confirmed in a streptavidin-shifting SDS-PAGE gel. The recombinant human and mouse antigens were confirmed to bind anti-CD137 positive-control antibodies (20H4.9 (U.S. Pat. No. 7,288,638)) and Lob12.3 (University of Southampton), respectively) in vitro by surface-plasmon resonance (SPR) and to DO11.10 cells expressing human and mouse CD137 ligand by flow cytometry. Cells were incubated with the CD137 antigens for 1 hour, and then a fluorescently labelled anti mouse Fc fragment antibody was used to detect cell binding. To ensure as high a purity as possible for the materials used in selection protocols, thorough protein characterisation of the antigens was performed to ensure the presence of protein aggregates did not exceed 2%.

1.2 Cell-Expressed CD137 Antigens

DO11.10 cells (National Jewish Health) expressing full-length mouse (SEQ ID NO: 374) or human CD137 (SEQ ID NO: 373), designated 'DO11.10.mCD137' and 'DO11.10.hCD137' respectively, were produced in order to present the antigen in a membrane-bound conformation, most similar to its natural form, for selections and further characterisation of selected Fcabs, as listed in Table 2.

Lentiviral transduction was used to generate these DO11.10 cells over-expressing human or mouse CD137 receptors using the Lenti-X HTX Packaging System (Clontech, catalogue no. 631249). Lenti-X expression vector (pLVX) (Clontech, catalogue no. 631253) containing the human CD137 cDNA or mouse CD137 cDNA (was co-transfected with a Lenti-X HTX Packaging Mix into the Lenti-X 293T Cell Line (Clontech, catalogue no. 632180) to generate virus. The DO11.10 cell line was then transduced with these lentiviral vectors.

Expression of human CD137 or mouse CD137 on these cells was confirmed by binding of 20H4.9 and Lob12.3 anti-CD137 positive control antibodies, respectively, to the cells by flow cytometry. Cells were incubated with the human or mouse positive control antibodies for 1 hour and then a fluorescently-labelled anti-human Fc detection antibody (Stratech Scientific Ltd, catalogue no. 109-546-098-JIR) was used to detect cell binding.

TABLE 2

| Cell-expressed CD137 | | | |
|---|---|---|---|
| 42Type | Designation | Species | Presentation |
| Cell | DO11.10.hCD137 | Human | Cell-expressed |
| Cell | DO11.10.mCD137 | Mouse | Cell-expressed |

1.3 Human, Cyno and Mouse Mesothelin Antigens

Recombinant biotinylated human MSLN-His antigen, designated 'hMSLN-His Acro', was obtained from Acrobiosystems (cat no MSN-H8223) which lacks the C-terminal 18 amino acids. Full-length monomeric human MSLN antigen was generated and biotinylated in house for phage selections. Cynomolgus and mouse MSLN were produced to allow the isolation of binders that were capable of binding to human as well as cyno MSLN, and also for the isolation of murine MSLN binders respectively.

Briefly, MSLN antigens were produced by cloning DNA encoding full length human (SEQ ID NO: 142)(hMSLN-His-Avi), cynomolgus (SEQ ID NO:143)(cMSLN-His-Avi) or mouse (SEQ ID NO:144) (mMSLN-His-Avi) MSLN along with six C-terminal histidine residues and an Avi tag sequence into modified pFUSE vectors (InvivoGen, pfuse-mIgG2A-Fc2) using EcoRI-HF and BamHI-HF restriction enzymes. The vectors were transfected into HEK293-6E cells (National Research Council of Canada), and expressed MSLN was purified using HisTrap™ excel nickel column (GE Healthcare Life Sciences 29048586). Each of the antigens was biotinylated using a BirA biotin-protein ligase reaction kit (Avidity LLC, BirA500) to produce monomeric MSLN antigens labelled with a single biotin molecule.

Recombinant human, cyno or mouse MSLN was subsequently purified using HisTrap™ excel nickel column to remove excess free biotin.

SEC-HPLC of these antigens showed less than 10% aggregation and PAGE verified that the antigens were monomeric. ELISA and surface plasmon resonance (SPR) were used to confirm that the biotinylated MSLN antigens could be bound by MSLN-specific positive control antibodies SS1 (VH SEQ NO: 140; VL SEQ ID NO: 141) containing the same CDRs as SS1 scFv U.S. Pat. No. 7,081,518 B1; Hassan et al. 2002) and MOR6626 (Patent Publication No. WO 2009/068204 A1). Based on this data all antigens were deemed suitable for naïve selections Example 2: Selection and Characterisation of Anti-Human CD137 Fcabs 2.1 Naïve Selection of Anti-Human CD137 Fcabs In order to select Fcabs that bind to human CD137, yeast and phage display selection campaigns were employed, to maximise the diversity of Fcabs identified. Both cell surface displayed human CD137 and recombinant dimeric human CD137 and were used to provide a variety of antigen presentations, in order to exert avidity-driven selection pressure against dimeric or multimeric CD137 proteins. Obtaining an Fcab which bound avidly to CD137 complexes rather than with high affinity to monomeric CD137 was deemed beneficial because such Fcab would preferentially target activated and primed T cells only, where upregulation of CD137 occurs after T cell stimulation. Without wishing to be bound by theory, it was hypothesised that T cells with very low or negligible levels of CD137 membrane expression would be more likely to have CD137 in monomeric state, unlike activated T cells with highly upregulated CD137 where most of the protein would be in dimeric, trimeric, or higher multimeric states. As a result of the avidity-driven selections, the Fcab would preferentially bind activated T cells and not bind well to naïve T cells or other cells that present lower expression of CD137. By selecting an avid CD137 Fcab potential off-targeted T cell activation would be reduced, with associated reduced toxicity.

Naïve yeast libraries displaying CH1 to CH3 domains of human IgG1 were used for selection by yeast display. All libraries contained randomised AB loops (comprising residues at positions 14 to 18 according to IMGT numbering) and randomised EF loops (comprising residues at positions 92 to 101 according to IMGT numbering) in the CH3 domain. Two of the libraries further contained an insertion of five amino acid residues at position 16 in the AB loop of the CH3 domain (residues at positions 16.5 to 16.1 according to IMGT numbering).

Yeast single clones identified from library selections were screened for antigen binding using a flow cytometry antigen binding assay that involved incubating the cells with biotinylated recombinant dimeric human antigen or mouse Fc fragment to discriminate against yeast clones binding to the Fc portion of the recombinant hCD137 antigen. Selections were repeated with varying antigen concentrations and conditions, such as increasing induction temperature, decreasing the selection stringency or reducing the number of rounds in order to increase the number of hits. 9 Fcab clones having unique sequences were identified.

2.2 Preparation of Anti-Human CD137 Fcabs in "Mock" $mAb^2$ Format

"Mock" $mAb^2$ antibodies consisting of IgG1 molecules comprising 85 anti-human CD137 Fcab clones were produced to allow characterisation of the Fcabs in a $mAb^2$ format. The mock $mAb^2$ were prepared by substituting part of the CH3 domain Fcabs comprising the AB, CD and EF loops, for the corresponding region of the CH3 domain of the anti-hen egg lysozyme antibody HelD1.3. Generation of the HelD1.3 antibody is described in Tello et al. 1993. The heavy and light chain sequences of antibody HelD1.3 are shown in SEQ ID 138 and 139, respectively. The mock $mAb^2$ molecules were produced by transient expression in HEK293-6E cells. and purified by protein A affinity chromatography using mAb SelectSure columns. These $mAb^2$ were then tested for binding to human recombinant antigen (biotinylated hCD137-mFc-Avi) by biolayer interferometry (BLI).

2.3 Activity of Selected Anti-CD137 Mock $mAb^2$ in a Human NF-κB Reporter Assay Multimerisation and clustering is required for TNFR signalling (Bitra et al., 2017). CD137 clusters and activates the NF-κB signalling pathway when it interacts with its cognate ligand, CD137L. Agonist molecules mimic the ligand in driving clustering and activation of CD137, thereby activating the NF-κB signalling pathway. It is known that some agonistic antibodies can inherently cause CD137 clustering upon binding for example, urelumab whereas as others require additional crosslinking of the antibody itself to induce CD137 clustering, such as utomilumab (Fisher et al., 2012). Fc gamma receptors on effector cells are known to induce such crosslinking in vivo, though this is inefficient and may occur away from the site of therapeutic interest. Since dose limiting toxicities have been associated with urelumab but not utolimumab, it was decided to select for anti-CD137 binding Fcabs which did not have the ability to inherently agonise, but to select only those that required additional crosslinking in order to induce CD137 clustering. Therefore, an assay that can detect the activation of the NF-κB signalling pathway in a cell upon clustering of CD137 expressed on the cell surface by crosslinked antibodies, but that showed little activity when the antibodies were not crosslinked, was developed. This assay was then used to test the agonistic functional activity of anti-CD137 Fcab clones $mAb^2$ format, irrespective of whether the Fcabs were found to bind recombinant antigen by BLI or not. Protein L was used as a crosslinking agent to drive cross linking of the mock $mAb^2$ via the Fab portions in the assay and NF-κB activation was measured.

HEK.FRT.luc.hCD137 cells were produced by subcloning the cDNA sequence encoding human CD137 sequence (SEQ ID 149 into pMSCV-neomycin vector (Takara Clontech, Cat. 634401) using EcoRI-HF and XhoI restriction enzymes. RetroPack PT67 cell line (Clontech, Cat. 631510) was used to produce retroviral particles following the manufacturer's protocol. This retro virus was subsequently used to transduce HEK.FRT.luc cells that were previously generated by transducing a Flp-In T-REx 293 HEK cell line (Life Technologies, R780-07) with Qiagen Cignal Lenti NFkB Reporter (luc) (Qiagen, cat no 336851) lentivirus containing a NF-κB-sensitive promoter controlling the expression of luciferase. These HEK.FRT.luc.hCD137 cells were used to screen the mock $mAb^2$ containing the CD137 binders identified in selections.

A 2 μM dilution of each mock $mAb^2$ was prepared in DPBS (Life Technologies, 14190169) and further diluted 1:3 in reporter cell medium (DMEM (Gibco, Cat. 61965-026); 10% FCS (Gibco, Cat. 10270-106); 1× PennStrep (Gibco, Cat. 15140-122); Blasticidin 15 μg/ml (Melford Laboratories Ltd. Cat. B1105); Puromycin 5 μg/ml (Life technologies, Cat. A11113803); Zeocin 100 μg/ml (InvivoGen, Cat. 11006-33-0); Geneticin 500 μg/ml (Life Technologies, Cat. 10131-027). Protein L (Life Technologies, 21189), was used as an artificial crosslinking agent and was mixed with the $mAb^2$ molecules in a 1:4 molar ratio. After a 24-hour incubation, cells were treated with 100 μl Promega Bio-Glo™ luciferase assay reagent (Promega cat no G7941) according to manufacturer's instructions and luminescence was measured with an integration time of 0.5 seconds on a plate reader with the Gen5 Software, BioTek. Luminescence values are a measure of the luciferase produced in response to the activation of the NF-κB signalling pathway by the clustering of CD137 induced by crosslinked Fcabs. The luminescence values were plotted versus the log concentration of Fcab and the resulting curves were fitted using the log (agonist) vs response equation in GraphPad Prism.

Hits were identified by having at least a 10-fold increase in luciferase signal when crosslinked with protein L as compared to when not crosslinked as these clones were determined to be capable of inducing CD137 clustering and subsequent activation of downstream signalling pathways. Of all clones tested, two were able to induce this 10-fold increase in luciferase on crosslinking, including FS22-172, though an EC50 could not be determined for either. Both were selected for further characterisation in a DO11.10 T cell activation assay. Surprisingly, activity was not observed for the remaining clones in crosslinked conditions despite binding to CD137 target by BLI, perhaps indicating they were binding at an irrelevant epitope on CD137, or that the affinity of such clones was not sufficient to bind CD137 strongly enough to initiate the NF-κB signalling cascade.

Overall, two Fcabs (including FS22-172) were identified from the naïve selections which exhibited the desired function in the NF-κB reporter assay when crosslinked and had little activity when not cross-linked.

Example 3: Affinity Maturation of the Anti-Human CD137 Fcab and Subsequent Characterisation

3.1 Affinity Maturation of FS22-172

Four yeast displayed libraries were constructed from the FS22-172 Fcab clone. Seven residues (at positions 15-16.1 according to IMGT) were randomised using ELLA primers in the AB loop of the CH3 domain of each clone to make library FS22-172 AB. Five residues (at positions 92-94 and 97-98 according to IMGT) were randomised using ELLA primers in the EF loop of the CH3 domain resulting in library FS22-172 EF.

For libraries FS22-172 AB and FS22-172 EF, three or four selection rounds were performed on the yeast libraries to select for affinity matured clones using either dimeric hCD137-mFc-Avi antigen or monomeric hCD137-Avi-His antigen. Monomeric antigen was alternated with dimeric antigens to ensure clones retained affinity to the antigen and did not bind exclusively through avidity. The use of monomeric or dimeric antigen, as well as the concentration used was determined empirically during each round by flow cytometry, determined by whether enrichment against the monomeric or dimeric antigen was observed in the previous round. Whenever possible, a sorting gate above the parental was used to isolate affinity matured clones compared to the parental molecule. Selection pressure was increased up to 1 nM of dimeric antigen. During each selection round, individual clones were spotted on agar plates to assess the progress of the selection. Each clone was grown and induced individually and next its binding and structural parameters were determined by flow cytometry using biotinylated dimeric antigen as well as anti-CH2 structural markers as described earlier. This screening cascade was followed to allow the determination of selection success based on a sample of clones from the selection output and to allow for early screening of individual clones that could be subsequently produced as soluble proteins.

Yeast single clones were screened for binding to biotinylated recombinant antigen in an antigen binding flow cytometry as described earlier. 30 unique loop sequences were isolated from the FS22-172 AB library. The FS22-172 EF library did not contain any clones which showed any binding improvement over the parental clones.

3.2 Construction of Anti-Human CD137 Fcabs in "Mock" $mAb^2$ Format

"Mock" $mAb^2$ antibodies comprising the anti-human CD137 Fcabs in HelD1.3 were prepared for further characterisation of the affinity matured Fcabs in $mAb^2$ format. These $mAb^2$ were prepared as described in Example 2.2. The CD137/HelD1.3 "mock" $mAb^2$ were produced by transient expression in HEK293-6E cells and purified using mAb Select SuRe protein A columns.

3.3 Activity of Human Fcabs in Mock $mAb^2$ Format in Human NF-κB Reporter Cell Assay The functional activity of the affinity-matured anti-human CD137 Fcabs in mock $mAb^2$ (HelD1.3) format listed was tested in the same NF-κB luciferase assay described in Example 2.3. Luminescence was measured with an integration time of 0.5 seconds in a plate reader with the Gen5 Software, BioTek. As expected, none of the Fcabs showed activity without Protein L crosslinking (-XL). All affinity matured CD137 Fcabs showed a vast improvement over parental CD137 Fcabs for which, while positive in this assay, calculation of an $EC_{50}$ value was not possible (see Example 2.3). FS22-172-003 showed the best activity from each family with the lowest $EC_{50}$ (32.64 nM), when crosslinked with Protein L (+XL).

3.4 Specificity Determination of Anti-Human CD137 Fcabs by Surface Plasmon Resonance (SPR)

The specificity of the anti-human CD137 Fcabs for human CD137 compared to other related TNFSFR family members was tested. 8 of the Fcabs were tested in mock $mAb^2$ (HelD1.3) format and measured by SPR in a Biacore T200 (GE Healthcare) by testing for binding to other human TNFRSF receptors: CD40, OX40 and GITR. Amine coupling (amine coupling kit, GE Healthcare, BR-1000-50) was used to coat human CD40, GITR and OX40 to approximately 1000 RU in Biacore CM5 chips (GE Healthcare, cat no 29149603). Dilutions of anti-human CD137 Fcab in mock $mAb^2$ format (FS22-172-003/HelD1.3) starting at 1 μM were prepared in HBS-EP+ buffer (BR100669) and injected for 3 min at 30 μl/min and then allowed to dissociate in buffer for 4 min. The chip was regenerated by injection of 10 mM glycine pH 2.5 for 12 s at 30 μl/min. Antibodies specific to the different TNFRSF members were used as positive controls to verify Biacore chip coating. Data was double reference subtracted and analysed using BIAevaluation 3.2 software. The Fcabs did not bind to any of the TNFRSF receptors tested, demonstrating their specificity for CD137. As a result, it is not expected that the Fcabs, or $mAb^2$ comprising the antigen-binding sites from these Fcabs, will elicit binding to anything other than CD137.

3.5 Binding Affinity of Anti-Human CD137 Fcabs in Mock $mAb^2$ Format for Human, Cynomolgus and Mouse CD137 by SPR The affinity of the anti-human CD137 Fcabs in a mock $mAb^2$ format (see Example 3.2) for human, cynomolgus (cyno) and mouse CD137 was measured by SPR, to determine whether the Fcabs may be useful for testing in animal studies. An anti-human Fab capture antibody was immobilised on all four flow cells of a CM5 series S chip (GE Healthcare #BR-1005-30) to an average surface density of 6000 RU following the manufacturer's recommendations (GE Healthcare, human Fab capture Kit, #28958325). Immobilization at 25° C. and 10 μl/min flow rate achieved an average final response of 6000 RUs. Each $mAb^2$ was captured to approximately 150 RU by injecting a 3 μg/ml solution of $mAb^2$ diluted in HBS-EP+buffer (GE Healthcare #BR1006-69) for 60 seconds at 30 μl/min. Then different concentrations of human, cyno or mouse CD137 antigen (unbiotinylated human, cyno or mouse CD137-mFc-Avi or human CD137-Avi-His) in HBS-EP+buffer were flowed over the chip for 3 min at 60 μl/min and then allowed to dissociate for 10 minutes. After each antigen concentration the chip was regenerated by injecting 10 mM glycine pH 2.1 at a flow rate of 30 μl/min for 30 seconds. Buffer HBS-EP+ was injected before the highest concentration of antigen and after the lowest concentration of antigen for reference subtraction, and one of the concentrations at random was repeated twice. The binding kinetics were fit with a 1:1 Langmuir model to generate equilibrium binding constants ($K_D$) for each sample. Data analysis was performed with BiaEvaluation software version 3.2. The results are shown in Table 3.

Analysis of the results revealed an improved binding for both human and cynomolgus CD137 by all affinity matured clones, compared to the respective parent molecules. The binding affinity for the monomeric human CD137 antigens was weaker (by at least 100-fold) than for the dimeric human and cyno Fc-fusion antigens. As discussed in Example 2.1, the Fcabs were selected to preferentially bind to dimeric over monomeric forms of CD137 and this data confirms that the selection strategy was successful. This kinetic behaviour makes them less likely to bind to monomeric CD137 expressed at minimal levels on unstimulated T cells to result in reduced risk of liver or systemic toxicities associated with some anti-CD137 monoclonal antibody therapies.

The data also shows that the anti-human CD137 Fcabs bound to cynomolgus dimeric CD137 with comparable affinity to human dimeric CD137.

TABLE 3

Kinetic analysis of CD137 Fcabs

| Fcab | Human dimeric CD137 $K_D$ (nM) | Cynomolgus dimeric CD137 $K_D$ (nM) | Human monomeric CD137 $K_D$ fold difference relative to human dimeric $K_D$ | Mouse dimeric CD137 $K_D$ (nM) |
|---|---|---|---|---|
| FS22-172 | 52 | 203 | N/A | N/A |
| FS22-172-003 | 1.5 | 1.3 | >200-fold | N/A |

N/A-not applicable as low signal did not allow $K_D$ determination

The ability of the Fcabs to bind to mouse dimeric CD137 was also tested. None of the clones showed strong binding to the mouse antigen (as shown in Table 3 where N/A indicates that no $K_D$ could be calculated).

3.6 Summary of Affinity Maturation and Characterisation of Anti-Human CD137 Fcabs In summary, affinity matured anti-CD137 Fcabs were generated and prepared in a $mAb^2$ format, which were then characterised. $mAb^2$ containing these CD137 antigen-binding domain in the CH3 domain showed high levels of activity in a human NF-κB Reporter Cell assay and this activity was shown to be crosslink dependent.

The $mAb^2$ containing the anti-human CD137 antigen-binding domain were also shown to be specific for CD137 and did not bind to other TNFRSF receptors. The $mAb^2$ were shown to preferentially bind human dimeric CD137 antigen over human monomeric CD137 antigen. Finally, these $mAb^2$ were shown to bind cynomolgus dimeric CD137 with comparable affinity to human dimeric CD137.

Having demonstrated that $mAb^2$ containing the anti-human CD137 antigen-binding domain require crosslinking in order to cluster and activate CD137, the next aim was to prepare a $mAb^2$ that binds human MSLN in addition to CD137. It was hypothesised that binding of the $mAb^2$ to human MSLN via the Fab arms would cause crosslinking of the antibody molecules, which in turn leads to clustering and activation of CD137 and that this activation would be dependent on the presence of human MSLN expression.

In order to prepare $mAb^2$ that bind human MSLN in addition to CD137, it was first necessary to generate mAbs that were able to bind MSLN. The generation of these mAbs is described below.

Example 4: Isolation of Anti-Human MSLN Antibodies: Antigens, Selections and Screening Mesothelin is a glycosylphosphatidylinositol (GPI)-linked glycoprotein synthesized as a 69 kDa precursor and proteolytically processed into a 30 kDa NH2-terminal secreted form (referred to as megakaryocyte potentiating factor or MPF) and a 40 kDa membrane-bound mesothelin (MSLN). Soluble forms of MSLN, shed from the tumour cell surface and generated by alternative splicing or tumour necrosis factor-a converting enzymes (TACE) of the membrane-bound MSLN, are found in patient serum. This tumour-shed antigen is known to create a ‘sink’ which can act as a decoy for therapeutic antibodies (Lee et al., 2018) such that this must be overcome to allow the antibodies to bind to MSLN on the tumour. To avoid this sink effect, novel anti-mesothelin antibodies that preferentially bound to immobilised MSLN compared to soluble MSLN were obtained, with the intention that this would translate to preferential binding to membrane-bound MSLN over soluble MSLN in the sink. To this end, different forms of MSLN antigens were employed in phage selections and subsequent screening campaigns. A panel of antibodies were identified that bound to membrane-bound human and cyno MSLN, with a variety of affinities, and that were able to target different areas of MSLN. A set of screening assays including ELISA, Biacore blocking assays and cell binding were performed as well as assays in which the binding regions to MSLN were compared.

4.1 Phagemid Library Selections

Synthetic naive phagemid libraries displaying the Fab domain of human IgG1 germlines with randomisation in the CDR1, CDR2 and CDR3 (MSM Technologies) were used for selections with the MSLN antigens described in Example 1.3.

Fab libraries were initially selected in multiple campaigns each in three or four rounds using Streptavidin Dynabeads (Thermo Fisher, 11205D), Neutravidin-binding protein coupled to Dynabeads (Thermo Fisher, 31000) or anti-His Dynabeads (Thermo Fisher, 10103D) to isolate the phage bound to biotinylated human, cyno or mouse MSLN-His-Avi or hMSLN-His Acro. Selection campaigns were also performed using full-length MSLN antigens produced in-house in which human MSLN selection rounds were alternated with cyno MSLN antigen with an aim to isolate human and cyno cross-reactive clones. Selections for binders to mouse MSLN (R&D mMSLN-His 8604-MS) were also performed. Standard phage selection and phage recovery procedures were used.

In an effort to obtain clones that bind to different regions of MSLN antigen, an epitope masking strategy was adopted using anti-MSLN antibodies from the initial selection campaigns described above. Briefly, a first round of selection of the naïve Fab libraries was performed using biotinylated human MSLN-His-Avi at 500 nM. In round 2 and 3 the phage binding of biotinylated cyno MSLN-His-Avi at 500 nM (round 2) or 100 nM (round 3) was tested in the presence of a mixture of naïve anti-mesothelin mAb proteins isolated from the initial selection campaign. These epitope masking selections resulted in reduced output titers, indicating that the selection strategy was working as fewer binders were identified, and led to the identification of 3 additional clones that target additional areas of MSLN compared to the clones from the earlier selection campaign.

4.2 Screening to Identify Anti-MSLN Antibodies

About 2000 clones from round 3 and 4 outputs of all selections were screened by phage ELISA for binding to 25 nM immobilised biotinylated hMSLN-His Acro, full-length biotinylated human or cyno MSLN-His-Avi, consistent with the antigen used in the round of selections. Streptavidin plates or plates immobilised with irrelevant biotinylated His tagged antigens were included as negative controls. Clones which had an MSLN binding signal at least 4-fold higher than signal to negative controls were selected and their variable regions sequenced, leading to the identification of 156 unique VH/VL sequence combinations, which were subsequently selected for soluble expression. Clones were chosen from all selection campaigns including epitope masking selections. For each clone, the VH and VL were individually cloned into pTT5 expression vector (National Research Council of Canada) containing either CH1, CH2 (with a LALA mutation in the CH2 domain (Bruhns et al., 2009; Hezareh et al., 2001) and CH3 domain, or CL domains respectively. The resulting pTT5-FS28 VH with LALA mutation (AA) and pTT5-FS28 VL vectors were transiently cotransfected into HEK293-6E cells and the clones were produced as complete IgG1 molecules. Using the same method, the VH and VL regions of SS1 and anti-hen egg white lysozyme antibody HeID1.3 were cloned and expressed in IgG1 LALA format, yielding G1-AA/SS1 (SEQ ID No 140 (heavy chain) and 141 (light chain)) and G1-AA/HeID1.3 (SEQ ID No 138 (heavy chain) and 139 (light chain)), to serve as positive and negative controls respectively.

4.3 Screening for Binding to Recombinant MSLN 4.3.1 Binding ELISA

HEK293 supernatants containing soluble anti-MSLN binding clones or purified clones were screened for binding to human MSLN-His Acro, hMSLN-His-Avi and, for some campaigns, cMSLN-His-Avi by ELISA. Briefly, hMSLN-His Acro, hMSLN-His-Avi, cMSLN-His-Avi or an irrelevant His tagged antigen were coated on maxisorp plates at 25 nM overnight at 4° C. Next day, plates were blocked with 300 μl PBS containing 0.05% Tween20 and 2% Marvel milk (Marvel dried milk). Anti-MSLN mAb containing supernatants or purified proteins were incubated for 1 hour at room temperature and their binding was detected with a mouse anti human Fc-IgG antibody conjugated to horse radish peroxidase (HRP). Clones that showed binding to the irrelevant antigen or were not cross reactive to both the human and cynomolgus antigens were discarded. In addition, clones that bound to the truncated MSLN antigen, hMSLN-His Acro, but not to the full length MSLN antigen, MSLN-His-Avi, were not taken forward to as it was expected that the full-length antigen would be more representative of antigen conformation on the cell surface of MSLN-expressing cells.

To ensure that the antibodies had specificity for binding to MSLN, the anti-MSLN binding clones were also tested for differential binding to glycosylated and deglycosylated MSLN. Biotinylated hMSLN-His-Avi was deglycosylated using PNGase F enzyme (NEB, P0704L) for 24 hr at 37° C., purified using Amicon ultra centrifugal filters (Millipore, UFC901024) and coated on maxisorp plates at 25 nM. ELISA binding of the unique anti-mesothelin mAbs to MSLN was detected using mouse anti-human Fc-IgG-HRP (Sigma, A0170). Clones that showed a more than 2-fold reduction in binding signal to deglycosylated compared to glycosylated MSLN antigen were excluded from the panel of naïve anti-MSLN binding mAbs.

4.3.2 BIAcore Screening

Human MSLN-His-Avi was immobilised on flow cell 2 on a CM5 Series S BIAcore sensor chip (GE Healthcare, BR100530) using an amine coupling kit (GE Healthcare, BR10050) to approximately 200 response units (RU). Flow cell 1 was left blank for subtraction. HEK293 supernatants or purified proteins were adjusted with HBS-EP+(GE Healthcare) to approximately 50 nM anti-MSLN mAb per sample. Samples were injected over flow cell 1 and 2 for 2.5 min at 30 μl/min and then allowed to dissociate in HBS-EP buffer for 2.5 min. Regeneration was achieved by injecting 10 mM glycine pH 1.5 (GE Healthcare, BR100354) for 30 seconds at a rate of 30 μl/min. Subtracted data (flow cell 2-flow cell 1) were analysed using BIAevaluation 3.2 Software (GE Healthcare). Of the 86 clones tested in this assay from the binding ELISA, 39 clones showed a binding response of greater than 10 RU at 50 nM and were therefore selected for re-expression, purification and further screening.

4.3.3 Binning of Antibodies Based on the Region of MSLN Bound

Based on the ELISA and Biacore screening data, clones were then tested in binning assays in which the binding of the mAbs to human MSLN was tested in the presence of another mAb by Bio-Layer Interferometry (BLI) on an Octet (ForteBio).

Briefly, biotinylated hMSLN-His-Avi (5 μg/ml) was bound on streptavidin tips (ForteBIO, 18-5020) for 5 min. G1-AA/SS1 was diluted to 200 nM in 1× kinetic buffer (FortéBIO, 18-1092) and allowed to bind to hMSLN-His-Avi for 5 minutes. Next, binding of a mixture containing 200 nM of the test mAb and 200 nM of G1-AA/SS1, was assessed for 5 minutes. This was compared with the binding of the test mAb to hMSLN-His-Avi in the absence of bound G1-AA/SS1 to determine the maximal extent of possible binding in the absence of SS1 (i.e. where there was no competition for binding). If both antibodies competed for binding to the same region of MSLN, the test antibody would not be able to bind.

These binning experiments with G1-AA/SS1 revealed that the majority (19 out of 23) of FS28 binders tested were unable to bind MSLN in the presence of G1-AA/SS1 and could therefore be attributed to bind a similar region as G1-AA/SS1. The MSLN binding site for the SS1 antibody in Fab format has been reported (Ma et al., 2012) and is defined as an N-terminal region comprising of amino acid 7 to 64 that are also involved in MUC16 binding. Additional clones, FS28-185 and FS28-256, were identified that showed partial or no competition for binding with SS1. Binning of these clones against each other revealed that these clones represented two additional independent bins, i.e. were capable of binding to a further two different regions of MSLN. FS28-185 was assigned to one bin ('bin 2') whereas FS28-256 was assigned to a separate bin ('bin 3'). These results showed that the epitope masking selections in section 1.2 were successful as antibodies which bound to multiple regions of MSLN were identified.

4.3.4 Affinities

For each bin described in Example 4.3.3, the binding kinetics were determined using the same method as described in Example 4.3.2, except that human or cyno MSLN-His-Avi was immobilised at 50 or 100 RU. Clones were tested at a concentration range of 81 nM to 0.33 nM in 3-fold dilutions. The binders were ranked and the best from each bin were selected: FS28-024 from bin 1; FS28-185 from bin 2, and FS28-256 for bin 3. All of these clones were cyno cross-reactive (data not shown), but affinities were not calculated under these test conditions. As shown in Table 4, the affinities obtained at 50 RU of immobilised MSLN were lower than those at 100 RU of immobilised MSLN antigen showing increased binding at higher levels of MSLN.

TABLE 4

Kinetic analysis of parental MSLN mAbs

| mAb (in G1-AA format) | $K_D$ to immobilised human MSLN-His-Avi (nM) | |
|---|---|---|
| | 50 RU | 100 RU |
| FS28-024 | 0.77 | 0.23 |
| FS28-185 | 37.00 | 29.57 |
| FS28-256 | 26.20 | 23.16 |

4.4 MUC16-MSLN Blocking Assays

FS28-024, FS28-185 and FS28-256 were tested for their ability to block the binding of MUC16 to mesothelin in a blocking assay. SS1 is known from the literature to block MUC16 binding to MSLN (Ma et al., 2012). G1-AA/SS1, containing the same CDRs as SS1 and would also be expected to block MUC16 binding, and a control IgG1 antibody (G1AA/HeID1.3) were included as positive and negative controls respectively.

Briefly, recombinant human MUC16 (R&D Systems, 5809-MU-050) was coated on maxisorp plates at 0.65 μg/ml in 1×PBS overnight at 4° C. Plates were washed 3× with 1×PBS and blocked with 300 μl PBS containing 2% Tween 20 and 2% Marvel Milk. A concentration of anti-MSLN mAbs (0.23 nM to 500 nM, 3-fold dilutions) were pre-mixed with biotinylated hMSLN-His-Avi antigen (final concentration 2 μg/ml) in a volume of 100 μl for 1 hr at room temperature. After removal of the blocking solution, the mAb/MSLN mixture was added to the plates and incubated for 1 hr at room temperature. Plates were washed 3× with PBST (1×PBS and 0.05% Tween20) and incubated with streptavidin-HRP (Thermo Scientific, 21126, 1:1000 dilution in 1×PBS) for 1 hr at room temperature. Finally, plates were washed 3 times with PBST and 3 times with PBS. MSLN bound to MUC16 was visualised by adding 100 μl TMB for 15 min, followed by 100 μl 1 M sulphuric acid solution. Absorbances were read at 450-630 nm (Gen5 software, BioTek).

Bin 1 clones FS28-024 showed dose-dependent blocking of the MUC16-MSLN interaction, similar to that of G1-AA/SS1. FS28-256 did not show any blocking activity similarly to the negative control G1-AA/HeID1.3. Whereas FS28-185 promoted the binding of MUC16 to MSLN. These results were consistent with the binning data in Example 4.3.3 in that clones which bound to three different regions of MSLN showed three different behaviours in the ligand blocking assay.

In conclusion, the results show that a panel of clones was selected that bind to 3 different regions of MSLN (bins); antibodies binding to one region of MSLN blocks the binding of MUC16 to MSLN, whereas antibodies binding to the other two regions does not.

4.5 Specificity

In light of the different areas of MSLN bound by the panel of antibodies, their specificity for binding to MSLN was tested. Specificity of FS28-024, FS28-185 and FS28-256 was tested by ELISA by comparing the binding to MSLN with binding to other molecules involved in cell adhesion such as CEACAM-5, E-Cadherin, Thrombomodulin and EpCAM.

A similar protocol was used as described in Example 4.3.1 in which maxisorp plates were coated with 1 μg/ml of recombinant human MSLN-His-Avi, human CEACAM-5-His-Fc (Sino Biological, 1077-H03H), human E-Cadherin (R&D systems, 8505-EC), human Thrombomodulin (Peprotech, 100-58) or human EpCAM-hFc (in-house production). Binding of the anti-MSLN mAbs, tested at a concentration range of 0.02 to 1000 nM (3-fold dilutions) was detected using anti-human Fab-HRP (Sigma, A0293). FS28-024, and FS28-185 and FS28-256 bound to human MSLN-His-Avi ($EC_{50}$ around 0.5 nM and maximum binding signal of 3) but no binding was observed to any of the cell adhesion molecules tested up to 1000 nM. Positive control antibodies bound to their respective targets, as expected. Thus, the anti-MSLN antibodies showed a high level of specificity.

4.6 Cell Binding

The panel of selected anti-mesothelin mAbs (FS28-024, FS28-185 and FS28-256) were analysed for binding to endogenous cell surface MSLN on the human lung cancer cell line NCI-H226.

Briefly, NCI-H226 cells (ATCC CRL-5826) were harvested from T175 cell culture flasks using Accutase (Gibco, A11105-01). Cells were centrifuged at 1200 rpm for 3 min and resuspended in ice cold FACS buffer made up of DPBS (Life Technologies, 14190169) and 1% BSA (Sigma-Aldrich, A7906) at $2\times10^6$ cells/ml and 50 μl per well was seeded in a 96-well V-bottom plate (Costar, 3894). All mAbs tested were diluted in FACS buffer in 120 μl at a concentration range of 0.01-200 nM (4-fold dilutions). The NCI-H226 cells were then centrifuged, supernatant removed and cells resuspended in 100 μl of each mAb dilution and incubated at 4° C. for 45 min. Cells were washed twice by centrifugation with 150 μl FACS buffer, resuspended in 100 μl containing goat anti-human IgG (γ-chain specific) F(ab')2 fragment-R-Phycoerythrin antibody (Sigma, P8047) diluted 1:1000 in FACS buffer and incubated at 4° C. for 45 min. The cells were washed once with 150 μl FACS buffer and then with 150 μl DPBS, resuspended in 150 μl DPBS containing DAPI (Biotium, 40043) at 1:10.000 and read on the BDCantoll or iQue (Intellicyt). Data was analysed using FlowJo v10 to determine the signal geometric mean for PE for live cells in each well.

$mAb^2$ FS28-024 bound to cell-surface MSLN on NCI-H226 cells, as did the positive control G1-AA/SS1. In comparison, FS28-185 and FS28-256 demonstrated weaker binding to cell-surface MSLN.

Summary of Naïve Screening Procedure

From the 156 mAbs identified by the initial screen of the naïve phage libraries, three anti-human MSLN mAb clones (FS28-024, FS28-185 and FS28-256) were selected based on a set of screening assays that first confirmed binding to full-length, deglycosylated recombinant MSLN as well as the ability to bind to cyno MSLN. Secondly, clones were grouped based on diversity of the region of MSLN they bound (bins) and MUC16 blocking activity and from within these groups, the highest affinity binders were selected. The resulting panel of mAb clones FS28-024, FS28-185 and FS28-256 bound three different regions of MSLN, one of which (bin 1, FS28-024) blocked the binding of MUC16 to MSLN in vitro. The panel of five anti-MSLN antibodies showed specific binding to MSLN, different affinities for recombinant and cell-surface MSLN and were selected for further characterisation and/or optimisation as described in Example 5, below.

Example 5: Affinity Maturation and Sequence Optimisation of Naïve Anti-MSLN mAbs 5.1 Affinity Maturation of Clone FS28-024 Using NNK Walk Strategy Whereas FS28-024 bound to human MSLN with sub-nanomolar affinities, its affinity for cyno MSLN was about 5-fold lower. To improve binding to cyno MSLN, an NNK walk strategy on five residues in the VH CDR3 region was used.

The sequence of the FS28-024 VH and VL was optimised. Parsimonious mutagenesis libraries were generated by diversifying one amino acid residue at a time on the RATLF residues (Kabat numbering 95-99) in the VH CDR3, leading to a total of five individual libraries. The libraries were made with low redundancy NNK codons to represent all possible amino acids in the position of interest. Forward and reverse primers were designed according to the guidelines of Quick-change Lightning Site-Directed Mutagenesis Kit (Agilent, 200518), which was used to create the libraries. Each mutant was expressed in small scale in HEK293 cells and supernatants were screened by BIAcore for retained or improved binding to human and cyno MSLN-His-Avi. Of the 84 clones screened, few retained binding, most of them being substitutes of T98 residue. Four clones, FS28-024-051, FS28-024-052, FS28-024-053 and FS28-024-060 were re-expressed, purified and their affinities for human and cyno MSLN determined. Only one clone, FS28-024-053 showed an improvement in cyno crossreactivity which was achieved by a single T98V mutation (Kabat numbering). All four clones were taken forward as they might provide alternative sequences and characteristics.

5.2 Affinity Maturation of FS28-185 and FS28-256

In comparison to FS28-024, clones FS28-185 and FS28-256 had weaker affinity for both recombinant and cell surface MSLN and were therefore subjected to affinity maturation.

The VH and VL CDR3 regions were affinity matured in parallel in scFv format by randomising overlapping cassettes of five to six amino acids using NNK primers. The regions randomised for FS28-185 were VH G95-M100F and VL S91-A95 and for FS28-256 they were VH Y95-L100B and VL S91-196 (Kabat numbering). Before library generation, parsimonious mutagenesis was performed on potential methionine oxidation and deamidation sites in the CDR1 and CDR3 regions (except for the FS28-256 VL CDR3 library). Two rounds of selections were performed as described for the naïve campaigns, using 20 nM biotinylated human MSLN-His-Avi in round 1 and either 20 or 2 nM cyno MSLN-His-Avi in round 2. Soluble scFv (single point concentration) were then tested for binding to an ovarian cancer cell line OVCAR-3 (ATCC® HTB-161™). OVCAR-3 cells were harvested using StemPro Accustase (Gibco, A11105-01), centrifuged at 1200 rpm for 3 min and resuspended in FACS buffer (DPS containing 2% BSA) at $2\times10^6$ cells/ml. 100 μl of OVCAR-3 cells were added to 96-well V-bottom plates. Plates were centrifuged at 1200 rpm for 3 mins and the buffer was discarded. 150 μl of scFv was added to the cells and incubated at 4° C. for one hour. ScFvs of parental clones FS28-185 and 256 were included as controls. After washing, cells were resuspended in 100 μl of Penta His Alexa-Fluor 647 (Qiagen, 109-546-098), and washed before being resuspended in 100 μl DPBS containing Sytox Green Nucleic Acid Stain (Invitrogen S7020, 1:10000 dilution). Samples were run on the iQue (Intellicyt Corporation, IQue Plus) and the geometric mean for APC was recorded.

For both FS28-185 and FS28-256, affinity matured clones with improved binding to OVCAR-3 cells were identified. On the basis of cell binding (MFI greater than 850) and sequence diversity, 10 clones were selected from the FS28-256 VH CDR3 and 9 from the VL CDR3 selections. Of the 38 FS28-185 affinity matured clones tested in this assay, 14 were selected from the VH CDR3 selections and one from the VL CDR3 selections. Selected clones were further characterised in a $mAb^2$ bispecific antibody format.

5.3 Generation of FS28-185 and FS28-256 Based $mAb^2$

For further characterisation of the anti-MSLN binders, the affinity matured VH or VL region of FS28-024, FS28-185 or 256, as well as the parental clones, were produced in $mAb^2$ format. The resulting $mAb^2$ are IgG1 antibodies comprising of the CDRs of FS28-024, FS28-185 or FS28-256 clones or the affinity matured variants derived from them, included the LALA mutation in the CH2 domain, and a human CD137 receptor-binding site in the CH3 domain. The heavy and light chain sequences of the resulting $mAb^2$ molecules are shown in the following SEQ ID NOS:

- FS22-172-003-AA/FS28-024 $mAb^2$: SEQ ID NOs 94 and 85
- FS22-172-003-AA/FS28-024-051 $mAb^2$: SEQ ID NOs 98 and 85
- FS22-172-003-AA/FS28-024-052 $mAb^2$: SEQ ID NOs 102 and 85
- FS22-172-003-AA/FS28-024-053 $mAb^2$: SEQ ID NOs 106 and 85
- FS22-172-003-AA/FS28-024-060 $mAb^2$: SEQ ID NOs 108 and 85
- FS22-172-003-AA/FS28-026 $mAb^2$: 270 SEQ ID NOs 109 and 87
- FS22-172-003-AA/FS28-091 $mAb^2$: SEQ ID NOs 110 and 88
- FS22-172-003-AA/FS28-185 $mAb^2$: SEQ ID NOs 111 and 89
- FS22-172-003-AA/FS28-256 $mAb^2$: SEQ ID NOs 114 and 116
- FS22-172-003-AA/FS28-256-001 $mAb^2$: SEQ ID NOs 120 and 82
- FS22-172-003-AA/FS28-256-005 $mAb^2$: SEQ ID NOs 120 and 83
- FS22-172-003-AA/FS28-256-012 $mAb^2$: SEQ ID NOs 125 and 116
- FS22-172-003-AA/FS28-256-014 $mAb^2$: SEQ ID NOs 129 and 116
- FS22-172-003-AA/FS28-256-018 $mAb^2$: SEQ ID NOs 133 and 116
- FS22-172-003-AA/FS28-256-021 $mAb^2$: SEQ ID NOs 125 and 82
- FS22-172-003-AA/FS28-256-023 $mAb^2$: SEQ ID NOs 133 and 82
- FS22-172-003-AA/FS28-256-024 $mAb^2$: SEQ ID NOs 125 and 83
- FS22-172-003-AA/FS28-256-026 $mAb^2$: SEQ ID NOs 133 and 83
- FS22-172-003-AA/FS28-256-027 $mAb^2$: SEQ ID NOs 125 and 84
- FS22-172-003-AA/FS28-256-271 $mAb^2$: 3 and 84
- FS22-172-003-AA/FS28-256-272 $mAb^2$: 158 and 84
- FS22-172-003-AA/FS28-256-273 $mAb^2$: 163 and 84

These $mAb^2$ were produced by transient expression in HEK293-6E cells and, where indicated, purified using mAb Select SuRe protein A columns.

5.4 Sequence Optimisation of FS28-256 Affinity Matured Clones

All FS28-256 lineage clones contained a potential N-linked glycosylation site in the VH CDR2 (IMGT numbering N55-X-S57, wherein X is any residue). Four variants of clone FS28-256-027 were obtained by substituting the N55 in the VH CDR2 to Alanine, Histidine, Serine and Threonine. These clones were named FS28-256-271, FS28-256-272, FS28-256-273, and FS28-256-274, respectively. The clones were characterised by SPR for binding to immobilised and in-solution MSLN. Table 5 shows the SPR results. FS28-256-274 had a much weaker affinity to immobilised MSLN than the other clones and was therefore not progressed. FS28-256-272 and FS28-256-273 bound to soluble MSLN either more strongly or with a similar strength as they did to immobilised MSLN. Consequently, it's likely that binding of both of these clones to cell surface expressed MSLN will be impacted by the presence of soluble MSLN. In contrast FS28-256-271 had the strongest binding to immobilised MSLN and weaker binding to soluble MSLN such that it preferentially targets immobilised MSLN over MSLN in-solution.

TABLE 1

Binding to immobilised and in-solution human mesothelin

| Clone (in CD137 $mAb^2$ format) | Mutation in Heavy Chain CDR2 | Affinity to immobilised human MSLN-His-Avi $K_D$ (nM) | Affinity to human MSLN-His-Avi in solution $K_D$ (nM) | Ratio of $K_D$ in solution/ immobilised for human MSLN-His-Avi |
|---|---|---|---|---|
| FS28-256-271 | N55A | 5.9 | 18.2 | 3 |
| FS28-256-272 | N55H | 10.7 | 7.6 | 0.7 |
| FS28-256-273 | N55S | 6.0 | 7.4 | 1.2 |
| FS28-256-274 | N55T | 19.8 | 55.9 | 2.8 |

Summary of Fcab and mAb Selections and Screening

The anti-CD137 Fcabs identified in the previous examples were shown to have agonistic activity in NF-κB reporter assays when crosslinked either by an external cross-linking agent such as Protein L (Example 2). Of the panel of anti-human CD137 Fcabs identified, FS22-172-003 was selected for pairing with MSLN-targeting Fabs, as this clone presented the most favourable functional and biophysical properties.

To localise this CD137-driven agonistic activity to the tumour microenvironment, it was decided to pair the Fcab in $mAb^2$ format with Fabs which specifically target the tumour associated antigen, mesothelin (MSLN). This may be beneficial because expression of MSLN on tumour cells would be expected to result in cross-linking of the $mAb^2$, such that the Fcab would be capable of inducing agonistic activity when bound to CD137.

A panel of MSLN binding Fabs was selected that bind to different regions of MSLN and preferentially bind immobilised MSLN over soluble mesothelin, as identified in the previous examples.

Example 6: Production of $mAb^2$ Targeting CD137 and Mesothelin (MSLN)

CD137/MSLN $mAb^2$ consisting of IgG1 molecules comprising the anti-CD137 Fcab FS22-172-003, and a panel of anti-MSLN Fabs (listed in Table 6) were produced to allow characterisation of the pairing in $mAb^2$ format. They were prepared by substituting part of the CH3 domain Fcabs comprising the AB, CD and EF loops, for the corresponding region of the CH3 domain of the MSLN binding antibody. These CD137/MSLN $mAb^2$ comprised a LALA mutation in the CH2 domain (AA). The isotype of $mAb^2$ is human IgG1, which is capable of inducing ADCC against the cells to which it binds. Since the CD137/MSLN $mAb^2$ will bind immune cells expressing CD137, it was decided to decrease the possibility of the $mAb^2$ inducing ADCC against the immune cells by inclusion of the LALA mutation. Further, Fc gamma receptors on effector cells are known to induce crosslinking of antibodies in vivo, though this is inefficient and may occur away from the site of therapeutic interest. Since the CD137 antibodies in the clinic have been associated with dose-limiting toxicities, it was decided to include the LALA mutation so that the CD137/MSLN $mAb^2$ would only exert agonistic activity through crosslinking by binding to MSLN. All $mAb^2$ and control antibodies were produced by transient expression in HEK293-6E cells and purified using mAb Select Sure Protein A columns. $mAb^2$ were then assessed for purity by SEC-HPLC, ensuring the monomeric percentage of the molecules exceeded 98%.

TABLE 6 list of $mAb^2$ molecules studied in terms of their binding characteristics and functionality.

| $mAb^2$ |
|---|
| FS22-172-003-AA/FS28-024 |
| FS22-172-003-AA/FS28-024-051 |
| FS22-172-003-AA/FS28-024-052 |
| FS22-172-003-AA/FS28-024-053 |
| FS22-172-003-AA/FS28-024-060 |
| FS22-172-003-AA/FS28-185 |
| FS22-172-003-AA/FS28-185-002 |
| FS22-172-003-AA/FS28-185-003 |
| FS22-172-003-AA/FS28-256 |
| FS22-172-003-AA/FS28-256-012 |
| FS22-172-003-AA/FS28-256-021 |
| FS22-172-003-AA/FS28-256-023 |
| FS22-172-003-AA/FS28-256-024 |
| FS22-172-003-AA/FS28-256-026 |
| FS22-172-003-AA/FS28-256-027 |
| FS22-172-003-AA/FS28-256-271 |
| FS22-172-003-AA/FS28-256-272 |
| FS22-172-003-AA/FS28-256-273 |

Example 7: Characterisation of CD137/MSLN $mAb^2$

The binding strength of CD137/MSLN $mAb^2$ to CD137 and MSLN was tested by Surface Plasmon Resonance using a BIAcore instrument, as well as binding to cell surface expressed MSLN by flow cytometry on relevant cell lines that endogenously express MSLN. Since soluble forms of MSLN, generated by alternative splicing or tumour necrosis factor-a converting enzymes (TACE) of the membrane-bound MSLN, are found in serum of MSLN positive cancer patients it is postulated that this might act as a decoy for therapeutic antibodies (Lee et al., 2018). We investigated the binding characteristics and avidity of the $mAb^2$, in particular, the difference in binding affinity to soluble and immobilised MSLN. This was measured in BIAcore binding experiments set up in two ways: Firstly, to reproduce the kinetic profile of a $mAb^2$ that binds antigen present on the cell surface, recombinant antigen was immobilised at moderate density on a SPR chip, followed by injection of $mAb^2$ at varying concentrations (see Example 7.1). Secondly, to simulate the potential sink effect caused by circulating soluble MSLN on $mAb^2$ binding to cell-surface bound MSLN, the $mAb^2$ were captured on the chip and then recombinant antigen flowed over at varying concentrations (see Example 7.2). Furthermore, the effect of soluble recombinant MSLN added at a level which is representative of that which is typically found in MSLN positive patient serum (Onda et al., 2006, 10.1158/1078-0432.CCR-05-1477) was also thoroughly investigated in binding studies to cell surface expressed MSLN and in $CD8^+$ T cell assays.

7.1 Binding of CD137/MSLN mAb2 to Human MSLN Under Avid Conditions—Antigen Capture Method Binding of all $mAb^2$ to MSLN immobilised on a BIAcore chip was tested to determine the binding affinity to human MSLN under avid conditions, where a high concentration of immobilised antigen is available to allow the antibody to bind avidly. A CM5 chip (GE Healthcare BR-1005-30) was coated with hMSLN-His-Avi at approximately 100 RU according to manufacturer's instructions. The panel of CD137/MSLN $mAb^2$ described in Table 6, as well as control antibodies G1-AA/HelD1.3 and G1-AA/SS1 (Hassan et al. 2002) were injected at a range of concentrations in a three-fold dilution series starting at 300 nM, at a flow rate of 70 μl/min. The association time was 5 min and the dissociation time was 10 min. Running buffer was HBS-EP (GE Healthcare BR100188). Flow cells were regenerated by injecting Glycine-HCl pH1.5 at a flow rate of 30 μl/min for 30 seconds. Data were analysed by double referencing against a flow cell which was intentionally left blank (no antigen coating). The binding kinetics were fitted with a 1:1 Langmuir model to generate binding association ($k_a$) and dissociation ($k_d$) rates. Equilibrium binding constants ($K_D$) were calculated by dividing the dissociation rate by the association rate for each sample. Data analysis was performed with BiaEvaluation software version 3.2. Results are shown in Table 7.

FS22-172-003-AA/FS28-185 and FS22-172-003-AA/FS28-256 $mAb^2$ comprising the FS28-185 and FS28-256 parental MSLN Fab arms showed binding affinities between 36 and 50 nM. Otherwise, all $mAb^2$, including the affinity matured progeny of FS28-256, presented MSLN binding affinities ($K_D$) lower than 10 nM. Indeed, a subnanomolar $K_D$ was determined for those $mAb^2$ containing MSLN Fab arms from lineage FS28-024.

For $mAb^2$ FS22-172-003-AA/FS28-256-271, cyno cross-reactivity was determined by SPR using a steady-state kinetic analysis. A CM5 chip (GE Healthcare BR-1005-30) was coated with hMSLN-His-Avi or cMSLN-His-Avi at approximately 50 RU according to manufacturer's instructions. $mAb^2$ were injected at a range of concentrations in a three-fold dilution series starting at 243 nM, at a flow rate of 10 μl/min. The association time was 1000 sec to steady state and the dissociation time was 30 sec. Running buffer was HBS-EP (GE Healthcare BR100188). Flow cells were regenerated by injecting Glycine-HCl pH1.5 at a flow rate of 30 μl/min for 30 seconds. Data were analysed by double referencing against a flow cell which was intentionally left blank (no antigen coating). Steady state affinity model was used to analyse kinetic data using the BiaEvaluation software version 3.2. Binding to cMSLN-Avi-His was within 3 fold of binding to hMSLN-Avi-His.

7.2 Binding of CD137/MSLN $mAb^2$ to Soluble Human MSLN—Antibody Capture Method

CD137/MSLN $mAb^2$ described in Table 7 as well as control antibodies G1-AA/HelD1.3 and G1-AA/SS1 were also tested for binding to human MSLN and cynomolgus MSLN by SPR where the antibodies were captured to assess their binding to MSLN in solution ($K_D$ in solution). Protein G (GE Healthcare 29179315) was used to capture mAb or $mAb^2$ samples at approximately 100 RU after which hMSLN-His-Avi or cMSLN-His-Avi was injected at a range of concentrations in a three-fold dilution series starting at 1000 nM, at a flow rate of 70 μl/min. The association time was 5 min and the dissociation time was 5 min. Running buffer was HBS-EP (GE Healthcare BR100188). Flow cells were regenerated by injecting Glycine-HCl pH2.1 at a flow rate of 30 μl/min for 15 seconds. The data was analysed as described in Example 7.1. The results are shown in Table 7. From the antibody capture method, the majority of the $mAb^2$ had significantly reduced binding affinities, supporting the screening strategy implemented for generating the avid anti-MSLN antibodies with differential binding for immobilised versus soluble MSLN. $K_D$ values for binding to soluble MSLN were between 4.27 nM for the best $mAb^2$ FS22-172-003-AA/FS28-024-060 and 1.2 μM for $mAb^2$ FS22-172-003-AA/FS28-256 which had the lowest affinity.

All tested $mAb^2$ were cyno cross-reactive within 10-fold of the affinity to human MSLN with the exception of $mAb^2$ FS22-172-003-AA/FS28-024-060 which was 54-fold less cross reactive compared to human MSLN and so was not pursued further.

TABLE 7

Binding to immobilised MSLN and MSLN in solution of human CD137/MSLN $mAb^2$ as measured by SPR

| $mAb^2$ | $K_D$ to immobilised human MSLN (nM) | $K_D$ to human MSLN in solution (nM) | $K_D$ to cyno MSLN in solution (nM) | $K_D$ Ratio in solution/ immobilised human MSLN |
|---|---|---|---|---|
| FS22-172-003-AA/FS28-024 | 0.39 | 46.53 | 169.7 | 119 |
| FS22-172-003-AA/FS28-024-051 | 0.40 | 42.35 | 153.4 | 105 |
| FS22-172-003-AA/FS28-024-052 | 0.39 | 33.12 | 239.1 | 85 |
| FS22-172-003-AA/FS28-024-053 | 0.42 | 46.42 | 165.6 | 111 |
| FS22-172-003-AA/FS28-024-060 | 0.13 | 4.27 | 230.4 | 33 |
| FS22-172-003-AA/FS28-185 | 50.52 | 247.90 | 294.3 | 5 |
| FS22-172-003-AA/FS28-256 | 36.01 | 1212.00 | 848.3 | 34 |
| FS22-172-003-AA/FS28-256-012 | 3.12 | 809.10 | 711.7 | 259 |
| FS22-172-003-AA/FS28-256-021 | 2.30 | 19.55 | 14.17 | 9 |
| FS22-172-003-AA/FS28-256-023 | 3.09 | 56.16 | 44.23 | 18 |
| FS22-172-003-AA/FS28-256-024 | 4.74 | 86.56 | 57.24 | 18 |
| FS22-172-003-AA/FS28-256-026 | 3.19 | 57.86 | 33.13 | 18 |
| FS22-172-003-AA/FS28-256-027 | 0.78 | 5.84 | 1.057 | 7 |

TABLE 7-continued

Binding to immobilised MSLN and MSLN in solution of human CD137/MSLN $mAb^2$ as measured by SPR

| $mAb^2$ | $K_D$ to immobilised human MSLN (nM) | $K_D$ to human MSLN in solution (nM) | $K_D$ to cyno MSLN in solution (nM) | $K_D$ Ratio in solution/ immobilised human MSLN |
|---|---|---|---|---|
| FS22-172-003-AA/FS28-256-271 | 5.9 | 18.2 | N/A | 3 |
| FS22-172-003-AA/FS28-256-272 | 10.7 | 7.6 | N/A | 0.7 |
| FS22-172-003-AA/FS28-256-273 | 6.0 | 7.4 | N/A | 1.2 |

N/A-not tested

The affinity (as measured by $K_D$) of MSLN binding Fab arms of all $mAb^2$ has been confirmed by both antigen capture (immobilised MSLN) and antibody capture (MSLN in solution) methods. In solution versus immobilised $K_D$ values varied for each antibody. A ratio was calculated from these $K_D$ values which gave an indication for each $mAb^2$ of its behaviour in terms of whether its binding was altered by the presence of soluble MSLN (Table 7). Without wishing to be bound by theory, we postulate that there is a threshold of binding affinity that needs to be overcome for the $mAb^2$ to be able to crosslink efficiently but the difference in binding affinity to immobilised versus in solution MSLN also plays an important role in terms of how this functionality may be affected by the shed MSLN-driven sink effect.

7.3 Biacore Binding to CD137: Binding Affinity Retained in $mAb^2$ Format

In addition to the binding strength towards MSLN, the $K_D$ of the CD137 Fcab towards human CD137 was also tested to demonstrate the binding properties of the Fcab are retained when paired with new Fabs. A Biacore CM5 chip was coated with anti-human Fab using a Human Fab Capture Kit (GE Healthcare 28958325) according to manufacturer's conditions, to a surface density of approximately 9000 RU. Samples of the FS22-172-003-AA/FS28-024-052 and FS22-172-003-AA/FS28-256-271 were captured to approximately 100 RU and then human CD137 antigen (hCD137-mFc-Avi) was flowed over at a range of concentrations in a three-fold dilution series starting at 81 nM at a flow rate of 70 μl/min. The association time was 5 min and the dissociation time was 5 min. Running buffer was HBS-EP. Flow cells were regenerated by injecting two repeat injections of 10 mM glycine-HCl at pH 2.1 at a flow rate of 30 μl/min for 30 seconds. Data analysis was performed as described in earlier examples (see e.g. Example 7.1). The results in Table 8 show consistent affinities to CD137 between $mAb^2$ containing the same Fcab but different Fabs. The anti-CD137 Fcabs were selected so that they preferentially bound dimeric or multimeric CD137 over monomeric CD137, via avid binding interactions. It is hypothesised that this avidity mode of action is beneficial to preferentially target cells with upregulated CD137 expression, such as activated T cells, over other cells that express CD137 at much lower levels. This may be beneficial to minimise off-tumour T cell activation that could lead to undesired effects such as toxicity. Further, the Fcabs were designed to have activity only when crosslinked such that they are not capable of inducing agonism simply by binding to CD137. In the context of these CD137/MSLN $mAb^2$, it is thought that the kinetic mode of action of both specificities of the molecule may result in the $mAb^2$ preferentially binding to upregulated MSLN expressed at high levels on tumour cells, followed by binding to activated T cells with upregulated CD137 expression. Due to the binding dynamics of the Fcab domains of the molecule, in the event that the $mAb^2$ molecule binds CD137 on T cells first, lack of MSLN-mediated crosslinking ensures that T cell agonism is not triggered.

TABLE 8

Binding of $mAb^2$ to dimeric CD137 antigens as measured by SPR

| $mAb^2$ | Affinity to hCD137-mFc-Avi $K_D$ (nM) |
|---|---|
| FS22-172-003-AA/FS28-024-052 | 1.51 |
| FS22-172-003-AA/FS28-256-271 | 1.26 |

7.4 Binding to Cell Surface Expressed MSLN and Interference by Soluble MSLN

To confirm binding to cell surface MSLN, $mAb^2$ listed in Table 9 were analysed for binding to endogenous cell surface MSLN on the human lung cancer cell line NCI-H226. In addition, and because MSLN can be found in blood in a shed soluble form, there is a risk that this circulating MSLN might affect exposure and ultimately potency of our $mAb^2$. To confirm that presence of soluble MSLN has minimal impact, additional binding experiments to NCI-H226 cells were performed in the presence of 20 nM soluble MSLN which is 10-20 times the level of soluble MSLN found to be of diagnostic value for defining malignant mesothelioma and lung cancer patients as MSLN positive (Cui et al., 2014). Briefly, NCI-H226 cells (ATCC CRL-5826) were harvested from T175 cell culture flasks using Accutase (Gibco, A11105-01). The antibody preparation protocol was slightly altered when supplementing with soluble MSLN: antibodies were diluted in FACS buffer to give a 2× final concentration in a 96-well V-bottom plate and 60 μl from each well was then added to either FACS buffer alone or to FACS buffer containing 60 μl of 40 nM recombinant hMSLN-His (R&D systems, 3265-MS-050) (to give a final concentration of 20 nM hMSLN) and pre-incubated at room temperature for 1 hour before 100 μl was added to the cells.

In both cases, cells were centrifuged at 1200 rpm for 3 min and resuspended in ice cold FACS buffer made up of DPBS (Life Technologies, 14190169) and 1% BSA (Sigma-Aldrich, A7906) at $2 \times 10^6$ cells/ml and 50 μl per well was seeded in a 96-well V-bottom plate (Costar, 3894). All antibodies tested were diluted in FACS buffer in 120 μl at a concentration range of 0.01-200 nM (4-fold dilutions). The NCI-H226 cells were then centrifuged, supernatant removed and cells resuspended in 100 μl of each mAb dilution and incubated at 4° C. for 45 min. Cells were washed twice by centrifugation with 150 μl FACS buffer, resuspended in 100 μl containing goat anti-human IgG (γ-chain specific) F(ab')2 fragment-R-Phycoerythrin antibody (Sigma, P8047) diluted 1:1000 in FACS buffer and incubated at 4° C. for 45 min. The cells were washed once with 150 µl FACS buffer and then with 150 µl DPBS, resuspended in 150 µl DPBS containing DAPI (Biotium, 40043) at 1:10.000 and read on the BDCantoll or iQue (Intellicyt). Data was analysed using FlowJo v10 to determine the signal geometric mean for PE for live cells in each well.

According to the cell binding results in Table 9, binding to cell surface MSLN on endogenously expressing cell line NCI-H226 was confirmed for all $mAb^2$ with $EC_{50}$ values ranging from 0.3 to greater than 47 nM. The impact of the presence of soluble recombinant MSLN on cell binding affinity was generally low with minimal (less than 3-fold) increases in EC50 observed for most clones.

FS22-172-003-AA/FS28-256 had higher $EC_{50}$ in the presence and absence of soluble MSLN than the majority of other clones tested, indicating that the parental FS28-256 antibody had weaker binding. However, affinity matured variants of this parental antibody displayed stronger binding. In particular, the cell binding affinities of $mAb^2$ containing FS28-256 derived clones, such as FS28-256-001, FS28-256-005, FS28-256-012, FS28-256-014, FS28-256-018, FS28-256-023, FS28-256-024 and FS28-256-026 were much better than the parent and were not affected by the presence of soluble MSLN. This demonstrates that even in the presence of an excess of soluble MSLN, most $mAb^2$ bound preferentially to the membrane bound form of MSLN. $mAb^2$ containing FS28-024-060 and FS28-256-027 were the most affected when binding to cells in the presence of soluble MSLN, indicating that higher affinity binders to MSLN in solution are more likely to be impacted by the presence of shed MSLN. $mAb^2$ containing the parental FS28-185 clone (i.e. FS22-172-003-AA/FS28-185) also had higher $EC_{50}$ values and so showed weaker binding in the presence and absence of soluble, recombinant MSLN. Affinity matured variants of the parental clone were also tested. An improvement in binding in the absence of soluble MSLN was observed for these affinity matured clones in $mAb^2$.

TABLE 9

CD137/MSLN $mAb^2$ binding to NCI-H226 cells

| $mAb^2$ | NCI-H226 $EC_{50}$ (nM) | NCI-H226 $E_{max}$ (MFI) | NCI-H226 + 20 nM soluble MSLN $EC_{50}$ (nM) | NCI-H226 + 20 nM soluble MSLN $E_{max}$ (MFI) |
|---|---|---|---|---|
| FS22-172-003-AA/FS28-024 | 0.3886 | 772808 | 3.049 | 791715 |
| FS22-172-003-AA/FS28-024-051 | 0.4774 | 767620 | 3.061 | 797595 |
| FS22-172-003-AA/FS28-024-052 | 0.8844 | 752345 | 3.639 | 799055 |
| FS22-172-003-AA/FS28-024-053 | 0.5789 | 783415 | 2.77 | 787914 |
| FS22-172-003-AA/FS28-024-060 | 0.6945 | 840057 | 4.691 | 930443 |
| FS22-172-003-AA/FS28-185 | 22.95 | 4926 | 28.43 | 4926 |
| FS22-172-003-AA/FS28-256 | 47.07 | 174359 | 52.87 | 200240 |
| FS22-172-003-AA/FS28-256-001 | N/A | N/A | N/A | N/A |
| FS22-172-003-AA/FS28-256-005 | 0.7293 | 440704 | 0.8561 | 423827 |
| FS22-172-003-AA/FS28-256-012 | 5.696 | 515615 | 6.364 | 485690 |
| FS22-172-003-AA/FS28-256-014 | 0.727 | 476372 | 1.095 | 514410 |
| FS22-172-003-AA/FS28-256-018 | 3.601 | 347878 | 4.09 | 357365 |
| FS22-172-003-AA/FS28-256-021 | 4.02 | 689367 | 9.489 | 773900 |
| FS22-172-003-AA/FS28-256-023 | 1.286 | 618097 | 2.134 | 624592 |
| FS22-172-003-AA/FS28-256-024 | 3.405 | 647114 | 5.236 | 674662 |
| FS22-172-003-AA/FS28-256-026 | 1.47 | 634311 | 2.683 | 687574 |
| FS22-172-003-AA/FS28-256-027 | 0.613 | 800727 | 2.305 | 685895 |

ND-tested, no activity so EC50 Emax not determined

N/A-not tested 7.5 $mAb^2$ Bind Cell Lines with a Wide Range of Endogenous Mesothelin Expression Levels To demonstrate the ability of the anti-MSLN Fab clone FS28-256-271 to bind cells expressing a range of MSLN cell densities, the $mAb^2$ was tested in a cell binding flow cytometry assay similar to the one described in Example 7.3 in which the following human carcinoma cells were utilised: NCI-H226 [H226](ATCC® CRL-5826), OVCAR-3 [OVCAR3] (ATCC® HTB-161), and AsPC-1 [AsPC-1] (ATCC® CRL-1682™). A MSLN negative cell line HEK-.FRT, described in Example 2, was also used as negative control. To determine the relative expression of MSLN in each cell line, the antibody binding capacity (ABC) was used following the protocol recommended by the manufacturer (Quantum™ Simply Cellular® #816 Bangs Labs). The cell lines were ranked in order of MSLN expression levels with H226 having the highest MSLN of those tested (ABC 315,478), OVCAR3 having medium levels (ABC 103,444), AsPC-1 having low levels (ABC 20,999).

The results of the cell binding assay are shown in Table 10. In terms of expression levels, the FS28-256-271 binds stronger to the H226 which has the highest MSLN expression of the cell lines tested. The $mAb^2$ has comparable binding to OVCAR-3 and AsPC-1 cells. As expected, FS28-256-271 selectively binds to cells that express MSLN but not to the negative HEK.FRT cell line. Consequently, the CD137/MSLN $mAb^2$ will have the potential to work on cells expressing a range of levels of membrane MSLN expression.

TABLE 10

Cell binding strength of CD137/MSLN $mAb^2$ on cells expressing a wide range of MSLN density.

| Cell Line | Binding EC50 (nM) |
|---|---|
| NCI-H226 | 0.3041 |
| OVCAR-3 | 0.3058 |

TABLE 10-continued

| Cell binding strength of CD137/MSLN mAb$^2$ on cells expressing a wide range of MSLN density. | |
|---|---|
| Cell Line | Binding EC50 (nM) |
| AsPC-1 | 0.2934 |
| HEK.FRT | ND |

ND-tested, no binding detected so $EC_{50}$ not determined

Example 8: Functional Activity of CD137/MSLN mAb2

To demonstrate that cell lines with endogenous levels of MSLN can crosslink CD137/MSLN mAb$^2$ resulting in CD137 agonism and subsequent T cell activation, a cytotoxic $CD8^+$ T cell assay was developed where IL-2 or TNFγ cytokine release was used as the assay endpoint. NCI-H226, OVCAR-3, AsPC-1, and HEK.FRT described in Example 7 were used to test the CD137/MSLN mAb$^2$ in this T cell assay.

To isolate T cells, peripheral blood mononuclear cells (PBMCs) were isolated from leukocyte depletion cones, a by-product of platelet donations. Briefly, leukocyte cones contents were flushed with PBS and overlaid on a Ficoll (Sigma-Aldrich, 1440-02) gradient. PBMCs were isolated by centrifugation and the cells that did not cross the Ficoll gradient were recovered. PBMCs were further washed with PBS and remaining red blood cells were lysed through the addition of 10 ml 1× red blood cell lysis buffer (eBioscience, 00-4300-54) according to the manufacturer's instructions. $CD8^+$ T cells were isolated from the PBMCs present in the eluant using the $CD8^+$ T cell isolation kit II (Miltenyi Biotec Ltd, 130-096-495) according to the manufacturer's instructions.

Incubation with an anti-CD3 antibody was used as a first signal to drive initial activation of the T cells. 96-well flat bottom tissue culture plates were coated with 8 μg/ml anti-CD3 antibody (Clone UCHT1, R&D Systems, MAB100-SP) in PBS overnight at 4° C. The plates were then washed 3 times with 200 μl PBS.

8.1 $CD8^+$ T Cell Assay Using NCI-H226 for MSLN Cross-linking

Cytotoxic $CD8^+$ T cells were then isolated from the PBMCs as described above. NCI-H226 cells were plated at $2\times10^4$ cells per well on to anti-CD3 antibody-coated (8 μg/ml) 96 well flat bottom plates in 100 μl T cell culture medium (RPMI medium (Life Technologies, 61870-044) with 10% FBS (Life Technologies), 1× Penicillin Streptomycin (Life Technologies, 15140122), 1 mM Sodium Pyruvate (Gibco, 11360-070), 10 mM Hepes (Sigma-Aldrich, H0887), 2 mM L-Glutamine (Sigma-Aldrich, G7513) and 50 μM 2-mercaptoethanol (Gibco, M6250)). Once cells had adhered after 4 hours incubation, all T cell culture medium was removed and replaced with 50 μl T cell culture medium containing T cells at a concentration of $4.0\times10^5$ cells/ml resulting in $2.0\times10^4$ cells/well. mAb$^2$ were diluted in T cell medium at a 2× final concentration starting at 60 nM and 1:3 or 1:7 serial dilutions were carried out. 50 μl of mAb$^2$ titration was added to the cells for a total assay volume of 200 μl and 1× concentration of antibody. Details of the molecules tested in this assay are provided in Table 11, G1-AA/20H4.9 was used as positive control in each assay (data not shown).

The assay was incubated at 37° C., 5% $CO_2$ for 72 hours. Supernatants were collected and assayed with a V-PLEX IL-2 kit from Meso Scale Discovery (K151QQD-4) following the manufacturer's instructions. The concentration of human IL-2 (hIL-2) was plotted vs the log concentration of antibody and the resulting curves were fitted using the log (agonist) vs response equation in GraphPad Prism.

Table 11 shows the $EC_{50}$ values and maximum response of IL-2 release observed in the T cell activation assay across different repeats of the assay. Due to the number of assays performed, T cells from multiple donors were used. In each case, positive and negative controls were utilised in each assay to ensure consistent data sets across assays and donors. The positive control anti-human CD137 antibody, 20H4.9, shows an increase in hIL-2 release with an EC50 of 0.5 nM. Lack of off-targeted CD137-mediated T cell agonism was confirmed in a $CD8^+$ T cell assay similar to that described above but with HEK-FRT which were not transduced to express MSLN cells instead of the MSLN positive NCI-H226. Avoidance of off-targeted activation is highly desirable particularly with CD137 antibodies due to the instances of dose-limiting toxicities observed in some other CD137 molecules in the clinic, and therefore this factor was used in determining which mAb$^2$ combinations were selected. The following mAb$^2$ showed an increase of IL-2 release, each with a subnanomolar EC50: FS22-172-003-AA/FS28-024-051, FS22-172-003-AA/FS28-024-052, FS22-172-003-AA/FS28-024-053, FS22-172-003-AA/FS28-024-060, FS22-172-003-AA/FS28-256-021, FS22-172-003-AA/FS28-256-023, FS22-172-003-AA/FS28-256-026, FS22-172-003-AA/FS28-256-027. FIG. 1 shows representative plots of IL-2 release for the T cell activation assay. These results suggest that mAb$^2$ comprising Fabs from the FS28-185 lineage (FIG. 1B) did not show functional activity in this particular assay. Surprisingly, all mAb$^2$ paired with Fabs from the FS28-185 lineage show very limited and reduced, or none at all, IL-2 release. This suggests that while Fabs in that lineage are able to bind MSLN, binding to this particular region of MSLN appears not to be able to crosslink CD137/MSLN mAb$^2$ in a way that results in increased potency upon MSLN crosslinking in this assay. All mAb$^2$ comprising Fabs from lineage FS28-024 (FIG. 1A) and FS28-256-021, FS28-256-023, FS28-256-023, FS28-256-026, and FS28-256-027 from lineage FS28-256 (FIG. 1C) show an increase of hIL-2 release with subnamolar $EC_{50}$.

TABLE 11

Functional screening of CD137/MSLN mAb$^2$ in a $CD8^+$ T cell assay in co-culture with NCI-H226 lung adenocarcinoma cells.

| | NCI-H226 Donor A | | NCI-H226 Donor B | |
|---|---|---|---|---|
| mAb$^2$ FS22-172-003-AA/ | $EC_{50}$ (nM) | $E_{max}$ (IL-2 pg/ml) | $EC_{50}$ (nM) | $E_{max}$ (IL-2 pg/ml) |
| FS28-024 | 0.02 | 1122 | 0.03 | 1381 |
| FS28-024-051 | 0.08 | 1129 | 0.04 | 1800 |
| FS28-024-052 | 0.04 | 1067 | 0.05 | 1689 |
| FS28-024-053 | 0.07 | 1007 | 0.04 | 1441 |
| FS28-024-060 | 0.04 | 1401 | 0.06 | 1942 |
| FS28-185 | ND | ND | ND | ND |
| FS28-185-002 | ND | ND | ND | ND |
| FS28-185-003 | ND | ND | ND | ND |
| FS28-256 | 34.01 | 1260 | 22.21 | 8586 |
| FS28-256-005 | 1.63 | 1099 | N/A | N/A |
| FS28-256-012 | 1.56 | 1550 | 1.67 | 1100 |
| FS28-256-014 | 3.58 | 1358 | N/A | N/A |
| FS28-256-018 | 3.22 | 1256 | 3.71 | 903 |
| FS28-256-021 | 0.06 | 1784 | 0.04 | 1005 |
| FS28-256-023 | 0.64 | 1964 | 0.23 | 975 |
| FS28-256-024 | 1.29 | 2121 | 0.61 | 1086 |

TABLE 11-continued

Functional screening of CD137/MSLN mAb[2] in a CD8+ T cell assay in co-culture with NCI-H226 lung adenocarcinoma cells.

| | NCI-H226 Donor A | | NCI-H226 Donor B | |
|---|---|---|---|---|
| mAb² FS22-172-003-AA/ | $EC_{50}$ (nM) | $E_{max}$ (IL-2 pg/ml) | $EC_{50}$ (nM) | $E_{max}$ (IL-2 pg/ml) |
| FS28-256-026 | 0.67 | 2055 | 0.23 | 932.5 |
| FS28-256-027 | 0.05 | 2112 | N/A | N/A |

ND-tested, no activity so EC50 Emax not determined
N/A-not tested
$CD8^+$ T cell assay using NCI-H226 in the presence of soluble MSLN The $CD8^+$ T cell functional assay described above was repeated in the presence of hMSLN-His at a 20 mM concentration, which is 10-20 times the level of soluble MSLN found to be of diagnostic value for defining malignant mesothelioma and lung cancer patients as MSLN positive (Cui et al., 2014).

Figure 2:
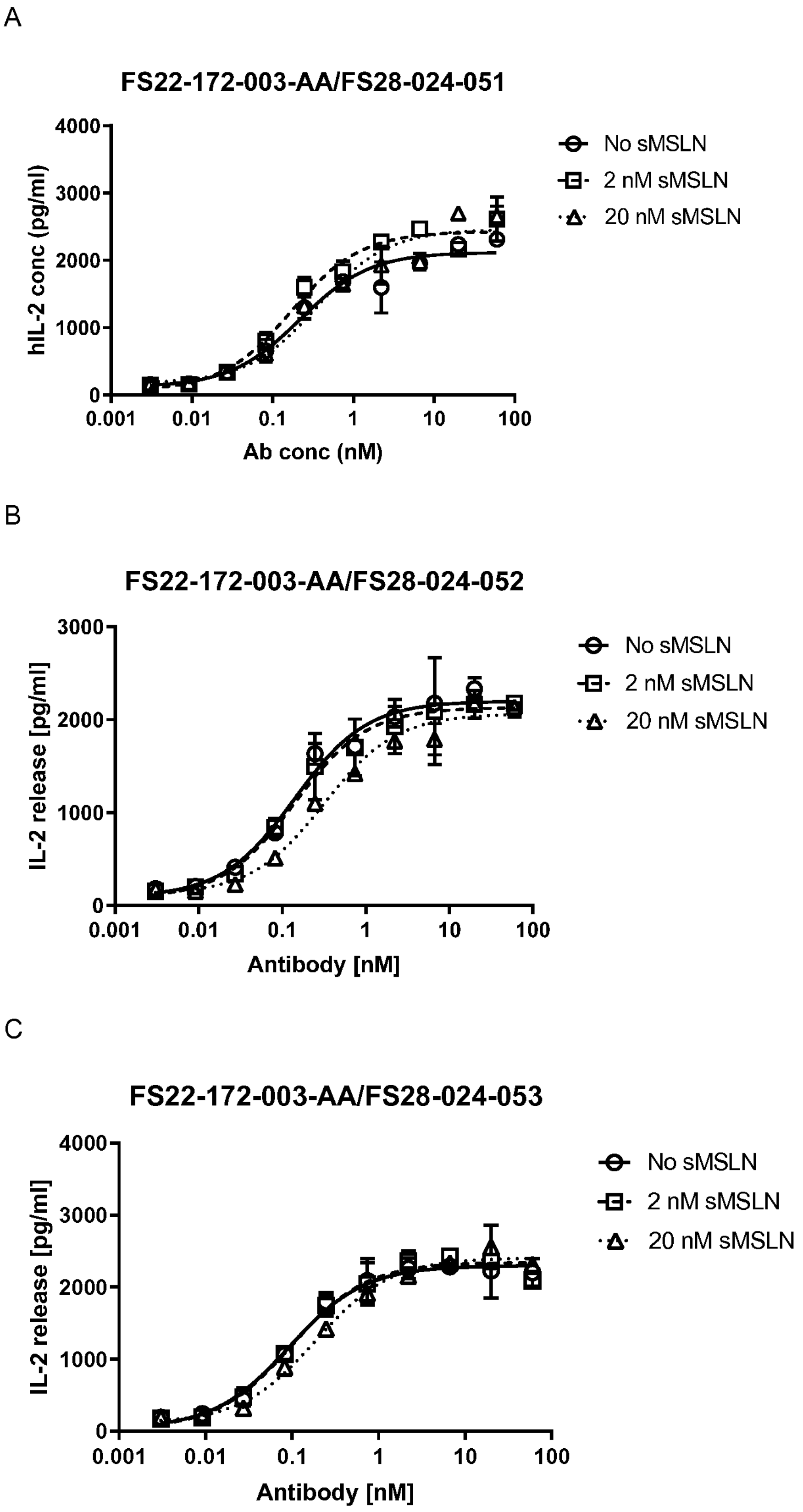
FIG. 2 shows the results of T cell activation assays in the presence of different concentration of soluble MSLN (sMSLN) (no sMSLN, 2 nM, and 20 nM sMSLN). $mAb^2$ which showed preferential binding to membrane-bound MSLN ($mAb^2$ comprising FS28-024-051, FS28-024-052, FS28-024-053, FS28-256-021, and FS28-256-023) were less affected by the presence of soluble MSLN (A-E) than FS22-172-003-AA/FS28-256-027 (F) for which a significant shift in the $EC_{50}$ was observed in the presence of 20 nM sMSLN compared to when no sMSLN was present.
Figure 2:
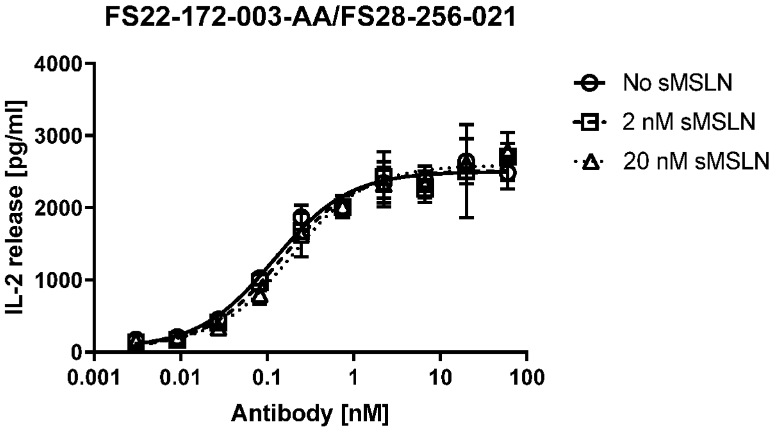
Figure 2:
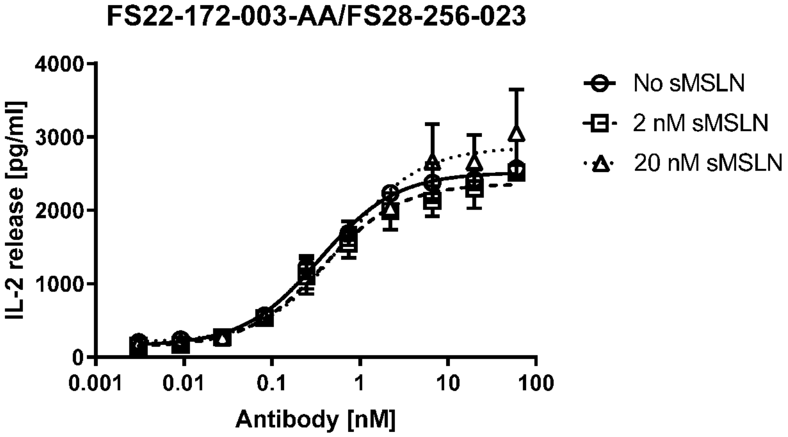
Figure 2:
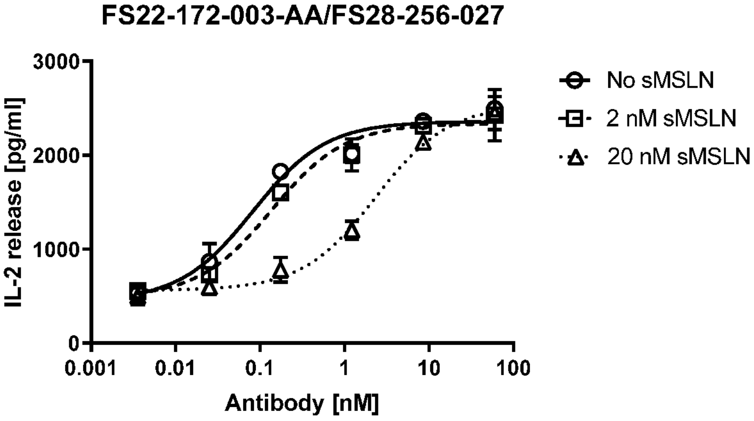

FIG. 2 shows the activity of a subset of $mAb^2$ in the presence or absence of soluble MSLN. As expected, soluble MSLN does not change the potency of those $mAb^2$ paired with Fabs that preferentially bind to immobilised versus soluble MSLN. Specifically, $mAb^2$ comprising the MSLN Fabs FS28-024-051, FS28-024-052, FS28-024-053, FS28-256-021, and FS28-256-023 were not affected by the presence of up to 20 nM soluble MSLN, this is consistent with affinity and cell binding data described in Examples 7.1 and 7.2.

Interestingly, $mAb^2$ FS22-172-003-AA/FS28-256-027 exhibited the biggest loss of potency when incubated with 20 nM of soluble MSLN resulting in a significant shift in $EC_{50}$. This is consistent with the affinity results in Examples 7.1 and 7.2, where FS28-256-027 exhibited high affinity to both immobilised and soluble MSLN, thereby supporting the theory that high affinity to soluble MSLN is not desirable. Results are consistent with the hypothesis described earlier in which clones with preferential binding to membrane MSLN are less interfered by the presence of soluble MSLN. In this context, clone FS28-256-027 shows high affinity binding to both immobilised and MSLN in solution and the functional data with the $mAb^2$ FS22-172-003-AA/FS28-256-027 reveals a significant shift in $EC_{50}$ when treated with 20 nM sMSLN. The remaining $mAb^2$ comprising the MSLN Fabs FS28-024-051, FS28-024-052, FS28-024-053, FS28-256-021, and FS28-256-023 were not affected in the presence of up to 20 nM and this is consistent with affinity and cell binding data described above.

8.2 CD8. T Cell Assay Using OVCAR-3 for Crosslinking

Figure 3:
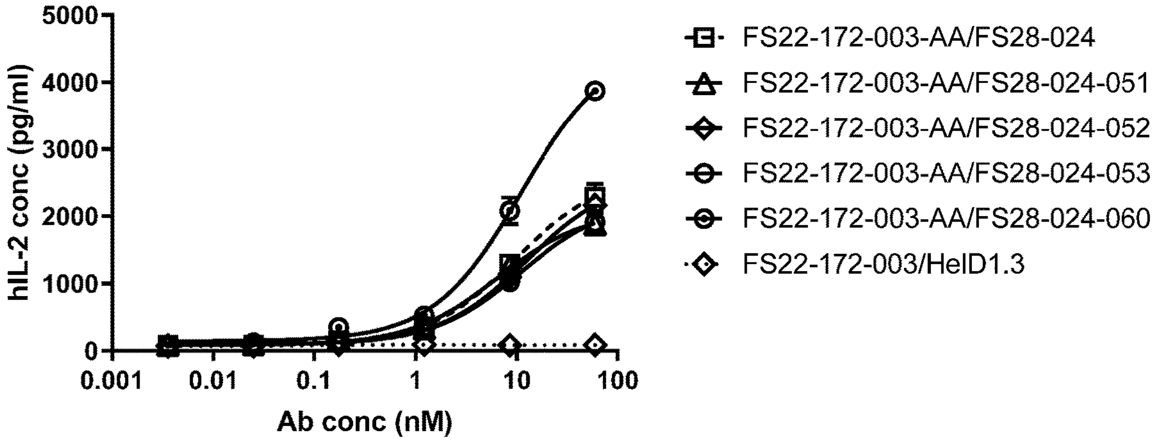
FIGS. 3 A and B shows the result of a T cell activation assay where the $mAb^2$ drive CD137-mediated activation of $CD8^+$ T cells when the $mAb^2$ are crosslinked by OVCAR-3 cells. These results show that the $mAb^2$ are able to drive CD137-mediated agonism in the context of cells expressing lower MSLN density on their cell membranes. The anti-CD137 Fcab FS22-172-003 in mock $mAb^2$ format (FS22-172-003/HeID1.3) was also tested in this assay and the lack of IL-2 release indicated that the anti-human CD137 Fcab is only functional when crosslinked via the Fab arms of the molecule.
Figure 3:
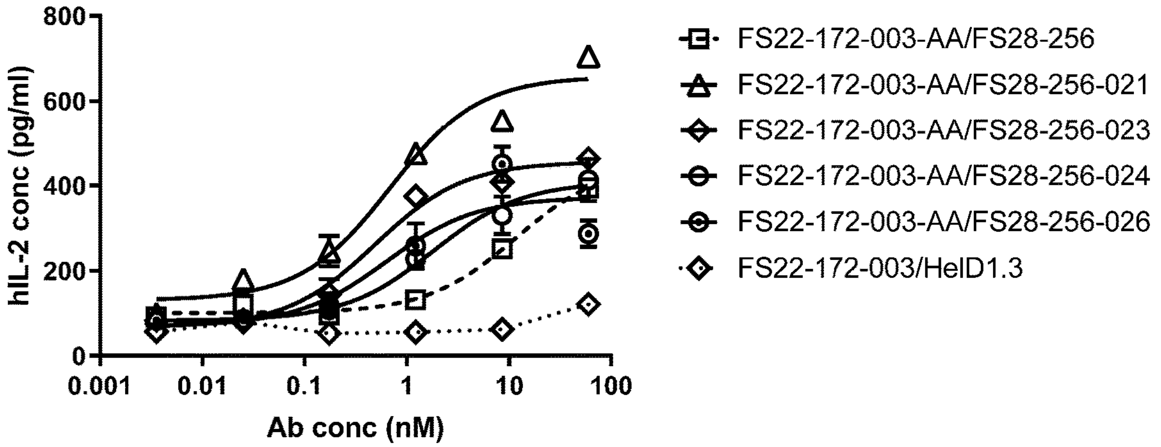

Mesothelin positive cancers have a wide range of expression levels, and so it was desirable to evaluate the functionality of some of the $mAb^2$ which were identified to have subnanomolar potency in Example 8.1 using cells which have a lower MSLN density on their cell surface. To achieve this, T cell activation assays were performed as described in Example 8.1 above, but this time using the OVCAR-3 cell line (ATCC® HTB-161). These are MSLN positive ovarian carcinoma cells that endogenously express lower levels of MSLN than NCI-H226 cells. The same protocol described in Example 8.1 was followed with the following change: due to differences in cell size and morphology, OVCAR-3 cells were plated at $1\times10^4$ cells per well on to anti-CD3 antibody-coated (8 μg/ml) 96 well flat bottom plates in 100 μl T cell culture medium. Once cells had adhered after 4 hours incubation, all T cell culture medium was removed and replaced with 50 μl T cell culture medium containing T cells at a concentration of $8.0\times10^5$ cells/ml resulting in $4.0\times10^4$ cells/well. The results confirm the ability of all tested $mAb^2$ to drive IL-2 release when cross-linked with OVCAR-3 cells (see FIG. 3). These data suggest that these $mAb^2$ have the potential to work across a wide range of MSLN densities across different tumour cell lines. The Fcab FS22-172-003 in HelD1.3 Mock $mAb^2$ format (FS22-172-003/HelD1.3) was also tested in this assay as this does not bind to MSLN and the lack of IL-2 release indicated that the anti-human CD137 Fcab is only functional when crosslinked through the Fab arms (MSLN in this case).

8.3 Functional Screening of Sequence-Optimised FS28-256 Affinity-Matured Clones

All $mAb^2$ containing anti-MSLN Fabs from the FS28-256 lineage described in Example 8.2 contain a potential N-linked glycosylation site in the VH CDR2 that was removed as described in Example 5.4. Three $mAb^2$ variants with the following substitutions were produced: FS22-172-003-AA/FS28-256-271, FS22-172-003-AA/FS28-256-272, and FS22-172-003-AA/FS28-256-273 which contained the amino acid substitutions, according to IMGT nomenclature, N55A, N55H, or H55S, respectively. To demonstrate the potency of these sequence optimised $mAb^2$, $CD8^+$ T cell activation assays were performed in co-culture with MSLN+ NCI-H226 cells as described in Example 8.1. $mAb^2$ were also tested in the presence of soluble MSLN.

TABLE 12

Functional screening of optimised FS28-256 clones using NCI-H226 cells, in the presence and absence of soluble MSLN.

| | EC50 (nM) | | |
|---|---|---|---|
| mAb² | No sMSLN | +2 nM sMSLN | +20 nM sMSLN |
| FS22-172-003-AA/FS28-256-271 | 0.1166 | 0.1390 | 0.3530 |
| FS22-172-003-AA/FS28-256-272 | 0.1216 | 0.1299 | 0.6840 |
| FS22-172-003-AA/FS28-256-273 | 0.0791 | 0.0616 | 0.3663 |

Figure 4:
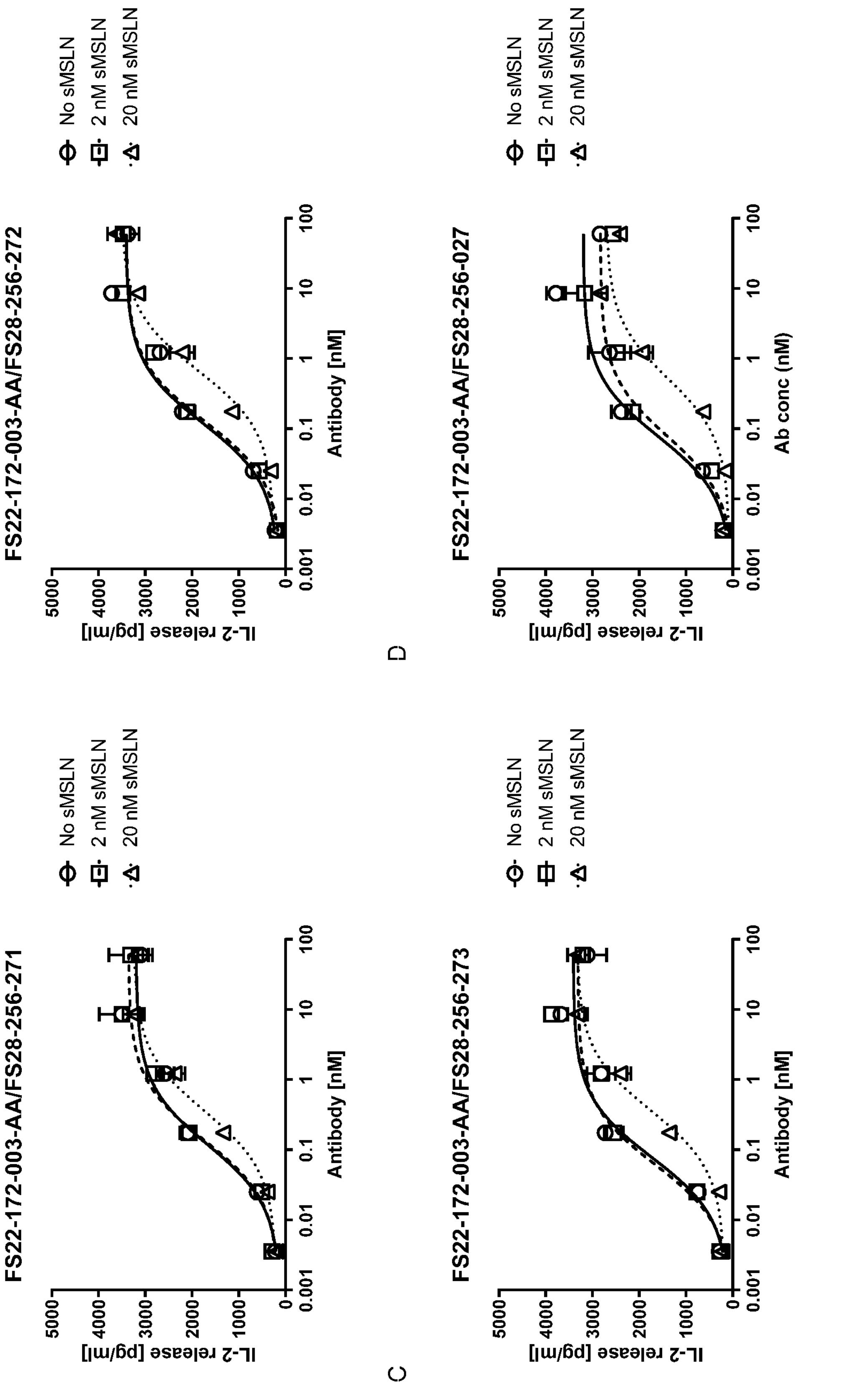
FIG. 4 shows the results of a $CD8^+$ T cell activation assay where the sequence optimised $mAb^2$ FS22-172-003-AA/FS28-256-271 (A), FS22-172-003-AA/FS28-256-272 (B), and FS22-172-003-AA/FS28-256-273 (C), were crosslinked with NCI-H226 cells expressing human MSLN in absence or presence of up to 20 nM of sMSLN. For $mAb^2$ FS22-172-003-AA/FS28-256-271 sMSLN concentrations of up to 20 nM result in minimal reduction in T cell activation activity in terms of the observed $EC_{50}$. The $mAb^2$ FS22-172-003-AA/FS28-256-272 and FS22-172-003-AA/FS28-256-273 showed a more pronounced reduction in T cell activation activity in the presence of 20 nM sMSLN with a higher than 4-fold reduction in the $EC_{50}$ observed, as did the parental clone FS22-172-003-AA/FS28-256-027 (D) which showed a 6.6-fold reduction in the $EC_{50}$.

FIG. 4 and Table 12 shows the potency of these $mAb^2$ and the effect of soluble MSLN on overall potency of the molecule. $mAb^2$ FS22-172-003-AA/FS28-256-271 showed the smallest decrease in potency of the three $mAb^2$ tested. Consistent with data described Examples 8.1 and 7.2, MSLN Fabs which bind with higher affinity to immobilised MSLN compared to MSLN in-solution were less affected by the presence of soluble MSLN: $mAb^2$ FS22-172-003-AA/FS28-256-271 showed the smallest change in $EC_{50}$ in the presence of soluble MSLN compared to the absence of soluble MSLN, with a 3-fold decrease in $EC_{50}$ being observed. Consistent with the affinity measurements reported in Example 7.1, this $mAb^2$ showed stronger affinity for immobilised MSLN compared to in-solution MSLN. Also consistent with Example 7.1, $mAb^2$ FS22-172-003-AA/FS28-256-272 and FS22-172-003-AA/FS28-256-273 bound in-solution MSLN with stronger affinity and this translated to a great impact on $EC_{50}$ for these clones in this assay in the presence of soluble MSLN compared to when no soluble MSLN was present, as shown in FIG. 4. $mAb^2$ FS22-172-003-AA/FS28-256-271 was therefore selected for further characterisation.

8.4 Expression-Dependent CD137/MSLN $mAb^2$ Potency Across Endogenous Cell Lines Expressing a Wide Range of MSLN Levels and Across Multiple PBMC Donors As mentioned in Examples 8.1 and 8.2, cancer patients express heterogeneous levels of MSLN. It was therefore desirable to determine the potency of FS22-172-003-AA/FS28-256-271 $mAb^2$ across a range of cells expressing varying levels of MSLN. $CD8^+$ T cell assays were performed as described in Examples 8.1 and 8.2. In addition to IL-2 measurement after 72 hours, IFNγ production was also measured after 96 hours using the V-PLEX human IFNγ MSD kit (Meso Scale Discovery, K151QOD-4) following the manufacturer's instructions.

TABLE 13

MSLN-dependent $mAb^2$ activity across different tumour cell lines.

| | NCI-H226 | OVCAR-3 | AsPC-1 | HEK.FRT |
|---|---|---|---|---|
| | IL-2 Production (nM) | | | |
| Donor C | 0.1111 | N/A | 0.7784 | ND |
| Donor D | 0.1122 | N/A | 0.8409 | N/A |
| Donor E | 0.0722 | 0.1453 | N/A | ND |
| Donor F | 0.0723 | 0.0693 | N/A | ND |
| | IFNγ Production (nM) | | | |
| Donor G | 0.0332 | N/A | 0.1475 | ND |
| Donor H | 0.0732 | 0.0840 | 0.1636 | N/A |
| Donor J | N/A | N/A | 0.3443 | N/A |

ND-tested, and no activity was detected, therefore $EC_{50}$ not determined
N/A-not tested In all assays reported in Table 13, $mAb^2$ FS22-172-003-AA/FS28-256-271 was able to induce potent T cell activation when crosslinked by cells expressing different levels of MSLN, as evidenced by subnanomolar potency for production of IL-2 (72 h) and IFNγ (96 h) (see Table 13). Interestingly, IL-2 and IFNγ production decreased with the amount of MSLN present on the crosslinking cells, e.g. when crosslinked with cells expressing low levels of MSLN (AsPC-1). This decrease was less pronounced when measuring IFNγ compared to IL-2 production, however in all cases the $mAb^2$ showed subnanomoalar potencies. In addition, when the $mAb^2$ were tested in co-culture with MSLN negative HEK.FRT cells, the $mAb^2$ did not elicit any agonist activity as evidenced by the lack of cytokine production. Overall, these results suggest that the $mAb^2$ can induce T cell activation even with low levels of MSLN and that the level of T cell activation induced by the $mAb^2$ is dependent on the level of MSLN present to crosslink the $mAb^2$, and therefore demonstrate that potency of the $mAb^2$ correlates with MSLN expression density on cells.

Example 9: Production of an Anti-Mouse CD137 Fcab in vivo Due to the low sequence homology between the mouse and human CD137 sequences, Fcabs which specifically bound to mouse CD137 were generated and characterised to allow the activity of $mAb^2$ containing a CD137 antigen-binding region in a constant domain to be tested in in vivo mouse models.

9.1 Naïve Selection of Anti-Mouse CD137 Fcabs

In order to select Fcabs that bind to human CD137, yeast display selection campaigns were employed, similar to that previously described for selection of Fcabs binding to human CD137 (see Example 2.1). Recombinant mouse dimeric was used as antigen (see Example 1).

The four naïve yeast libraries displaying CH1 to CH3 domains of human IgG1 previously used for selection of Fcabs binding to human CD137 were used for selections of Fcabs binding to mouse CD137. A total of 53 separate rounds of selections were performed to identify anti-mouse CD137 binders. In-house-produced, recombinant, dimeric, biotinylated mouse CD137 (mCD137-mFc-Avi) antigen was used to select binders from the yeast naïve libraries.

9.2 Characterisation of Anti-Mouse CD137 Fcabs from Naïve Selections

The specificity of the anti-mouse CD137 Fcabs for mouse CD137 were tested in HeID1.3 "mock" $mAb^2$ format and measured by BLI in an Octet QKe system by testing for binding of the Fcabs to other mouse TNFRSF receptors (CD40, OX40, GITR). Streptavidin biosensors (PALL ForteBio 18-5021) to coat 10 ng/μl mouse CD40, GITR, OX40 receptors (all obtained from R&D Systems and biotinylated using an EZ-Link Sulfo-NHS-SS-Biotin kit from Thermoscientific #21328). Anti-mouse CD137 Fcabs in mock $mAb^2$ format were diluted 1:1 in kinetic buffer (PALL 18-1092) to a final concentration of at least 1 μM. Antigen-coated sensors were dipped into the $mAb^2$ solutions for 180 seconds followed by 180 seconds in 1× kinetic buffer. Antibodies for each of the TNFRSF receptors were used as positive controls. The Fcab clones FS22m-055, FS22m-063, FS22m-066, FS22m-075, FS22m-135, FS22m-055, FS22m-063, FS22m-066 did not bind to any of the TNFRSF receptors tested, thus demonstrating their specificity for mouse CD137.

HEK.FRT.luc cells expressing the mouse CD137 sequence (SEQ ID NO: 150 were produced following the same methodology as previously described in Example 2.3. The $mAb^2$ containing the anti-mouse CD137 Fcabs previously selected were screened using this cell line, HEK.FRT-.luc.mCD137, according to the method described in Example 2.3. 56 $mAb^2$ were tested of which 29 were positive for NF-κB activity. Lob12.3 containing a human IgG1 Fc with a LALA mutation (G1AA/Lob12.3), was used as a positive control anti-mouse CD137 mAb and showed an increase in luminescence confirming the assay's validity. HeID1.3, also containing a human IgG1 Fc with a LALA mutation, was used as a negative control human IgG isotype to rule out interference from the human IgG mock Fab in this assay. $EC_{50}$ were calculated where possible and $mAb^2$ which did not reach a plateau in activity were disregarded in favour of $mAb^2$ which showed classic sigmoidal activity kinetics. $mAb^2$ were ranked in order of EC50 and fold-change in activity upon Protein L crosslinking. FS22m-063 was selected based on it having the best EC50 upon crosslinking (1.44 nM) and highest fold-change in activity upon crosslinking (27-fold).

Example 10: Selection and Characterisation of Anti-Mouse MSLN Antibodies

10.1 Naïve Selection of Anti-Mouse MSLN mAbs

The amino acid identity between mouse and human MSLN is low (60%). To enable in vivo Proof of Concept (PoC) studies in mice, the inventors set out to isolate anti-mouse MSLN mAbs with similar properties as the anti-human MSLN mAbs described in Example 4 and 5.

Phage selections, using the synthetic naive phagemid libraries displaying the Fab domain of human IgG1 germlines with randomisation in the CDR1, CDR2 and CDR3 (MSM Technologies) were used for selections with biotinylated mouse MSLN-His-Avi (SEQ ID NO143, see section 1.1) as described in section 1.2. Four rounds of selections were performed with decreasing concentrations of biotinylated mMSLN-His-Avi and similarly to the anti-human MSLN selections, epitope masking strategies were performed in a subsequent campaign. In addition, after a first round of using recombinant antigen, HEK293-mMSLN cells were generated and used in round 2, 3 and 4.

Briefly, cDNA encoding mouse MSLN (SEQ ID NO: 145 sequence was subcloned into the pcDNA5/FRT/TO vector (Life Technologies, V652020) and then co-transfected with the FIp recombinase expression plasmid, pOG44 (Life Technologies, V600520) into FIp-In TREx 293 cell lines (Life Technologies, R78007). Cells were grown in DMEM containing 10% FBS, 100 μg/ml Hygromycin B (Melford Laboratories Ltd, Z2475) and 15 μg/ml Blasticidin (Melford Laboratories Ltd, B1105) for 3-4 weeks until colonies of stably transformed cells had formed. These colonies were amplified in the presence of 1 μg/ml Doxycyclin (Sigma Aldrich, D9891) and tested for expression of MSLN using anti-mouse MSLN (LS Bio, LS-C179484).

In total 47 individual mAbs from enriched populations were screened for antigen binding and 45 unique positive binders were subcloned and expressed as soluble mAbs in IgG1 LALA format as previously described in Example 1.3. mAbs were characterised for specific binding to immobilised mMSLN-His-Avi by ELISA and ranked based on affinity to about 50 or 200 RU of immobilized mMSLN-His-Avi in kinetic experiments using Biacore analysis. This identified a panel of mAbs, including FS28m-228, with affinities ranging from 1 to 25 nM. In addition, binding to different regions of MSLN was tested as described in section 2.1.3. A mouse crossreactive mAb G1-AA/MOR6626, generated by cloning the VH and VL of MOR6626 clone (Patent publication no WO 2009/068204 A1) was used as positive control. Most clones, amongst which was FS28m-228, failed to bind to MSLN that is already bound to MOR6626, whereas others like FS28-194 or FS28-261 showed partial or full binding respectively. Thus, clones binding to different regions (bins) were isolated.

Summary: Anti-Mouse Fcab and mAb Selection and Screening

The anti-mouse CD137 Fcabs identified in the previous examples were shown to have agonistic activity in NF-κB reporter assays when crosslinked either by an external cross-linking agent such as Protein L (Example 9). Of the panel of anti-human CD137 Fcabs identified, FS22m-066 was selected for pairing with mouse MSLN-targeting Fabs, as this clone presented the most favourable functional and biophysical properties.

Phage selection and antibody screening strategies led to the identification of a panel of anti-mouse mesothelin binding clones with a range of affinities and which bind to different regions of mMSLN. Like the anti-human MSLN binders, the clones showed binding characteristics favouring binding to immobilised mMSLN than soluble mMSLN rendering them suitable molecules for studying in murine in vivo PoC studies.

Example 11: Production of Anti-Mouse CD137/MSLN mAb$^2$

As described in Example 10, a panel of naïve anti-mouse MSLN antibodies were discovered and screened for beneficial binding and targeting properties. An anti-mouse CD137 Fcab was selected as described in Example 9. The anti-mouse CD137 Fcab (FS22m-063) and anti-mouse MSLN Fabs (FS28m-228 and FS28m-228-010) were used to generate mouse mAb$^2$ for full in vitro characterisation as well as in vivo proof of concept MSLN-targeted CD137 agonism in syngeneic mouse tumour models. The Fabs were chosen to investigate the relationship between binding affinity, avidity and functional activity. The mAb$^2$ have the LALA mutation in the CH2 region of the heavy chain, with the purpose of minimising the contribution of Fc-gamma receptor driven cross-linking as well as effector function, were constructed as described in Example 6 and given the identifiers FS22m-063-AA/FS28m-228 (SEQ ID NO 136 (light chain), 137 (heavy chain)), and FS22m-063-AA/FS28m-228-010 (SEQ ID NO 136 (light chain) and 166 (heavy chain), respectively. The mAb$^2$ were produced by transient expression in HEK293-6E cells, and purified using mAb Select Sure protein A columns.

11.1 Binding Kinetics

Like the anti-human MSLN binders, the affinity of the mAb$^2$ for binding to immobilised and soluble MSLN was tested by SPR using a Biacore instrument.

The procedure for binding to immobilised was similar to the method described in Example 7.1 and 7.2 with mMSLN-His-Avi immobilised at 50 RU. To determine the affinity for soluble MSLN the mAb$^2$ was captured via an anti-human Fc. Briefly, 25 μg/ml anti-human IgG (Fc) antibody (GE Healthcare, Human Antibody Capture Kit, BR100839) was immobilised on a Biacore sensor chip CM5 (GE Healthcare, BR100530) achieving a final response of approximately 750 RU. The mAb$^2$ molecule, diluted in HBS-EP buffer (GE Healthcare, BR100188) at 50 nM, was injected individually at 30 μl/min to achieve a response of approximately 100 RU. The recombinant mMSLN-His-Avi antigen, diluted in HBS-EP buffer, was injected at a concentration range of 243 nM to 0.11 nM with 3-fold dilutions for 5 minutes at 70 μl/min and then allowed to dissociate in buffer for 5 minutes. Regeneration was achieved by injecting 3 M magnesium chloride (GE Healthcare, Human Antibody Capture Kit, BR100839) for 30 seconds at a rate of 30 μl/min.

The kinetic data is shown in Table 14. FS22m-063-AA/FS28m-228-010 showed stronger binding to membrane bound MSLN than soluble shed MSLN, likely due to enhanced avid binding interactions. The affinity matured mAb$^2$ FS22m-063-AA/FS28m-228-010 showed improvement in binding to both immobilised MSLN and MSLN in solution. FS28m-228-010 was chosen as it binds preferentially to immobilised MSLN which is was deemed beneficial to avoid a sink effect by circulating MSLN in blood. This clone, like the human Fab FS28-256-271, bound immobilised MSLN in the single-digit nanomolar range, preferentially targeting immobilised MSLN over MSLN in solution.

TABLE 14

| Binding of mouse CD137/MSLN $mAb^2$ to immobilised MSLN and MSLN in solution as measured by SPR | | | |
|---|---|---|---|
| $mAb^2$ (FS22m-063-AA/) | Affinity to immobilised mMSLN-His-Avi $K_D$ (nM) | Affinity to in-solution mMSLN-His-Avi $K_D$ (nM) | Ratio of $K_D$ in solution/immobilised for human MSLN-His-Avi |
| FS28m-228 | 7.90 | 252 | 31.9 |
| FS28m-228-010 | 2.6 | 60.24 | 23.2 |

11.2 Functional Activity of Mouse CD137/MSLN $mAb^2$ Using Mouse MSLN Positive Cells Activated cytotoxic $CD8^+$ T cells are responsible for directly killing cancer cells and express CD137 on their cell surface (Ye et al., 2014). Clustering of CD137 is known to be essential to induce downstream signalling and further $CD8^+$ T cell activation. A $CD8^+$ T cell activation assay was therefore used to assess the ability of $mAb^2$ to drive clustering and subsequent downstream signalling of CD137. $CD8^+$ T cell activation was achieved by antigen stimulation of genetically modified OT-1 T cells isolated from C57 BL/6-Tg(TcraTcrb)1100Mjb/Crl OT-I mice (Jackson Laboratory, Cat no. 003831) that have a T cell receptor specific for ovalbumin peptide 257-264, and was determined by the release of IFNγ.

To isolate T cells, splenocytes were isolated from fresh OT-1 mouse spleens. Briefly, each spleen from a C57Bl/6 OT-1 mouse was collected and stored in PBS before being transferred to a well of a 6-well tissue culture plate and mechanically disrupted with 2 needles. The disrupted spleen was passed through a 70 μm cell strainer and the strainer was rinsed with PBS. The cell suspension was then pelleted by centrifugation, the supernatant removed and red blood cells were lysed through the addition of 10 ml 1× red blood cell lysis buffer (eBioscience, 00-4300-54) according to the manufacturer's instructions. Splenocytes were plated for T cell activation at $2\times10^6$ cells per well in medium (IMDM, 5% FCS, 50 μM 2-Mercapto Ethanol, 1× Penstrep) containing 10 nM SIINFEKL peptide in 6-well plates at $10\times10^6$ cells per well. Plates were incubated for 48 hours at 37'C with 5% CO2. After 48 hours CD8 T cells were isolated by using a $CD8^+$ T cell Isolation Kit (Milentyi Biotec, 130-104-075) following manufacturer's instructions. Isolated and activated CD8 T cells were plated in medium (IMDM, 5% FCS, 50 μM 2-Mercapto Ethanol, 1× Penstrep) supplemented with 30 U/ml IL-2 (Peprotech, AF-200-02) and kept at less than $1\times10^6$ per ml at each daily split for 3 further days. After the three days of expansion cells were then used in the following assay.

$CD8^+$ T cells used in this example originated from two separate animals and splenocyte expansions performed 18 months apart and therefore variance in T cell activation between specimen A and B is expected.

CT26 colon carcinoma cells (ATCC, CRL-2638) expressing full-length mouse mesothelin (SEQ ID NO:145), were produced to present the antigen in a membrane-bound conformation. Lipofection (Lipofectamine 3000, Thermo Fisher Scientific, catalogue number L3000008) was used to generate these cells using the pcDNA3.1 vector (+) (Thermo Fisher Scientific, catalogue number V79020). Following the manufacturer's protocol, the CT26 cells were transfected with the pcDNA3.1 vectors containing the mouse MSLN cDNA A stable transfection was then achieved using geneticin as the selection antibiotic (at 600 μg/ml) in complete media (RPMI, 10% FBS).

Expression of mouse MSLN on the CT26 cells was confirmed by flow cytometry by using the positive control antibody MOR6626. Cells were incubated with the positive control antibody for 1 hour and then a fluorescently-labelled anti-human IgG detection antibody (Stratech Scientific Ltd, catalogue no. 109-546-098-JIR) was used to detect cell binding. Clonal populations were expanded and subsequently analysed to determine the relative expression levels using the same flow cytometric procedure, after which two clones expressing mouse MSLN at different levels were progressed as tools to study the anti-mouse MSLN Fabs: CT26.B2 (High MSLN expression) and CT26.G10 (Medium/Low MSLN expression). To provide cells having a range of MSLN expression Panc02 cells NIC/NIH (Maryland, USA) which express MSLN endogenously were also used. These cells expressed lower levels of MSLN in vitro and ex vivo showed cytosolic expression as determined by IHC (data not shown). Mesothelin expression was subsequently also confirmed ex vivo by IHC (data not shown)

CT26.B2, CT26.G10 and Panc02 cells were incubated with the SIINFEKL peptide (500 nM), $2\times10^4$ OT-1 cells per well were added to the $MSLN^+$ cells in 50 μl media. Test antibodies were prepared in a 1:4 titration starting at 60 nM (4× final concentration) and 50 μl of antibody mix was added to each well accordingly resulting in a final assay volume of 200 μl. The assay was incubated for 3 days at 37° C. with 5% CO2. After 3 days, supernatants were harvested and an ELISA for mIFNγ (eBioscience, cat no. 88-7314-88) was performed according to manufacturer's instructions.

The mouse CD137/MSLN $mAb^2$ were screened in this T cell assay in the absence and presence of soluble mouse MSLN. Commercially available mouse mMSLN-His Biolegend (#594008). Analysis of blood serum from mice carrying CT26.G10 tumours determined the median concentration of MSLN in blood to be 100 μM (data not shown). Therefore, in order to study interference with soluble MSLN, up to 2 nM was used in the functional assay.

Figure 5:
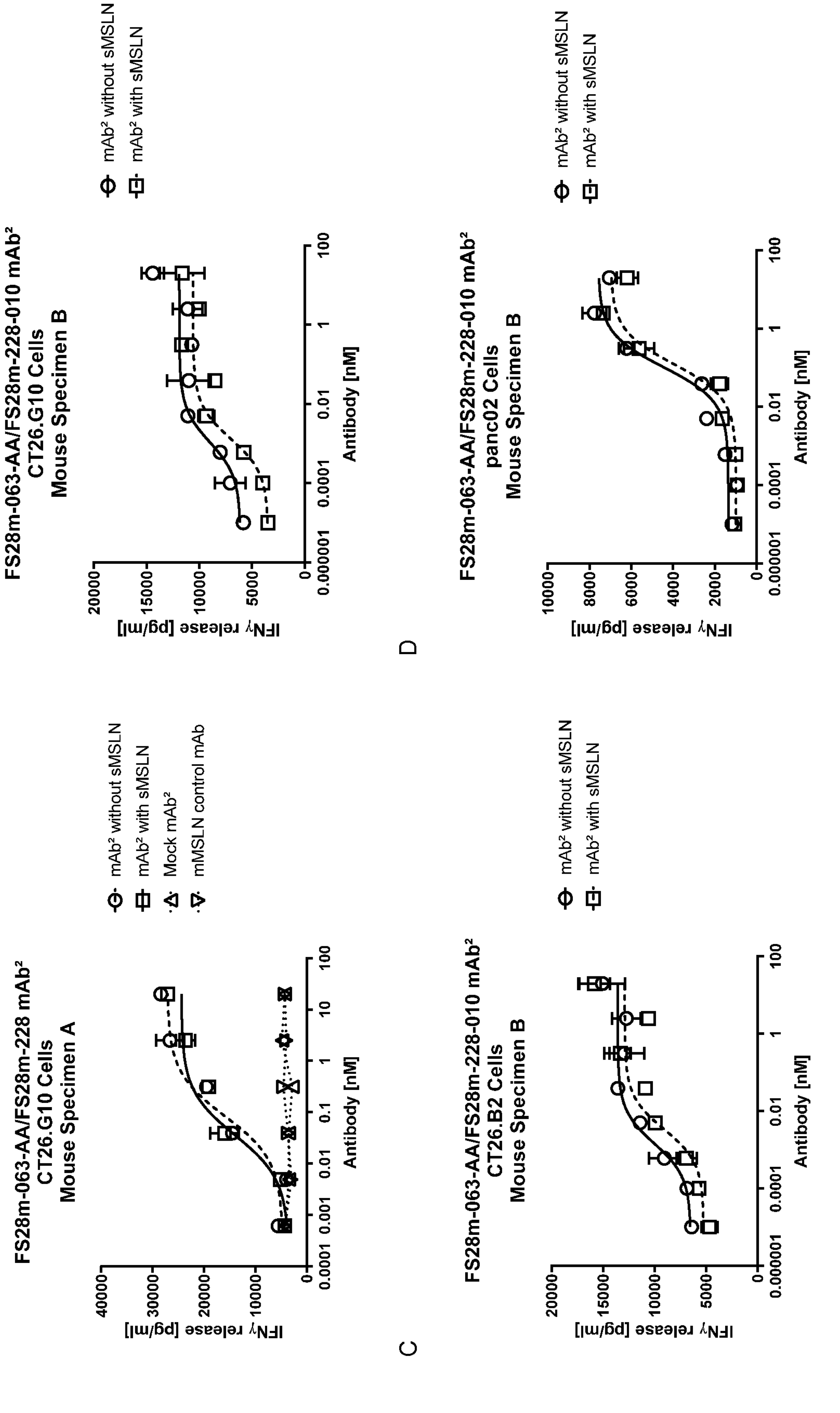
FIG. 5 shows IFNγ release in a T cell activation assay when the $mAb^2$ FS22m-063-AA/FS28m-228-010 and FS22m-063-AA/FS28m-228 were crosslinked with CT26.G10, CT26.B2 or Panc02 cells in the presence or absence of 2 nM soluble mouse MSLN (A to D). The experiment for $mAb^2$ FS22m-063-AA/FS28m-228 included the following negative controls: an anti-MSLN control antibody in IgG1 format lacking any CD137-targeting Fcab, and the mock $mAb^2$ FS22m-063/HeID1.3 (i.e. CD137 Fcab without MSLN targeting). The results showed that at even relatively high concentrations of soluble MSLN there was negligible impact in the potency of the $mAb^2$ in this assay. This data also showed subnanomolar potencies ($EC_{50}$) across all of the MSLN-expressing cell lines tested.

As shown in Table 15 and FIG. 5, $mAb^2$ FS22m-063-AA/FS28m-228-010 had greater potency than the parental FS22m-063-AA/FS28m-228 when crosslinked by the CT26.G10 cell line. The following negative controls were also tested in one assay, which as expected did not result in any cytokine readout: the FS22m-063 Fcab in mock $mAb^2$ format (HelD1.3), and a MSLN-targeting positive control (G1/MOR6626). As shown in FIG. 5, the presence of 2 nM soluble MSLN had minimal impact on IFNγ release with all $EC_{50}$ values in the low picomolar range with the exception of Panc02 cells which express less membrane MSLN than the engineered $MSLN^+$ CT26 cells. Similarly to the human mAb2, the level of T cell activation induced by the mAb2 is dependent on the level of MSLN present on the crosslinking cells.

TABLE 15

| Mouse CD137/MSLN $mAb^2$ potency with MSLN positive cells in an OT-1 T cell assay | | | | | | |
|---|---|---|---|---|---|---|
| | CT26.G10 | | CT26.B2 | | Panc02 | |
| $mAb^2$ | −sMSLN | +sMSLN | −sMSLN | +sMSLN | −sMSLN | +sMSLN |
| FS22m-063-AA/FS28m-228 | 0.0357 | 0.0836 | NM | | NM | |
| FS22m-063-AA/FS28m-228-010 | 0.0010 | 0.0013 | 0.0014 | 0.0033 | 0.1034 | 0.1251 |

NM = Not measured

Example 12: In Vivo Proof of Concept

Having shown that the $mAb^2$ had function in a T cell assay, it was desirable to test the function of the $mAb^2$ FS22m-063-AA/FS28m-228 in vivo in a syngeneic immunocompetent tumour model.

12.1 Efficacy of FS22m-063-AA/FS28m-228 In Vivo in a CT26.B2 Syngeneic Tumour Model In order to determine anti-tumour efficacy of FS22m-063-AA/FS28m-228 in a high MSLN-expressing tumour model, Balb/C female mice (Charles River) aged 9-10 weeks were acclimatised for one week prior to the study start. All animals were micro-chipped and given a unique identifier. Each cohort had either 15 or 20 mice. CT26.B2 cells were expanded and cell banks generated, then pre-screened by IDEXX Bioresearch for pathogens using the IMPACT I protocol and shown to be pathogen-free. Each animal received $1\times10^1$ cells injected subcutaneously in the left flank in 100 μl serum free media. 17 days following tumour cell inoculation, mice which did not have tumours were removed from the study.

The FS22m-063-AA/FS28-228 $mAb^2$ (SEQ ID NO: 360 and 361) or human IgG1 isotype control (G1-AA/4420) were injected with 200 μl of antibodies at a fixed concentration of 200 μg per dose (approximately 10 mg/kg in a 20 g mouse) in DPBS+1 mM arginine+0.05% Tween 80. Mice were dosed by intraperitoneal injection with the $mAb^2$ molecule on days 17, 19 and 21 days post inoculation, whereas mice were dosed with the control human IgG1 antibody on days 7, 9 and 11 post inoculation. Tumour volume measurements were taken three times per week with calipers to determine the longest axis and the shortest axis of the longest axis and the shortest axis of the tumour. The following formula was used to calculate the tumour volume:

$$L\times(S^2)/2$$

Where L=longest axis; S=shortest axis

The study endpoint was determined by humane endpoints based on tumour volume and condition.

Figure 6:
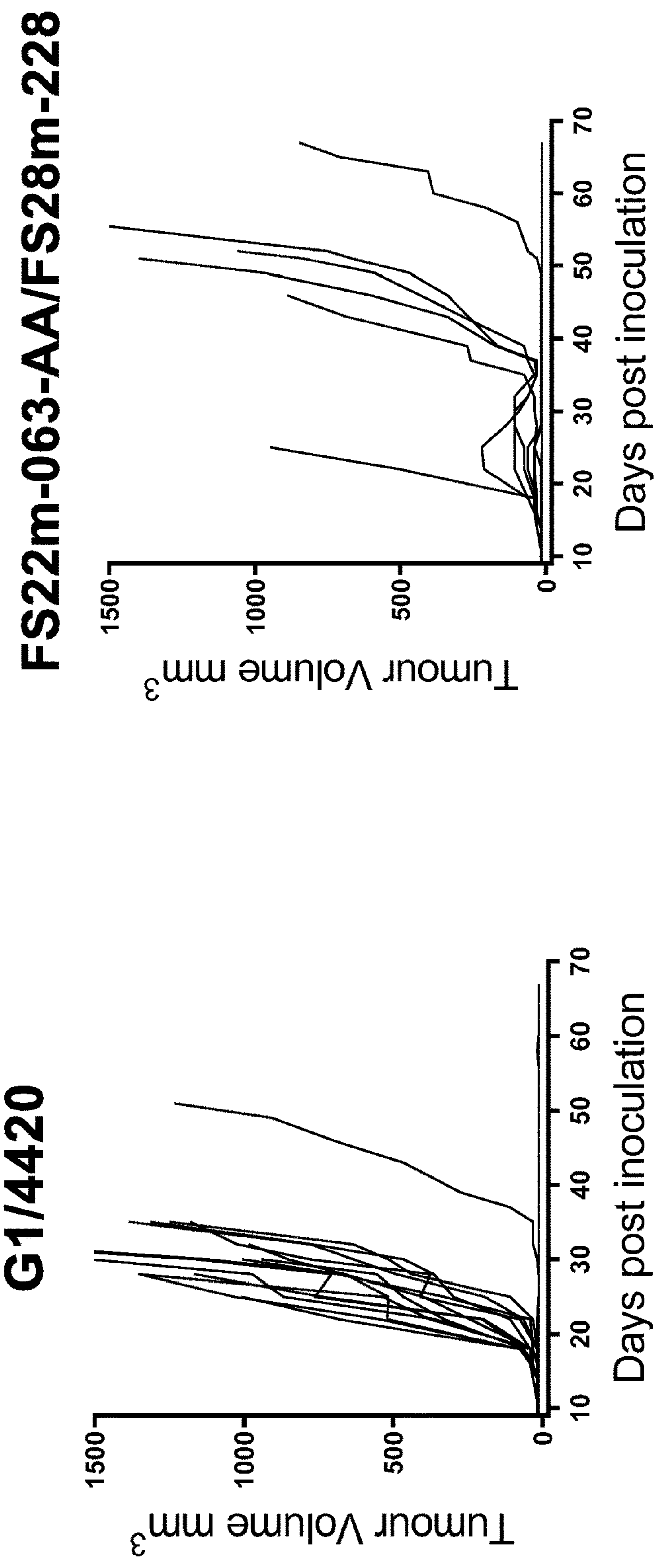
FIG. 6 shows individual tumour volume measurements in the CT26.B2 syngeneic mouse tumour model for mice treated with G1/4420 (human IgG1 isotype control antibody) (A) or FS22m-063-AA/FS28m-228 (anti-mouse CD137/MSLN $mAb^2$) (B). Treatment with FS22m-063-AA/FS28m-228 resulted in reduced tumour growth compared to the isotype control.

As shown in FIG. 6, treatment with the FS22m-063-AA/FS28m-228 $mAb^2$ showed a visual delay in tumour growth compared to mice treated with isotype control (G1/4420).

Figure 7:
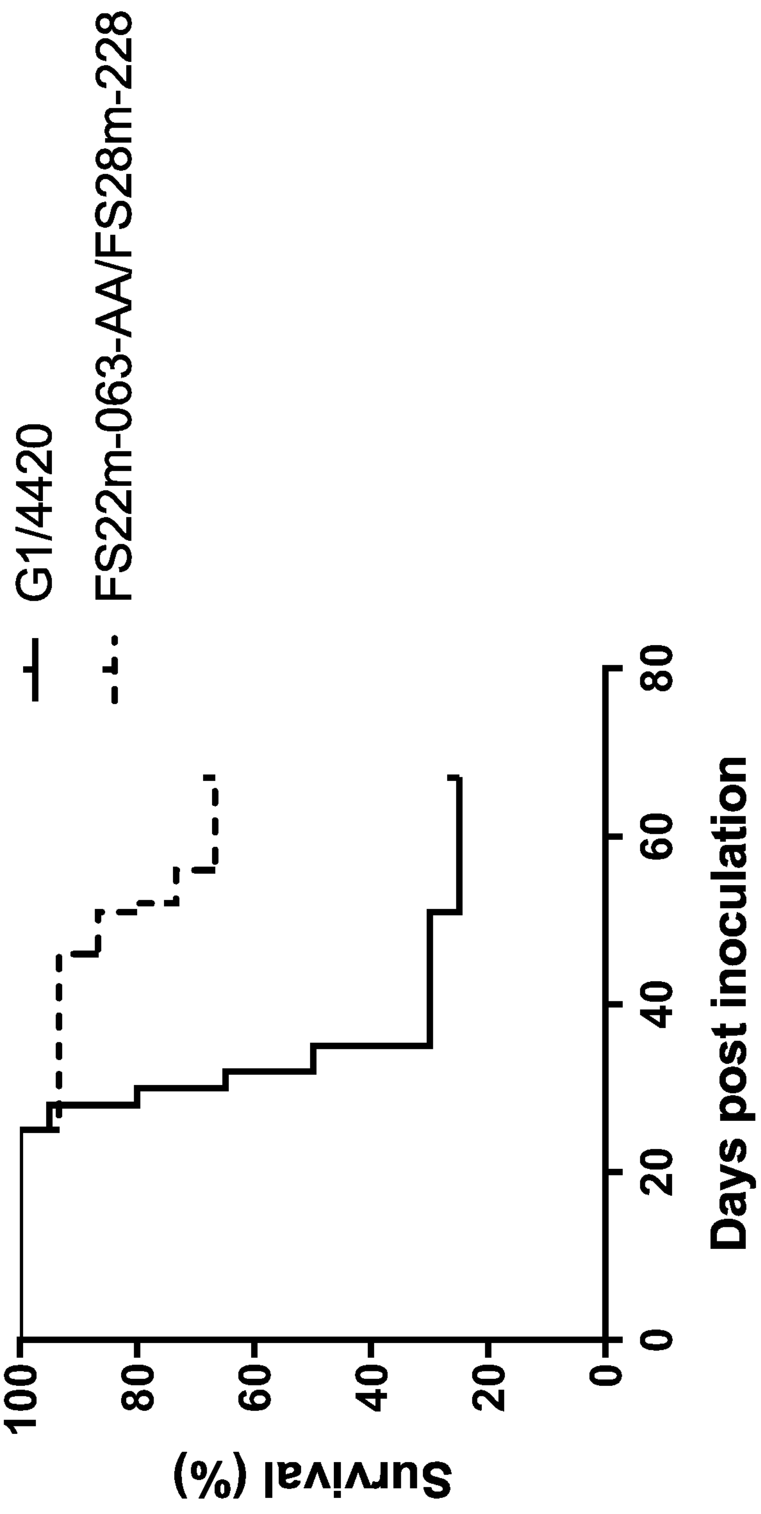
FIG. 7 shows a Kaplan Meier survival plot of mice in the CT26.B2 syngeneic mouse tumour model treated with G1/4420 (human IgG1 isotype control antibody) or FS22m-063-AA/FS28m-228 (anti-mouse CD137/MSLN $mAb^2$). Treatment with FS22m-063-AA/FS28m-228 showed a significant improvement in survival compared to treatment with the human IgG1 isotype control antibody. (Log-rank analysis, **p<0.01)

Time-to-Endpoint (survival) analysis was performed using GraphPad Prism 8.0 software. Data shown in FIG. 7 and Table 15 were analysed using the Log-rank (Mantel-Cox) test. Data showed that the FS22m-063-AA/FS28m-228 $mAb^2$ induced a significant survival benefit compared to isotype control (G1/4420), by log-rank analysis. The median survival of the IgG1 control group was 33.5 days, whereas the median survival of FS22m-063-AA/FS28m-228 was not reached.

TABLE 15

| Time to endpoint pairwise statistical analyses (Log-rank) in CT26.B2 syngeneic tumour model | |
|---|---|
| Groups | P-values Log-rank |
| G1/4420<br>FS22m-063-AA/FS28m-228 | 0.0052 ** |

NS $p \geq 0.05$;
* $p < 0.05$;
** $p < 0.01$;
*** $p < 0.001$;
**** $p < 0.0001$

12.2 Efficacy of FS22m-063-AA/FS28m-228 In Vivo in a CT26.G10 Syngeneic Tumour Model The efficacy of the FS22m-063-AA/FS28m-228 $mAb^2$ was also tested in CT26.G10 syngeneic tumour model. CT26.G10 cells express lower levels of MSLN compared with CT26.B2 cells. The same procedure as described in Example 12.1 was followed, except that the CT26.G10 cell line was used to inoculate the mice. Mice were dosed with a 200 μl intraperitoneal injection of FS22m-063-AA/FS28m-228 $mAb^2$ on days 12, 14 and 16 days post inoculation, and or G1/4420 control antibody on days 7, 9 and 11 post inoculation. Mice were administered with a fixed dose of 200 μg/mouse (equivalent to approximately 10 mg/kg in a 20 g mouse).

Figure 8:
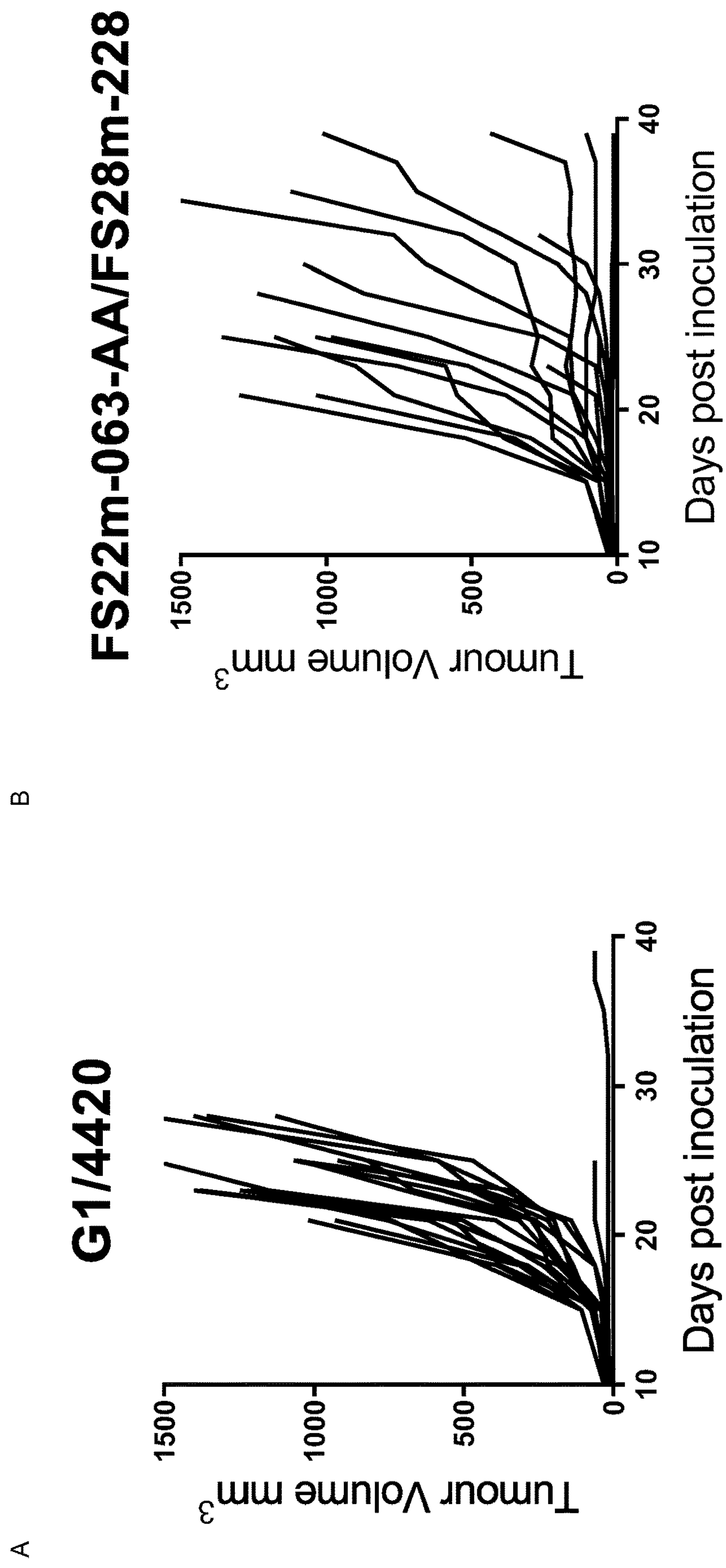
FIG. 8 shows individual tumour volume measurements in the CT26.G10 syngeneic mouse tumour model for mice treated with G1/4420 (human IgG1 isotype control antibody) (A) or FS22m-063-AA/FS28m-228 (anti-mouse CD137/MSLN $mAb^2$) (B). Mice treated with FS22m-063-AA/FS28m-228 showed reduced tumour growth compared with the isotype control, with no palpable tumours being present in 4/20 (25%) mice at the end of study, compared to (1/20, 5%) in the isotype control treated group.
Figure 9:
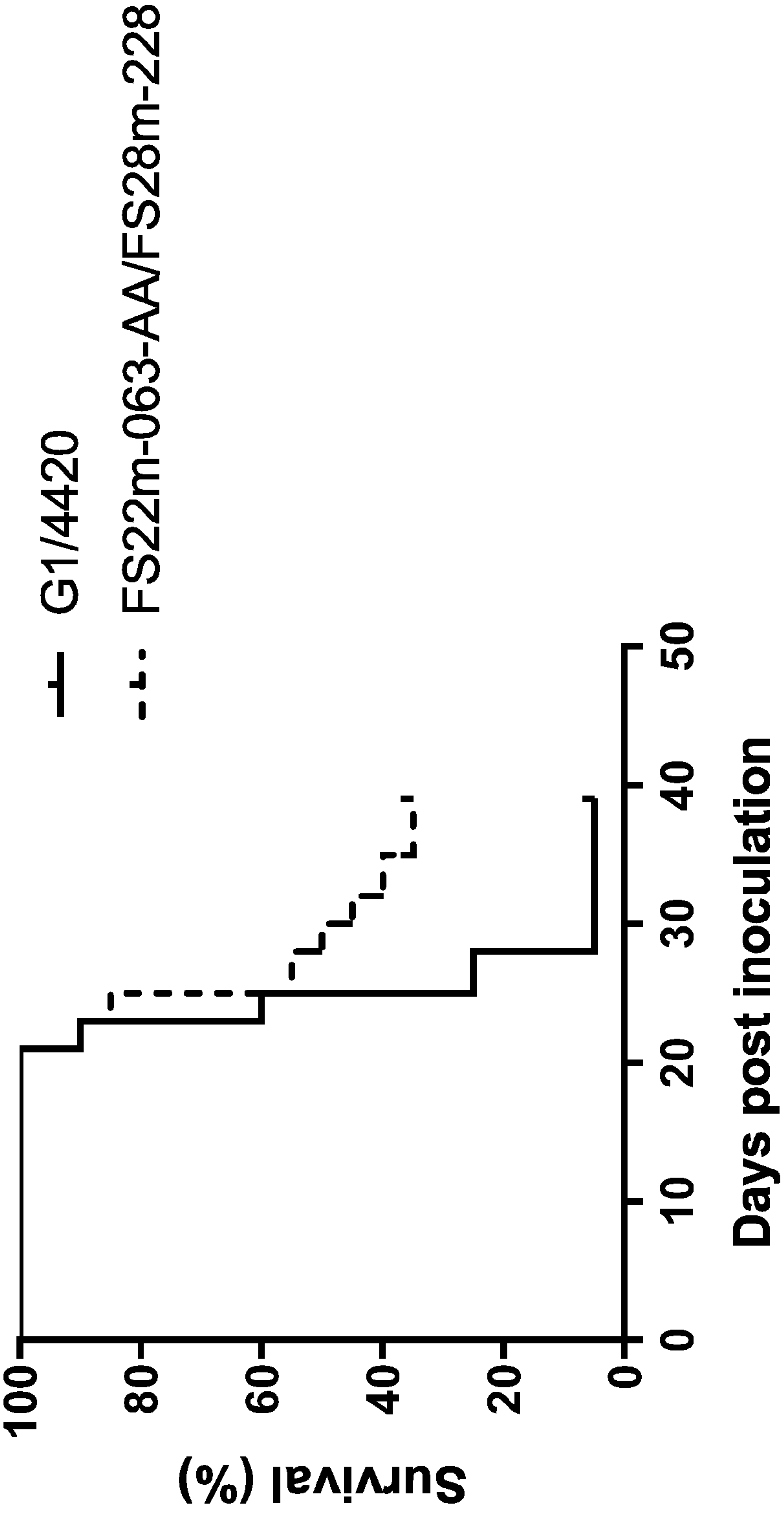
FIG. 9 shows a Kaplan Meier survival plot of mice in the CT26.G10 syngeneic mouse tumour model treated with G1/4420 (human IgG1 isotype control antibody) or FS22m-063-AA/FS28m-228 (anti-mouse CD137/MSLN $mAb^2$). Treatment with FS22m-063-AA/FS28m-228 showed a significant improvement in survival compared to treatment with the human IgG1 isotype control antibody. (Log-rank analysis, **p<0.01)

As shown in FIG. 8, the FS22m-063-AA/FS28m-228 $mAb^2$ treated mice showed reduced tumour growth compared to mice treated with isotype control, with a notable delay in tumour volume increase being observed in FS22m-063-AA/FS28m-228-treated mice compared to the G1/4420-treated group. Moreover, whereas 1/20 (5%) of mice were tumour-free following treatment with G1/4420, 4/20 (20%) of mice were tumour-free following treatment with FS22m-063-AA/FS28m-228 at the end of the study. In addition, as shown in FIG. 9 and Table 16, this translated to a significant improvement in tumour-free survival, as assessed using pairwise log-rank analysis. Specifically, the median survival increased from 25 days (G1/4420) to 29 days with FS22m-063-AA/FS28m-228.

TABLE 16

Number and percentage of tumour-free mice (tumours ≤ 62.5 $mm^3$) by the end of study, median survival (in days) and pairwise statistical analyses (Log-rank) of survival in CT26.G10 syngeneic tumour model

| Groups | Tumour-free mice at study end | Median Survival (Days) | P-values Log-rank |
|---|---|---|---|
| G1/4420 | 1/20 (5%) | 25 | 0.0062 ** |
| FS22m-063-AA/ FS28m-228 | 4/20 (20%) | 29 | |

NS p ≥ 0.05;
* p < 0.05;
** p < 0.01;
*** p < 0.001;
**** p < 0.0001

The $mAb^2$ and isotype controls contained the LALA mutation, so the observed tumour growth inhibition cannot have been the result of ADCC activity as the LALA mutation significantly reduced the ability of the antibodies to bind to Fcγ receptors. It is therefore assumed that no anti-tumour activity would be seen in mice treated with the the LALA mutation-containing anti-MSLN mAb alone. However, the $mAb^2$ containing the LALA mutation was capable of significant tumour growth inhibition even when the LALA mutation was present, which is thought to be due to cross-linking of the $mAb^2$ by the Fab arms binding to MSLN on the cell surface driving clustering and activation of CD137 on immune cells, resulting in the anti-tumour activity of the $mAb^2$.

Example 13: In Vivo Characterisation of Affinity Matured Anti-Mouse CD137/MSLN (FS22m-063-AA/FS28m-228-010) $mAb^2$

13.1 Dose-Response Activity of an Affinity Matured CD137/MSLN $mAb^2$ in a CT26.G10 Syngeneic Mouse Tumour Model Significant anti-tumour efficacy and improvement in survival was observed in syngeneic tumour models expressing high levels of mouse MSLN (CT26.B2) as well as in tumours expressing lower levels of mouse MSLN (CT26.G10) when treated with FS22m-063-AA/FS28m-228 $mAb^2$ (Example 12). It was therefore desirable to investigate the anti-tumour efficacy of the affinity matured FS22m-063-AA/FS28m-228-010 in vivo at a range of doses (6, 20, 60 and 200 μg/mouse, equivalent to approximately 0.3, 1, 3 and 10 mg/kg in a 20 g mouse).

Balb/c female mice (Charles River) aged 9-11 weeks and weighing 17.0-25.2 g each were acclimatised for one week prior to the study start. All animals were micro-chipped and given a unique identified. Each cohort had 20 mice. The CT26.G10 colon carcinoma cell line described in Example 11.2, was expanded and cell banks generated. Each animal received $1\times10^5$ cells injected subcutaneously in the left flank in 100 μl serum free media. 12 days following tumour cell inoculation, mice which did not have tumours were removed from the study.

The FS22m-063-AA/FS28m-228-010 $mAb^2$ was prepared and injected intraperitoneally (IP) into mice at a fixed final concentration according to the dose range described above. The human IgG1 isotype control, (G1-AA/4420) and the anti-CD137 positive control antibody Lob12.3 (G1/Lob12.3) both in human IgG1 backbone and containing the LALA, were included at a dose of 20 μg (~1 mg/kg in a 20 g mouse). All antibodies were prepared in DPBS+1 mM arginine+0.05% Tween 80. Each mouse received the $mAb^2$ molecule or the control antibody by 200 μl IP injection on days 12, 14 and 16 following tumour inoculation. Tumour volume measurements were taken three times per week using calipers as described in Example 12.1, and mice were monitored closely. The study endpoint was determined by humane endpoints based on tumour volume and condition.

STATA/IC 15.1 software was used to implement a mixed model for analysis of the tumour growth rate. Statistical significance was shown pairwise for growth rates over the full time of study using the Mixed Model analysis comparing all groups. A separate model was fitted to each pair of treatments of interest. The model was:

log 10(volume)=A+B×(day−start day)+EA and B are the intercept and slope respectively; they are different for each mouse, and include a fixed effect for the group and a random effect for the animal:

$$A=A0+A1T+\varepsilon A$$

$$B=B0+B1T+\varepsilon B$$

T is a dummy variable representing the treatment group with value 0 in one group and 1 in the other. The random effects are distributed with a normal distribution:

$$\varepsilon A\sim(0,\sigma A),\varepsilon B\sim N(0,\sigma B)$$

where σA and σB are the standard deviations of the inter-animal variability in the intercept and slope respectively. The intra-animal variability is also normally distributed with standard deviation σ:ε~(0,σ)

For each pair of treatments, the model above was fitted to the data. For A1 and B1, the (two-sided) p-value for a difference from zero was calculated; a p-value below 0.05 is statistically significant evidence for a difference between the treatment groups.

Figure 10:
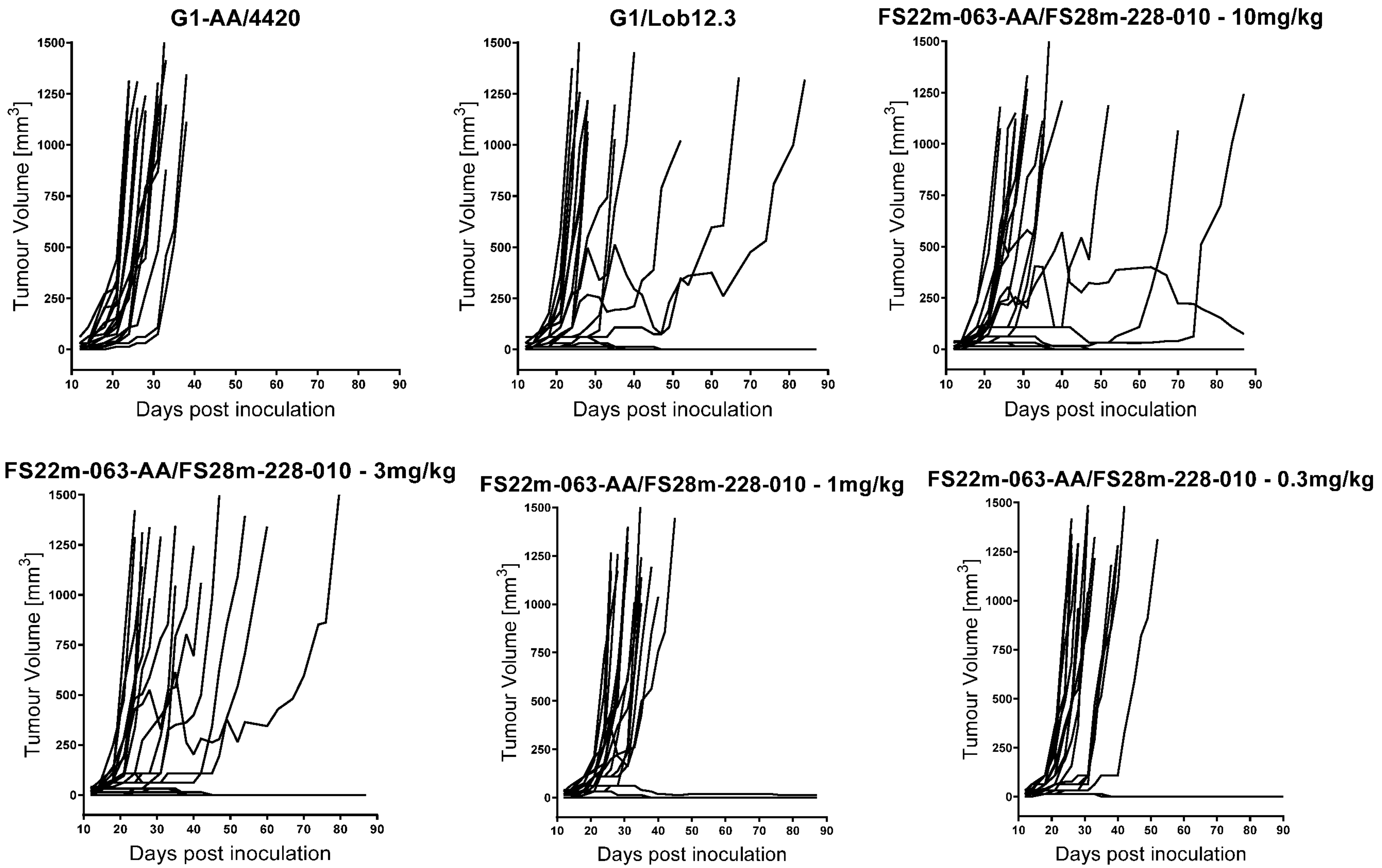
FIG. 10 shows individual tumour volume measurements in the CT26.G10 syngeneic mouse tumour model for mice treated with G1-AA/4420 (IgG control; 20 μg, equivalent to 1 mg/kg in a 20 g mouse), G1/Lob12.3 (wild-type human IgG1 anti-CD137 positive control; 20 μg, equivalent to 1 mg/kg in a 20 g mouse), and FS22m-063-AA/FS28m-228-010 (anti-mouse CD137/MSLN $mAb^2$). Treatment with FS22m-063-AA/FS28m-228-010 showed a dose-dependent reduction in tumour growth compared to human IgG1 isotype control-treated mice.

As shown in FIG. 10, the FS22m-063-AA/FS28m-228-010 $mAb^2$ reduced tumour growth at all dose levels in comparison to the mice treated with the isotype control. All animals bearing tumours measuring equal or below 62.5 $mm^3$ at the end of the study were counted as fully responding animals (see Table 17). 30%, 20%, 20% and 10% of animals treated with FS22m-063-AA/FS28m-228-010 $mAb^2$ at 10, 3, 1 and 0.3 mg/kg, respectively, were deemed to be tumour-free, in comparison to anti-CD137 antibody, G1/Lob12.3 (15%) and G1-AA/4420 isotype control treated animals (0%).

In addition, Table 17 shows a pairwise comparison of the growth rates over the full course of the study using Mixed Model analysis, comparing all groups to the human IgG1 isotype control treatment group. None of the mice showed signs of overt toxicity nor adverse effects, and all treatments were well tolerated in mice.

Figure 11:
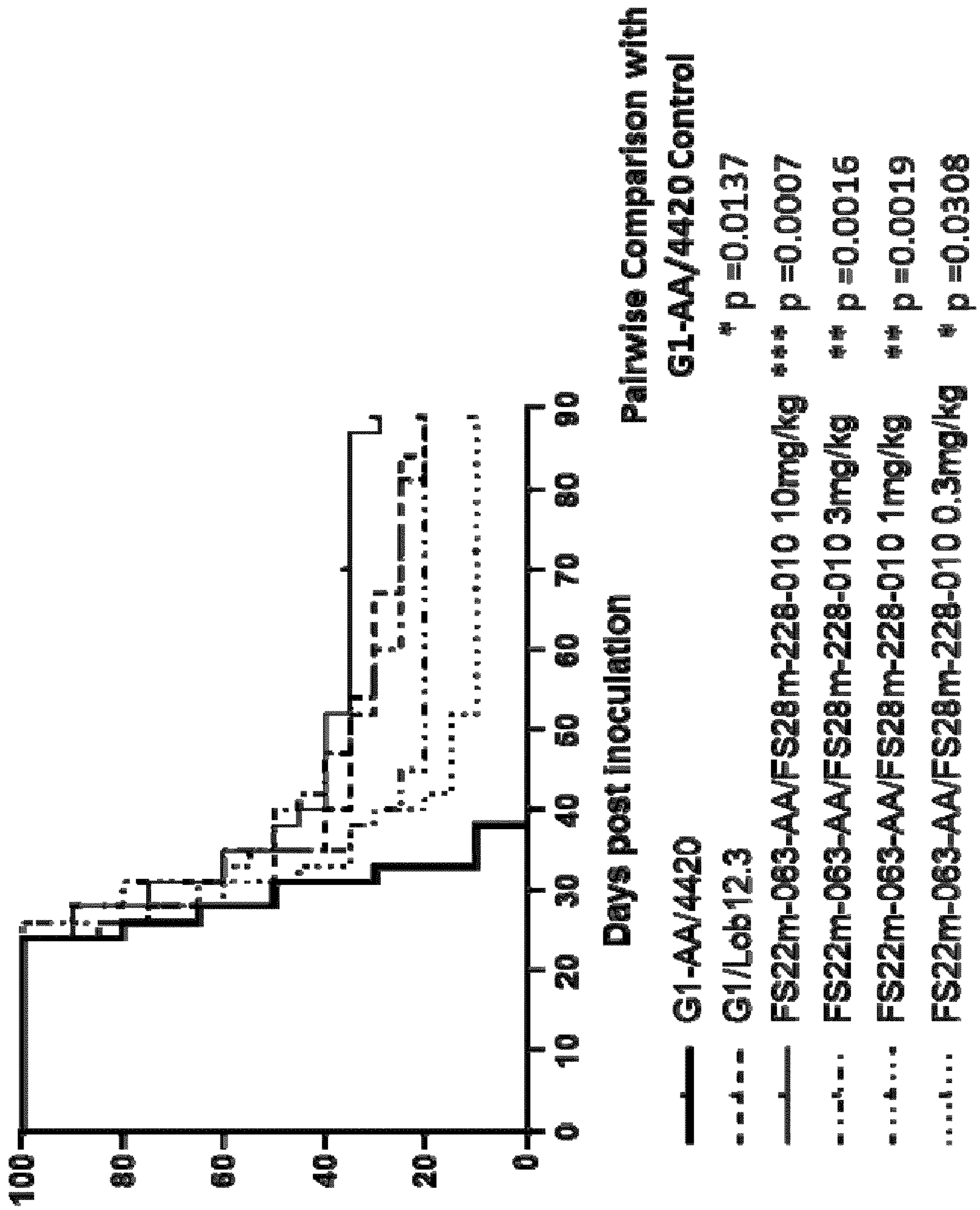
FIG. 11 shows a Kaplan Meier survival plot of mice in the CT26.G10 syngeneic mouse tumour model treated with G1-AA/4420 (human IgG1 control; 20 μg, equivalent to 1 mg/kg in a 20 g mouse), G1/Lob12.3 (wild-type human IgG1 anti-CD137 positive control; 20 μg, equivalent to 1 mg/kg in a 20 g mouse), and FS22m-063-AA/FS28m-228-010 (anti-mouse CD137/MSLN $mAb^2$). Treatment with FS22m-063-AA/FS28m-228-010 at all dose levels tested resulted in a significant improvement in survival compared to the IgG control, and the improvement in survival was dose-dependent. (Log-rank pairwise analysis comparing treatment groups to G1-AA/4420 isotype control, p<0.05, p<0.01, *p<0.001)

Survival analysis (FIG. 11 and Table 18) showed that at all dose levels the FS22m-063-AA/FS28m-228-010 $mAb^2$ induced a significant anti-tumour response in comparison to isotype control (G1-AA/4420)-treated mice, and this response appeared to be dose-dependent. In addition, Table 18 shows a summary of median survival in days for each group, where treatment with 10 mg/kg, 3 mg/kg, 1 mg/kg and 0.3 mg/kg of the mouse CD137/MSLN $mAb^2$ increased the median survival from 29.5 days (G1-AA/4420) to 36.5, 37.5, 35 and 31 days, respectively.

TABLE 17

Number and percentage of tumour-free mice (tumours ≤ 62.5 $mm^3$) by the end of study, and pairwise statistical analyses (Mixed model) comparing all treatment groups to G1-AA/4420 control in CT26.G10 syngeneic tumour model.

| Groups | Tumour-free mice at study end | P-values Mixed Model Analysis comparing treatment groups to G1-AA/4420 control |
|---|---|---|
| G1-AA/4420 1 mg/kg | 1/19 (0%) | |
| G1/Lob12.3 1 mg/kg | 3/20 (15%) | <0.0001 **** |
| FS22m-063-AA/FS28m-228-010 10 mg/kg | 6/20 (30%) | <0.0001 **** |
| FS22m-063-AA/FS28m-228-010 3 mg/kg | 4/20 (20%) | <0.0001 **** |
| FS22m-063-AA/FS28m-228-010 1 mg/kg | 4/20 (20%) | <0.0001 **** |
| FS22m-063-AA/FS28m-228-010 0.3 mg/kg | 2/20 (10%) | <0.0001 **** |

NS p ≥ 0.05;
* p < 0.05;
** p < 0.01;
*** p < 0.001;
**** p < 0.0001

TABLE 18

Median survival times for animals treated with each compound, and pairwise statistical analyses (Log-rank) comparing all treatment groups to G1-AA/4420 control in CT26.G10 syngeneic tumour model.

| Groups | Median Survival (Days) | P-values Log-rank Analysis comparing treatment groups to G1-AA/4420 control |
|---|---|---|
| G1-AA/4420 1 mg/kg | 29.5 | |
| G1/Lob12.3 1 mg/kg | 31.5 | 0.0137 * |
| FS22m-063-AA/FS28m-228-010 10 mg/kg | 36.5 | 0.0007 *** |
| FS22m-063-AA/FS28m-228-010 3 mg/kg | 37.5 | 0.0016 ** |
| FS22m-063-AA/FS28m-228-010 1 mg/kg | 35 | 0.0019 ** |
| FS22m-063-AA/FS28m-228-010 0.3 mg/kg | 31 | 0.0308 * |

NS p ≥ 0.05;
* p < 0.05;
** p < 0.01;
*** p < 0.001;
**** p < 0.0001

Similar to the FS28m-228 MSLN Fab in CD137/MSLN $mAb^2$ format, the FS28m-228-010 Fab in CD137/MSLN $mAb^2$ format also resulted in a significant reduction in tumour growth compared to isotype control. Moreover, the dose-dependent significant improvement in survival with $mAb^2$ suggests that cross-linking of the $mAb^2$ to MSLN target by the Fab arms drives agonism of CD137, and therefore the anti-tumour efficacy observed in vivo.

13.2 Anti-Tumour Efficacy of FS22m-063-AA/FS28m-228-010 in Comparison with its Component Parts in a CT26.G10 Syngeneic Tumour Model Having shown that FS22m-063-AA/FS28m-228-010, had significant anti-tumour efficacy and improved survival in tumour-bearing mice, it was desirable to determine whether the $mAb^2$ demonstrated superior anti-tumour activity in vivo compared to its individual component parts. Treatment with the mouse MSLN antibody (G1-AA/FS28m-228-010), the CD137 Fcab in "mock" $mAb^2$ formats (FS22m-063-AA/HelD1.3 and FS22m-063-AA/4420), combinations of the Mouse MSLN antibody and the CD137 Fcab in mock $mAb^2$ format (i.e. G1-AA/FS28m-228-010 plus FS22m-063-AA/HelD1.3), and FS22m-063-AA/FS28m-228-010 $mAb^2$ were compared to treatment with the human isotype control antibody (G1-AA/HelD1.3).

Mice were prepared according to Example 13.1 and inoculated with the CT26.G10 colon carcinoma cell line. All cohorts had 20 mice, with the exception of FS22m-063-AA/4420 which had 10 mice.

FS22m-063-AA/FS28-228-010 $mAb^2$, G1-AA/FS28m-228-010, FS22m-063-AA/HelD1.3, FS22m-063-AA/4420 and G1-AA/HelD1.3 antibodies were all prepared at 200 μg per dose (approximately 10 mg/kg in a 20 g mouse) and injected at a fixed dose intraperitoneally (IP) into mice. In addition, both the CD137 mock $mAb^2$ and MSLN antibody were prepared at 200 μg per dose (approximately 10 mg/kg in a 20 g mouse) for the combination groups. All antibodies were prepared in DPBS+1 mM arginine+0.05% Tween 80. Similar to the dosing regimen in Example 13.1, each mouse received the antibodies by 200 μl intraperitoneal injection on days 12, 14 and 16 (q2dx3) following tumour inoculation. Tumour volume measurements were made three times per week using calipers as described in Example 12.1, and mice were monitored closely. The study endpoint was determined by humane endpoints based on tumour volume and condition.

Figure 12:
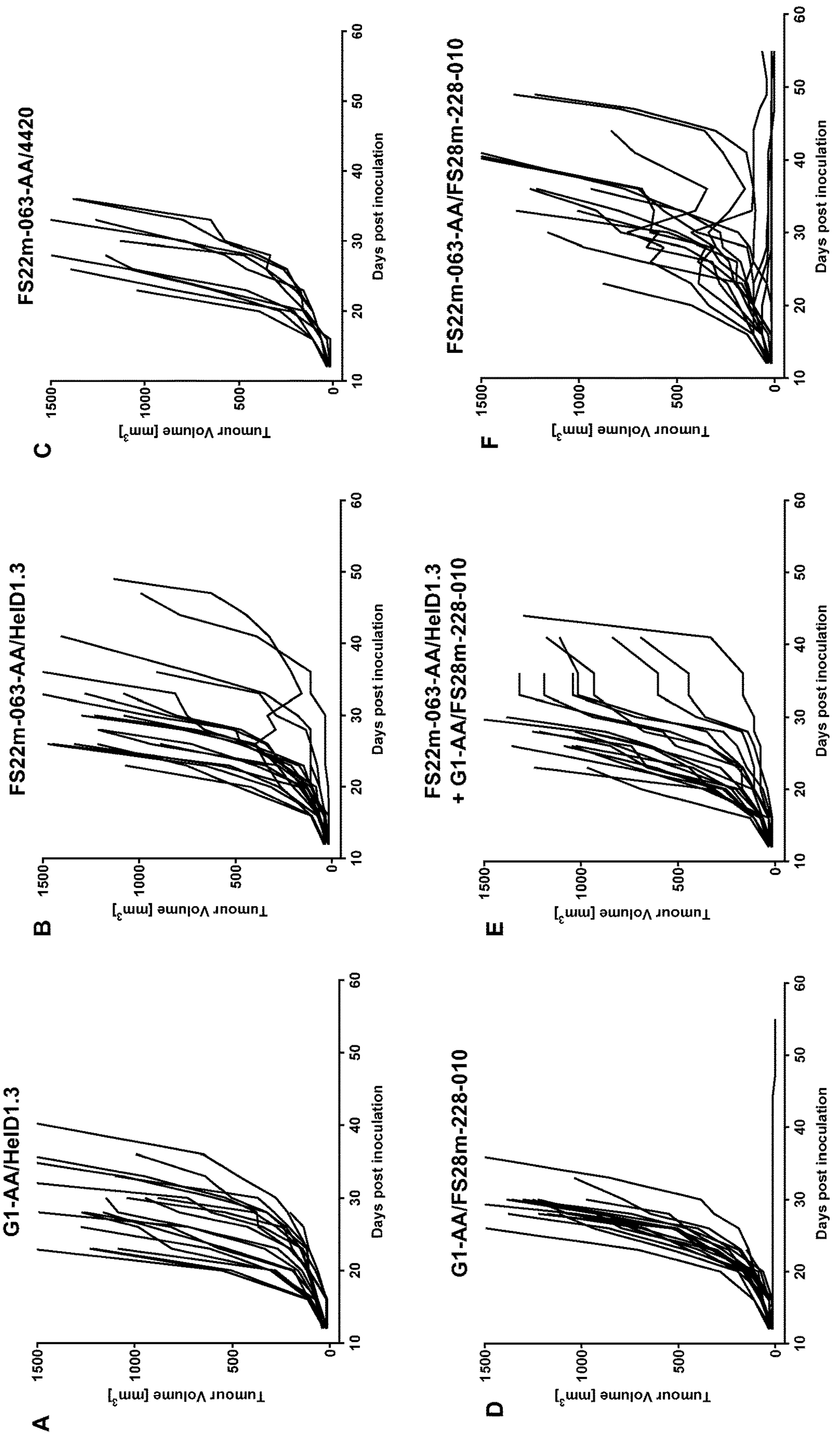
FIG. 12 shows individual tumour volume measurements in the CT26.G10 syngeneic mouse tumour model for mice treated with (A) G1-AA/HelD1.3 (human IgG1 control), (B) FS22m-063-AA/HelD1.3 (anti-mouse CD137 Fcab in 'mock' $mAb^2$ format), (C) FS22m-063-AA/4420 (anti-mouse CD137 Fcab in $mAb^2$ format), (D) G1-AA/FS28m-228-010 (anti-mouse MSLN antibody), (E) combination of FS22m-063-AA/HelD1.3 plus G1-AA/FS28m-228-010 (anti-mouse CD137 Fcab in 'mock' $mAb^2$ format plus anti-mouse MSLN Fab), and (F) FS22m-063-AA/FS28m-228-010 (anti-mouse CD137/MSLN $mAb^2$). The results show that whilst 7/20 (35%) of mice treated with FS22m-063-AA/FS28m-228-010 had no palpable tumours at the end of the study, with the exception of G1-AA/FS28m-228-010 (1/20, 5%), all mice dosed with the other treatments had tumours ≥62.5 $mm^3$ at the end of study.

As shown in FIG. 12, treatment with the FS22m-063-AA/FS28m-228-010 $mAb^2$ resulted in significantly reduced tumour growth compared to mice treated with the G1-AA/HelD1.3 isotype control. All animals bearing tumours measuring equal or below 62.5 $mm^3$ at the end of the study were counted as fully responding animals (see Table 19). 7/20 (35%) of FS22m-063-AA/FS28-228-010 $mAb^2$-treated animals were deemed to be complete responders to treatment at the end of study, compared to 1/20 (5%) of the G1-AA/FS28m-228-010-treated mice and 0/20 (0%) of the G1-AA/HelD1.3 isotype control, FS22m-063-AA/HelD1.3, FS22m-063-AA/4420, and combination of FS22m-063-AA/HelD1.3 plus G1-AA/FS28m-228-010-treated mice.

In addition, Table 19 shows pairwise comparison of the growth rates over the full course of the study using Mixed Model analysis, comparing all groups to the G1-AA/HelD1.3 isotype control.

Figure 13:
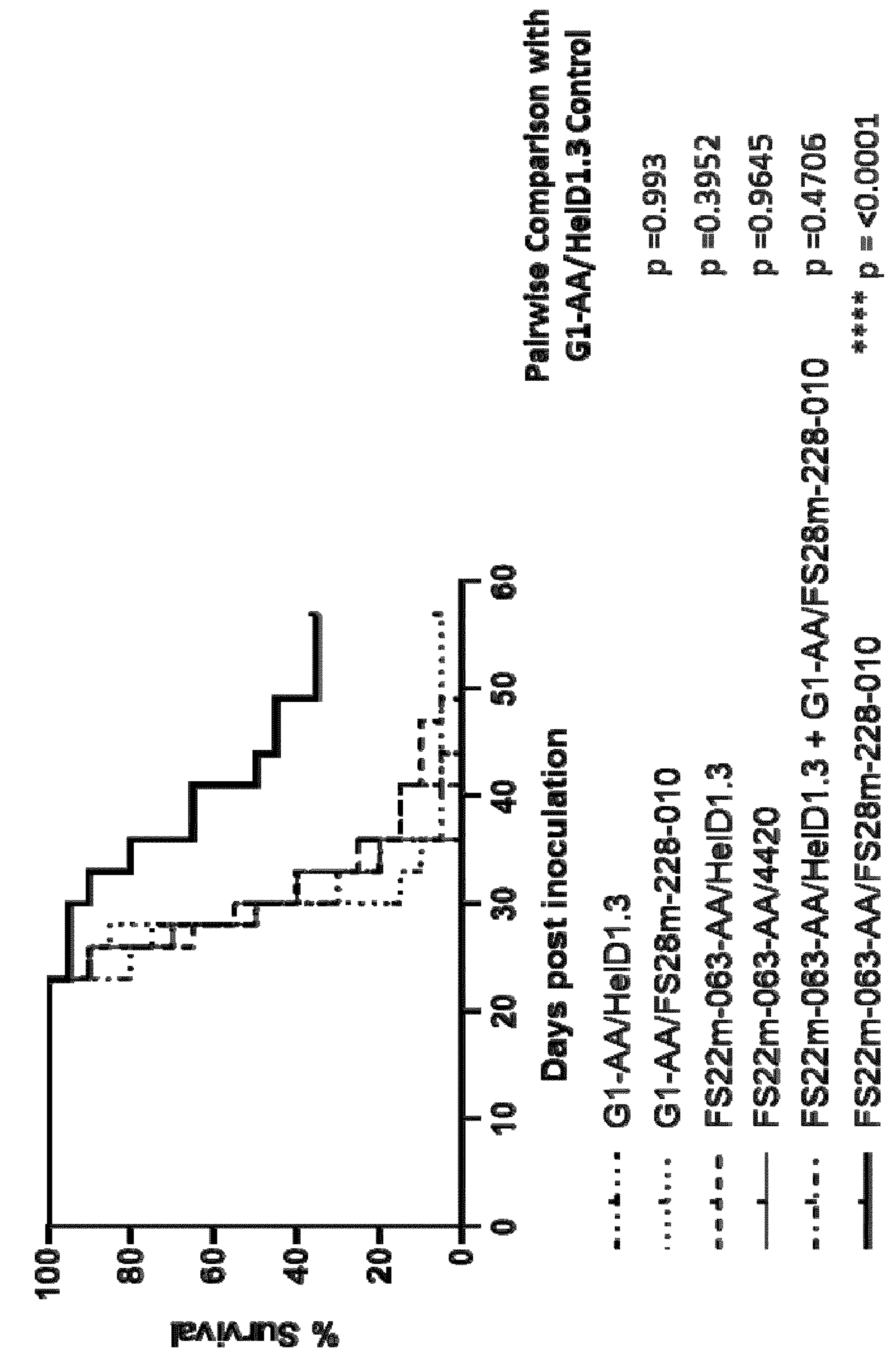
FIG. 13 shows a Kaplan Meier survival plot of mice in the CT26.G10 syngeneic mouse tumour model treated with G1-AA/HelD1.3 (IgG control), FS22m-063-AA/HelD1.3 (anti-mouse CD137 Fcab in 'mock' $mAb^2$ format with non-binder Fab, anti-HelD1.3), FS22m-063-AA/4420 (anti-mouse CD137 Fcab in 'mock' $mAb^2$ format with non-binder Fab, anti-4420), G1-AA/FS28m-228-010 (anti-mouse MSLN antibody), combination of FS22m-063-AA/HelD1.3 plus G1-AA/FS28m-228-010 (anti-mouse CD137 Fcab plus anti-mouse MSLN antibody), and FS22m-063-AA/FS28m-228-010 (anti-mouse CD137/MSLN $mAb^2$). The results show that whereas mice treated with one of the two anti-mouse CD137 Fcabs in 'mock' $mAb^2$ format, or the anti-mouse MSLN antibody, as well as mice in the the combination treatment group did not show any improvement in survival compared to the isotype control treated mice, mice treated with FS22m-063-AA/FS28m-228-010-showed improved survival compared to the isotype control treated mice. (Log-rank pairwise analysis comparing treatment groups to G1-AAHelD1.3 isotype control, ****p<0.0001).

Survival analysis (FIG. 13 and Table 20) showed that the FS22m-063-AA/FS28m-228-010 $mAb^2$ induced a significant survival benefit in comparison to the G1-AA/HelD1.3 antibody, whereas the components did not result in a survival advantage. In addition, treatment with the FS22m-063-AA/FS28m-228-010 $mAb^2$ resulted in an improved median survival of 42.5 days compared with G1-AA/HelD1.3 (29 days), FS22m-063-AA/HelD1.3 (30 days), FS22m-063-AA/4420 (29 days), G1-AA/FS28m-228-010 (30 days) and combination of FS22m-063-AA/HelD1.3 with G1-AA/FS28m-228-010 (29 days).

TABLE 19

Number and percentage of tumour-free mice (tumours ≤ 62.$mm^3$) by the end of study, and pairwise statistical analyses (Mixed model) comparing all treatment groups to G1-AA/HelD1.3 control in CT26.G10 syngeneic tumour model.

| Groups | Tumour-free mice at study end | P-values Mixed Model Analysis comparing all treatment groups to G1-AA/HelD1.3 control |
|---|---|---|
| G1-AA/HelD1.3 10 mg/kg | 0/20 (0%) | |
| G1-AA/FS28m-228-010 10 mg/kg | 1/20 (5%) | 0.4367 NS |
| FS22m-063-AA/HelD1.3 10 mg/kg | 0/20 (0%) | 0.0017 *** |
| FS22m-063-AA/4420 10 mg/kg | 0/10 (0%) | 0.7067 NS |
| G1-AA/FS28m-228-010 10 mg/kg + FS22m-063-AA/HelD1.3 10 mg/kg | 0/20 (0%) | 0.2093 NS |
| FS22m-063-AA/FS28m-228-010 10 mg/kg | 7/20 (35%) | 0.0000 **** |

NS $p \geq 0.05$;
* $p < 0.05$;
** $p < 0.01$;
*** $p < 0.001$;
**** $p < 0.0001$

TABLE 20

Median survival times for animals treated with each compound, and pairwise statistical analyses (Log-rank) comparing all treatment groups to G1-AA/HelD1.3 control in CT26.G10 syngeneic tumour model.

| Groups | Median Survival (Days) | P-values Log-rank Analysis comparing all treatment groups to G1-AA/HelD1.3 control |
|---|---|---|
| G1-AA/HelD1.3 10 mg/kg | 29 | |
| G1-AA/FS28m-228-010 10 mg/kg | 30 | 0.993 NS |
| FS22m-063-AA/HelD1.3 10 mg/kg | 30 | 0.3952 NS |
| FS22m-063-AA/4420 10 mg/kg | 29 | 0.9645 NS |
| G1-AA/FS28m-228-010 10 mg/kg + FS22m-063-AA/HelD1.3 10 mg/kg | 29 | 0.4706 NS |
| FS22m-063-AA/FS28m-228-010 10 mg/kg | 42.5 | <0.0001 **** |

NS $p \geq 0.05$;
* $p < 0.05$;
** $p < 0.01$;
*** $p < 0.001$;
**** $p < 0.0001$ These data demonstrate that a bispecific molecule targeting both CD137 and MSLN is required for in vivo activity, since the $mAb^2$ results in tumour growth inhibition at a level which is not observed when the individual components of the mAb2 are administered either alone or in combination.

13.3 Liver Pharmacology of Anti-Mouse CD137/MSLN $mAb^2$ in CT26.G10 Syngeneic Mouse Tumour Bearing Model Anti-CD137 mAb treatment of solid tumour patients with urelumab in investigative clinical trials has resulted in severe treatment related immune events which have been shown to be related to the dose of urelumab administered. The effects of these immune events manifested in the liver as severe hepatoxicity (Segal, N. H., et al., 2017).

Preclinical mechanistic work undertaken in mice wherein animals were dosed using CD137 agonistic tool antibodies has shown similar hepatotoxicity. These studies showed a requirement for T cells and CD137 in the resultant hepatotoxicity (Niu, L., et al. 2007 and Dubrot J, et al. 2010). Although poorly understood, the interplay between the myeloid and T cell compartments has also been shown to be important in initiating the inflammatory cascade leading to liver damage and hepatotoxicity (Bartkowiak, T et al., 2018). Therefore, these animal models have translational relevance for the clinic in predicting the risk of hepatoxicity in human patients following administration of other CD137 agonists, such as a CD137/MSLN $mAb^2$.

Mice from the CT26.G10 syngeneic tumour studies described in Examples 13.1 and 13.2, showed no overt signs of toxicity following repeated dosing with FS22m-063-AA/FS28m-228-010 $mAb^2$. To determine whether in these animals the immune activation correlated with hepatotoxicity mice were dosed following a similar dosing regimen as shown in Examples 13.1 and 13.2, mice were culled at four time-points post dosing and liver samples were taken at necropsy for histological assessment.

Mice were prepared as described in Example 13.1, and mice were inoculated with the CT26.G10 colon carcinoma cell line. Each cohort consisted of 24 mice. FS22m-063-AA/FS28-228-010 $mAb^2$ (CD137/MSLN) and G1-AA/4420 (human IgG1 isotype control) antibodies were prepared in DPBS+1 mM arginine+0.05% Tween 80 at 200 μg per dose (approximately 10 mg/kg in a 20 g mouse) and injected intraperitoneally (IP) into mice at a fixed dose. Each mouse received the antibodies by 200 μl intraperitoneal injection on days 12, 14 and 16) following tumour inoculation. Tumour volume measurements were made three times per week using calipers as described in Example 12.1, and mice were monitored closely. Six mice per group were necropsied 2, 5, 8 and 11 days after the last dose administration, and liver samples were formed fixed and paraffin embedded. Sections of liver were then cut and subjected to histopathological evaluation via haematoxylin and eosin staining and scoring of liver inflammation and damage by an independent, certified veterinary pathologist.

A scoring system was used to assess liver pathology in the haematoxylin and eosin stained sections. Liver was scored for pathology corresponding to multifocal mixed inflammatory cells, multifocal degenerate hepatocytes, increased hepatocyte mitoses and portal mixed inflammatory cell infiltrate. The frequency of mice showing minimal, mild and moderate effects within each group are shown in Table 21.

FS22m-063-AA/FS28-228-010 $mAb^2$ treated animals presented with minimal liver pathology, specifically:

- Minimal multifocal mixed inflammatory cells (primarily granulocytes) located throughout the parenchyma
- Minimal degenerating hepatocytes scattered throughout the parenchyma
- Minimal degenerating hepatocytes
- Minimal mixed inflammatory cells in portal tracts

TABLE 21

Liver pharmacology results

| Liver histopathology | G1-AA/4420 10 mg/kg D2 | D5 | D8 | D11 | FS22m-063-AA/FS28m-228-010 10 mg/kg D2 | D5 | D8 | D11 |
|---|---|---|---|---|---|---|---|---|
| Multifocal mixed inflammatory cells (primarily granulocytes, parenchymal/central vein) | | | | | | | | |
| Minimal | 0 | 0 | 0 | 0 | 0 | 1 | 2 | 4 |
| Mild | 0 | 0 | 0 | 0 | 0 | 0 | 0 | 0 |
| Multifocal degenerate hepatocytes (parenchymal) | | | | | | | | |
| Minimal | 0 | 0 | 0 | 0 | 0 | 2 | 2 | 4 |
| Mild | 0 | 0 | 0 | 0 | 0 | 0 | 0 | 0 |
| Increased hepatocyte mitoses (parenchymal) | | | | | | | | |
| Minimal | 1 | 1 | 4 | 1 | 0 | 4 | 4 | 3 |
| Mild | 0 | 1 | 1 | 0 | 1 | 0 | 1 | 2 |
| Moderate | 0 | 0 | 0 | 0 | 0 | 1 | 0 | 1 |
| Portal mixed inflammatory cell infiltrate | | | | | | | | |
| Minimal | 0 | 1 | 0 | 2 | 1 | 2 | 1 | 2 |

These findings do not represent hepatotoxicity, as observed with other examples of anti-CD137 agonist antibodies. In addition, given that the $mAb^2$ agonizes CD137 via crosslinking mediated through MSLN binding, and MSLN is predominantly overexpressed on the cell surface of tumour cells, but not in the liver (Ordóñez 2003, 14576474), it is expected that CD137 agonism will be limited to the tumour microenvironment.

13.4 Mechanism of Action of Anti-Mouse CD137/MSLN $mAb^2$ in a CT26.G10 Syngeneic Mouse Tumour Model With limited liver pharmacology observed following repeated dosing with the CD137/MSLN $mAb^2$ (Example 13.3), and to further understand the pharmacology of the anti-tumour response observed with FS22m-063-AA/FS28m-228-010, the mechanism of action of CD137/MSLN $mAb^2$ in a MSLN-positive syngeneic tumour model was investigated.

Mice were prepared as described in Example 13.1, and inoculated with the CT26.G10 colon carcinoma cell line. Each cohort consisted of 20 mice. FS22m-063-AA/FS28-228-010 (CD137/MSLN) $mAb^2$, human IgG1 isotype control (G1-AA/4420) and an anti-CD137 agonist antibody (clone 3H3; G1/3H3) was also included for comparison. All three antibodies were prepared at 134 μg per dose (approximately 6.7 mg/kg in a 20 g mouse) in DPBS+1 mM arginine+0.05% Tween 80 and injected intraperitoneally (IP) into mice. Each mouse received the antibodies by one 200 μl intraperitoneal injection at a fixed dose of 134 μg on day 20 following tumour inoculation. Tumour volume measurements were made three times per week using calipers as described in Example 12.1, and mice were monitored closely.

Six mice per group were necropsied 24, 72, 144 and 192 hours post dose at day 20 following tumour inoculation. Spleen, blood and tumour tissue were taken for analysis from CT26.G10 tumour-bearing mice treated with either FS22m-063-AA/FS28-228-010, G1-AA/4420, or G1/3H3. All samples were investigated for T cell abundance and proliferation by flow cytometry, as T cell activation and proliferation markers are known to be downstream effects of CD137 agonism (Fisher et al., 2012). In addition, serum from blood was also collected for detection and quantification of soluble MSLN expression. Spleen and tumour tissue were disaggregated to single cell suspension by standard mechanical and enzymatic methods, and red blood cells were lysed once in red blood cell lysis buffer (Miltenyi Biotec Ltd., 130-094-183). Blood was collected by terminal cardiac bleed, and half collected into EDTA-containing tubes for single cell analysis by flow cytometry and half of blood was collected into clotting activator/serum tubes for analysis of soluble MSLN. Whole blood collected in EDTA-containing tubes were lysed three times in red blood cell lysis buffer (Miltenyi Biotec Ltd., 130-094-183) according to Manufacturer's instructions. Blood collected in serum tubes was fractionated by centrifugation and serum removed for analysis of soluble MSLN.

Single cells from spleen, tumour and blood were then treated the same, and cells were washed once with PBS and samples stained with fixable viability dye (eBioscience, 65-0865-14). Cells were subsequently stained for cell surface markers with an antibody staining panel shown in Table 22 (all but intracellular markers, Ki67 and FoxP3), in the presence of Fc block (eBioscience, 16-0161-85 at 1:25) for 45 minutes at 4° C. Cells were then fixed and permeabilised with the eBioscience FoxP3 staining kit (eBioscience, 00-5523-00) according to manufacturer's instructions. Cells were resuspended in 100 μl permeabilization buffer with intracellular markers Ki67 and FoxP3 antibodies and incubated overnight at 4° C. in the dark. Prior to acquisition on a BD Fortessa flow cytometer, cells were washed once with permeabilization buffer and resuspended in 120 μl PBS containing 0.5% BSA. Data was acquired using BD FACS Diva software, and analysed with FlowJo (V10), and Microsoft Excel. The data shows the abundance and proliferation of $CD8^+$ T cells at 144 hours following dosing, as a percentage of the parental population.

TABLE 22

Flow Cytometry panel

| Target | Clone | Fluorophore | Manufacturer | Cat No. |
|---|---|---|---|---|
| CD45 | 30-F11 | Alexa700 | eBioscience | 56-0451 |
| CD3e | 145-2C11 | PE-Cy7 | eBioscience | 25-0031-82 |
| CD8 | 53-6.7 | BUV737 | BD Bioscience | 564297 |
| CD4 | RM4-5 | BUV395 | BD Bioscience | 740208 |
| FoxP3 | FJK-16s | PerCP-Cy5.5 | eBioscience | 45-5773 |
| CD49b | DX5 | BV421 | Biolegend | 563063 |
| CD103 | M290 | BV786 | BD Bioscience | 564322 |
| CD137 | 17B5 | APC | eBioscience | 106110 |
| CD69 | H1.2F3 | BV510 | Biolegend | 104505 |
| PD1 | 29F.1A12 | FITC | Biolegend | 135220 |
| Ki67 | SolA15 | PE | eBioscience | 12-5698-82 |
| Viability | N/A | eFluor780 | eBioscience | 65-0865-14 |

As shown in Table 23, an increase in the percentage of $CD8^+$ T cells in the tumour was observed at 144 hours following dosing with G1/3H3 and FS22m-063-AA/FS28-228-010 $mAb^2$, compared to the control treatment group (G1-AA/4420). The mean percentage of $CD8^+$ T cells in the tumour increased from 32.1% (G1-AA/4420) to 56.1% with G1/3H3 and 58.4% with FS22m-063-AA/FS28m-228-010 at 144 hours post dose.

In addition, an increase in the abundance of $CD8^+$ T cells was also observed in the blood and spleen, but only with G1/3H3 in comparison to IgG1 control. In the blood at 144 hours post dose, the mean percentage of $CD8^+$ T cells increased from 22.6% (G1-AA/4420) to 57.0% (G1/3H3), yet this increase was not observed with FS22m-063-AA/FS28m-228-010 (25.8%). Similarly, in the spleen, the mean percentage of $CD8^+$ T cells increased from 28.8% (G1-AA/4420) to 38.0% with G1/3H3, yet this increase was not observed with FS22m-063-AA/FS28m-228-010 (29%).

This suggests that the FS22m-063-AA/FS28m-228-010 $mAb^2$ increases $CD8^+$ T cells specifically in the tumour, where MSLN is expressed, whereas the CD137-targeting antibody, G1/3H3, also demonstrates peripheral (blood and spleen) increases in $CD8^+$ T cells.

To identify whether there were any differences in the proliferation of $CD8^+$ T cells following dosing, proliferation marker, Ki67, was analysed on $CD8^+$ T cells in tumour, blood and spleen. As shown in Table 24, a high proportion of $CD8^+$ T cells expressed $Ki67^+$ in the control group (mean expression of 75.1%), suggesting a high level of proliferating $CD8^+$ T cells in the tumour in the CT26.G10 model. This may contribute to the unclear differences in Ki67 expression on $CD8^+$ T cells between dose groups in the tumour.

In comparison, a clear increase in $Ki67^+$ expression on $CD8^+$ T cells in the blood and spleen was observed at 144 hours post dosing with G1/3H3 in comparison to the IgG1 control. In the blood, whereas the isotype control-treated mice show a mean $Ki67^+$ expression on $CD8^+$ T cells of 10.4%, the mean expression of Ki67 on $CD8^+$ T cells following dosing with G1/3H3 is shown to be 86.3% at 144 hours post dose. In comparison, this increase was not observed with FS22m-063-AA/FS28m-228-010, where the mean $Ki67^+$ expression on $CD8^+$ T cells was observed at 13.1% following dosing with $mAb^2$ in the blood. Similarly, in the spleen, mean $Ki67^+$ expression was observed on 36.1% of $CD8^+$ T cells following dosing with G1/3H3, in comparison to 8.1% observed following dosing with isotype control and 11.4% observed with FS22m-063-AA/FS28m-228-010.

TABLE 23

The mean percentage of $CD8^+$ T cells of total $CD3^+$ cells in the tumour, blood and spleen at 144 hours post dosing with G1-AA/4420, G1/3H3 or FS22m-063-AA/FS28m-228-010. Data shows mean percentage $CD8^+$ T cells of total $CD3^+$ T cells ± standard error of the mean.

| | G1-AA/4420 % ± SEM | G1/3H3 % ± SEM | FS22m-063-AA/FS28m-228-010 % ± SEM |
|---|---|---|---|
| Tumour | 32.1 ± 5.8 | 56.1 ± 2.8 | 58.4 ± 5.0 |
| Blood | 22.6 ± 0.6 | 57.0 ± 1.6 | 25.8 ± 0.6 |
| Spleen | 28.8 ± 0.4 | 38.0 ± 0.8 | 29.0 ± 0.9 |

TABLE 24

The mean percentage of Ki67 expressed on CD8+ T cells in the tumour, blood and spleen at 144 hours post dosing with G1-AA/4420, G1/3H3 or FS22m-063-AA/FS28m-228-010. Data shows mean percentage of Ki67+ of total CD8+ T cells ± standard error of the mean.

| | G1-AA/4420 % ± SEM | G1/3H3 % ± SEM | FS22m-063-AA/FS28m-228-010 % ± SEM |
|---|---|---|---|
| Tumour | 75.1% ± 2.9 | 85.1% ± 2.8 | 77.6% ± 5.0 |
| Blood | 10.4% ± 1.0 | 86.3% ± 0.7 | 13.1 ± 3.4 |
| Spleen | 8.1% ± 0.3 | 36.1 ± 1.7 | 11.4% ± 1.4 |

Serum collected from six mice per group dosed with either FS22m-063-AA/FS28-228-010, G1-AA/4420 or G1/3H3 was analysed for levels of soluble MSLN using a Mesothelin Mouse SimpleStep ELISA Kit (Abcam, ab204528), according to manufacturer's instructions for serum. Data were plotted in Prism and concentration of serum MSLN levels shown over time. As shown in Table 25, there was an increase in serum levels of MSLN with G1/3H3 and FS22m-063-AA/FS28m-228-010, compared to isotype control G1-AA/4420, at 144 hour post dosing. As this similar increase is observed for both G1/3H3 and FS22m-063-AA/FS28m-228-010 mAb$^2$, and MSLN is predominantly expressed on tumour cells in the CT26.G10 syngeneic mouse model, this suggests that CD137-agonism in the tumour may be increasing soluble MSLN which is detected in the serum.

TABLE 25

Mean soluble MSLN in serum, relative to G1-AA/4420 levels, at 144 hours post dosing with G1-AA/4420, G1/3H3 or FS22m-063-AA/FS28m-228-010. Data shows mean relative to G1-AA/4420 levels ± standard error of the mean.

| | G1-AA/4420 | G1/3H3 | FS22m-063-AA/FS28m-228-010 |
|---|---|---|---|
| sMSLN | 1.0 | 9.5 ± 1.6 | 7.6 ± 1.2 |

Taken together, these data show that FS22m-063-AA/FS28m-228-010 mediated a tumour-specific increase in cytotoxic CD8+ T cells in the tumour. Although this was also observed with G1/3H3, unlike the FS22m-063-AA/FS28m-228-010 mAb$^2$, G1/3H3 also promoted a peripheral increase in CD8+ T cells in the blood and spleen. Furthermore, these CD8+ T cells also showed increased proliferation following dosing with G1/3H3. The main role of CD8+ T cells (also called cytotoxic lymphocytes) is the killing of infected or malignant cells via three main mechanisms: 1) release of cytokines e.g. TNFα and IFNγ, 2) production and release of cytotoxic granules and 3) expression of FasL. The increase in CD8+ T cells in the tumour following treatment may therefore result in cytotoxic activity via these mechanisms against the tumour, which may consequently lead to an increased release of mesothelin, as a result of tumour cell killing, as observed in this example. Since the tumours do not express CD137, it is hypothesised the release of mesothelin is an indirect PD response brought about by T cell-mediated cytotoxicity.

Example 14: Pharmacokinetics of Anti-Mouse CD137/MSLN mAb$^2$ and Anti-Human CD137/MSLN mAb$^2$ in Mice

14.1 Pharmacokinetics of Anti-Mouse CD137/MSLN mAb$^2$ (FS22m-063-AA/FS28-228-010) in Non-Tumour Bearing Mice In order to determine the pharmacokinetics of the anti-mouse CD137/MSLN mAb$^2$ in mice, non-tumour bearing C57BL/6 female mice were dosed once intravenously with 10 mg/kg of anti-mouse CD137/MSLN mAb$^2$ (FS22m-063-AA/FS28m-228-010) or human IgG1 control antibody (G1/4420) and monitored for up to 144 hrs.

Microsampling of approximately 20 μl of whole blood was performed at 0.5, 1, 6, 24, 48, 96 and 144 hours, and processed to isolate approximately 5 μl of serum for analysis. The amount of antibody present at each time point was determined using the Gyrolab xPlore system (system name XPS1055) by Gyros Protein Technologies. A sandwich assay was performed using Gyrolab Bioaffy 200 CDs (Gyros Protein Technologies, P0004180) with biotinylated goat anti-human IgG-(heavy and light chain) monkey adsorbed antibody (Cambridge Biosciences, A80-319B) as capture antibody and goat anti-human IgG-AlexaFluor® 647 (Cambridge Biosciences, 2040-31) as detection antibody. A standard curve generated in the range of 4000 ng/mL to 0.0677 ng/mL of each compound was prepared in 0.1% mouse serum (Sigma-Aldrich M5905) in Rexxip AN buffer (Gyros Protein Technologies, P0004994) to determine sample concentration, with samples undergoing 1:1000 dilution in Rexxip AN (Gyros Protein Technologies, P0004994). The average sample concentration from individual mice per time point (three mice per time point) was plotted.

Figure 14:
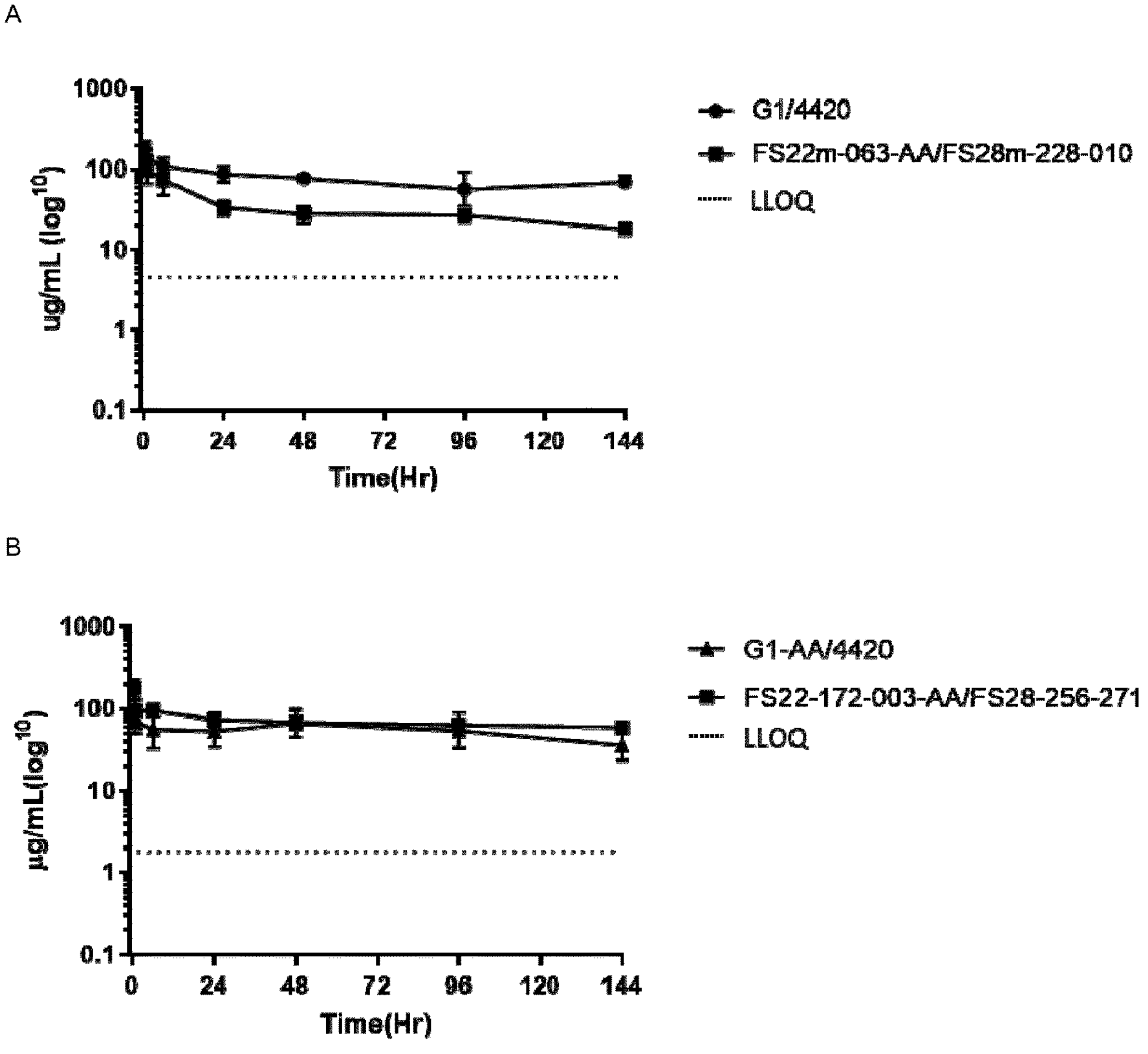
FIG. 14 shows the pharmacokinetic profile of anti-human CD137/MSLN $mAb^2$ and anti-mouseCD137/MSLN $mAb^2$ in a non-tumour bearing C57BL/6 mouse model. A: shows anti-mouse CD137/MSLN $mAb^2$ (FS22m-063-AA/FS28m-228-010) at 10 mg/kg, in comparison with 10 mg/kg human IgG1 isotype control (G1/4420), after a single intravenous dose (n=3 per group). Both the human IgG1 isotype control and the FS22m-063-AA/FS28m-228-010 $mAb^2$ maintained high levels of exposure at 70.30 and 18.11 μg/ml, respectively, at 144 hours post dose. The lower limit of quantification (LLOQ) is shown at 5.48 ng/mL. B: shows the levels of anti-human CD137/MSLN $mAb^2$ (FS22-172-003-AA/FS28-256-271) following an intravenous dose of 6.7 mg/kg, in comparison with 6.7 mg/kg human IgG1 isotype control (G1/4420), after a single intravenous dose administered to non-tumour bearing C57BL/6 mice. Both the human IgG1 isotype control and the anti-human CD137/MSLN $mAb^2$ maintained high levels of exposure at 28.36 and 60.26 μg/ml, respectively, at 144 hours post dose. The lower limit of quantification (LLOQ) is shown at 1.82 ng/mL.

FIG. 14 A shows the pharmacokinetics of anti-mouse CD137/MSLN mAb$^2$ and demonstrates that the mAb$^2$ had a slightly lower systemic exposure over the dosing period than a non-MSLN binding human IgG1 antibody. This may be explained by target-mediated clearance mechanisms.

14.2 Pharmacokinetics of Anti-Human CD137/MSLN $mAb^2$ in Non-Tumour Bearing Mice For comparison, the pharmacokinetic profile of the anti-human CD137/MSLN $mAb^2$ in non-tumour bearing C57BL/6 female mice was determined. Mice were dosed intravenously with 6.7 mg/kg of anti-human CD137/MSLN (FS22-172-003-AA/FS28-256-271) $mAb^2$ or human IgG1 control antibody (G1-AA/4420) and monitored for up to 144 hrs. Microsampling of approximately 20 μl of whole blood was performed at 0.5, 1, 6, 24, 48, 96 and 144 hours, and processed to isolate approximately 5 μl of serum for analysis. Analysis was performed as described in Example 14.1.

FIG. 14B shows the pharmacokinetics of anti-human CD137/MSLN $mAb^2$ and demonstrates that the $mAb^2$ had comparable exposure in the blood to a standard human IgG1 antibody which does not bind MSLN (Bergman et al., 1998).

Sequence Listing

Heavy Chain Annotations i. In amino acid sequences of the heavy chain of $mAb^2$, the variable domain is shown in italics, CDRs according to IMGT are shown in bold italics, CDRs according to Kabat are shown in italics and underlined (therefore any overlapping IMGT and Kabat CDR sequences are shown in bold, italics and underlined), CH1 domains are underlined, hinge regions are doubly underlined, CH2 domains are shown in bold (and, where applicable, location of the LALA mutation is shown in bold and underlined), CH3 domains are shown in plain font, and modified regions of CH3 structural loops are underlined (no underlining if loop is unchanged).

ii. In amino acid sequences of variable domains, CDRs according to IMGT are shown in bold and italics, CDRs according to Kabat are shown in italics and underlined (therefore any overlapping IMGT and Kabat CDR sequences are shown in bold, italics and underlined).

iii. CDR amino acid sequences according to both IMGT and Kabat are provided.

Light Chain Annotations i. In the amino acid sequence of the light chain of $mAb^2$, variable domains are shown in italics, CDRs according to IMGT are shown in bold and italics, and CDRs according to Kabat are shown in italics and underlined (therefore any overlapping IMGT and Kabat CDR sequences are shown in bold, italics and underlined).

ii. In the amino acid sequence of the variable domain, CDRs according to IMGT are shown in bold and italics, and CDRs according to Kabat are shown in italics and underlined (therefore any overlapping IMGT and Kabat CDR sequences are shown in bold, italics and underlined).

iii. CDR amino acid sequences according to both IMGT and Kabat are provided.

Amino acid and cDNA sequences of CH3 domain and amino acid sequence of modified regions of CH3 AB and EF structural loops of all FS22-172-003 Fcab-containing $mAb^2$ clones and the FS22-172-003 Fcab

CH3
AA

SEQ ID NO: 8

GQPREPQVYTLPPSRDELPYIIPPYNQVSLTCLVKGFYPSDIAVEWESNGQPENNYKTTPPV
LDSDGSFFLYSKLTVGADRWLEGNVFSCSVMHEALHNHYTQKSLSLSPG

CH3
DNA

SEQ ID NO: 9

GGACAGCCTCGAGAACCACAGGTGTACACCCTGCCCCCATCCCGGGATGAGCTGCCA
TACATCATCCCACCATACAACCAGGTCAGCCTGACCTGCCTGGTCAAAGGCTTCTATCCCAGCG
ACATCGCCGTGGAGTGGGAGAGCAATGGGCAGCCGGAGAACAACTACAAGACCACGCCTCCCG
TGCTGGACTCCGACGGCTCCTTCTTCCTCTACAGCAAGCTCACCGTGGGCGCAGATAGGTGGCT
GGAAGGGAACGTCTTCTCATGCTCCGTGATGCATGAGGCGCTGCACAACCACTACACTCAGAAG
AGCTTGTCCCTGTCGCCCGGT

| | | |
|---|---|---|
| SEQ ID NO: 10 | Loop AB (AA) | PYIIPPY |
| SEQ ID NO: 11 | Loop EF (AA) | GADRWLE |

Amino acid and cDNA sequences of heavy chain of FS22-172-003-AA/FS28-024 $mAb^2$ Heavy chain AA (without LALA)

SEQ ID NO: 92

*EVQLLESGGGLVQPGGSLRLSCAASGFTLSYSSMSWVRQAPGKGLEW*
*VSFITPSTGYTHYADSVKGRFTISRDNSKNTLYLQMNSLRAEDTAVYYCARRALTFDYWGQGTLVTV*
*SS*ASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELPYIIPPYNQVSLTCLVKGFYPSDIAV
EWESNGQPENNYKTTPPVLDSDGSFFLYSKLTVGADRWLEGNVFSCSVMHEALHNHYTQKSLSLSP
G

Heavy chain DNA (without LALA)

SEQ ID NO: 93

GAAGTGCAACTGCTGGAGTCCGGTGGTGGTCTGGTACAGCCGGGTG
GTTCTCTGCGTCTGAGTTGCGCGGCCAGTGGCTTTACCCTCAGTTATTCTTCTATGTCATGGGTG
CGTCAGGCTCCGGGCAAAGGTCTGGAATGGGTTAGCTTTATTACTCCGTCTACTGGCTATACCC

-continued

Amino acid and cDNA sequences of heavy chain of FS22-172-003-AA/ FS28-024 mAb[2]

ACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGACGGGCGCT
GACGTTCGACTACTGGGGCCAGGGAACCTTGGTCACCGTCTCGAGTGCTAGCACTAAGGGCCC
GTCGGTGTTCCCGCTGGCCCCATCGTCCAAGAGCACATCAGGGGGTACCGCCGCCCTGGGCTG
CCTTGTGAAGGATTACTTTCCCGAGCCCGTCACAGTGTCCTGGAACAGCGGAGCCCTGACCTCC
GGAGTGCATACTTTCCCGGCTGTGCTTCAGTCCTCTGGCCTGTACTCATTGTCCTCCGTGGTCAC
CGTCCCTTCGTCCTCCCTGGGCACCCAGACCTATATCTGTAATGTCAACCATAAGCCCTCGAACA
CCAAGGTCGACAAGAAGGTCGAGCCGAAGTCGTGCGACAAGACTCACACTTGCCCGCCTTGCC
CAGCCCCGGAACTGCTGGGTGGTCCTTCGGTGTTCCTCTTCCCGCCCAAGCCGAAGGATACCCT
GATGATCTCACGGACCCCCGAAGTGACCTGTGTGGTGGTGGACGTGTCCCACGAGGACCCGGA
AGTGAAATTCAATTGGTACGTGGATGGAGTGGAAGTGCACAACGCCAAGACCAAGCCACGGGAA
GAACAGTACAACTCTACCTACCGCGTGGTGTCCGTGCTCACTGTGCTGCACCAAGACTGGCTGA
ACGGGAAGGAGTACAAGTGCAAAGTGTCCAACAAGGCGCTGCCTGCCCCAATTGAGAAAACTAT
CTCGAAAGCCAAGGGACAGCCTCGAGAACCACAGGTGTACACCCTGCCCCCATCCCGGGATGA
GCTGCCATACATCATCCCACCATACAACCAGGTCAGCCTGACCTGCCTGGTCAAAGGCTTCTATC
CCAGCGACATCGCCGTGGAGTGGGAGAGCAATGGGCAGCCGGAGAACAACTACAAGACCACGC
CTCCCGTGCTGGACTCCGACGGCTCCTTCTTCCTCTACAGCAAGCTCACCGTGGGCGCAGATAG
GTGGCTGGAAGGGAACGTCTTCTCATGCTCCGTGATGCATGAGGCGCTGCACAACCACTACACT
CAGAAGAGCTTGTCCCTGTCGCCCGGT

Heavy chain AA (with LALA)

SEQ ID NO: 94

*EVQLLESGGGLVQPGGSLRLSCAAS*GFTLSYSS*MSWVRQAPGKGLEW*
*VSF*ITPSTGYT*HYADSVKGRFTISRDNSKNTLYLQMNSLRAEDTAVYYC*ARRALTFDY*WGQGTLVTV*
*SS*ASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPEAAGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELPYIIPPYNQVSLTCLVKGFYPSDIAV
EWESNGQPENNYKTTPPVLDSDGSFFLYSKLTVGADRWLEGNVFSCSVMHEALHNHYTQKSLSLSP
G

Heavy chain DNA (with LALA)

SEQ ID NO: 95

GAAGTGCAACTGCTGGAGTCCGGTGGTGGTCTGGTACAGCCGGGTG
GTTCTCTGCGTCTGAGTTGCGCGGCCAGTGGCTTTACCCTCAGTTATTCTTCTATGTCATGGGTG
CGTCAGGCTCCGGGCAAAGGTCTGGAATGGGTTAGCTTTATTACTCCGTCTACTGGCTATACCC
ACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGACGGGCGCT
GACGTTCGACTACTGGGGCCAGGGAACCTTGGTCACCGTCTCGAGTGCTAGCACTAAGGGCCC
GTCGGTGTTCCCGCTGGCCCCATCGTCCAAGAGCACATCAGGGGGTACCGCCGCCCTGGGCTG
CCTTGTGAAGGATTACTTTCCCGAGCCCGTCACAGTGTCCTGGAACAGCGGAGCCCTGACCTCC
GGAGTGCATACTTTCCCGGCTGTGCTTCAGTCCTCTGGCCTGTACTCATTGTCCTCCGTGGTCAC
CGTCCCTTCGTCCTCCCTGGGCACCCAGACCTATATCTGTAATGTCAACCATAAGCCCTCGAACA
CCAAGGTCGACAAGAAGGTCGAGCCGAAGTCGTGCGACAAGACTCACACTTGCCCGCCTTGCC
CAGCCCCGGAAGCTGCCGGTGGTCCTTCGGTGTTCCTCTTCCCGCCCAAGCCGAAGGATACCC
TGATGATCTCACGGACCCCCGAAGTGACCTGTGTGGTGGTGGACGTGTCCCACGAGGACCCGG
AAGTGAAATTCAATTGGTACGTGGATGGAGTGGAAGTGCACAACGCCAAGACCAAGCCACGGGA
AGAACAGTACAACTCTACCTACCGCGTGGTGTCCGTGCTCACTGTGCTGCACCAAGACTGGCTG
AACGGGAAGGAGTACAAGTGCAAAGTGTCCAACAAGGCGCTGCCTGCCCCAATTGAGAAAACTA
TCTCGAAAGCCAAGGGACAGCCTCGAGAACCACAGGTGTACACCCTGCCCCCATCCCGGGATG
AGCTGCCATACATCATCCCACCATACAACCAGGTCAGCCTGACCTGCCTGGTCAAAGGCTTCTAT
CCCAGCGACATCGCCGTGGAGTGGGAGAGCAATGGGCAGCCGGAGAACAACTACAAGACCACG
CCTCCCGTGCTGGACTCCGACGGCTCCTTCTTCCTCTACAGCAAGCTCACCGTGGGCGCAGATA
GGTGGCTGGAAGGGAACGTCTTCTCATGCTCCGTGATGCATGAGGCGCTGCACAACCACTACAC
TCAGAAGAGCTTGTCCCTGTCGCCCGGT

VH domain AA

SEQ ID NO: 12

*EVQLLESGGGLVQPGGSLRLSCAAS*GFTLSYSS*MSWVRQAPGKGLEW*
*VSF*ITPSTGYT*HYADSVKGRFTISRDNSKNTLYLQMNSLRAEDTAVYYC*ARRALTFDY*WGQGTLVTV*
*SS*

VH domain DNA

SEQ ID NO: 13

GAAGTGCAACTGCTGGAGTCCGGTGGTGGTCTGGTACAGCCGGGTG
GTTCTCTGCGTCTGAGTTGCGCGGCCAGTGGCTTTACCCTCAGTTATTCTTCTATGTCATGGGTG
CGTCAGGCTCCGGGCAAAGGTCTGGAATGGGTTAGCTTTATTACTCCGTCTACTGGCTATACCC
ACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGACGGGCGCT
GACGTTCGACTACTGGGGCCAGGGAACCTTGGTCACCGTCTCGAGT

| | | |
|---|---|---|
| SEQ ID NO: 14 | HCDR1 (AA) (IMGT) | GFTLSYSS |
| SEQ ID NO: 15 | HCDR1 (AA) (Kabat) | YSSMS |
| SEQ ID NO: 16 | HCDR2 (AA) (IMGT) | ITPSTGYT |

-continued

| Amino acid and cDNA sequences of heavy chain of FS22-172-003-AA/ FS28-024 mAb[2] | | |
|---|---|---|
| SEQ ID NO: 17 | HCDR2 (AA) Kabat) | FITPSTGYTHYADSVKG |
| SEQ ID NO: 18 | HCDR3 (AA) (IMGT) | ARRALTFDY |
| SEQ ID NO: 19 | HCDR3 (AA) (Kabat) | RALTFDY |

Amino acid and cDNA sequences of light chain of FS22-172-003-AA/ FS28-024 mAb[2]

Light chain AA

SEQ ID NO: 85

*EIVLTQSPGTLSLSPGERATLSCRASQSVSSSYLAWYQQKPGQAPRLLIY*
*GASSRATGIPDRFSGSGSGTDFTLTISRLEPEDFAVYYCQQASSYPLTFGQGTKVEIK*RTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light chain DNA

SEQ ID NO: 86

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAGCTTCTTCTTATCCTCTCACGTTCGGCCAAG
GGACCAAGGTGGAAATCAAACGTACTGTGGCCGCTCCTAGCGTGTTCATTTTTCCGCCATCCGA
CGAGCAGCTCAAGTCCGGCACCGCCTCCGTGGTCTGCCTGCTCAACAACTTCTACCCTCGCGAA
GCTAAGGTCCAGTGGAAGGTCGACAATGCCCTGCAGTCCGGAAACTCGCAGGAAAGCGTGACT
GAACAGGACTCCAAGGACTCCACCTATTCACTGTCCTCGACTCTGACCCTGAGCAAGGCGGATT
ACGAAAAGCACAAAGTGTACGCATGCGAAGTGACCCACCAGGGTCTTTCGTCCCCCGTGACCAA
GAGCTTCAACAGAGGAGAGTGT

VL domain AA

SEQ ID NO: 54

*EIVLTQSPGTLSLSPGERATLSCRASQSVSSSYLAWYQQKPGQAPRLLIY*
*GASSRATGIPDRFSGSGSGTDFTLTISRLEPEDFAVYYCQQASSYPLTFGQGTKVEIK*

VL domain DNA

SEQ ID NO: 55

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAGCTTCTTCTTATCCTCTCACGTTCGGCCAAG
GGACCAAGGTGGAAATCAAA

| | | |
|---|---|---|
| SEQ ID NO: 20 | LCDR1 (AA) (IMGT) | QSVSSSY |
| SEQ ID NO: 21 | LCDR1 (AA) (Kabat) | RASQSVSSSYLA |
| SEQ ID NO: 22 | LCDR2 (AA) (IMGT) | GAS |
| SEQ ID NO: 23 | LCDR2 (AA) (Kabat) | GASSRAT |
| SEQ ID NO: 24 | LCDR3 (AA) (IMGT) | QQASSYPLT |
| SEQ ID NO: 24 | LCDR3 (AA) (Kabat) | QQASSYPLT |

Amino acid and cDNA sequences of heavy chain of FS22-172-003-AA/ FS28-024-051 mAb[2]

Heavy chain AA (without LALA)

SEQ ID NO: 96

*EVQLLESGGGLVQPGGSLRLSCAASGFTLSYSSMSWVRQAPGKGLEW*
*VSFITPSTGYTHYADSVKGRFTISRDNSKNTLYLQMNSLRAEDTAVYYCARRALIFDYWGQGTLVTVS*
*S*ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYNSTYRVVSVLTVLHQDWLN

-continued

| Amino acid and cDNA sequences of heavy chain of FS22-172-003-AA/ FS28-024-051 mAb[2] |
|---|

GKEYKCKVSNKALPAPIEKTISKAKGQPREPQVYTLPPSRDELPYIIPPYNQVSLTCLVKGFYPSDIAV
EWESNGQPENNYKTTPPVLDSDGSFFLYSKLTVGADRWLEGNVFSCSVMHEALHNHYTQKSLSLSP
G

Heavy chain DNA (without LALA)

SEQ ID NO: 97

GAAGTGCAACTGCTGGAGTCCGGTGGTGGTCTGGTACAGCCGGGTGGTTCTCTGCGTC
TGAGTTGCGCGGCCAGTGGCTTTACCCTCAGTTATTCTTCTATGTCATGGGTGCGTCAGGCTCC
GGGCAAAGGTCTGGAATGGGTTAGCTTTATTACTCCGTCTACTGGCTATACCCACTATGCGGATA
GCGTGAAAGGCCGTTTTACCATTTCTCGCGACAACAGCAAGAACACGCTGTACCTGCAGATGAA
CTCACTGCGTGCCGAAGATACGGCCGTGTATTACTGTGCGAGACGGGCGCTGATTTTCGACTAC
TGGGGCCAGGGAACCCTGGTCACCGTCTCGAGTGCTAGCACTAAGGGCCCGTCGGTGTTCCCG
CTGGCCCCATCGTCCAAGAGCACATCAGGGGGTACCGCCGCCCTGGGCTGCCTTGTGAAGGAT
TACTTTCCCGAGCCCGTCACAGTGTCCTGGAACAGCGGAGCCCTGACCTCCGGAGTGCATACTT
TCCCGGCTGTGCTTCAGTCCTCTGGCCTGTACTCATTGTCCTCCGTGGTCACCGTCCCTTCGTC
CTCCCTGGGCACCCAGACCTATATCTGTAATGTCAACCATAAGCCCTCGAACACCAAGGTCGAC
AAGAAGGTCGAGCCGAAGTCGTGCGACAAGACTCACACTTGCCCGCCTTGCCCAGCCCCGGAA
CTGCTGGGTGGTCCTTCGGTGTTCCTCTTCCCGCCCAAGCCGAAGGATACCCTGATGATCTCAC
GGACCCCCGAAGTGACCTGTGTGGTGGTGGACGTGTCCCACGAGGACCCGGAAGTGAAATTCA
ATTGGTACGTGGATGGAGTGGAAGTGCACAACGCCAAGACCAAGCCACGGGAAGAACAGTACA
ACTCTACCTACCGCGTGGTGTCCGTGCTCACTGTGCTGCACCAAGACTGGCTGAACGGGAAGGA
GTACAAGTGCAAAGTGTCCAACAAGGCGCTGCCTGCCCCAATTGAGAAAACTATCTCGAAAGCC
AAGGGACAGCCTCGAGAACCACAGGTGTACACCCTGCCCCCATCCCGGGATGAGCTGCCATAC
ATCATCCCACCATACAACCAGGTCAGCCTGACCTGCCTGGTCAAAGGCTTCTATCCCAGCGACA
TCGCCGTGGAGTGGGAGAGCAATGGGCAGCCGGAGAACAACTACAAGACCACGCCTCCCGTGC
TGGACTCCGACGGCTCCTTCTTCCTCTACAGCAAGCTCACCGTGGGCGCAGATAGGTGGCTGGA
AGGGAACGTCTTCTCATGCTCCGTGATGCATGAGGCGCTGCACAACCACTACACTCAGAAGAGC
TTGTCCCTGTCGCCCGGT

Heavy chain AA (with LALA)

SEQ ID NO: 98

*EVQLLESGGGLVQPGGSLRLSCAASGFTLSYSSMSWVRQAPGKGLEW*
*VSFITPSTGYTHYADSVKGRFTISRDNSKNTLYLQMNSLRAEDTAVYYCARRALIFDYWGQGTLVTVS*
*S*ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPEAAGGPSVFLFPPKPKDT
LMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELPYIIPPYNQVSLTCLVKGFYPSDIAV
EWESNGQPENNYKTTPPVLDSDGSFFLYSKLTVGADRWLEGNVFSCSVMHEALHNHYTQKSLSLSP
G

Heavy chain DNA (with LALA)

SEQ ID NO: 99

GAAGTGCAACTGCTGGAGTCCGGTGGTGGTCTGGTACAGCCGGGTGGTTCTCTGCGTC
TGAGTTGCGCGGCCAGTGGCTTTACCCTCAGTTATTCTTCTATGTCATGGGTGCGTCAGGCTCC
GGGCAAAGGTCTGGAATGGGTTAGCTTTATTACTCCGTCTACTGGCTATACCCACTATGCGGATA
GCGTGAAAGGCCGTTTTACCATTTCTCGCGACAACAGCAAGAACACGCTGTACCTGCAGATGAA
CTCACTGCGTGCCGAAGATACGGCCGTGTATTACTGTGCGAGACGGGCGCTGATTTTCGACTAC
TGGGGCCAGGGAACCCTGGTCACCGTCTCGAGTGCTAGCACTAAGGGCCCGTCGGTGTTCCCG
CTGGCCCCATCGTCCAAGAGCACATCAGGGGGTACCGCCGCCCTGGGCTGCCTTGTGAAGGAT
TACTTTCCCGAGCCCGTCACAGTGTCCTGGAACAGCGGAGCCCTGACCTCCGGAGTGCATACTT
TCCCGGCTGTGCTTCAGTCCTCTGGCCTGTACTCATTGTCCTCCGTGGTCACCGTCCCTTCGTC
CTCCCTGGGCACCCAGACCTATATCTGTAATGTCAACCATAAGCCCTCGAACACCAAGGTCGAC
AAGAAGGTCGAGCCGAAGTCGTGCGACAAGACTCACACTTGCCCGCCTTGCCCAGCCCCGGAA
GCTGCCGGTGGTCCTTCGGTGTTCCTCTTCCCGCCCAAGCCGAAGGATACCCTGATGATCTCAC
GGACCCCCGAAGTGACCTGTGTGGTGGTGGACGTGTCCCACGAGGACCCGGAAGTGAAATTCA
ATTGGTACGTGGATGGAGTGGAAGTGCACAACGCCAAGACCAAGCCACGGGAAGAACAGTACA
ACTCTACCTACCGCGTGGTGTCCGTGCTCACTGTGCTGCACCAAGACTGGCTGAACGGGAAGGA
GTACAAGTGCAAAGTGTCCAACAAGGCGCTGCCTGCCCCAATTGAGAAAACTATCTCGAAAGCC
AAGGGACAGCCTCGAGAACCACAGGTGTACACCCTGCCCCCATCCCGGGATGAGCTGCCATAC
ATCATCCCACCATACAACCAGGTCAGCCTGACCTGCCTGGTCAAAGGCTTCTATCCCAGCGACA
TCGCCGTGGAGTGGGAGAGCAATGGGCAGCCGGAGAACAACTACAAGACCACGCCTCCCGTGC
TGGACTCCGACGGCTCCTTCTTCCTCTACAGCAAGCTCACCGTGGGCGCAGATAGGTGGCTGGA
AGGGAACGTCTTCTCATGCTCCGTGATGCATGAGGCGCTGCACAACCACTACACTCAGAAGAGC
TTGTCCCTGTCGCCCGGT

VH domain AA

SEQ ID NO: 56

*EVQLLESGGGLVQPGGSLRLSCAASGFTLSYSSMSWVRQAPGKGLEW*
*VSFITPSTGYTHYADSVKGRFTISRDNSKNTLYLQMNSLRAEDTAVYYCARRALIFDYWGQGTLVTVS*

VH domain DNA

SEQ ID NO: 57

GAAGTGCAACTGCTGGAGTCCGGTGGTGGTCTGGTACAGCCGGGTG
GTTCTCTGCGTCTGAGTTGCGCGGCCAGTGGCTTTACCCTCAGTTATTCTTCTATGTCATGGGTG
CGTCAGGCTCCGGGCAAAGGTCTGGAATGGGTTAGCTTTATTACTCCGTCTACTGGCTATACCC
ACTATGCGGATAGCGTGAAAGGCCGTTTTACCATTTCTCGCGACAACAGCAAGAACACGCTGTA

-continued

| Amino acid and cDNA sequences of heavy chain of FS22-172-003-AA/ FS28-024-051 mAb² | | |
|---|---|---|
| CCTGCAGATGAACTCACTGCGTGCCGAAGATACGGCCGTGTATTACTGTGCGAGACGGGCGCT GATTTTCGACTACTGGGGCCAGGGAACCCTGGTCACCGTCTCGAGT | | |
| SEQ ID NO: 14 | HCDR1 (AA) (IMGT) | GFTLSYSS |
| SEQ ID NO: 15 | HCDR1 (AA) (Kabat) | YSSMS |
| SEQ ID NO: 16 | HCDR2 (AA) (IMGT) | ITPSTGYT |
| SEQ ID NO: 17 | HCDR2 (AA) Kabat) | FITPSTGYTHYADSVKG |
| SEQ ID NO: 25 | HCDR3 (AA) (IMGT) | ARRALIFDY |
| SEQ ID NO: 26 | HCDR3 (AA) (Kabat) | RALIFDY |

Amino acid and cDNA sequences of light chain of FS22-172-003-AA/ FS28-024-051 mAb²

Light chain AA

SEQ ID NO: 85

*EIVLTQSPGTLSLSPGERATLSC*RAS*QSVSSSY*L*AWYQQKPGQAPRLLIY*
*GASSRATGIPDRFSGSGSGTDFTLTISRLEPEDFAVYYC***QQASSYPLT**FGQGTKVEIK*RTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light chain DNA

SEQ ID NO: 86

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAGCTTCTTCTTATCCTCTCACGTTCGGCCAAG
GGACCAAGGTGGAAATCAAACGTACTGTGGCCGCTCCTAGCGTGTTCATTTTTCCGCCATCCGA
CGAGCAGCTCAAGTCCGGCACCGCCTCCGTGGTCTGCCTGCTCAACAACTTCTACCCTCGCGAA
GCTAAGGTCCAGTGGAAGGTCGACAATGCCCTGCAGTCCGGAAACTCGCAGGAAAGCGTGACT
GAACAGGACTCCAAGGACTCCACCTATTCACTGTCCTCGACTCTGACCCTGAGCAAGGCGGATT
ACGAAAAGCACAAAGTGTACGCATGCGAAGTGACCCACCAGGGTCTTTCGTCCCCCGTGACCAA
GAGCTTCAACAGAGGAGAGTGT

VL domain AA

SEQ ID NO: 54

*EIVLTQSPGTLSLSPGERATLSC*RAS*QSVSSSY*L*AWYQQKPGQAPRLLIY*
*GASSRATGIPDRFSGSGSGTDFTLTISRLEPEDFAVYYC**QQASSYPLT**FGQGTKVEIK*

VL domain DNA

SEQ ID NO: 55

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAGCTTCTTCTTATCCTCTCACGTTCGGCCAAG
GGACCAAGGTGGAAATCAAA

| | | |
|---|---|---|
| SEQ ID NO: 20 | LCDR1 (AA) (IMGT) | QSVSSSY |
| SEQ ID NO: 21 | LCDR1 (AA) (Kabat) | RASQSVSSSYLA |
| SEQ ID NO: 22 | LCDR2 (AA) (IMGT) | GAS |
| SEQ ID NO: 23 | LCDR2 (AA) (Kabat) | GASSRAT |
| SEQ ID NO: 24 | LCDR3 (AA) (IMGT) | QQASSYPLT |
| SEQ ID NO: 24 | LCDR3 (AA) (Kabat) | QQASSYPLT |

Amino acid and cDNA sequences of heavy chain of FS22-172-003-AA/ FS28-024-052 mAb[2]

Heavy chain AA (without LALA)

SEQ ID NO: 100

EVQLLESGGGLVQPGGSLRLSCAASGFTLSYSSMSWVRQAPGKGLEW
VSFITPSTGYTHYADSVKGRFTI
SRDNSKNTLYLQMNSLRAEDTAVYYCARRALLFDYWGQGTLVTVSSASTKGPSVFPLAPSSKSTSG
GTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKVSNKALPAPIEKTIS
KAKGQPREPQVYTLPPSRDELPYIIPPYNQVSLTCLVKGFYPSDIAVEWESNGQPENNYKTTPPVLDS
DGSFFLYSKLTVGADRWLEGNVFSCSVMHEALHNHYTQKSLSLSPG

Heavy chain DNA (without LALA)

SEQ ID NO: 101

GAAGTGCAACTGCTGGAGTCCGGTGGTGGTCTGGTACAGCCGGGTGGTTCTCTGCGTC
TGAGTTGCGCGGCCAGTGGCTTTACCCTCAGTTATTCTTCTATGTCATGGGTGCGTCAGGCTCC
GGGCAAAGGTCTGGAATGGGTTAGCTTTATTACTCCGTCTACTGGCTATACCCACTATGCGGATA
GCGTGAAAGGCCGTTTTACCATTTCTCGCGACAACAGCAAGAACACGCTGTACCTGCAGATGAA
CTCACTGCGTGCCGAAGATACGGCCGTGTATTACTGTGCGAGACGGGCGCTGCTTTTCGACTAC
TGGGGCCAGGGAACCCTGGTCACCGTCTCGTCGGCTAGCACTAAGGGCCCGTCGGTGTTCCCG
CTGGCCCCATCGTCCAAGAGCACATCAGGGGGTACCGCCGCCCTGGGCTGCCTTGTGAAGGAT
TACTTTCCCGAGCCCGTCACAGTGTCCTGGAACAGCGGAGCCCTGACCTCCGGAGTGCATACTT
TCCCGGCTGTGCTTCAGTCCTCTGGCCTGTACTCATTGTCCTCCGTGGTCACCGTCCCTTCGTC
CTCCCTGGGCACCCAGACCTATATCTGTAATGTCAACCATAAGCCCTCGAACACCAAGGTCGAC
AAGAAGGTCGAGCCGAAGTCGTGCGACAAGACTCACACTTGCCCGCCTTGCCCAGCCCCGGAA
CTGCTGGGTGGTCCTTCGGTGTTCCTCTTCCCGCCCAAGCCGAAGGATACCCTGATGATCTCAC
GGACCCCCGAAGTGACCTGTGTGGTGGTGGACGTGTCCCACGAGGACCCGGAAGTGAAATTCA
ATTGGTACGTGGATGGAGTGGAAGTGCACAACGCCAAGACCAAGCCACGGGAAGAACAGTACA
ACTCTACCTACCGCGTGGTGTCCGTGCTCACTGTGCTGCACCAAGACTGGCTGAACGGGAAGGA
GTACAAGTGCAAAGTGTCCAACAAGGCGCTGCCTGCCCCAATTGAGAAAACTATCTCGAAAGCC
AAGGGACAGCCTCGAGAACCACAGGTGTACACCCTGCCCCCATCCCGGGATGAGCTGCCATAC
ATCATCCCACCATACAACCAGGTCAGCCTGACCTGCCTGGTCAAAGGCTTCTATCCCAGCGACA
TCGCCGTGGAGTGGGAGAGCAATGGGCAGCCGGAGAACAACTACAAGACCACGCCTCCCGTGC
TGGACTCCGACGGCTCCTTCTTCCTCTACAGCAAGCTCACCGTGGGCGCAGATAGGTGGCTGGA
AGGGAACGTCTTCTCATGCTCCGTGATGCATGAGGCGCTGCACAACCACTACACTCAGAAGAGC
TTGTCCCTGTCGCCCGGT

Heavy chain AA (with LALA)

SEQ ID NO: 102

EVQLLESGGGLVQPGGSLRLSCAASGFTLSYSSMSWVRQAPGKGLEW
VSFITPSTGYTHYADSVKGRFTISRDNSKNTLYLQMNSLRAEDTAVYYCARRALLFDYWGQGTLVTV
SSASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPEAAGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELPYIIPPYNQVSLTCLVKGFYPSDIAV
EWESNGQPENNYKTTPPVLDSDGSFFLYSKLTVGADRWLEGNVFSCSVMHEALHNHYTQKSLSLSP
G

Heavy chain DNA (with LALA)

SEQ ID NO: 103

GAAGTGCAACTGCTGGAGTCCGGTGGTGGTCTGGTACAGCCGGGTG
GTTCTCTGCGTCTGAGTTGCGCGGCCAGTGGCTTTACCCTCAGTTATTCTTCTATGTCATGGGTG
CGTCAGGCTCCGGGCAAAGGTCTGGAATGGGTTAGCTTTATTACTCCGTCTACTGGCTATACCC
ACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGACGGGCGCT
GCTTTTCGACTACTGGGGCCAGGGAACCCTGGTCACCGTCTCGTCGGCTAGCACTAAGGGCCC
GTCGGTGTTCCCGCTGGCCCCATCGTCCAAGAGCACATCAGGGGGTACCGCCGCCCTGGGCTG
CCTTGTGAAGGATTACTTTCCCGAGCCCGTCACAGTGTCCTGGAACAGCGGAGCCCTGACCTCC
GGAGTGCATACTTTCCCGGCTGTGCTTCAGTCCTCTGGCCTGTACTCATTGTCCTCCGTGGTCAC
CGTCCCTTCGTCCTCCCTGGGCACCCAGACCTATATCTGTAATGTCAACCATAAGCCCTCGAACA
CCAAGGTCGACAAGAAGGTCGAGCCGAAGTCGTGCGACAAGACTCACACTTGCCCGCCTTGCC
CAGCCCCGGAAGCTGCCGGTGGTCCTTCGGTGTTCCTCTTCCCGCCCAAGCCGAAGGATACCC
TGATGATCTCACGGACCCCCGAAGTGACCTGTGTGGTGGTGGACGTGTCCCACGAGGACCCGG
AAGTGAAATTCAATTGGTACGTGGATGGAGTGGAAGTGCACAACGCCAAGACCAAGCCACGGGA
AGAACAGTACAACTCTACCTACCGCGTGGTGTCCGTGCTCACTGTGCTGCACCAAGACTGGCTG
AACGGGAAGGAGTACAAGTGCAAAGTGTCCAACAAGGCGCTGCCTGCCCCAATTGAGAAAACTA
TCTCGAAAGCCAAGGGACAGCCTCGAGAACCACAGGTGTACACCCTGCCCCCATCCCGGGATG
AGCTGCCATACATCATCCCACCATACAACCAGGTCAGCCTGACCTGCCTGGTCAAAGGCTTCTAT
CCCAGCGACATCGCCGTGGAGTGGGAGAGCAATGGGCAGCCGGAGAACAACTACAAGACCACG
CCTCCCGTGCTGGACTCCGACGGCTCCTTCTTCCTCTACAGCAAGCTCACCGTGGGCGCAGATA
GGTGGCTGGAAGGGAACGTCTTCTCATGCTCCGTGATGCATGAGGCGCTGCACAACCACTACAC
TCAGAAGAGCTTGTCCCTGTCGCCCGGT

VH domain AA

SEQ ID NO: 58

EVQLLESGGGLVQPGGSLRLSCAASGFTLSYSSMSWVRQAPGKGLEW
VSFITPSTGYTHYADSVKGRFTISRDNSKNTLYLQMNSLRAEDTAVYYCARRALLFDYWGQGTLVTV
SS

-continued

Amino acid and cDNA sequences of heavy chain of FS22-172-003-AA/ FS28-024-052 mAb[2]

VH domain DNA

SEQ ID NO: 59

GAAGTGCAACTGCTGGAGTCCGGTGGTGGTCTGGTACAGCCGGGTG
GTTCTCTGCGTCTGAGTTGCGCGGCCAGTGGCTTTACCCTCAGTTATTCTTCTATGTCATGGGTG
CGTCAGGCTCCGGGCAAAGGTCTGGAATGGGTTAGCTTTATTACTCCGTCTACTGGCTATACCC
ACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGACGGGCGCT
GCTTTTCGACTACTGGGGCCAGGGAACCCTGGTCACCGTCTCGTCG

| | | |
|---|---|---|
| SEQ ID NO: 14 | HCDR1 (AA) (IMGT) | GFTLSYSS |
| SEQ ID NO: 15 | HCDR1 (AA) (Kabat) | YSSMS |
| SEQ ID NO: 16 | HCDR2 (AA) (IMGT) | ITPSTGYT |
| SEQ ID NO: 17 | HCDR2 (AA) Kabat) | FITPSTGYTHYADSVKG |
| SEQ ID NO: 27 | HCDR3 (AA) (IMGT) | ARRALLFDY |
| SEQ ID NO: 28 | HCDR3 (AA) (Kabat) | RALLFDY |

Amino acid and cDNA sequences of light chain of FS22-172-003-AA/ FS28-024-052 mAb[2]

Light chain AA

SEQ ID NO: 85

*EIVLTQSPGTLSLSPGERATLSCRASQSVSSSYLAWYQQKPGQAPRLLIY*
*GASSRATGIPDRFSGSGSGTDFTLTISRLEPEDFAVYYCQQASSYPLTFGQGTKVEIK*RTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light chain DNA

SEQ ID NO: 86

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAGCTTCTTCTTATCCTCTCACGTTCGGCCAAG
GGACCAAGGTGGAAATCAAACGTACTGTGGCCGCTCCTAGCGTGTTCATTTTTCCGCCATCCGA
CGAGCAGCTCAAGTCCGGCACCGCCTCCGTGGTCTGCCTGCTCAACAACTTCTACCCTCGCGAA
GCTAAGGTCCAGTGGAAGGTCGACAATGCCCTGCAGTCCGGAAACTCGCAGGAAAGCGTGACT
GAACAGGACTCCAAGGACTCCACCTATTCACTGTCCTCGACTCTGACCCTGAGCAAGGCGGATT
ACGAAAAGCACAAAGTGTACGCATGCGAAGTGACCCACCAGGGTCTTTCGTCCCCCGTGACCAA
GAGCTTCAACAGAGGAGAGTGT

VL domain AA

SEQ ID NO: 54

*EIVLTQSPGTLSLSPGERATLSCRASQSVSSSYLAWYQQKPGQAPRLLIY*
*GASSRATGIPDRFSGSGSGTDFTLTISRLEPEDFAVYYCQQASSYPLTFGQGTKVEIK*

VL DNA

SEQ ID NO: 55

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAGCTTCTTCTTATCCTCTCACGTTCGGCCAAG
GGACCAAGGTGGAAATCAAA

| | | |
|---|---|---|
| SEQ ID NO: 20 | LCDR1 (AA) (IMGT) | QSVSSSY |
| SEQ ID NO: 21 | LCDR1 (AA) (Kabat) | RASQSVSSSYLA |
| SEQ ID NO: 22 | LCDR2 (AA) (IMGT) | GAS |
| SEQ ID NO: 23 | LCDR2 (AA) (Kabat) | GASSRAT |
| SEQ ID NO: 24 | LCDR3 (AA) (IMGT) | QQASSYPLT |
| SEQ ID NO: 24 | LCDR3 (AA) (Kabat) | QQASSYPLT |

Amino acid and cDNA sequences of heavy chain of FS22-172-003-AA/ FS28-024-053 mAb[2]

Heavy chain AA (without LALA)

SEQ ID NO: 104

*EVQLLESGGGLVQPGGSLRLSCAASGFTLSYSSMSWVRQAPGKGLEW*
*VSFITPSTGYTHYADSVKGRFTISRDNSKNTLYLQMNSLRAEDTAVYYCARRALVFDYWGQGTLVTV*
*SS*ASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELPYIIPPYNQVSLTCLVKGFYPSDIAV
EWESNGQPENNYKTTPPVLDSDGSFFLYSKLTVGADRWLEGNVFSCSVMHEALHNHYTQKSLSLSP
G

Heavy chain DNA
(without LALA)

SEQ ID NO: 105

GAAGTGCAACTGCTGGAGTCCGGTGGTGGTCTGGTACAGCCGGGTG
GTTCTCTGCGTCTGAGTTGCGCGGCCAGTGGCTTTACCCTCAGTTATTCTTCTATGTCATGGGTG
CGTCAGGCTCCGGGCAAAGGTCTGGAATGGGTTAGCTTTATTACTCCGTCTACTGGCTATACCC
ACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGACGGGCGCT
GGTGTTCGACTACTGGGGCCAGGGAACCCTGGTCACCGTCTCGTCGGCTAGCACTAAGGGCCC
GTCGGTGTTCCCGCTGGCCCCATCGTCCAAGAGCACATCAGGGGGTACCGCCGCCCTGGGCTG
CCTTGTGAAGGATTACTTTCCCGAGCCCGTCACAGTGTCCTGGAACAGCGGAGCCCTGACCTCC
GGAGTGCATACTTTCCCGGCTGTGCTTCAGTCCTCTGGCCTGTACTCATTGTCCTCCGTGGTCAC
CGTCCCTTCGTCCTCCCTGGGCACCCAGACCTATATCTGTAATGTCAACCATAAGCCCTCGAACA
CCAAGGTCGACAAGAAGGTCGAGCCGAAGTCGTGCGACAAGACTCACACTTGCCCGCCTTGCC
CAGCCCCGGAACTGCTGGGTGGTCCTTCGGTGTTCCTCTTCCCGCCCAAGCCGAAGGATACCCT
GATGATCTCACGGACCCCCGAAGTGACCTGTGTGGTGGTGGACGTGTCCCACGAGGACCCGGA
AGTGAAATTCAATTGGTACGTGGATGGAGTGGAAGTGCACAACGCCAAGACCAAGCCACGGGAA
GAACAGTACAACTCTACCTACCGCGTGGTGTCCGTGCTCACTGTGCTGCACCAAGACTGGCTGA
ACGGGAAGGAGTACAAGTGCAAAGTGTCCAACAAGGCGCTGCCTGCCCCAATTGAGAAAACTAT
CTCGAAAGCCAAGGGACAGCCTCGAGAACCACAGGTGTACACCCTGCCCCCATCCCGGGATGA
GCTGCCATACATCATCCCACCATACAACCAGGTCAGCCTGACCTGCCTGGTCAAAGGCTTCTATC
CCAGCGACATCGCCGTGGAGTGGGAGAGCAATGGGCAGCCGGAGAACAACTACAAGACCACGC
CTCCCGTGCTGGACTCCGACGGCTCCTTCTTCCTCTACAGCAAGCTCACCGTGGGCGCAGATAG
GTGGCTGGAAGGGAACGTCTTCTCATGCTCCGTGATGCATGAGGCGCTGCACAACCACTACACT
CAGAAGAGCTTGTCCCTGTCGCCCGGT

Heavy chain AA (with LALA)

SEQ ID NO: 106

*EVQLLESGGGLVQPGGSLRLSCAASGFTLSYSSMSWVRQAPGKGLEW*
*VSFITPSTGYTHYADSVKGRFTISRDNSKNTLYLQMNSLRAEDTAVYYCARRALVFDYWGQGTLVTV*
*SS*ASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPEAAGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELPYIIPPYNQVSLTCLVKGFYPSDIAV
EWESNGQPENNYKTTPPVLDSDGSFFLYSKLTVGADRWLEGNVFSCSVMHEALHNHYTQKSLSLSP
G

Heavy chain DNA
(with LALA)

SEQ ID NO: 107

GAAGTGCAACTGCTGGAGTCCGGTGGTGGTCTGGTACAGCCGGGTG
GTTCTCTGCGTCTGAGTTGCGCGGCCAGTGGCTTTACCCTCAGTTATTCTTCTATGTCATGGGTG
CGTCAGGCTCCGGGCAAAGGTCTGGAATGGGTTAGCTTTATTACTCCGTCTACTGGCTATACCC
ACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGACGGGCGCT
GGTGTTCGACTACTGGGGCCAGGGAACCCTGGTCACCGTCTCGTCGGCTAGCACTAAGGGCCC
GTCGGTGTTCCCGCTGGCCCCATCGTCCAAGAGCACATCAGGGGGTACCGCCGCCCTGGGCTG
CCTTGTGAAGGATTACTTTCCCGAGCCCGTCACAGTGTCCTGGAACAGCGGAGCCCTGACCTCC
GGAGTGCATACTTTCCCGGCTGTGCTTCAGTCCTCTGGCCTGTACTCATTGTCCTCCGTGGTCAC
CGTCCCTTCGTCCTCCCTGGGCACCCAGACCTATATCTGTAATGTCAACCATAAGCCCTCGAACA
CCAAGGTCGACAAGAAGGTCGAGCCGAAGTCGTGCGACAAGACTCACACTTGCCCGCCTTGCC
CAGCCCCGGAAGCTGCCGGTGGTCCTTCGGTGTTCCTCTTCCCGCCCAAGCCGAAGGATACCC
TGATGATCTCACGGACCCCCGAAGTGACCTGTGTGGTGGTGGACGTGTCCCACGAGGACCCGG
AAGTGAAATTCAATTGGTACGTGGATGGAGTGGAAGTGCACAACGCCAAGACCAAGCCACGGGA
AGAACAGTACAACTCTACCTACCGCGTGGTGTCCGTGCTCACTGTGCTGCACCAAGACTGGCTG
AACGGGAAGGAGTACAAGTGCAAAGTGTCCAACAAGGCGCTGCCTGCCCCAATTGAGAAAACTA
TCTCGAAAGCCAAGGGACAGCCTCGAGAACCACAGGTGTACACCCTGCCCCCATCCCGGGATG
AGCTGCCATACATCATCCCACCATACAACCAGGTCAGCCTGACCTGCCTGGTCAAAGGCTTCTAT
CCCAGCGACATCGCCGTGGAGTGGGAGAGCAATGGGCAGCCGGAGAACAACTACAAGACCACG
CCTCCCGTGCTGGACTCCGACGGCTCCTTCTTCCTCTACAGCAAGCTCACCGTGGGCGCAGATA
GGTGGCTGGAAGGGAACGTCTTCTCATGCTCCGTGATGCATGAGGCGCTGCACAACCACTACAC
TCAGAAGAGCTTGTCCCTGTCGCCCGGTf

-continued

| Amino acid and cDNA sequences of heavy chain of FS22-172-003-AA/ FS28-024-053 mAb[2] |
|---|

VH domain AA

SEQ ID NO: 60

*EVQLLESGGGLVQPGGSLRLSCAASGFTLSYSSMSWVRQAPGKGLEW*
*VSFITPSTGYTHYADSVKGRFTISRDNSKNTLYLQMNSLRAEDTAVYYCARRALVFDYWGQGTLVTV*
*SS*

VH domain DNA

SEQ ID NO: 61

GAAGTGCAACTGCTGGAGTCCGGTGGTGGTCTGGTACAGCCGGGTG
GTTCTCTGCGTCTGAGTTGCGCGGCCAGTGGCTTTACCCTCAGTTATTCTTCTATGTCATGGGTG
CGTCAGGCTCCGGGCAAAGGTCTGGAATGGGTTAGCTTTATTACTCCGTCTACTGGCTATACCC
ACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGACGGGCGCT
GGTGTTCGACTACTGGGGCCAGGGAACCCTGGTCACCGTCTCGTCG

| | | |
|---|---|---|
| SEQ ID NO: 14 | HCDR1 (AA) (IMGT) | GFTLSYSS |
| SEQ ID NO: 15 | HCDR1 (AA) (Kabat) | YSSMS |
| SEQ ID NO: 16 | HCDR2 (AA) (IMGT) | ITPSTGYT |
| SEQ ID NO: 17 | HCDR2 (AA) Kabat) | FITPSTGYTHYADSVKG |
| SEQ ID NO: 29 | HCDR3 (AA) (IMGT) | ARRALVFDY |
| SEQ ID NO: 30 | HCDR3 (AA) (Kabat) | RALVFDY |

| Amino acid and cDNA sequences of light chain of FS22-172-003-AA/ FS28-024-053 mAb[2] |
|---|

Light chain AA

SEQ ID NO: 85

*EIVLTQSPGTLSLSPGERATLSCRASQSVSSSYLAWYQQKPGQAPRLLIY*
*GASSRATGIPDRFSGSGSGTDFTLTISRLEPEDFAVYYCQQASSYPLTFGQGTKVEIK*RTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light chain DNA

SEQ ID NO: 86

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAGCTTCTTCTTATCCTCTCACGTTCGGCCAAG
GGACCAAGGTGGAAATCAAACGTACTGTGGCCGCTCCTAGCGTGTTCATTTTTCCGCCATCCGA
CGAGCAGCTCAAGTCCGGCACCGCCTCCGTGGTCTGCCTGCTCAACAACTTCTACCCTCGCGAA
GCTAAGGTCCAGTGGAAGGTCGACAATGCCCTGCAGTCCGGAAACTCGCAGGAAAGCGTGACT
GAACAGGACTCCAAGGACTCCACCTATTCACTGTCCTCGACTCTGACCCTGAGCAAGGCGGATT
ACGAAAAGCACAAAGTGTACGCATGCGAAGTGACCCACCAGGGTCTTTCGTCCCCCGTGACCAA
GAGCTTCAACAGAGGAGAGTGT

VL domain AA

SEQ ID NO: 54

*EIVLTQSPGTLSLSPGERATLSCRASQSVSSSYLAWYQQKPGQAPRLLIY*
*GASSRATGIPDRFSGSGSGTDFTLTISRLEPEDFAVYYCQQASSYPLTFGQGTKVEIK*

VL domain DNA

SEQ ID NO: 55

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAGCTTCTTCTTATCCTCTCACGTTCGGCCAAG
GGACCAAGGTGGAAATCAAA

| | | |
|---|---|---|
| SEQ ID NO: 20 | LCDR1 (AA) (IMGT) | QSVSSSY |
| SEQ ID NO: 21 | LCDR1 (AA) (Kabat) | RASQSVSSSYLA |
| SEQ ID NO: 22 | LCDR2 (AA) (IMGT) | GAS |

-continued

| Amino acid and cDNA sequences of light chain of FS22-172-003-AA/ FS28-024-053 mAb[2] | | |
|---|---|---|
| SEQ ID NO: 23 | LCDR2 (AA) (Kabat) | GASSRAT |
| SEQ ID NO: 24 | LCDR3 (AA) (IMGT) | QQASSYPLT |
| SEQ ID NO: 24 | LCDR3 (AA) (Kabat) | QQASSYPLT |

Amino acid sequences of the heavy and light chain of FS22-172-003-AA/ FS28-024-060 mAb[2]

Heavy chain AA (with LALA)

SEQ ID NO: 108

*EVQLLESGGGLVQPGGSLRLSCAAS*GFTLSYSS*MSWVRQAPGKGLEW*
*VSF*ITPSTGYT*HYADSVKGRFTISRDNSKNTLYLQMNSLRAEDTAVYYC*ARRALWFDY*WGQGTLVTV*
*SS*ASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPEAAGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELPYIIPPYNQVSLT-
CLVKGFYPSDIAV
EWESNGQPENNYKTTPPVLDSDGSFFLYSKLTVGADRWLEGNVFSCSVMHEALHNHYTQKSLSLSP
G

Light chain AA

SEQ ID NO: 85

*EIVLTQSPGTLSLSPGERATLSCRAS*QSVSSSY*LAWYQQKPGQAPRLLIY*
*GASSRATGIPDRFSGSGSGTDFTLTISRLEPEDFAVYYC*QQASSY-**
*PLT**FGQGTKVEIK*RTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Amino acid sequences of the heavy and light chain of FS22-172-003-AA/ FS28-026 mAb[2]

Heavy chain AA (with LALA)

SEQ ID NO: 109

*EVQLLESGGGLVQPGGSLRLSCAAS*GFTFSNYA*MTWVRQAPGKGLEW*
*VSS*ITPYYSKT*DYADSVKGRFTISRDNSKNTLYLQMNSLRAEDTAVYYC*ARNWYRFDY*WGQGTLVTV*
*SS*ASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPEAAGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELPYIIPPYNQVSLT-
CLVKGFYPSDIAV
EWESNGQPENNYKTTPPVLDSDGSFFLYSKLTVGADRWLEGNVFSCSVMHEALHNHYTQKSLSLSP
G

Light chain AA

SEQ ID NO: 87

*EIVLTQSPGTLSLSPGERATLSCRAS*QSVSSSY*LAWYQQKPGQAPRLLIY*
*GASSRATGIPDRFSGSGSGTDFTLTISRLEPEDFAVYYC*QQASSYP-**
*IT**FGQGTKVEIK*RTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

| Amino acid sequences of the heavy and light chain of FS22-172-003-AA/ FS28-091 mAb[2] |
|---|
| Heavy chain AA (with LALA)<br>SEQ ID NO: 110<br>*EVQLLESGGGLVQPGGSLRLSCAAS**GFTFTNYA**MSWVRQAPGKGLEW VSS**IKPYDGNT**YYADSVKGRFTISRDNSKNTLYLQMNSLRAEDTAVYYC**ARNRWVFDY**WGQGTLVTV SS*ASTKGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCP**APEAAGGPSVFLFPPKPKD TLMISRTPEVTCVVVDVSHEDPEVKFNWYVDGVEVHNAKTKPREEQYNSTYRVVSVLTVLHQDWLN GKEYKCKVSNKALPAPIEKTISKAK**GQPREPQVYTLPPSRDELPYIIPPYNQVSLT-CLVKGFYPSDIAV EWESNGQPENNYKTTPPVLDSDGSFFLYSKLTVGADRWLEGNVFSCSVMHEALHNHYTQKSLSLSP G<br><br>Light chain AA<br>SEQ ID NO: 88<br>*EIVLTQSPGTLSLSPGERATLSC**RASQSVSSSYLA**WYQQKPGQAPRLLIY **GAS**SRATGIPDRFSGSGSGTDFTLTISRLEPED-FAVYYC**QQYSSSPFT**FGQGTKVEIK*RTVAAPSVFIF PPSDEQLKSGTASVVCLLNNFYPREAKVQWKVDNALQSGNSQESVTEQDSKDSTYSLSSTLTLSKA DYEKHKVYACEVTHQGLSSPVTKSFNRGEC |

| Amino acid sequences of the heavy and light chain of FS22-172-003-AA/ FS28-185 mAb[2] |
|---|
| Heavy chain AA (with LALA)<br>SEQ ID NO: 111<br>*EVQLLESGGGLVQPGGSLRLSCAAS**GFTFTTSA**MSWVRQAPGKGLEW VSR**INPYEGET**NYADSVKGRFTISRDNSKNTLYLQMNSLRAEDTAVYYC**ARGWSIATYYKSAMDY**WG QGTLVTVSS*ASTKGPSVFPLAPSSKSTSGGTAALGCLVKDYFPEPVTVSWNSGALTSGVHTFPAVLQ SSGLYSLSSVVTVPSSSLGTQTYICNVNHKPSNTKVDKKVEPKSCDKTHTCPPCP**APEAAGGPSVFL FPPKPKDTLMISRTPEVTCVVVDVSHEDPEVKFNWYVDGVEVHNAKTKPREEQYNSTYRVVSVLTVL HQDWLNGKEYKCKVSNKALPAPIEKTISKAK**GQPREPQVYTLPPSRDELPYIIPPYNQVSLTCLVKG FYPSDIAVEWESNGQPENNYKTTPPVLDSDGSFFLYSKLTVGADRWLEGNVFSCSVMHEALHNHYTQ KSLSLSPG<br><br>Light chain AA<br>SEQ ID NO: 89<br>*EIVLTQSPGTLSLSPGERATLSC**RASQSVSSSYLA**WYQQKPGQAPRLLIY **GAS**SRATGIPDRFSGSGSGTDFTLTISRLEPEDFAVYYC**QQSSYSAPVT**FGQGTKVEIK*RTVAAPS VFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC |

| Amino acid and cDNA sequences of heavy chain of FS22-172-003-AA/ FS28-256 mAb[2] |
|---|
| Heavy chain AA (without LALA)<br>SEQ ID NO: 112<br>*EVQLLESGGGLVQPGGSLRLSCAAS**GFTFTNTY**MSWVRQAPGKGLEWV SN**ISPTYSTT**NYADSVKGRFTISRDNSKNTLYLQMNSLRAEDTAVYYC**ARYNSYQGGLDY**WGQGTL VTVSS*ASTKGPSVFPLAPSSKSTSGGTAALGCLVKDYFPEPVTVSWNSGALTSGVHTFPAVLQSSGL YSLSSVVTVPSSSLGTQTYICNVNHKPSNTKVDKKVEPKSCDKTHTCPPCP**APELLGGPSVFLFPPK PKDTLMISRTPEVTCVVVDVSHEDPEVKFNWYVDGVEVHNAKTKPREEQYNSTYRVVSVLTVLHQD WLNGKEYKCKVSNKALPAPIEKTISKAK**GQPREPQVYTLPPSRDELPYIIPPYNQVSLTCLVKGFYPS DIAVEWESNGQPENNYKTTPPVLDSDGSFFLYSKLTVGADRWLEGNVFSCSVMHEALHNHYTQKSL SLSPG<br><br>Heavy chain DNA (without lala)<br>SEQ ID NO: 113<br>GAAGTGCAACTGCTGGAGTCCGGTGGTGGTCTGGTACAGCCGGGTG GTTCTCTGCGTCTGAGTTGCGCGGCCAGTGGCTTTACCTTCACTAACACTTATATGAGCTGGGTG CGTCAGGCTCCGGGCAAAGGTCTGGAATGGGTTAGCAATATTTCTCCGACTTATAGCACTACCAA CTATGCGGATAGCGTGAAAGGCCGTTTTACCATTTCTCGCGACAACAGCAAGAACACGCTGTAC CTGCAGATGAACTCACTGCGTGCCGAAGATACGGCCGTGTATTACTGTGCGAGATACAACTCTTA CCAGGGTGGCTTGGACTACTGGGGCCAGGGAACCTTGGTCACCGTCTCGAGTGCTAGCACTAA GGGCCCGTCGGTGTTCCCGCTGGCCCCATCGTCCAAGAGCACATCAGGGGGTACCGCCGCCCT GGGCTGCCTTGTGAAGGATTACTTTCCCGAGCCCGTCACAGTGTCCTGGAACAGCGGAGCCCT GACCTCCGGAGTGCATACTTTCCCGGCTGTGCTTCAGTCCTCTGGCCTGTACTCATTGTCCTCC GTGGTCACCGTCCCTTCGTCCTCCCTGGGCACCCAGACCTATATCTGTAATGTCAACCATAAGCC CTCGAACACCAAGGTCGACAAGAAGGTCGAGCCGAAGTCGTGCGACAAGACTCACACTTGCCC |

-continued

Amino acid and cDNA sequences of heavy chain of FS22-172-003-AA/ FS28-256 mAb[2]

GCCTTGCCCAGCCCCGGAACTGCTGGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

Heavy chain AA (with LALA)

SEQ ID NO: 114

*EVQLLESGGGLVQPGGSLRLSCAAS**GFTFTNTY**MSWVRQAPGKGLEWV*
*SN**ISPTYSTTNYADSVKGRFTISRDNSKNTLYLQMNSLRAEDTAVYYCARYNSYQGGLDY**WGQGTL*
*VTVSS*ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPEAAGGPSVFLFPPK
PKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (with LALA)

SEQ ID NO: 115

GAAGTGCAACTGCTGGAGTCCGGTGGTGGTCTGGTACAGCCGGGTG
GTTCTCTGCGTCTGAGTTGCGCGGCCAGTGGCTTTACCTTCACTAACACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAGCAAGAACACGCTGTAC
CTGCAGATGAACTCACTGCGTGCCGAAGATACGGCCGTGTATTACTGTGCGAGATACAACTCTTA
CCAGGGTGGCTTGGACTACTGGGGCCAGGGAACCTTGGTCACCGTCTCGAGTGCTAGCACTAA
GGGCCCGTCGGTGTTCCCGCTGGCCCCATCGTCCAAGAGCACATCAGGGGGTACCGCCGCCCT
GGGCTGCCTTGTGAAGGATTACTTTCCCGAGCCCGTCACAGTGTCCTGGAACAGCGGAGCCCT
GACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC
GCCTTGCCCAGCCCCGGAAGCTGCCGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

VH domain AA

SEQ ID NO: 62

*EVQLLESGGGLVQPGGSLRLSCAAS**GFTFTNTY**MSWVRQAPGKGLEWV*
*SN**ISPTYSTTNYADSVKGRFTISRDNSKNTLYLQMNSLRAEDTAVYYCARYNSYQGGLDY**WGQGTL*
*VTVSS*

VH domain DNA

SEQ ID NO: 63

GAAGTGCAACTGCTGGAGTCCGGTGGTGGTCTGGTACAGCCGGGTG
GTTCTCTGCGTCTGAGTTGCGCGGCCAGTGGCTTTACCTTCACTAACACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAGCAAGAACACGCTGTAC
CTGCAGATGAACTCACTGCGTGCCGAAGATACGGCCGTGTATTACTGTGCGAGATACAACTCTTA
CCAGGGTGGCTTGGACTACTGGGGCCAGGGAACCTTGGTCACCGTCTCGAGT

| | | |
|---|---|---|
| SEQ ID NO: 31 | HCDR1 (AA) (IMGT) | GFTFTNTY aaaaa |
| SEQ ID NO: 32 | HCDR1 (AA) (Kabat) | NTYMS |
| SEQ ID NO: 33 | HCDR2 (AA) (IMGT) | ISPTYSTT |
| SEQ ID NO: 34 | HCDR2 (AA) Kabat) | NISPTYSTTNYADSVKG |
| SEQ ID NO: 35 | HCDR3 (AA) (IMGT) | ARYNSYQGGLDY |
| SEQ ID NO: 36 | HCDR3 (AA) (Kabat) | YNSYQGGLDY |

Amino acid and cDNA sequences of light chain of FS22-172-003-AA/ FS28-256 mAb[2]

Light chain AA

SEQ ID NO: 116

EIVLTQSPGTLSLSPGERATLSCRASQSVSSSYLAWYQQKPGQAPRLLIY
GASSRATGIPDRFSGSGSGTDFTLTISRLEPEDFAVYYCQQSYYYPITFGQGTKVEIKRTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light chain DNA

SEQ ID NO: 117

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAATCTTATTATTATCCTATCACGTTCGGCCAAG
GGACCAAGGTGGAAATCAAACGTACTGTGGCCGCTCCTAGCGTGTTCATTTTTCCGCCATCCGA
CGAGCAGCTCAAGTCCGGCACCGCCTCCGTGGTCTGCCTGCTCAACAACTTCTACCCTCGCGAA
GCTAAGGTCCAGTGGAAGGTCGACAATGCCCTGCAGTCCGGAAACTCGCAGGAAAGCGTGACT
GAACAGGACTCCAAGGACTCCACCTATTCACTGTCCTCGACTCTGACCCTGAGCAAGGCGGATT
ACGAAAAGCACAAAGTGTACGCATGCGAAGTGACCCACCAGGGTCTTTCGTCCCCCGTGACCAA
GAGCTTCAACAGAGGAGAGTGT

VL domain AA

SEQ ID NO: 64

EIVLTQSPGTLSLSPGERATLSCRASQSVSSSYLAWYQQKPGQAPRLLIY
GASSRATGIPDRFSGSGSGTDFTLTISRLEPEDFAVYYCQQSYYYPITFGQGTKVEIK

VL domain DNA

SEQ ID NO: 65

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAATCTTATTATTATCCTATCACGTTCGGCCAAG
GGACCAAGGTGGAAATCAAA

| | | | |
|---|---|---|---|
| SEQ ID NO: 20 | LCDR1 (AA) (IMGT) | QSVSSSY aaa |
| SEQ ID NO: 21 | LCDR1 (AA) (Kabat) | RASQSVSSSYLA |
| SEQ ID NO: 22 | LCDR2 (AA) (IMGT) | GAS |
| SEQ ID NO: 23 | LCDR2 (AA) (Kabat) | GASSRAT |
| SEQ ID NO: 37 | LCDR3 (AA) (IMGT) | QQSYYYPIT |
| SEQ ID NO: 37 | LCDR3 (AA) (Kabat) | QQSYYYPIT |

Amino acid and cDNA sequences of heavy chain of FS22-172-003-AA/ FS28-256-001 mAb[2]

Heavy chain AA (without LALA)

SEQ ID NO: 118

EVQLLESGGGLVQPGGSLRLSCAASGFTFTETYMSWVRQAPGKGLEWV
SNISPTYSTTNYADSVKGRFTISRDNSKNTLYLQMNSLRAEDTAVYYCARYNSYQGGLDYWGQGTL
VTVSSASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (Without LALA)

SEQ ID NO: 119

GAAGTGCAACTGCTGGAGTCCGGTGGTGGTCTGGTACAGCCGGGTG
GTTCTCTGCGTCTGAGTTGCGCGGCCAGTGGCTTTACCTTCACTGAGACTTATATGAGCTGGGT
GCGTCAGGCTCCGGGCAAAGGTCTGGAATGGGTTAGCAATATTTCTCCGACTTATAGCACTACC
AACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGATACAACTCT
TACCAGGGTGGCTTGGACTACTGGGGCCAGGGAACCTTGGTCACCGTCTCGAGTGCTAGCACT
AAGGGCCCGTCGGTGTTCCCGCTGGCCCCATCGTCCAAGAGCACATCAGGGGGTACCGCCGCC
CTGGGCTGCCTTGTGAAGGATTACTTTCCCGAGCCCGTCACAGTGTCCTGGAACAGCGGAGCCC
TGACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC

-continued

| Amino acid and cDNA sequences of heavy chain of FS22-172-003-AA/ FS28-256-001 mAb[2] |
|---|
| GCCTTGCCCAGCCCCGGAACTGCTGGGTGGTCCTTCGGTGTTCCTCTTCCCGCCCAAGCCGAA<br>GGATACCCTGATGATCTCACGGACCCCCGAAGTGACCTGTGTGGTGGTGGACGTGTCCCACGA<br>GGACCCGGAAGTGAAATTCAATTGGTACGTGGATGGAGTGGAAGTGCACAACGCCAAGACCAAG<br>CCACGGGAAGAACAGTACAACTCTACCTACCGCGTGGTGTCCGTGCTCACTGTGCTGCACCAAG<br>ACTGGCTGAACGGGAAGGAGTACAAGTGCAAAGTGTCCAACAAGGCGCTGCCTGCCCCAATTGA<br>GAAAACTATCTCGAAAGCCAAGGGACAGCCTCGAGAACCACAGGTGTACACCCTGCCCCCATCC<br>CGGGATGAGCTGCCATACATCATCCCACCATACAACCAGGTCAGCCTGACCTGCCTGGTCAAAG<br>GCTTCTATCCCAGCGACATCGCCGTGGAGTGGGAGAGCAATGGGCAGCCGGAGAACAACTACA<br>AGACCACGCCTCCCGTGCTGGACTCCGACGGCTCCTTCTTCCTCTACAGCAAGCTCACCGTGGG<br>CGCAGATAGGTGGCTGGAAGGGAACGTCTTCTCATGCTCCGTGATGCATGAGGCGCTGCACAA<br>CCACTACACTCAGAAGAGCTTGTCCCTGTCGCCCGGT |
| Heavy chain AA (with LALA)<br>SEQ ID NO: 120<br>*EVQLLESGGGLVQPGGSLRLSCAAS**GFTFTETY**MSWVRQAPGKGLEWV*<br>*SN**ISPTYSTT**NYADSVKGRFTISRDNSKNTLYLQMNSLRAEDTAVYYC**ARYNSYQGGLDY**WGQGTL*<br>*VTVSS*ASTKGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKKVEPKSCDKTHTCPPCP**APEAAGGPSVFLFPPK**<br>**PKDTLMISRTPEVTCVVVDVSHEDPEVKFNWYVDGVEVHNAKTKPREEQYNSTYRVVSVLTVLHQD**<br>**WLNGKEYKCKVSNKALPAPIEKTISKAK**GQPREPQVYTLPPSRDELPYIIPPYNQVSLTCLVKGFYPS<br>DIAVEWESNGQPENNYKTTPPVLDSDGSFFLYSKLTVGADRWLEGNVFSCSVMHEALHNHYTQKSL<br>SLSPG |
| Heavy chain DNA (with LALA)<br>SEQ ID NO: 121<br>GAAGTGCAACTGCTGGAGTCCGGTGGTGGTCTGGTACAGCCGGGTG<br>GTTCTCTGCGTCTGAGTTGCGCGGCCAGTGGCTTTACCTTCACTGAGACTTATATGAGCTGGGT<br>GCGTCAGGCTCCGGGCAAAGGTCTGGAATGGGTTAGCAATATTTCTCCGACTTATAGCACTACC<br>AACTATGCGGATAGCGTGAAAGGCCGTTTTACCATTTCTCGCGACAACAGCAAGAACACGCTGTA<br>CCTGCAGATGAACTCACTGCGTGCCGAAGATACGGCCGTGTATTACTGTGCGAGATACAACTCT<br>TACCAGGGTGGCTTGGACTACTGGGGCCAGGGAACCTTGGTCACCGTCTCGAGTGCTAGCACT<br>AAGGGCCCGTCGGTGTTCCCGCTGGCCCCATCGTCCAAGAGCACATCAGGGGGTACCGCCGCC<br>CTGGGCTGCCTTGTGAAGGATTACTTTCCCGAGCCCGTCACAGTGTCCTGGAACAGCGGAGCCC<br>TGACCTCCGGAGTGCATACTTTCCCGGCTGTGCTTCAGTCCTCTGGCCTGTACTCATTGTCCTCC<br>GTGGTCACCGTCCCTTCGTCCTCCCTGGGCACCCAGACCTATATCTGTAATGTCAACCATAAGCC<br>CTCGAACACCAAGGTCGACAAGAAGGTCGAGCCGAAGTCGTGCGACAAGACTCACACTTGCCC<br>GCCTTGCCCAGCCCCGGAAGCTGCCGGTGGTCCTTCGGTGTTCCTCTTCCCGCCCAAGCCGAA<br>GGATACCCTGATGATCTCACGGACCCCCGAAGTGACCTGTGTGGTGGTGGACGTGTCCCACGA<br>GGACCCGGAAGTGAAATTCAATTGGTACGTGGATGGAGTGGAAGTGCACAACGCCAAGACCAAG<br>CCACGGGAAGAACAGTACAACTCTACCTACCGCGTGGTGTCCGTGCTCACTGTGCTGCACCAAG<br>ACTGGCTGAACGGGAAGGAGTACAAGTGCAAAGTGTCCAACAAGGCGCTGCCTGCCCCAATTGA<br>GAAAACTATCTCGAAAGCCAAGGGACAGCCTCGAGAACCACAGGTGTACACCCTGCCCCCATCC<br>CGGGATGAGCTGCCATACATCATCCCACCATACAACCAGGTCAGCCTGACCTGCCTGGTCAAAG<br>GCTTCTATCCCAGCGACATCGCCGTGGAGTGGGAGAGCAATGGGCAGCCGGAGAACAACTACA<br>AGACCACGCCTCCCGTGCTGGACTCCGACGGCTCCTTCTTCCTCTACAGCAAGCTCACCGTGGG<br>CGCAGATAGGTGGCTGGAAGGGAACGTCTTCTCATGCTCCGTGATGCATGAGGCGCTGCACAA<br>CCACTACACTCAGAAGAGCTTGTCCCTGTCGCCCGGT |
| VH domain AA<br>SEQ ID NO: 66<br>*EVQLLESGGGLVQPGGSLRLSCAAS**GFTFTETY**MSWVRQAPGKGLEWV*<br>*SN**ISPTYSTT**NYADSVKGRFTISRDNSKNTLYLQMNSLRAEDTAVYYC**ARYNSYQGGLDY**WGQGTL*<br>*VTVSS* |
| VH domain DNA<br>SEQ ID NO: 67<br>GAAGTGCAACTGCTGGAGTCCGGTGGTGGTCTGGTACAGCCGGGTG<br>GTTCTCTGCGTCTGAGTTGCGCGGCCAGTGGCTTTACCTTCACTGAGACTTATATGAGCTGGGT<br>GCGTCAGGCTCCGGGCAAAGGTCTGGAATGGGTTAGCAATATTTCTCCGACTTATAGCACTACC<br>AACTATGCGGATAGCGTGAAAGGCCGTTTTACCATTTCTCGCGACAACAGCAAGAACACGCTGTA<br>CCTGCAGATGAACTCACTGCGTGCCGAAGATACGGCCGTGTATTACTGTGCGAGATACAACTCT<br>TACCAGGGTGGCTTGGACTACTGGGGCCAGGGAACCTTGGTCACCGTCTCGAGT |

| | | |
|---|---|---|
| SEQ ID NO: 38 | HCDR1 (AA) (IMGT) | GFTFTETY |
| SEQ ID NO: 39 | HCDR1 (AA) (Kabat) | ETYMS |
| SEQ ID NO: 33 | HCDR2 (AA) (IMGT) | ISPTYSTT |
| SEQ ID NO: 34 | HCDR2 (AA) Kabat) | NISPTYSTTNYADSVKG |
| SEQ ID NO: 35 | HCDR3 (AA) (IMGT) | ARYNSYQGGLDY |
| SEQ ID NO: 36 | HCDR3 (AA) (Kabat) | YNSYQGGLDY |

Amino acid and cDNA sequences of light chain of FS22-172-003-AA/FS28-256-001 mAb[2]

Light chain AA

SEQ ID NO: 82

EIVLTQSPGTLSLSPGERATLSCRASQSVSSSYLAWYQQKPGQAPRLLIY
GASSRATGIPDRFSGSGSGTDFTLTISRLEPEDFAVYYCQQHNQYPNTFGQGTKVEIKRTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light chain DNA

SEQ ID NO: 122

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAACATAATCAGTATCCGAATACGTTCGGCCAAG
GGACCAAGGTGGAAATCAAACGTACTGTAGCAGCTCCTTCCGTGTTCATCTTTCCGCCCAGTGAT
GAGCAGCTGAAGTCAGGTACTGCTTCCGTGGTTTGCCTGCTCAACAACTTTTACCCCAGAGAAG
CCAAAGTCCAGTGGAAAGTGGACAATGCGTTGCAAAGCGGGAACTCTCAGGAATCCGTCACAGA
GCAGGACTCTAAGGACTCCACCTATAGCCTCTCTAGTACGCTGACACTGAGCAAAGCCGATTAC
GAGAAGCACAAGGTGTATGCCTGTGAGGTTACCCATCAAGGCCTTAGCTCACCAGTGACCAAGA
GCTTCAATAGGGGAGAATGC

VL domain AA

SEQ ID NO: 68

EIVLTQSPGTLSLSPGERATLSCRASQSVSSSYLAWYQQKPGQAPRLLIY
GASSRATGIPDRFSGSGSGTDFTLTISRLEPEDFAVYYCQQHNQYPNTFGQGTKVEIK

VL domain DNA

SEQ ID NO: 69

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAACATAATCAGTATCCGAATACGTTCGGCCAAG
GGACCAAGGTGGAAATCAAA

| | | |
|---|---|---|
| SEQ ID NO: 20 | LCDR1 (AA) (IMGT) | QSVSSSY |
| SEQ ID NO: 21 | LCDR1 (AA) (Kabat) | RASQSVSSSYLA |
| SEQ ID NO: 22 | LCDR2 (AA) (IMGT) | GAS |
| SEQ ID NO: 23 | LCDR2 (AA) (Kabat) | GASSRAT |
| SEQ ID NO: 40 | LCDR3 (AA) (IMGT) | QQHNQYPNT |
| SEQ ID NO: 40 | LCDR3 (AA) (Kabat) | QQHNQYPNT |

Amino acid and cDNA sequences of heavy chain of FS22-172-003-AA/FS28-256-005 mAb[2]

Heavy chain AA (without LALA)

SEQ ID NO: 118

EVQLLESGGGLVQPGGSLRLSCAASGFTFTETYMSWVRQAPGKGLEWV
SNISPTYSTTNYADSVKGRFTISRDNSKNTLYLQMNSLRAEDTAVYYCARYNSYQGGLDYWGQGTL
VTVSSASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (without LALA)

SEQ ID NO: 119

GAAGTGCAACTGCTGGAGTCCGGTGGTGGTCTGGTACAGCCGGGTG
GTTCTCTGCGTCTGAGTTGCGCGGCCAGTGGCTTTACCTTCACTGAGACTTATATGAGCTGGGT
GCGTCAGGCTCCGGGCAAAGGTCTGGAATGGGTTAGCAATATTTCTCCGACTTATAGCACTACC
AACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGATACAACTCT
TACCAGGGTGGCTTGGACTACTGGGGCCAGGGAACCTTGGTCACCGTCTCGAGTGCTAGCACT
AAGGGCCCGTCGGTGTTCCCGCTGGCCCCATCGTCCAAGAGCACATCAGGGGGTACCGCCGCC
CTGGGCTGCCTTGTGAAGGATTACTTTCCCGAGCCCGTCACAGTGTCCTGGAACAGCGGAGCCC
TGACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC

-continued

Amino acid and cDNA sequences of heavy chain of FS22-172-003-AA/ FS28-256-005 mAb[2]

GCCTTGCCCAGCCCCGGAACTGCTGGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

Heavy chain AA (with LALA)

SEQ ID NO: 120

EVQLLESGGGLVQPGGSLRLSCAASGFTFTETYMSWVRQAPGKGLEWV
SNISPTYSTTNYADSVKGRFTISRDNSKNTLYLQMNSLRAEDTAVYYCARYNSYQGGLDYWGQGTL
VTVSSASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPEAAGGPSVFLFPPK
PKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (with LALA)

SEQ ID NO: 121

GAAGTGCAACTGCTGGAGTCCGGTGGTGGTCTGGTACAGCCGGGTG
GTTCTCTGCGTCTGAGTTGCGCGGCCAGTGGCTTTACCTTCACTGAGACTTATATGAGCTGGGT
GCGTCAGGCTCCGGGCAAAGGTCTGGAATGGGTTAGCAATATTTCTCCGACTTATAGCACTACC
AACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGATACAACTCT
TACCAGGGTGGCTTGGACTACTGGGGCCAGGGAACCTTGGTCACCGTCTCGAGTGCTAGCACT
AAGGGCCCGTCGGTGTTCCCGCTGGCCCCATCGTCCAAGAGCACATCAGGGGGTACCGCCGCC
CTGGGCTGCCTTGTGAAGGATTACTTTCCCGAGCCCGTCACAGTGTCCTGGAACAGCGGAGCCC
TGACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC
GCCTTGCCCAGCCCCGGAAGCTGCCGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

VH domain AA

SEQ ID NO: 66

EVQLLESGGGLVQPGGSLRLSCAASGFTFTETYMSWVRQAPGKGLEWV
SNISPTYSTTNYADSVKGRFTISRDNSKNTLYLQMNSLRAEDTAVYYCARYNSYQGGLDYWGQGTL
VTVSS

VH domain DNA

SEQ ID NO: 67

GAAGTGCAACTGCTGGAGTCCGGTGGTGGTCTGGTACAGCCGGGTG
GTTCTCTGCGTCTGAGTTGCGCGGCCAGTGGCTTTACCTTCACTGAGACTTATATGAGCTGGGT
GCGTCAGGCTCCGGGCAAAGGTCTGGAATGGGTTAGCAATATTTCTCCGACTTATAGCACTACC
AACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGATACAACTCT
TACCAGGGTGGCTTGGACTACTGGGGCCAGGGAACCTTGGTCACCGTCTCGAGT

| | | |
|---|---|---|
| SEQ ID NO: 38 | HCDR1 (AA) (IMGT) | GFTFTETY |
| SEQ ID NO: 39 | HCDR1 (AA) (Kabat) | ETYMS |
| SEQ ID NO: 33 | HCDR2 (AA) (IMGT) | ISPTYSTT |
| SEQ ID NO: 34 | HCDR2 (AA) Kabat) | NISPTYSTTNYADSVKG |
| SEQ ID NO: 35 | HCDR3 (AA) (IMGT) | ARYNSYQGGLDY |
| SEQ ID NO: 36 | HCDR3 (AA) (Kabat) | YNSYQGGLDY |

Amino acid and cDNA sequences of light chain of FS22-172-003-AA/ FS28-256-005 mAb[2]

SEQ ID NO: 83

Light chain AA
*EIVLTQSPGTLSLSPGERATLSCRASQSVSSSYLAWYQQKPGQAPRLLIY*
*GASSRATGIPDRFSGSGSGTDFTLTISRLEPEDFAVYYCQQALGYPHTFGQGTKVEIK*RTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC Light chain DNA

SEQ ID NO: 90

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAGCTTTGGGTTATCCTCATACGTTCGGCCAAG
GGACCAAGGTGGAAATCAAACGTACTGTAGCAGCTCCTTCCGTGTTCATCTTTCCGCCCAGTGAT
GAGCAGCTGAAGTCAGGTACTGCTTCCGTGGTTTGCCTGCTCAACAACTTTTACCCCAGAGAAG
CCAAAGTCCAGTGGAAAGTGGACAATGCGTTGCAAAGCGGGAACTCTCAGGAATCCGTCACAGA
GCAGGACTCTAAGGACTCCACCTATAGCCTCTCTAGTACGCTGACACTGAGCAAAGCCGATTAC
GAGAAGCACAAGGTGTATGCCTGTGAGGTTACCCATCAAGGCCTTAGCTCACCAGTGACCAAGA
GCTTCAATAGGGGAGAATGC

VL domain AA

SEQ ID NO: 78

*EIVLTQSPGTLSLSPGERATLSCRASQSVSSSYLAWYQQKPGQAPRLLIY*
*GASSRATGIPDRFSGSGSGTDFTLTISRLEPEDFAVYYCQQALGYPHTFGQGTKVEIK*

VL domain DNA

SEQ ID NO: 79

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAGCTTTGGGTTATCCTCATACGTTCGGCCAAG
GGACCAAGGTGGAAATCAAA

| | | |
|---|---|---|
| SEQ ID NO: 20 | LCDR1 (AA) (IMGT) | QSVSSSY |
| SEQ ID NO: 21 | LCDR1 (AA) (Kabat) | RASQSVSSSYLA |
| SEQ ID NO: 22 | LCDR2 (AA) (IMGT) | GAS |
| SEQ ID NO: 23 | LCDR2 (AA) (Kabat) | GASSRAT |
| SEQ ID NO: 41 | LCDR3 (AA) (IMGT) | QQALGYPHT |
| SEQ ID NO: 41 | LCDR3 (AA) (Kabat) | QQALGYPHT |

Amino acid and cDNA sequences of heavy chain of FS22-172-003-AA/ FS28-256-012 mAb[2]

Heavy chain AA (without LALA)

SEQ ID NO: 123

*EVQLLESGGGLVQPGGSLRLSCAASGFTFTHTYMSWVRQAPGKGLEWV*
*SNISPTYSTTNYADSVKGRFTISRDNSKNTLYLQMNSLRAEDTAVYYCARYNAYHAALDYWGQGTL*
*VTVSS*ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (without LALA)

SEQ ID NO: 124

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAACAAGAACACGCTGTACC
TGCAGATGAACTCACTGCGTGCCGAAGATACGGCCGTGTATTACTGTGCGAGATACAACGCGTA
TCATGCTGCTCTGGACTACTGGGGCCAGGGAACCCTGGTCACCGTCTCGAGTGCTAGCACTAAG
GGCCCGTCGGTGTTCCCGCTGGCCCCATCGTCCAAGAGCACATCAGGGGGTACCGCCGCCCTG
GGCTGCCTTGTGAAGGATTACTTTCCCGAGCCCGTCACAGTGTCCTGGAACAGCGGAGCCCTGA
CCTCCGGAGTGCATACTTTCCCGGCTGTGCTTCAGTCCTCTGGCCTGTACTCATTGTCCTCCGTG
GTCACCGTCCCTTCGTCCTCCCTGGGCACCCAGACCTATATCTGTAATGTCAACCATAAGCCCTC
GAACACCAAGGTCGACAAGAAGGTCGAGCCGAAGTCGTGCGACAAGACTCACACTTGCCCGCC

-continued

Amino acid and cDNA sequences of heavy chain of FS22-172-003-AA/ FS28-256-012 mAb[2]

TTGCCCAGCCCCGGAACTGCTGGGTGGTCCTTCGGTGTTCCTCTTCCCGCCCAAGCCGAAGGAT
ACCCTGATGATCTCACGGACCCCCGAAGTGACCTGTGTGGTGGTGGACGTGTCCCACGAGGAC
CCGGAAGTGAAATTCAATTGGTACGTGGATGGAGTGGAAGTGCACAACGCCAAGACCAAGCCAC
GGGAAGAACAGTACAACTCTACCTACCGCGTGGTGTCCGTGCTCACTGTGCTGCACCAAGACTG
GCTGAACGGGAAGGAGTACAAGTGCAAAGTGTCCAACAAGGCGCTGCCTGCCCCAATTGAGAAA
ACTATCTCGAAAGCCAAGGGACAGCCTCGAGAACCACAGGTGTACACCCTGCCCCCATCCCGG
GATGAGCTGCCATACATCATCCCACCATACAACCAGGTCAGCCTGACCTGCCTGGTCAAAGGCT
TCTATCCCAGCGACATCGCCGTGGAGTGGGAGAGCAATGGGCAGCCGGAGAACAACTACAAGA
CCACGCCTCCCGTGCTGGACTCCGACGGCTCCTTCTTCCTCTACAGCAAGCTCACCGTGGGCG
CAGATAGGTGGCTGGAAGGGAACGTCTTCTCATGCTCCGTGATGCATGAGGCGCTGCACAACCA
CTACACTCAGAAGAGCTTGTCCCTGTCGCCCGGT

Heavy chain AA (with LALA)

SEQ ID NO: 125

*EVQLLESGGGLVQPGGSLRLSCAAS*__GFTFTHTY__*MSWVRQAPGKGLEWV*
*SN*__ISPTYSTT__*NYADSVKGRFTISRDNSKNTLYLQMNSLRAEDTAVYYC*__ARYNAYHAALDY__*WGQGTL*
*VTVSS*ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPEAAGGPSVFLFPPK
PKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (with LALA)

SEQ ID NO: 126

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAACAAGAACACGCTGTACC
TGCAGATGAACTCACTGCGTGCCGAAGATACGGCCGTGTATTACTGTGCGAGATACAACGCGTA
TCATGCTGCTCTGGACTACTGGGGCCAGGGAACCCTGGTCACCGTCTCGAGTGCTAGCACTAAG
GGCCCGTCGGTGTTCCCGCTGGCCCCATCGTCCAAGAGCACATCAGGGGGTACCGCCGCCCTG
GGCTGCCTTGTGAAGGATTACTTTCCCGAGCCCGTCACAGTGTCCTGGAACAGCGGAGCCCTGA
CCTCCGGAGTGCATACTTTCCCGGCTGTGCTTCAGTCCTCTGGCCTGTACTCATTGTCCTCCGTG
GTCACCGTCCCTTCGTCCTCCCTGGGCACCCAGACCTATATCTGTAATGTCAACCATAAGCCCTC
GAACACCAAGGTCGACAAGAAGGTCGAGCCGAAGTCGTGCGACAAGACTCACACTTGCCCGCC
TTGCCCAGCCCCGGAAGCTGCCGGTGGTCCTTCGGTGTTCCTCTTCCCGCCCAAGCCGAAGGA
TACCCTGATGATCTCACGGACCCCCGAAGTGACCTGTGTGGTGGTGGACGTGTCCCACGAGGA
CCCGGAAGTGAAATTCAATTGGTACGTGGATGGAGTGGAAGTGCACAACGCCAAGACCAAGCCA
CGGGAAGAACAGTACAACTCTACCTACCGCGTGGTGTCCGTGCTCACTGTGCTGCACCAAGACT
GGCTGAACGGGAAGGAGTACAAGTGCAAAGTGTCCAACAAGGCGCTGCCTGCCCCAATTGAGA
AAACTATCTCGAAAGCCAAGGGACAGCCTCGAGAACCACAGGTGTACACCCTGCCCCCATCCCG
GGATGAGCTGCCATACATCATCCCACCATACAACCAGGTCAGCCTGACCTGCCTGGTCAAAGGC
TTCTATCCCAGCGACATCGCCGTGGAGTGGGAGAGCAATGGGCAGCCGGAGAACAACTACAAG
ACCACGCCTCCCGTGCTGGACTCCGACGGCTCCTTCTTCCTCTACAGCAAGCTCACCGTGGGCG
CAGATAGGTGGCTGGAAGGGAACGTCTTCTCATGCTCCGTGATGCATGAGGCGCTGCACAACCA
CTACACTCAGAAGAGCTTGTCCCTGTCGCCCGGT

VH domain AA

SEQ ID NO: 70

*EVQLLESGGGLVQPGGSLRLSCAAS*__GFTFTHTY__*MSWVRQAPGKGLEWV*
*SN*__ISPTYSTT__*NYADSVKGRFTISRDNSKNTLYLQMNSLRAEDTAVYYC*__ARYNAYHAALDY__*WGQGTLV*
*TVSS*

VH domain DNA

SEQ ID NO: 71

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAACAAGAACACGCTGTACC
TGCAGATGAACTCACTGCGTGCCGAAGATACGGCCGTGTATTACTGTGCGAGATACAACGCGTA
TCATGCTGCTCTGGACTACTGGGGCCAGGGAACCCTGGTCACCGTCTCGAGT

| | | |
|---|---|---|
| SEQ ID NO: 42 | HCDR1 (AA) (IMGT) | GFTFTHTY |
| SEQ ID NO: 43 | HCDR1 (AA) (Kabat) | HTYMS |
| SEQ ID NO: 33 | HCDR2 (AA) (IMGT) | ISPTYSTT |
| SEQ ID NO: 34 | HCDR2 (AA) Kabat) | NISPTYSTTNYADSVKG |
| SEQ ID NO: 44 | HCDR3 (AA) (IMGT) | ARYNAYHAALDY |
| SEQ ID NO: 45 | HCDR3 (AA) (Kabat) | YNAYHAALDY |

| Amino acid and cDNA sequences of light chain of FS22-172-003-AA/ FS28-256-012 mAb[2] |
|---|

Light chain AA

SEQ ID NO: 116

EIVLTQSPGTLSLSPGERATLSCRASQSVSSSYLAWYQQKPGQAPRLLIY
GASSRATGIPDRFSGSGSGTDFTLTISRLEPEDFAVYYCQQSYYYPITFGQGTKVEIKRTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light chain DNA

SEQ ID NO: 117

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAATCTTATTATTATCCTATCACGTTCGGCCAAG
GGACCAAGGTGGAAATCAAACGTACTGTGGCCGCTCCTAGCGTGTTCATTTTTCCGCCATCCGA
CGAGCAGCTCAAGTCCGGCACCGCCTCCGTGGTCTGCCTGCTCAACAACTTCTACCCTCGCGAA
GCTAAGGTCCAGTGGAAGGTCGACAATGCCCTGCAGTCCGGAAACTCGCAGGAAAGCGTGACT
GAACAGGACTCCAAGGACTCCACCTATTCACTGTCCTCGACTCTGACCCTGAGCAAGGCGGATT
ACGAAAAGCACAAAGTGTACGCATGCGAAGTGACCCACCAGGGTCTTTCGTCCCCCGTGACCAA
GAGCTTCAACAGAGGAGAGTGT

VL domain AA

SEQ ID NO: 64

EIVLTQSPGTLSLSPGERATLSCRASQSVSSSYLAWYQQKPGQAPRLLIY
GASSRATGIPDRFSGSGSGTDFTLTISRLEPEDFAVYYCQQSYYYPITFGQGTKVEIK

VL domain DNA

SEQ ID NO: 65

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAATCTTATTATTATCCTATCACGTTCGGCCAAG
GGACCAAGGTGGAAATCAAA

| | | |
|---|---|---|
| SEQ ID NO: 20 | LCDR1 (AA) (IMGT) | QSVSSSY |
| SEQ ID NO: 21 | LCDR1 (AA) (Kabat) | RASQSVSSSYLA |
| SEQ ID NO: 22 | LCDR2 (AA) (IMGT) | GAS |
| SEQ ID NO: 23 | LCDR2 (AA) (Kabat) | GASSRAT |
| SEQ ID NO: 37 | LCDR3 (AA) (IMGT) | QQSYYYPIT |
| SEQ ID NO: 37 | LCDR3 (AA) (Kabat) | QQSYYYPIT |

| Amino acid and cDNA sequences of heavy chain of FS22-172-003-AA/ FS28-256-014 mAb[2] |
|---|

Heavy chain AA (without LALA)

SEQ ID NO: 127

EVQLLESGGGLVQPGGSLRLSCAASGFTFTDTYMSWVRQAPGKGLEWV
SNISPTYSTTNYADSVKGRFTISRDNSKNTLYLQMNSLRAEDTAVYYCARYNAYAAGLDYWGQGTL
VTVSSASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (without LALA)

SEQ ID NO: 128

GAAGTGCAACTGCTGGAGTCCGGTGGTGGTCTGGTACAGCCGGGTG
GTTCTCTGCGTCTGAGTTGCGCGGCCAGTGGCTTTACCTTCACTGATACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAGCAAGAACACGCTGTAC
CTGCAGATGAACTCACTGCGTGCCGAAGATACGGCCGTGTATTACTGTGCGAGATACAACGCGT
ATGCGGCGGGTCTTGACTACTGGGGCCAGGGAACCCTGGTCACCGTCTCGAGTGCTAGCACTA
AGGGCCCGTCGGTGTTCCCGCTGGCCCCATCGTCCAAGAGCACATCAGGGGGTACCGCCGCCC
TGGGCTGCCTTGTGAAGGATTACTTTCCCGAGCCCGTCACAGTGTCCTGGAACAGCGGAGCCCT
GACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC

-continued

Amino acid and cDNA sequences of heavy chain of FS22-172-003-AA/ FS28-256-014 mAb[2]

GCCTTGCCCAGCCCCGGAACTGCTGGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

Heavy chain AA (with LALA)

SEQ ID NO: 129

*EVQLLESGGGLVQPGGSLRLSCAASGFTFTDTYMSWVRQAPGKGLEWV*
*SNISPTYSTTNYADSVKGRFTISRDNSKNTLYLQMNSLRAEDTAVYYCARYNAYAAGLDYWGQGTL*
*VTVSS*ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPEAAGGPSVFLFPPK
PKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (with LALA)

SEQ ID NO: 130

GAAGTGCAACTGCTGGAGTCCGGTGGTGGTCTGGTACAGCCGGGTG
GTTCTCTGCGTCTGAGTTGCGCGGCCAGTGGCTTTACCTTCACTGATACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAGCAAGAACACGCTGTAC
CTGCAGATGAACTCACTGCGTGCCGAAGATACGGCCGTGTATTACTGTGCGAGATACAACGCGT
ATGCGGCGGGTCTTGACTACTGGGGCCAGGGAACCCTGGTCACCGTCTCGAGTGCTAGCACTA
AGGGCCCGTCGGTGTTCCCGCTGGCCCCATCGTCCAAGAGCACATCAGGGGGTACCGCCGCCC
TGGGCTGCCTTGTGAAGGATTACTTTCCCGAGCCCGTCACAGTGTCCTGGAACAGCGGAGCCCT
GACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC
GCCTTGCCCAGCCCCGGAAGCTGCCGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

VH domain AA

SEQ ID NO: 72

*EVQLLESGGGLVQPGGSLRLSCAASGFTFTDTYMSWVRQAPGKGLEWV*
*SNISPTYSTTNYADSVKGRFTISRDNSKNTLYLQMNSLRAEDTAVYYCARYNAYAAGLDYWGQGTLV*
*TVSS*

VH domain DNA

SEQ ID NO: 73

GAAGTGCAACTGCTGGAGTCCGGTGGTGGTCTGGTACAGCCGGGTG
GTTCTCTGCGTCTGAGTTGCGCGGCCAGTGGCTTTACCTTCACTGATACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAGCAAGAACACGCTGTAC
CTGCAGATGAACTCACTGCGTGCCGAAGATACGGCCGTGTATTACTGTGCGAGATACAACGCGT
ATGCGGCGGGTCTTGACTACTGGGGCCAGGGAACCCTGGTCACCGTCTCGAGT

| | | |
|---|---|---|
| SEQ ID NO: 46 | HCDR1 (AA) (IMGT) | GFTFTDTY |
| SEQ ID NO: 47 | HCDR1 (AA) (Kabat) | DTYMS |
| SEQ ID NO: 33 | HCDR2 (AA) (IMGT) | ISPTYSTT |
| SEQ ID NO: 34 | HCDR2 (AA) Kabat) | NISPTYSTTNYADSVKG |
| SEQ ID NO: 48 | HCDR3 (AA) (IMGT) | ARYNAYAAGLDY |
| SEQ ID NO: 49 | HCDR3 (AA) (Kabat) | YNAYAAGLDY |

| Amino acid and cDNA sequences of light chain of FS22-172-003-AA/ FS28-256-014 mAb[2] |
|---|

Light chain AA

SEQ ID NO: 116

*EIVLTQSPGTLSLSPGERATLSCRASQSVSSSYLAWYQQKPGQAPRLLIY*
*GASSRATGIPDRFSGSGSGTDFTLTISRLEPEDFAVYYCQQSYYYPITFGQGTKVEIK*RTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light chain DNA

SEQ ID NO: 117

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAATCTTATTATTATCCTATCACGTTCGGCCAAG
GGACCAAGGTGGAAATCAAACGTACTGTGGCCGCTCCTAGCGTGTTCATTTTTCCGCCATCCGA
CGAGCAGCTCAAGTCCGGCACCGCCTCCGTGGTCTGCCTGCTCAACAACTTCTACCCTCGCGAA
GCTAAGGTCCAGTGGAAGGTCGACAATGCCCTGCAGTCCGGAAACTCGCAGGAAAGCGTGACT
GAACAGGACTCCAAGGACTCCACCTATTCACTGTCCTCGACTCTGACCCTGAGCAAGGCGGATT
ACGAAAAGCACAAAGTGTACGCATGCGAAGTGACCCACCAGGGTCTTTCGTCCCCCGTGACCAA
GAGCTTCAACAGAGGAGAGTGT

VL domain AA

SEQ ID NO: 64

*EIVLTQSPGTLSLSPGERATLSCRASQSVSSSYLAWYQQKPGQAPRLLIY*
*GASSRATGIPDRFSGSGSGTDFTLTISRLEPEDFAVYYCQQSYYYPITFGQGTKVEIK*

VL domain DNA

SEQ ID NO: 65

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAATCTTATTATTATCCTATCACGTTCGGCCAAG
GGACCAAGGTGGAAATCAAA

| | | |
|---|---|---|
| SEQ ID NO: 20 | LCDR1 (AA) (IMGT) | QSVSSSY |
| SEQ ID NO: 21 | LCDR1 (AA) (Kabat) | RASQSVSSSYLA |
| SEQ ID NO: 22 | LCDR2 (AA) (IMGT) | GAS |
| SEQ ID NO: 23 | LCDR2 (AA) (Kabat) | GASSRAT |
| SEQ ID NO: 37 | LCDR3 (AA) (IMGT) | QQSYYYPIT |
| SEQ ID NO: 37 | LCDR3 (AA) (Kabat) | QQSYYYPIT |

| Amino acid and cDNA sequences of heavy chain of FS22-172-003-AA/ FS28-256-018 mAb[2] |
|---|

Heavy chain AA (without LALA)

SEQ ID NO: 131

*EVQLLESGGGLVQPGGSLRLSCAASGFTFTQTYMSWVRQAPGKGLEWV*
*SNISPTYSTTNYADSVKGRFTISRDNSKNTLYLQMNSLRAEDTAVYYCARYNAYQIGLDYWGQGTL*
*VTVSS*ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (without LALA)

SEQ ID NO: 132

GAAGTGCAACTGCTGGAGTCCGGTGGTGGTCTGGTACAGCCGGGTGGTTCTCTGCGTC
TGAGTTGCGCGGCCAGTGGCTTTACCTTCACTCAGACTTATATGAGCTGGGTGCGTCAGGCTCC
GGGCAAAGGTCTGGAATGGGTTAGCAATATTTCTCCGACTTATAGCACTACCAACTATGCGGATA
GCGTGAAAGGCCGTTTTACCATTTCTCGCGACAACAGCAAGAACACGCTGTACCTGCAGATGAA
CTCACTGCGTGCCGAAGATACGGCCGTGTATTACTGTGCGAGATACAACGCTTATCAGATTGGG
TTGGACTACTGGGGCCAGGGAACCCTGGTCACCGTCTCGAGTGCTAGCACTAAGGGCCCGTCG
GTGTTCCCGCTGGCCCCATCGTCCAAGAGCACATCAGGGGGTACCGCCGCCCTGGGCTGCCTT
GTGAAGGATTACTTTCCCGAGCCCGTCACAGTGTCCTGGAACAGCGGAGCCCTGACCTCCGGA
GTGCATACTTTCCCGGCTGTGCTTCAGTCCTCTGGCCTGTACTCATTGTCCTCCGTGGTCACCGT
CCCTTCGTCCTCCCTGGGCACCCAGACCTATATCTGTAATGTCAACCATAAGCCCTCGAACACCA
AGGTCGACAAGAAGGTCGAGCCGAAGTCGTGCGACAAGACTCACACTTGCCCGCCTTGCCCAG

-continued

| Amino acid and cDNA sequences of heavy chain of FS22-172-003-AA/ FS28-256-018 mAb[2] |
|---|
| CCCCGGAACTGCTGGGTGGTCCTTCGGTGTTCCTCTTCCCGCCCAAGCCGAAGGATACCCTGAT<br>GATCTCACGGACCCCCGAAGTGACCTGTGTGGTGGTGGACGTGTCCCACGAGGACCCGGAAGT<br>GAAATTCAATTGGTACGTGGATGGAGTGGAAGTGCACAACGCCAAGACCAAGCCACGGGAAGAA<br>CAGTACAACTCTACCTACCGCGTGGTGTCCGTGCTCACTGTGCTGCACCAAGACTGGCTGAACG<br>GGAAGGAGTACAAGTGCAAAGTGTCCAACAAGGCGCTGCCTGCCCCAATTGAGAAAACTATCTC<br>GAAAGCCAAGGGACAGCCTCGAGAACCACAGGTGTACACCCTGCCCCCATCCCGGGATGAGCT<br>GCCATACATCATCCCACCATACAACCAGGTCAGCCTGACCTGCCTGGTCAAAGGCTTCTATCCCA<br>GCGACATCGCCGTGGAGTGGGAGAGCAATGGGCAGCCGGAGAACAACTACAAGACCACGCCTC<br>CCGTGCTGGACTCCGACGGCTCCTTCTTCCTCTACAGCAAGCTCACCGTGGGCGCAGATAGGTG<br>GCTGGAAGGGAACGTCTTCTCATGCTCCGTGATGCATGAGGCGCTGCACAACCACTACACTCAG<br>AAGAGCTTGTCCCTGTCGCCCGGT |
| Heavy chain AA (with LALA) |
| SEQ ID NO: 133 |
| *EVQLLESGGGLVQPGGSLRLSCAAS**GFTFTQTY**MSWVRQAPGKGLEWV*<br>*SN**ISPTYSTT**NYADSVKGRFTISRDNSKNTLYLQMNSLRAEDTAVYYC**ARYNAYQIGLDY**WGQGTL*<br>*VTVSS*ASTKGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKKVEPKSCDKTHTCPPCP**APEAAGGPSVFLFPPK**<br>**PKDTLMISRTPEVTCVVVDVSHEDPEVKFNWYVDGVEVHNAKTKPREEQYNSTYRVVSVLTVLHQD**<br>**WLNGKEYKCKVSNKALPAPIEKTISKAK**GQPREPQVYTLPPSRDELPYIIPPYNQVSLTCLVKGFYPS<br>DIAVEWESNGQPENNYKTTPPVLDSDGSFFLYSKLTVGADRWLEGNVFSCSVMHEALHNHYTQKSL<br>SLSPG |
| Heavy chain DNA (with LALA) |
| SEQ ID NO: 134 |
| GAAGTGCAACTGCTGGAGTCCGGTGGTGGTCTGGTACAGCCGGGTG<br>GTTCTCTGCGTCTGAGTTGCGCGGCCAGTGGCTTTACCTTCACTCAGACTTATATGAGCTGGGT<br>GCGTCAGGCTCCGGGCAAAGGTCTGGAATGGGTTAGCAATATTTCTCCGACTTATAGCACTACC<br>AACTATGCGGATAGCGTGAAAGGCCGTTTTACCATTTCTCGCGACAACAGCAAGAACACGCTGTA<br>CCTGCAGATGAACTCACTGCGTGCCGAAGATACGGCCGTGTATTACTGTGCGAGATACAACGCT<br>TATCAGATTGGGTTGGACTACTGGGGCCAGGGAACCCTGGTCACCGTCTCGAGTGCTAGCACTA<br>AGGGCCCGTCGGTGTTCCCGCTGGCCCCATCGTCCAAGAGCACATCAGGGGGTACCGCCGCCC<br>TGGGCTGCCTTGTGAAGGATTACTTTCCCGAGCCCGTCACAGTGTCCTGGAACAGCGGAGCCCT<br>GACCTCCGGAGTGCATACTTTCCCGGCTGTGCTTCAGTCCTCTGGCCTGTACTCATTGTCCTCC<br>GTGGTCACCGTCCCTTCGTCCTCCCTGGGCACCCAGACCTATATCTGTAATGTCAACCATAAGCC<br>CTCGAACACCAAGGTCGACAAGAAGGTCGAGCCGAAGTCGTGCGACAAGACTCACACTTGCCC<br>GCCTTGCCCAGCCCCGGAAGCTGCCGGTGGTCCTTCGGTGTTCCTCTTCCCGCCCAAGCCGAA<br>GGATACCCTGATGATCTCACGGACCCCCGAAGTGACCTGTGTGGTGGTGGACGTGTCCCACGA<br>GGACCCGGAAGTGAAATTCAATTGGTACGTGGATGGAGTGGAAGTGCACAACGCCAAGACCAAG<br>CCACGGGAAGAACAGTACAACTCTACCTACCGCGTGGTGTCCGTGCTCACTGTGCTGCACCAAG<br>ACTGGCTGAACGGGAAGGAGTACAAGTGCAAAGTGTCCAACAAGGCGCTGCCTGCCCCAATTGA<br>GAAAACTATCTCGAAAGCCAAGGGACAGCCTCGAGAACCACAGGTGTACACCCTGCCCCCATCC<br>CGGGATGAGCTGCCATACATCATCCCACCATACAACCAGGTCAGCCTGACCTGCCTGGTCAAAG<br>GCTTCTATCCCAGCGACATCGCCGTGGAGTGGGAGAGCAATGGGCAGCCGGAGAACAACTACA<br>AGACCACGCCTCCCGTGCTGGACTCCGACGGCTCCTTCTTCCTCTACAGCAAGCTCACCGTGGG<br>CGCAGATAGGTGGCTGGAAGGGAACGTCTTCTCATGCTCCGTGATGCATGAGGCGCTGCACAA<br>CCACTACACTCAGAAGAGCTTGTCCCTGTCGCCCGGT |
| VH domain AA |
| SEQ ID NO: 74 |
| *EVQLLESGGGLVQPGGSLRLSCAAS**GFTFTQTY**MSWVRQAPGKGLEWV*<br>*SN**ISPTYSTT**NYADSVKGRFTISRDNSKNTLYLQMNSLRAEDTAVYYC**ARYNAYQIGLDY**WGQGTLV*<br>*TVSS* |
| VH domain DNA |
| SEQ ID NO: 75 |
| GAAGTGCAACTGCTGGAGTCCGGTGGTGGTCTGGTACAGCCGGGTG<br>GTTCTCTGCGTCTGAGTTGCGCGGCCAGTGGCTTTACCTTCACTCAGACTTATATGAGCTGGGT<br>GCGTCAGGCTCCGGGCAAAGGTCTGGAATGGGTTAGCAATATTTCTCCGACTTATAGCACTACC<br>AACTATGCGGATAGCGTGAAAGGCCGTTTTACCATTTCTCGCGACAACAGCAAGAACACGCTGTA<br>CCTGCAGATGAACTCACTGCGTGCCGAAGATACGGCCGTGTATTACTGTGCGAGATACAACGCT<br>TATCAGATTGGGTTGGACTACTGGGGCCAGGGAACCCTGGTCACCGTCTCGAGT |

| | | |
|---|---|---|
| SEQ ID NO: 50 | HCDR1 (AA) (IMGT) | GFTFTQTY |
| SEQ ID NO: 51 | HCDR1 (AA) (Kabat) | QTYMS |
| SEQ ID NO: 33 | HCDR2 (AA) (IMGT) | ISPTYSTT |
| SEQ ID NO: 34 | HCDR2 (AA) Kabat) | NISPTYSTTNYADSVKG |
| SEQ ID NO: 52 | HCDR3 (AA) (IMGT) | ARYNAYQIGLDY |
| SEQ ID NO: 53 | HCDR3 (AA) (Kabat) | YNAYQIGLDY |

Amino acid and cDNA sequences of light chain of FS22-172-003-AA/FS28-256-018 mAb[2]

Light chain AA

SEQ ID NO: 116

EIVLTQSPGTLSLSPGERATLSCRASQSVSSSYLAWYQQKPGQAPRLLIY
GASSRATGIPDRFSGSGSGTDFTLTISRLEPEDFAVYYCQQSYYYPITFGQGTKVEIKRTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light chain DNA

SEQ ID NO: 117

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAATCTTATTATTATCCTATCACGTTCGGCCAAG
GGACCAAGGTGGAAATCAAACGTACTGTGGCCGCTCCTAGCGTGTTCATTTTTCCGCCATCCGA
CGAGCAGCTCAAGTCCGGCACCGCCTCCGTGGTCTGCCTGCTCAACAACTTCTACCCTCGCGAA
GCTAAGGTCCAGTGGAAGGTCGACAATGCCCTGCAGTCCGGAAACTCGCAGGAAAGCGTGACT
GAACAGGACTCCAAGGACTCCACCTATTCACTGTCCTCGACTCTGACCCTGAGCAAGGCGGATT
ACGAAAAGCACAAAGTGTACGCATGCGAAGTGACCCACCAGGGTCTTTCGTCCCCCGTGACCAA
GAGCTTCAACAGAGGAGAGTGT

VL domain AA

SEQ ID NO: 64

EIVLTQSPGTLSLSPGERATLSCRASQSVSSSYLAWYQQKPGQAPRLLIY
GASSRATGIPDRFSGSGSGTDFTLTISRLEPEDFAVYYCQQSYYYPITFGQGTKVEIK

VL domain DNA

SEQ ID NO: 65

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAATCTTATTATTATCCTATCACGTTCGGCCAAG
GGACCAAGGTGGAAATCAAA

| | | |
|---|---|---|
| SEQ ID NO: 20 | LCDR1 (AA) (IMGT) | QSVSSSY |
| SEQ ID NO: 21 | LCDR1 (AA) (Kabat) | RASQSVSSSYLA |
| SEQ ID NO: 22 | LCDR2 (AA) (IMGT) | GAS |
| SEQ ID NO: 23 | LCDR2 (AA) (Kabat) | GASSRAT |
| SEQ ID NO: 37 | LCDR3 (AA) (IMGT) | QQSYYYPIT |
| SEQ ID NO: 37 | LCDR3 (AA) (Kabat) | QQSYYYPIT |

Amino acid and cDNA sequences of heavy chain of FS22-172-003-AA/FS28-256-021 mAb[2]

Heavy chain AA (without LALA)

SEQ ID NO: 123

EVQLLESGGGLVQPGGSLRLSCAASGFTFTHTYMSWVRQAPGKGLEWV
SNISPTYSTTNYADSVKGRFTISRDNNKNTLYLQMNSLRAEDTAVYYCARYNAYHAALDYWGQGTLV
TVSSASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (without LALA)

SEQ ID NO: 124

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAACAAGAACACGCTGTACC
TGCAGATGAACTCACTGCGTGCCGAAGATACGGCCGTGTATTACTGTGCGAGATACAACGCGTA
TCATGCTGCTCTGGACTACTGGGGCCAGGGAACCCTGGTCACCGTCTCGAGTGCTAGCACTAAG
GGCCCGTCGGTGTTCCCGCTGGCCCCATCGTCCAAGAGCACATCAGGGGGTACCGCCGCCCTG
GGCTGCCTTGTGAAGGATTACTTTCCCGAGCCCGTCACAGTGTCCTGGAACAGCGGAGCCCTGA
CCTCCGGAGTGCATACTTTCCCGGCTGTGCTTCAGTCCTCTGGCCTGTACTCATTGTCCTCCGTG
GTCACCGTCCCTTCGTCCTCCCTGGGCACCCAGACCTATATCTGTAATGTCAACCATAAGCCCTC
GAACACCAAGGTCGACAAGAAGGTCGAGCCGAAGTCGTGCGACAAGACTCACACTTGCCCGCC

-continued

| Amino acid and cDNA sequences of heavy chain of FS22-172-003-AA/ FS28-256-021 mAb[2] |
|---|

TTGCCCAGCCCCGGAACTGCTGGGTGGTCCTTCGGTGTTCCTCTTCCCGCCCAAGCCGAAGGAT
ACCCTGATGATCTCACGGACCCCCGAAGTGACCTGTGTGGTGGTGGACGTGTCCCACGAGGAC
CCGGAAGTGAAATTCAATTGGTACGTGGATGGAGTGGAAGTGCACAACGCCAAGACCAAGCCAC
GGGAAGAACAGTACAACTCTACCTACCGCGTGGTGTCCGTGCTCACTGTGCTGCACCAAGACTG
GCTGAACGGGAAGGAGTACAAGTGCAAAGTGTCCAACAAGGCGCTGCCTGCCCCAATTGAGAAA
ACTATCTCGAAAGCCAAGGGACAGCCTCGAGAACCACAGGTGTACACCCTGCCCCCATCCCGG
GATGAGCTGCCATACATCATCCCACCATACAACCAGGTCAGCCTGACCTGCCTGGTCAAAGGCT
TCTATCCCAGCGACATCGCCGTGGAGTGGGAGAGCAATGGGCAGCCGGAGAACAACTACAAGA
CCACGCCTCCCGTGCTGGACTCCGACGGCTCCTTCTTCCTCTACAGCAAGCTCACCGTGGGCG
CAGATAGGTGGCTGGAAGGGAACGTCTTCTCATGCTCCGTGATGCATGAGGCGCTGCACAACCA
CTACACTCAGAAGAGCTTGTCCCTGTCGCCCGGT

Heavy chain AA (with LALA)
SEQ ID NO: 125
*EVQLLESGGGLVQPGGSLRLSCAASGFTFTHTYMS*WVRQAPGKGLEWV
*SNISPTYSTTNYADSVKG*RFTISRDNNKNTLYLQMNSLRAEDTAVYYC*ARYNAYHAALDY*WGQGTLV*
*TVSS*ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPEAAGGPSVFLFPPKP
KDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG Heavy chain DNA (with LALA)
SEQ ID NO: 126
GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAACAAGAACACGCTGTACC
TGCAGATGAACTCACTGCGTGCCGAAGATACGGCCGTGTATTACTGTGCGAGATACAACGCGTA
TCATGCTGCTCTGGACTACTGGGGCCAGGGAACCCTGGTCACCGTCTCGAGTGCTAGCACTAAG
GGCCCGTCGGTGTTCCCGCTGGCCCCATCGTCCAAGAGCACATCAGGGGGTACCGCCGCCCTG
GGCTGCCTTGTGAAGGATTACTTTCCCGAGCCCGTCACAGTGTCCTGGAACAGCGGAGCCCTGA
CCTCCGGAGTGCATACTTTCCCGGCTGTGCTTCAGTCCTCTGGCCTGTACTCATTGTCCTCCGTG
GTCACCGTCCCTTCGTCCTCCCTGGGCACCCAGACCTATATCTGTAATGTCAACCATAAGCCCTC
GAACACCAAGGTCGACAAGAAGGTCGAGCCGAAGTCGTGCGACAAGACTCACACTTGCCCGCC
TTGCCCAGCCCCGGAAGCTGCCGGTGGTCCTTCGGTGTTCCTCTTCCCGCCCAAGCCGAAGGA
TACCCTGATGATCTCACGGACCCCCGAAGTGACCTGTGTGGTGGTGGACGTGTCCCACGAGGA
CCCGGAAGTGAAATTCAATTGGTACGTGGATGGAGTGGAAGTGCACAACGCCAAGACCAAGCCA
CGGGAAGAACAGTACAACTCTACCTACCGCGTGGTGTCCGTGCTCACTGTGCTGCACCAAGACT
GGCTGAACGGGAAGGAGTACAAGTGCAAAGTGTCCAACAAGGCGCTGCCTGCCCCAATTGAGA
AAACTATCTCGAAAGCCAAGGGACAGCCTCGAGAACCACAGGTGTACACCCTGCCCCCATCCCG
GGATGAGCTGCCATACATCATCCCACCATACAACCAGGTCAGCCTGACCTGCCTGGTCAAAGGC
TTCTATCCCAGCGACATCGCCGTGGAGTGGGAGAGCAATGGGCAGCCGGAGAACAACTACAAG
ACCACGCCTCCCGTGCTGGACTCCGACGGCTCCTTCTTCCTCTACAGCAAGCTCACCGTGGGCG
CAGATAGGTGGCTGGAAGGGAACGTCTTCTCATGCTCCGTGATGCATGAGGCGCTGCACAACCA
CTACACTCAGAAGAGCTTGTCCCTGTCGCCCGGT VH domain AA
SEQ ID NO: 70
*EVQLLESGGGLVQPGGSLRLSCAASGFTFTHTYMS*WVRQAPGKGLEWV
*SNISPTYSTTNYADSVKG*RFTISRDNNKNTLYLQMNSLRAEDTAVYYC*ARYNAYHAALDY*WGQGTLV*
TVSS VH domain DNA
SEQ ID NO: 71
GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAACAAGAACACGCTGTACC
TGCAGATGAACTCACTGCGTGCCGAAGATACGGCCGTGTATTACTGTGCGAGATACAACGCGTA
TCATGCTGCTCTGGACTACTGGGGCCAGGGAACCCTGGTCACCGTCTCGAGT

| | | |
|---|---|---|
| SEQ ID NO: 42 | HCDR1 (AA) (IMGT) | GFTFTHTY |
| SEQ ID NO: 43 | HCDR1 (AA) (Kabat) | HTYMS |
| SEQ ID NO: 33 | HCDR2 (AA) (IMGT) | ISPTYSTT |
| SEQ ID NO: 34 | HCDR2 (AA) Kabat) | NISPTYSTTNYADSVKG |
| SEQ ID NO: 44 | HCDR3 (AA) (IMGT) | ARYNAYHAALDY |
| SEQ ID NO: 45 | HCDR3 (AA) (Kabat) | YNAYHAALDY |

Amino acid and cDNA sequences of light chain of FS22-172-003-AA/ FS28-256-021 mAb$^{2}$ Light chain AA

SEQ ID NO: 82

EIVLTQSPGTLSLSPGERATLSCRASQSVSSSYLAWYQQKPGQAPRLLIY
GASSRATGIPDRFSGSGSGTDFTLTISRLEPEDFAVYYCQQHNQYPNTFGQGTKVEIKRTVAAPSVFI
FPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light chain DNA

SEQ ID NO: 122

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAACATAATCAGTATCCGAATACGTTCGGCCAAG
GGACCAAGGTGGAAATCAAACGTACTGTAGCAGCTCCTTCCGTGTTCATCTTTCCGCCCAGTGAT
GAGCAGCTGAAGTCAGGTACTGCTTCCGTGGTTTGCCTGCTCAACAACTTTTACCCCAGAGAAG
CCAAAGTCCAGTGGAAAGTGGACAATGCGTTGCAAAGCGGGAACTCTCAGGAATCCGTCACAGA
GCAGGACTCTAAGGACTCCACCTATAGCCTCTCTAGTACGCTGACACTGAGCAAAGCCGATTAC
GAGAAGCACAAGGTGTATGCCTGTGAGGTTACCCATCAAGGCCTTAGCTCACCAGTGACCAAGA
GCTTCAATAGGGGAGAATGC

VL domain AA

SEQ ID NO: 68

EIVLTQSPGTLSLSPGERATLSCRASQSVSSSYLAWYQQKPGQAPRLLIY
GASSRATGIPDRFSGSGSGTDFTLTISRLEPEDFAVYYCQQHNQYPNTFGQGTKVEIK

VL domain DNA

SEQ ID NO: 69

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAACATAATCAGTATCCGAATACGTTCGGCCAAG
GGACCAAGGTGGAAATCAAA

| | | | |
|---|---|---|---|
| SEQ ID NO: 20 | LCDR1 (AA) | (IMGT) | QSVSSSY |
| SEQ ID NO: 21 | LCDR1 (AA) | (Kabat) | RASQSVSSSYLA |
| SEQ ID NO: 22 | LCDR2 (AA) | (IMGT) | GAS |
| SEQ ID NO: 23 | LCDR2 (AA) | (Kabat) | GASSRAT |
| SEQ ID NO: 40 | LCDR3 (AA) | (IMGT) | QQHNQYPNT |
| SEQ ID NO: 40 | LCDR3 (AA) | (Kabat) | QQHNQYPNT |

Amino acid and cDNA sequences of heavy chain of FS22-172-003-AA/ FS28-256-023 mAb$^{2}$ Heavy chain AA (without LALA)

SEQ ID NO: 131

EVQLLESGGGLVQPGGSLRLSCAASGFTFTQTYMSWVRQAPGKGLEW
VSNISPTYSTTNYADSVKGRFTISRDNSKNTLYLQMNSLRAEDTAVYYCARYNAYQIGLDYWGQGTL
VTVSSASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (Without LALA)

SEQ ID NO: 132

GAAGTGCAACTGCTGGAGTCCGGTGGTGGTCTGGTACAGCCGGGTG
GTTCTCTGCGTCTGAGTTGCGCGGCCAGTGGCTTTACCTTCACTCAGACTTATATGAGCTGGGT
GCGTCAGGCTCCGGGCAAAGGTCTGGAATGGGTTAGCAATATTTCTCCGACTTATAGCACTACC
AACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGATACAACGCT
TATCAGATTGGGTTGGACTACTGGGGCCAGGGAACCCTGGTCACCGTCTCGAGTGCTAGCACTA
AGGGCCCGTCGGTGTTCCCGCTGGCCCCATCGTCCAAGAGCACATCAGGGGGTACCGCCGCCC
TGGGCTGCCTTGTGAAGGATTACTTTCCCGAGCCCGTCACAGTGTCCTGGAACAGCGGAGCCCT
GACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC
GCCTTGCCCAGCCCCGGAACTGCTGGGTGGTCCTTCGGTGTTCCTCTTCCCGCCCAAGCCGAA

-continued

Amino acid and cDNA sequences of heavy chain of FS22-172-003-AA/ FS28-256-023 mAb[2]

GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

Heavy chain AA (with LALA)

SEQ ID NO: 133

EVQLLESGGGLVQPGGSLRLSCAASGFTFTQTYMSWVRQAPGKGLEW
VSNISPTYSTTNYADSVKGRFTISRDNSKNTLYLQMNSLRAEDTAVYYCARYNAYQIGLDYWGQGTL
VTVSSASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPEAAGGPSVFLFPPK
PKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (with LALA)

SEQ ID NO: 134

GAAGTGCAACTGCTGGAGTCCGGTGGTGGTCTGGTACAGCCGGGTG
GTTCTCTGCGTCTGAGTTGCGCGGCCAGTGGCTTTACCTTCACTCAGACTTATATGAGCTGGGT
GCGTCAGGCTCCGGGCAAAGGTCTGGAATGGGTTAGCAATATTTCTCCGACTTATAGCACTACC
AACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGATACAACGCT
TATCAGATTGGGTTGGACTACTGGGGCCAGGGAACCCTGGTCACCGTCTCGAGTGCTAGCACTA
AGGGCCCGTCGGTGTTCCCGCTGGCCCCATCGTCCAAGAGCACATCAGGGGGTACCGCCGCCC
TGGGCTGCCTTGTGAAGGATTACTTTCCCGAGCCCGTCACAGTGTCCTGGAACAGCGGAGCCCT
GACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC
GCCTTGCCCAGCCCCGGAAGCTGCCGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

VH domain AA

SEQ ID NO: 74

EVQLLESGGGLVQPGGSLRLSCAASGFTFTQTYMSWVRQAPGKGLEW
VSNISPTYSTTNYADSVKGRFTISRDNSKNTLYLQMNSLRAEDTAVYYCARYNAYQIGLDYWGQGTL
VTVSS

VH domain DNA

SEQ ID NO: 75

GAAGTGCAACTGCTGGAGTCCGGTGGTGGTCTGGTACAGCCGGGTG
GTTCTCTGCGTCTGAGTTGCGCGGCCAGTGGCTTTACCTTCACTCAGACTTATATGAGCTGGGT
GCGTCAGGCTCCGGGCAAAGGTCTGGAATGGGTTAGCAATATTTCTCCGACTTATAGCACTACC
AACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGATACAACGCT
TATCAGATTGGGTTGGACTACTGGGGCCAGGGAACCCTGGTCACCGTCTCGAGT

| | | |
|---|---|---|
| SEQ ID NO: 50 | HCDR1 (AA) (IMGT) | ***GFTFTQTY*** |
| SEQ ID NO: 51 | HCDR1 (AA) (Kabat) | *QTYMS* |
| SEQ ID NO: 33 | HCDR2 (AA) (IMGT) | ***ISPTYSTT*** |
| SEQ ID NO: 34 | HCDR2 (AA) Kabat) | *NISPTYSTTNYADSVKG* |
| SEQ ID NO: 52 | HCDR3 (AA) (IMGT) | ***ARYNAYQIGLDY*** |
| SEQ ID NO: 53 | HCDR3 (AA) (Kabat) | *YNAYQIGLDY* |

| Amino acid and cDNA sequences of light chain of FS22-172-003-AA/ FS28-256-023 mAb[2] |
|---|

Light chain AA

SEQ ID NO: 82

*EIVLTQSPGTLSLSPGERATLSCRASQSVSSSYLAWYQQKPGQAPRLLIY*
*GASSRATGIPDRFSGSGSGTDFTLTISRLEPEDFAVYYCQQHNQYPNTFGQGTKVEIK*RTVAAPSVFI
FPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light chain DNA

SEQ ID NO: 122

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAACATAATCAGTATCCGAATACGTTCGGCCAAG
GGACCAAGGTGGAAATCAAACGTACTGTAGCAGCTCCTTCCGTGTTCATCTTTCCGCCCAGTGAT
GAGCAGCTGAAGTCAGGTACTGCTTCCGTGGTTTGCCTGCTCAACAACTTTTACCCCAGAGAAG
CCAAAGTCCAGTGGAAAGTGGACAATGCGTTGCAAAGCGGGAACTCTCAGGAATCCGTCACAGA
GCAGGACTCTAAGGACTCCACCTATAGCCTCTCTAGTACGCTGACACTGAGCAAAGCCGATTAC
GAGAAGCACAAGGTGTATGCCTGTGAGGTTACCCATCAAGGCCTTAGCTCACCAGTGACCAAGA
GCTTCAATAGGGGAGAATGC

VL domain AA

SEQ ID NO: 68

*EIVLTQSPGTLSLSPGERATLSCRASQSVSSSYLAWYQQKPGQAPRLLIY*
*GASSRATGIPDRFSGSGSGTDFTLTISRLEPEDFAVYYCQQHNQYPNTFGQGTKVEIK*

VL domain DNA

SEQ ID NO: 69

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAACATAATCAGTATCCGAATACGTTCGGCCAAG
GGACCAAGGTGGAAATCAAA

| | | | | |
|---|---|---|---|---|
| SEQ ID NO: 20 | LCDR1 | (AA) | (IMGT) | QSVSSSY |
| SEQ ID NO: 21 | LCDR1 | (AA) | (Kabat) | RASQSVSSSYLA |
| SEQ ID NO: 22 | LCDR2 | (AA) | (IMGT) | GAS |
| SEQ ID NO: 23 | LCDR2 | (AA) | (Kabat) | GASSRAT |
| SEQ ID NO: 40 | LCDR3 | (AA) | (IMGT) | QQHNQYPNT |
| SEQ ID NO: 40 | LCDR3 | (AA) | (Kabat) | QQHNQYPNT |

| Amino acid and cDNA sequences of heavy chain of FS22-172-003-AA/ FS28-256-024 mAb[2] |
|---|

Heavy chain AA (without LALA)

SEQ ID NO: 123

*EVQLLESGGGLVQPGGSLRLSCAASGFTFTHTYMSWVRQAPGKGLEWV*
*SNISPTYSTTNYADSVKGRFTISRDNNKNTLYLQMNSLRAEDTAVYYCARYNAYHAALDYWGQGTLV*
*TVSS*ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (without LALA)

SEQ ID NO: 124

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAACAAGAACACGCTGTACC
TGCAGATGAACTCACTGCGTGCCGAAGATACGGCCGTGTATTACTGTGCGAGATACAACGCGTA
TCATGCTGCTCTGGACTACTGGGGCCAGGGAACCCTGGTCACCGTCTCGAGTGCTAGCACTAAG
GGCCCGTCGGTGTTCCCGCTGGCCCCATCGTCCAAGAGCACATCAGGGGGTACCGCCGCCCTG
GGCTGCCTTGTGAAGGATTACTTTCCCGAGCCCGTCACAGTGTCCTGGAACAGCGGAGCCCTGA
CCTCCGGAGTGCATACTTTCCCGGCTGTGCTTCAGTCCTCTGGCCTGTACTCATTGTCCTCCGTG
GTCACCGTCCCTTCGTCCTCCCTGGGCACCCAGACCTATATCTGTAATGTCAACCATAAGCCCTC
GAACACCAAGGTCGACAAGAAGGTCGAGCCGAAGTCGTGCGACAAGACTCACACTTGCCCGCC

-continued

| Amino acid and cDNA sequences of heavy chain of FS22-172-003-AA/ FS28-256-024 mAb[2] |
|---|
| TTGCCCAGCCCCGGAACTGCTGGGTGGTCCTTCGGTGTTCCTCTTCCCGCCCAAGCCGAAGGAT<br>ACCCTGATGATCTCACGGACCCCCGAAGTGACCTGTGTGGTGGTGGACGTGTCCCACGAGGAC<br>CCGGAAGTGAAATTCAATTGGTACGTGGATGGAGTGGAAGTGCACAACGCCAAGACCAAGCCAC<br>GGGAAGAACAGTACAACTCTACCTACCGCGTGGTGTCCGTGCTCACTGTGCTGCACCAAGACTG<br>GCTGAACGGGAAGGAGTACAAGTGCAAAGTGTCCAACAAGGCGCTGCCTGCCCCAATTGAGAAA<br>ACTATCTCGAAAGCCAAGGGACAGCCTCGAGAACCACAGGTGTACACCCTGCCCCCATCCCGG<br>GATGAGCTGCCATACATCATCCCACCATACAACCAGGTCAGCCTGACCTGCCTGGTCAAAGGCT<br>TCTATCCCAGCGACATCGCCGTGGAGTGGGAGAGCAATGGGCAGCCGGAGAACAACTACAAGA<br>CCACGCCTCCCGTGCTGGACTCCGACGGCTCCTTCTTCCTCTACAGCAAGCTCACCGTGGGCG<br>CAGATAGGTGGCTGGAAGGGAACGTCTTCTCATGCTCCGTGATGCATGAGGCGCTGCACAACCA<br>CTACACTCAGAAGAGCTTGTCCCTGTCGCCCGGT |
| Heavy chain AA (with LALA)<br>SEQ ID NO: 125<br>*EVQLLESGGGLVQPGGSLRLSCAAS***GFTFTHTY***MSWVRQAPGKGLEWV*<br>*SN***ISPTYSTT***NYADSVKGRFTISRDNNKNTLYLQMNSLRAEDTAVYYC***ARYNAYHAALDY***WGQGTLV*<br>*TVSS*ASTKGPSVFPLAPSSKSTSGGTAALGCLVKDYFPEPVTVSWNSGALTSGVHTFPAVLQSSGLY<br>SLSSVVTVPSSSLGTQTYICNVNHKPSNTKVDKKVEPKSCDKTHTCPPC**PAPEAAGGPSVFLFPPKP**<br>**KDTLMISRTPEVTCVVVDVSHEDPEVKFNWYVDGVEVHNAKTKPREEQYNSTYRVVSVLTVLHQD**<br>**WLNGKEYKCKVSNKALPAPIEKTISKAK**GQPREPQVYTLPPSRDELPYIIPPYNQVSLTCLVKGFYPS<br>DIAVEWESNGQPENNYKTTPPVLDSDGSFFLYSKLTVGADRWLEGNVFSCSVMHEALHNHYTQKSL<br>SLSPG |
| Heavy chain DNA (with LALA)<br>SEQ ID NO: 126<br>GAAGTGCAACTGCTGGAGTCCGGTGGTGGTCTGGTACAGCCGGGTG<br>GTTCTCTGCGTCTGAGTTGCGCGGCCAGTGGCTTTACCTTCACTCATACTTATATGAGCTGGGTG<br>CGTCAGGCTCCGGGCAAAGGTCTGGAATGGGTTAGCAATATTTCTCCGACTTATAGCACTACCAA<br>CTATGCGGATAGCGTGAAAGGCCGTTTTACCATTTCTCGCGACAACAACAAGAACACGCTGTACC<br>TGCAGATGAACTCACTGCGTGCCGAAGATACGGCCGTGTATTACTGTGCGAGATACAACGCGTA<br>TCATGCTGCTCTGGACTACTGGGGCCAGGGAACCCTGGTCACCGTCTCGAGTGCTAGCACTAAG<br>GGCCCGTCGGTGTTCCCGCTGGCCCCATCGTCCAAGAGCACATCAGGGGGTACCGCCGCCCTG<br>GGCTGCCTTGTGAAGGATTACTTTCCCGAGCCCGTCACAGTGTCCTGGAACAGCGGAGCCCTGA<br>CCTCCGGAGTGCATACTTTCCCGGCTGTGCTTCAGTCCTCTGGCCTGTACTCATTGTCCTCCGTG<br>GTCACCGTCCCTTCGTCCTCCCTGGGCACCCAGACCTATATCTGTAATGTCAACCATAAGCCCTC<br>GAACACCAAGGTCGACAAGAAGGTCGAGCCGAAGTCGTGCGACAAGACTCACACTTGCCCGCC<br>TTGCCCAGCCCCGGAAGCTGCCGGTGGTCCTTCGGTGTTCCTCTTCCCGCCCAAGCCGAAGGA<br>TACCCTGATGATCTCACGGACCCCCGAAGTGACCTGTGTGGTGGTGGACGTGTCCCACGAGGA<br>CCCGGAAGTGAAATTCAATTGGTACGTGGATGGAGTGGAAGTGCACAACGCCAAGACCAAGCCA<br>CGGGAAGAACAGTACAACTCTACCTACCGCGTGGTGTCCGTGCTCACTGTGCTGCACCAAGACT<br>GGCTGAACGGGAAGGAGTACAAGTGCAAAGTGTCCAACAAGGCGCTGCCTGCCCCAATTGAGA<br>AAACTATCTCGAAAGCCAAGGGACAGCCTCGAGAACCACAGGTGTACACCCTGCCCCCATCCCG<br>GGATGAGCTGCCATACATCATCCCACCATACAACCAGGTCAGCCTGACCTGCCTGGTCAAAGGC<br>TTCTATCCCAGCGACATCGCCGTGGAGTGGGAGAGCAATGGGCAGCCGGAGAACAACTACAAG<br>ACCACGCCTCCCGTGCTGGACTCCGACGGCTCCTTCTTCCTCTACAGCAAGCTCACCGTGGGCG<br>CAGATAGGTGGCTGGAAGGGAACGTCTTCTCATGCTCCGTGATGCATGAGGCGCTGCACAACCA<br>CTACACTCAGAAGAGCTTGTCCCTGTCGCCCGGT |
| VH domain AA<br>SEQ ID NO: 70<br>*EVQLLESGGGLVQPGGSLRLSCAAS***GFTFTHTY***MSWVRQAPGKGLEWV*<br>*SN***ISPTYSTT***NYADSVKGRFTISRDNNKNTLYLQMNSLRAEDTAVYYC***ARYNAYHAALDY***WGQGTLV*<br>*TVSS* |
| VH domain DNA<br>SEQ ID NO: 71<br>GAAGTGCAACTGCTGGAGTCCGGTGGTGGTCTGGTACAGCCGGGTG<br>GTTCTCTGCGTCTGAGTTGCGCGGCCAGTGGCTTTACCTTCACTCATACTTATATGAGCTGGGTG<br>CGTCAGGCTCCGGGCAAAGGTCTGGAATGGGTTAGCAATATTTCTCCGACTTATAGCACTACCAA<br>CTATGCGGATAGCGTGAAAGGCCGTTTTACCATTTCTCGCGACAACAACAAGAACACGCTGTACC<br>TGCAGATGAACTCACTGCGTGCCGAAGATACGGCCGTGTATTACTGTGCGAGATACAACGCGTA<br>TCATGCTGCTCTGGACTACTGGGGCCAGGGAACCCTGGTCACCGTCTCGAGT |
| SEQ ID NO: 42 HCDR1 (AA) (IMGT) GFTFTHTY |
| SEQ ID NO: 43 HCDR1 (AA) (Kabat) HTYMS |
| SEQ ID NO: 33 HCDR2 (AA) (IMGT) ISPTYSTT |
| SEQ ID NO: 34 HCDR2 (AA) Kabat) NISPTYSTTNYADSVKG |
| SEQ ID NO: 44 HCDR3 (AA) (IMGT) ARYNAYHAALDY |
| SEQ ID NO: 45 HCDR3 (AA) (Kabat) YNAYHAALDY |

| Amino acid and cDNA sequences of light chain of FS22-172-003-AA/ FS28-256-024 mAb[2] |
|---|

Light chain AA

SEQ ID NO: 83

EIVLTQSPGTLSLSPGERATLSCRASQSVSSSYLAWYQQKPGQAPRLLIY
GASSRATGIPDRFSGSGSGTDFTLTISRLEPEDFAVYYCQQALGYPHTFGQGTKVEIKRTVAAPSVFI
FPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light chain DNA

SEQ ID NO: 90

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAGCTTTGGGTTATCCTCATACGTTCGGCCAAG
GGACCAAGGTGGAAATCAAACGTACTGTAGCAGCTCCTTCCGTGTTCATCTTTCCGCCCAGTGAT
GAGCAGCTGAAGTCAGGTACTGCTTCCGTGGTTTGCCTGCTCAACAACTTTTACCCCAGAGAAG
CCAAAGTCCAGTGGAAAGTGGACAATGCGTTGCAAAGCGGGAACTCTCAGGAATCCGTCACAGA
GCAGGACTCTAAGGACTCCACCTATAGCCTCTCTAGTACGCTGACACTGAGCAAAGCCGATTAC
GAGAAGCACAAGGTGTATGCCTGTGAGGTTACCCATCAAGGCCTTAGCTCACCAGTGACCAAGA
GCTTCAATAGGGGAGAATGC

VL domain AA

SEQ ID NO: 78

EIVLTQSPGTLSLSPGERATLSCRASQSVSSSYLAWYQQKPGQAPRLLIY
GASSRATGIPDRFSGSGSGTDFTLTISRLEPEDFAVYYCQQALGYPHTFGQGTKVEIK

VL domain DNA

SEQ ID NO: 79

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAGCTTTGGGTTATCCTCATACGTTCGGCCAAG
GGACCAAGGTGGAAATCAAA

| | | |
|---|---|---|
| SEQ ID NO: 20 | LCDR1 (AA) (IMGT) | QSVSSSY |
| SEQ ID NO: 21 | LCDR1 (AA) (Kabat) | RASQSVSSSYLA |
| SEQ ID NO: 22 | LCDR2 (AA) (IMGT) | GAS |
| SEQ ID NO: 23 | LCDR2 (AA) (Kabat) | GASSRAT |
| SEQ ID NO: 41 | LCDR3 (AA) (IMGT) | QQALGYPHT |
| SEQ ID NO: 41 | LCDR3 (AA) (Kabat) | QQALGYPHT |

| Amino acid and cDNA sequences of heavy chain of FS22-172-003-AA/ FS28-256-026 mAb[2] |
|---|

Heavy chain AA (without LALA)

SEQ ID NO: 131

EVQLLESGGGLVQPGGSLRLSCAASGFTFTQTYMSWVRQAPGKGLEW
VSNISPTYSTTNYADSVKGRFTISRDNSKNTLYLQMNSLRAEDTAVYYCARYNAYQIGLDYWGQGTL
VTVSSASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (without LALA)

SEQ ID NO: 132

GAAGTGCAACTGCTGGAGTCCGGTGGTGGTCTGGTACAGCCGGGTG
GTTCTCTGCGTCTGAGTTGCGCGGCCAGTGGCTTTACCTTCACTCAGACTTATATGAGCTGGGT
GCGTCAGGCTCCGGGCAAAGGTCTGGAATGGGTTAGCAATATTTCTCCGACTTATAGCACTACC
AACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGATACAACGCT
TATCAGATTGGGTTGGACTACTGGGGCCAGGGAACCCTGGTCACCGTCTCGAGTGCTAGCACTA
AGGGCCCGTCGGTGTTCCCGCTGGCCCCATCGTCCAAGAGCACATCAGGGGGTACCGCCGCCC
TGGGCTGCCTTGTGAAGGATTACTTTCCCGAGCCCGTCACAGTGTCCTGGAACAGCGGAGCCCT
GACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC

-continued

Amino acid and cDNA sequences of heavy chain of FS22-172-003-AA/FS28-256-026 mAb[2]

GCCTTGCCCAGCCCCGGAACTGCTGGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

Heavy chain AA (with LALA)

SEQ ID NO: 133

*EVQLLESGGGLVQPGGSLRLSCAASGFTFTQTYMS*WVRQAPGKGLEW
*VSNISPTYSTTNYADSVKG*RFTISRDNSKNTLYLQMNSLRAEDTAVYYC*ARYNAYQIGLDY*WGQGTL*
*VTVSS*ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPEAAGGPSVFLFPPK
PKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (with LALA)

SEQ ID NO: 134

GAAGTGCAACTGCTGGAGTCCGGTGGTGGTCTGGTACAGCCGGGTG
GTTCTCTGCGTCTGAGTTGCGCGGCCAGTGGCTTTACCTTCACTCAGACTTATATGAGCTGGGT
GCGTCAGGCTCCGGGCAAAGGTCTGGAATGGGTTAGCAATATTTCTCCGACTTATAGCACTACC
AACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGATACAACGCT
TATCAGATTGGGTTGGACTACTGGGGCCAGGGAACCCTGGTCACCGTCTCGAGTGCTAGCACTA
AGGGCCCGTCGGTGTTCCCGCTGGCCCCATCGTCCAAGAGCACATCAGGGGGTACCGCCGCCC
TGGGCTGCCTTGTGAAGGATTACTTTCCCGAGCCCGTCACAGTGTCCTGGAACAGCGGAGCCCT
GACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC
GCCTTGCCCAGCCCCGGAAGCTGCCGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

VH domain AA

SEQ ID NO: 74

*EVQLLESGGGLVQPGGSLRLSCAASGFTFTQTYMSWVRQAPGKGLEW*
*VSNISPTYSTTNYADSVKGRFTISRDNSKNTLYLQMNSLRAEDTAVYYCARYNAYQIGLDYWGQGTL*
*VTVSS*

VH domain DNA

SEQ ID NO: 75

GAAGTGCAACTGCTGGAGTCCGGTGGTGGTCTGGTACAGCCGGGTG
GTTCTCTGCGTCTGAGTTGCGCGGCCAGTGGCTTTACCTTCACTCAGACTTATATGAGCTGGGT
GCGTCAGGCTCCGGGCAAAGGTCTGGAATGGGTTAGCAATATTTCTCCGACTTATAGCACTACC
AACTATGCGGATAGCGTGAAAGGCCGTTTTACCATTTCTCGCGACAACAGCAAGAACACGCTGTA
CCTGCAGATGAACTCACTGCGTGCCGAAGATACGGCCGTGTATTACTGTGCGAGATACAACGCT
TATCAGATTGGGTTGGACTACTGGGGCCAGGGAACCCTGGTCACCGTCTCGAGT

| | | |
|---|---|---|
| SEQ ID NO: 50 | HCDR1 (AA) (IMGT) | GFTFTQTY |
| SEQ ID NO: 51 | HCDR1 (AA) (Kabat) | QTYMS |
| SEQ ID NO: 33 | HCDR2 (AA) (IMGT) | ISPTYSTT |
| SEQ ID NO: 34 | HCDR2 (AA) Kabat) | NISPTYSTTNYADSVKG |
| SEQ ID NO: 52 | HCDR3 (AA) (IMGT) | ARYNAYQIGLDY |
| SEQ ID NO: 53 | HCDR3 (AA) (Kabat) | YNAYQIGLDY |

Amino acid and cDNA sequences of light chain of FS22-172-003-AA/FS28-256-026 mAb[2]

Light chain AA

SEQ ID NO: 83

EIVLTQSPGTLSLSPGERATLSCRASQSVSSSYLAWYQQKPGQAPRLLIY
GASSRATGIPDRFSGSGSGTDFTLTISRLEPEDFAVYYCQQALGYPHTFGQGTKVEIKRTVAAPSVFI
FPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light chain DNA

SEQ ID NO: 90

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAGCTTTGGGTTATCCTCATACGTTCGGCCAAG
GGACCAAGGTGGAAATCAAACGTACTGTAGCAGCTCCTTCCGTGTTCATCTTTCCGCCCAGTGAT
GAGCAGCTGAAGTCAGGTACTGCTTCCGTGGTTTGCCTGCTCAACAACTTTTACCCCAGAGAAG
CCAAAGTCCAGTGGAAAGTGGACAATGCGTTGCAAAGCGGGAACTCTCAGGAATCCGTCACAGA
GCAGGACTCTAAGGACTCCACCTATAGCCTCTCTAGTACGCTGACACTGAGCAAAGCCGATTAC
GAGAAGCACAAGGTGTATGCCTGTGAGGTTACCCATCAAGGCCTTAGCTCACCAGTGACCAAGA
GCTTCAATAGGGGAGAATGC

VL domain AA

SEQ ID NO: 78

EIVLTQSPGTLSLSPGERATLSCRASQSVSSSYLAWYQQKPGQAPRLLIY
GASSRATGIPDRFSGSGSGTDFTLTISRLEPEDFAVYYCQQALGYPHTFGQGTKVEIK

VL domain DNA

SEQ ID NO: 79

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAGCTTTGGGTTATCCTCATACGTTCGGCCAAG
GGACCAAGGTGGAAATCAAA

| | | | | |
|---|---|---|---|---|
| SEQ ID NO: 20 | LCDR1 | (AA) | (IMGT) | QSVSSSY |
| SEQ ID NO: 21 | LCDR1 | (AA) | (Kabat) | RASQSVSSSYLA |
| SEQ ID NO: 22 | LCDR2 | (AA) | (IMGT) | GAS |
| SEQ ID NO: 23 | LCDR2 | (AA) | (Kabat) | GASSRAT |
| SEQ ID NO: 41 | LCDR3 | (AA) | (IMGT) | QQALGYPHT |
| SEQ ID NO: 41 | LCDR3 | (AA) | (Kabat) | QQALGYPHT |

Amino acid and cDNA sequences of heavy chain of FS22-172-003-AA/FS28-256-027 mAb[2]

Heavy chain AA (without LALA)

SEQ ID NO: 123

EVQLLESGGGLVQPGGSLRLSCAASGFTFTHTYMSWVRQAPGKGLEWV
SNISPTYSTTNYADSVKGRFTISRDNNKNTLYLQMNSLRAEDTAVYYCARYNAYHAALDYWGQGTLV
TVSSASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (without LALA)

SEQ ID NO: 124

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAACAAGAACACGCTGTACC
TGCAGATGAACTCACTGCGTGCCGAAGATACGGCCGTGTATTACTGTGCGAGATACAACGCGTA
TCATGCTGCTCTGGACTACTGGGGCCAGGGAACCCTGGTCACCGTCTCGAGTGCTAGCACTAAG
GGCCCGTCGGTGTTCCCGCTGGCCCCATCGTCCAAGAGCACATCAGGGGGTACCGCCGCCCTG
GGCTGCCTTGTGAAGGATTACTTTCCCGAGCCCGTCACAGTGTCCTGGAACAGCGGAGCCCTGA
CCTCCGGAGTGCATACTTTCCCGGCTGTGCTTCAGTCCTCTGGCCTGTACTCATTGTCCTCCGTG
GTCACCGTCCCTTCGTCCTCCCTGGGCACCCAGACCTATATCTGTAATGTCAACCATAAGCCCTC
GAACACCAAGGTCGACAAGAAGGTCGAGCCGAAGTCGTGCGACAAGACTCACACTTGCCCGCC

-continued

| Amino acid and cDNA sequences of heavy chain of FS22-172-003-AA/ FS28-256-027 mAb$^2$ |
|---|

TTGCCCAGCCCCGGAACTGCTGGGTGGTCCTTCGGTGTTCCTCTTCCCGCCCAAGCCGAAGGAT
ACCCTGATGATCTCACGGACCCCCGAAGTGACCTGTGTGGTGGTGGACGTGTCCCACGAGGAC
CCGGAAGTGAAATTCAATTGGTACGTGGATGGAGTGGAAGTGCACAACGCCAAGACCAAGCCAC
GGGAAGAACAGTACAACTCTACCTACCGCGTGGTGTCCGTGCTCACTGTGCTGCACCAAGACTG
GCTGAACGGGAAGGAGTACAAGTGCAAAGTGTCCAACAAGGCGCTGCCTGCCCCAATTGAGAAA
ACTATCTCGAAAGCCAAGGGACAGCCTCGAGAACCACAGGTGTACACCCTGCCCCCATCCCGG
GATGAGCTGCCATACATCATCCCACCATACAACCAGGTCAGCCTGACCTGCCTGGTCAAAGGCT
TCTATCCCAGCGACATCGCCGTGGAGTGGGAGAGCAATGGGCAGCCGGAGAACAACTACAAGA
CCACGCCTCCCGTGCTGGACTCCGACGGCTCCTTCTTCCTCTACAGCAAGCTCACCGTGGGCG
CAGATAGGTGGCTGGAAGGGAACGTCTTCTCATGCTCCGTGATGCATGAGGCGCTGCACAACCA
CTACACTCAGAAGAGCTTGTCCCTGTCGCCCGGT

Heavy chain AA (with LALA)

SEQ ID NO: 125

*EVQLLESGGGLVQPGGSLRLSCAAS**GFTFTHTY**MS*
*WVRQAPGKGLEWV*
*SN**ISPTYSTTNYADSVKGRFTISRDNNKNTLYLQMNSLRAEDTAVYYCARYNAYHAALDY**WGQGTLV*
*TVSS*ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPEAAGGPSVFLFPPKP
KDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (with LALA)

SEQ ID NO: 126

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAACAAGAACACGCTGTACC
TGCAGATGAACTCACTGCGTGCCGAAGATACGGCCGTGTATTACTGTGCGAGATACAACGCGTA
TCATGCTGCTCTGGACTACTGGGGCCAGGGAACCCTGGTCACCGTCTCGAGTGCTAGCACTAAG
GGCCCGTCGGTGTTCCCGCTGGCCCCATCGTCCAAGAGCACATCAGGGGGTACCGCCGCCCTG
GGCTGCCTTGTGAAGGATTACTTTCCCGAGCCCGTCACAGTGTCCTGGAACAGCGGAGCCCTGA
CCTCCGGAGTGCATACTTTCCCGGCTGTGCTTCAGTCCTCTGGCCTGTACTCATTGTCCTCCGTG
GTCACCGTCCCTTCGTCCTCCCTGGGCACCCAGACCTATATCTGTAATGTCAACCATAAGCCCTC
GAACACCAAGGTCGACAAGAAGGTCGAGCCGAAGTCGTGCGACAAGACTCACACTTGCCCGCC
TTGCCCAGCCCCGGAAGCTGCCGGTGGTCCTTCGGTGTTCCTCTTCCCGCCCAAGCCGAAGGA
TACCCTGATGATCTCACGGACCCCCGAAGTGACCTGTGTGGTGGTGGACGTGTCCCACGAGGA
CCCGGAAGTGAAATTCAATTGGTACGTGGATGGAGTGGAAGTGCACAACGCCAAGACCAAGCCA
CGGGAAGAACAGTACAACTCTACCTACCGCGTGGTGTCCGTGCTCACTGTGCTGCACCAAGACT
GGCTGAACGGGAAGGAGTACAAGTGCAAAGTGTCCAACAAGGCGCTGCCTGCCCCAATTGAGA
AAACTATCTCGAAAGCCAAGGGACAGCCTCGAGAACCACAGGTGTACACCCTGCCCCCATCCCG
GGATGAGCTGCCATACATCATCCCACCATACAACCAGGTCAGCCTGACCTGCCTGGTCAAAGGC
TTCTATCCCAGCGACATCGCCGTGGAGTGGGAGAGCAATGGGCAGCCGGAGAACAACTACAAG
ACCACGCCTCCCGTGCTGGACTCCGACGGCTCCTTCTTCCTCTACAGCAAGCTCACCGTGGGCG
CAGATAGGTGGCTGGAAGGGAACGTCTTCTCATGCTCCGTGATGCATGAGGCGCTGCACAACCA
CTACACTCAGAAGAGCTTGTCCCTGTCGCCCGGT

VH domain AA

SEQ ID NO: 70

*EVQLLESGGGLVQPGGSLRLSCAAS**GFTFTHTY**MSWVRQAPGKGLEWV*
*SN**ISPTYSTTNYADSVKGRFTISRDNNKNTLYLQMNSLRAEDTAVYYCARYNAYHAALDY**WGQGTLV*
*TVSS*

VH domain DNA

SEQ ID NO: 71

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAACAAGAACACGCTGTACC
TGCAGATGAACTCACTGCGTGCCGAAGATACGGCCGTGTATTACTGTGCGAGATACAACGCGTA
TCATGCTGCTCTGGACTACTGGGGCCAGGGAACCCTGGTCACCGTCTCGAGT

| | | |
|---|---|---|
| SEQ ID NO: 42 | HCDR1 (AA) (IMGT) | GFTFTHTY |
| SEQ ID NO: 43 | HCDR1 (AA) (Kabat) | HTYMS |
| SEQ ID NO: 33 | HCDR2 (AA) (IMGT) | ISPTYSTT |
| SEQ ID NO: 34 | HCDR2 (AA) Kabat) | NISPTYSTTNYADSVKG |
| SEQ ID NO: 44 | HCDR3 (AA) (IMGT) | ARYNAYHAALDY |
| SEQ ID NO: 45 | HCDR3 (AA) (Kabat) | YNAYHAALDY |

| Amino acid and cDNA sequences of light chain of FS22-172-003-AA/ FS28-256-027 mAb2 |
|---|

Light chain AA

SEQ ID NO: 84

*EIVLTQSPGTLSLSPGERATLSCRASQSVSSSYLAWYQQKPGQAPRLLIY*
*GASSRATGIPDRFSGSGSGTDFTLTISRLEPEDFAVYYCQQTVPYPYTFGQGTKVEIK*RTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light chain DNA

SEQ ID NO: 91

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAACTGTGCCGTATCCGTATACGTTCGGCCAA
GGGACCAAGGTGGAAATCAAACGTACTGTGGCCGCTCCTAGCGTGTTCATTTTTCCGCCATCCG
ACGAGCAGCTCAAGTCCGGCACCGCCTCCGTGGTCTGCCTGCTCAACAACTTCTACCCTCGCGA
AGCTAAGGTCCAGTGGAAGGTCGACAATGCCCTGCAGTCCGGAAACTCGCAGGAAAGCGTGAC
TGAACAGGACTCCAAGGACTCCACCTATTCACTGTCCTCGACTCTGACCCTGAGCAAGGCGGAT
TACGAAAAGCACAAAGTGTACGCATGCGAAGTGACCCACCAGGGTCTTTCGTCCCCCGTGACCA
AGAGCTTCAACAGAGGAGAGTGT

VL domain AA

SEQ ID NO: 76

*EIVLTQSPGTLSLSPGERATLSCRASQSVSSSYLAWYQQKPGQAPRLLIY*
*GASSRATGIPDRFSGSGSGTDFTLTISRLEPEDFAVYYCQQTVPYPYTFGQGTKVEIK*

VL domain DNA

SEQ ID NO: 77

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAAACTGTGCCGTATCCGTATACGTTCGGCCAA
GGGACCAAGGTGGAAATCAAA

| | | |
|---|---|---|
| SEQ ID NO: 20 | LCDR1 (AA) (IMGT) | QSVSSSY |
| SEQ ID NO: 21 | LCDR1 (AA) (Kabat) | RASQSVSSSYLA |
| SEQ ID NO: 22 | LCDR2 (AA) (IMGT) | GAS |
| SEQ ID NO: 23 | LCDR2 (AA) (Kabat) | GASSRAT |
| SEQ ID NO: 80 | LCDR3 (AA) (IMGT) | QQTVPYPYT |
| SEQ ID NO: 80 | LCDR3 (AA) (Kabat) | QQTVPYPYT |

Mouse mAb and mAb2

| Amino acid sequence of heavy chain of FS28m-228 mAb |
|---|

Heavy chain AA (with LALA)

SEQ ID NO: 135

*EVQLLESGGGLVQPGGSLRLSCAASGFTFSTYFMVWVRQAPGKGLEWV*
*SMISPKSSNTYYADSVKGRFTISRDNSKNTLYLQMNSLRAEDTAVYYCARWFTPARFDYWGQGTLVT*
*VSS*ASTKGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSCDKTHTCPPCPAPEAAGGPSVFLFPPKPK
DTLMISRTPEVTCVVVDVSHEDPEVKFNWYVDGVEVHNAKTKPREEQYNSTYRVVSVLTVLHQDWL
NGKEYKCKVSNKALPAPIEKTISKAKQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHYTQKSLSLSPG

Amino acid sequence of light chain of FS28m-228 mAb
Light chain AA

SEQ ID NO: 136

*EIVLTQSPGTLSLSPGERATLSCRASQSVSSSYLAWYQQKPGQAPRLLIY*
*GASSRATGIPDRFSGSGSGTDFTLTISRLEPEDFAVYYCQQPFPFSFTFGQGTKVEIK*RTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Amino acid sequence of heavy chain of FS22m-063-AA/FS28m-228 mAb2
Heavy chain AA (with LALA)

SEQ ID NO: 137

*EVQLLESGGGLVQPGGSLRLSCAASGFTFSTYFMVWVRQAPGKGLEWV*
*SMISPKSSNTYYADSVKGRFTISRDNSKNTLYLQMNSLRAEDTAVYYCARWFTPARFDYWGQGTLVT*
*VSS*ASTKGPSVFPLAPSSKSTSGGTAALGCLVKDYFPEPVTVSWNSGALTSGVHTFPAVLQSSGLYS

-continued

| Amino acid sequence of heavy chain of FS28m-228 mAb |
| --- |
| LSSVVTVPSSSLGTQTYICNVNHKPSNTKVDKKVEPKSCDKTHTCPPCPAPE**AA**GGPSVFLFPPKPK<br>DTLMISRTPEVTCVVVDVSHEDPEVKFNWYVDGVEVHNAKTKPREEQYNSTYRVVSVLTVLHQDWL<br>NGKEYKCKVSNKALPAPIEKTISKAKGQPREPQVYTLPPSRDEPYWSYVSLTCLVKGFYPSDIAVEWE<br>SNGQPENNYKTTPPVLDSDGSFFLYSKLTVMNYRWELGNVFSCSVMHEALHNHYTQKSLSLSPG |

Amino acid sequence of light chain of FS22m-063-AA/FS28m-228 mAb2
Light chain AA

SEQ ID NO: 136

*EIVLTQSPGTLSLSPGERATLSCRASQSVSSSYLAWYQQKPGQAPRLLIYGASSRATGIPDR*
*FSGSGSGTDFTLTISRLEPEDFAVYYCQQPFPFSFTFGQGTKVEIKR*TVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC

Amino acid sequence of heavy chain of G1AA/HelD1.3 mAb
Heavy chain AA (with LALA)

SEQ ID NO: 138

*QVQLQESGPGLVRPSQTLSLTCTVSGSTFSGYGVNWVRQPPGRGLEWI*
*GMIWGDGNTDYNSALKSRVTMLVDTSKNQFSLRLSSVTAADTAVYYCARERDYRLDYWGQGSLVTV*
*SS*ASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPEAAGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHYTQKSLSLSPG

Amino acid sequence of light chain of G1AA/HelD1.3 mAb
Light chain AA

SEQ ID NO: 139

*DIQMTQSPASLSASVGETVTITCRASGNIHNYLAWYQQKQGKSPQLLVY*
*NAKTLADGVPSRFSGSGSGTQYSLKINSLQPEDFGSYYCQHFWSTPRTFGGGTKLEIK*RTVAAPSVFI
FPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

G1AA/SS1 mAb
Heavy chain (with LALA)

SEQ ID NO: 140

*QVQLQQSGPELEKPGASVKISCKASGYSFTGYTMNWVKQSHGKSLEWI*
*GLITPYNGASSYNQKFRGKATLTVDKSSSTAYMDLLSLTSEDSAVYFCARGGYDGRGFDYWGSGTP*
*VTVSS*ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPEAAGGPSVFLFPPK
PKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHEALHNHYTQKSLSLSP
G

Light chain

SEQ ID NO: 141

*DIELTQSPAIMSASPGEKVTMTCSASSSVSYMHWYQQKSGTSPKRWIYD*
*TSKLASGVPGRFSGSGSGNSYSLTISSVEAEDDATYYCQQWSKHPLTFGSGTKVEIK*RTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

MSLN-His-Avi
Mesothelin (without MPF and C terminus) (shown); His and Avi tags (not shown)
Human

SEQ ID NO: 142

EVEKTACPSGKKAREIDESLIFYKKWELEACVDAALLATQMDRVNAIPFTY
EQLDVLKHKLDELYPQGYPESVIQHLGYLFLKMSPEDIRKWNVTSLETLKALLEVNKGHEMSPQVATL
IDRFVKGRGQLDKDTLDTLTAFYPGYLCSLSPEELSSVPPSSIWAVRPQDLDTCDPRQLDVLYPKARL
AFQNMNGSEYFVKIQSFLGGAPTEDLKALSQQNVSMDLATFMKLRTDAVLPLTVAEVQKLLGPHVEG
LKAEERHRPVRDWILRQRQDDLDTLGLGLQGGIPNGYLVLDLSMQEALS

Cyno

SEQ ID NO: 143

DVERTTCPPEKEVHEIDESLIFYKKRELEACVDAALLAAQMDRVDAIPFTY
EQLDVLKHKLDELYPQGYPESVIRHLGHLFLKMSPEDIRKWNVTSLETLKALLKVSKGHEMSAQVATLI
DRVVVGRGQLDKDTADTLTAFCPGCLCSLSPERLSSVPPSIIGAVRPQDLDTCGPRQLDVLYPKARLA
FQNMSGSEYFVKIRPFLGGAPTEDLKALSQQNVSMDLATFMKLRREAVLPLSVAEVQKLLGPHVEGL
KVEEQHSPVRDWILKQRQDDLDTLGLGLQGGIPNGYLILDLSVREALS

Mouse

SEQ ID NO: 144

DAEQKACPPGKEPYKVDEDLIFYQNWELEACVDGTMLARQMDLVNEIPF
TYEQLSIFKHKLDKTYPQGYPESLIQQLGHFFRYVSPEDIHQWNVTSPDTVKTLLKVSKGQKMNAQAI
ALVACYLRGGGQLDEDMVKALGDIPLSYLCDFSPQDLHSVPSSVMWLVGPQDLDKCSQRHLGLLYQ
KACSAFQNVSGLEYFEKIKTFLGGASVKDLRALSQHNVSMDIATFKRLQVDSLVGLSVAEVQKLLGPN
IVDLKTEEDKSPVRDWLFRQHQKDLDRLGLGLQGGIPNGYLVLDFNVREAFS

-continued

Amino acid sequence of heavy chain of FS28m-228 mAb

CD137-mFc-Avi and CD137-Avi-His
(Extracellular domain CD137 (shown); mFc, Avi tag, His tag (not shown)
Human

SEQ ID NO: 146

SLQDPCSNCPAGTFCDNNRNQICSPCPPNSFSSAGGQRTCDICRQCKG
VFRTRKECSSTSNAECDCTPGFHCLGAGCSMCEQDCKQGQELTKKGCKDCCFGTFNDQKRGICRP
WTNCSLDGKSVLVNGTKERDVVCGPSPADLSPGASSVTPPAPAREPGHSPQ

Cyno

SEQ ID NO: 147

SLQDLCSNCPAGTFCDNNRSQICSPCPPNSFSSAGGQRTCDICRQCKG
VFKTRKECSSTSNAECDCISGYHCLGAECSMCEQDCKQGQELTKKGCKDCCFGTFNDQKRGICRP
WTNCSLDGKSVLVNGTKERDVVCGPSPADLSPGASSATPPAPAREPGHSPQ

Mouse

SEQ ID NO: 148

AVQNSCDNCQPGTFCRKYNPVCKSCPPSTFSSIGGQPNCNICRVCAGY
FRFKKFCSSTHNAECECIEGFHCLGPQCTRCEKDCRPGQELTKQGCKTCSLGTFNDQNGTGVCRP
WTNCSLDGRSVLKTGTTEKDVVCGPPVVSFSPSTTISVTPEGGPGGHSLQVL

Cell-expressed antigens (CD137)
(Extracellular domain (italics); Transmembrane and intracellular domains (bold))
Human

SEQ ID NO: 149

*LQDPCSNCPAGTFCDNNRNQICSPCPPNSFSSAGGQRTCDICRQCKGV*
*FRTRKECSSTSNAECDCTPGFHCLGAGCSMCEQDCKQGQELTKKGCKDCCFGTFNDQKRGICRPW*
*TNCSLDGKSVLVNGTKERDVVCGPSPADLSPGASSVTPPAPAREPGHSPQ*IISFFLALTSTALLFLLF
FLTLRFSVVKRGRKKLLYIFKQPFMRPVQTTQEEDGCSCRFPEEEEGGCEL

Mouse

SEQ ID NO: 150

*VQNSCDNCQPGTFCRKYNPVCKSCPPSTFSSIGGQPNCNICRVCAGYF*
*RFKKFCSSTHNAECECIEGFHCLGPQCTRCEKDCRPGQELTKQGCKTCSLGTFNDQNGTGVCRPW*
*TNCSLDGRSVLKTGTTEKDVVCGPPVVSFSPSTTISVTPEGGPGGHSLQVL*TLFLALTSALLLALIFIT
LLFSVLKWIRKKFPHIFKQPFKKTTGAAQEEDACSCRCPQEEEGGGGGYEL

Cyno

SEQ ID NO: 153

*LQDLCSNCPAGTFCDNNRSQICSPCPPNSFSSAGGQRTCDICRQCKGV*
*FKTRKECSSTSNAECDCISGYHCLGAECSMCEQDCKQGQELTKKGCKDCCFGTFNDQKRGICRPW*
*TNCSLDGKSVLVNGTKERDVVCGPSPADLSPGASSATPPAPAREPGHSPQ*IIFFLALTSTVVLFLLFF
LVLRFSVVKRSRKKLLYIFKQPFMRPVQTTQEEDGCSCRFPEEEEGGCEL

Overexpressing cell lines - Membrane-bound mature form of Mesothelin (shown in bold italics)
[N.B. MPF and propeptide are shown in normal font before and after mesothelin sequence. Neither are present in the membrane-bound mature form of mesothelin.]
Human MPF + MSLN

SEQ ID NO: 151

MALPTARPLLGSCGTPALGSLLFLLFSLGWVQPSRTLAGETGQEAAPLDGVLANPPNISSLSPRQLLG
FPCAEVSGLSTERVRELAVALAQKNVKLSTEQLRCLAHRLSEPPEDLDALPLDLLLFLNPDAFSGPQA
CTRFFSRITKANVDLLPRGAPERQRLLPAALACWGVRGSLLSEADVRALGGLACDLPGRFVAESAEV
LLPRLVSCPGPLDQDQQEAARAALQGGGPPYGPPSTWSVSTMDALRGLLPVLGQPIIRSIPQGIVAA
WRQRSSRDPSWRQPERTILRPRFRR*EVEKTACPSGKKAREIDESLIFYKKWELEACVDAALLATQM*
*DRVNAIPFTYEQLDVLKHKLDELYPQGYPESVIQHLGYLFLKMSPEDIRKWNVTSLETLKALLEVNK*
*GHEMSPQVATLIDRFVKGRGQLDKDTLDTLTAFYPGYLCSLSPEELSSVPPSSIWAVRPQDLDTCD*
*PRQLDVLYPKARLAFQNMNGSEYFVKIQSFLGGAPTEDLKALSQQNVSMDLATFMKLRTDAVLPLT*
*VAEVQKLLGPHVEGLKAEERHRPVRDWILRQRQDDLDTLGLGLQGGIPNGYLVLDLSMQEALS*GT
PCLLGPGPVLTVLALLLASTLA

Mouse MPF + MSLN

SEQ ID NO: 145

MALPTARPLLGSCGSPICSRSFLLLLLSLGWIPRLQTQTTKTSQEATLLHAVNGAADFASLPTGLFLGL
TCEEVSDLSMEQAKGLAMAVRQKNITLRGHQLRCLARRLPRHLTDEELNALPLDLLLFLNPAMFPGQ
QACAHFFSLISKANVDVLPRRSLERQRLLMEALKCQGVYGFQVSEADVRALGGLACDLPGKFVARSS
EVLLPWLAGCQGPLDQSQEKAVREVLRSGRTQYGPPSKWSVSTLDALQSLVAVLDESIVQSIPKDVK
AEWLQHISRDPSRLGSKLTVIHPRFRR*DAEQKACPPGKEPYKVDEDLIFYQNWELEACVDGTMLAR*
*QMDLVNEIPFTYEQLSIFKHKLDKTYPQGYPESLIQQLGHFFRYVSPEDIHQWNVTSPDTVKTLLKVS*
*KGQKMNAQAIALVACYLRGGGQLDEDMVKALGDIPLSYLCDFSPQDLHSVPSSVMWLVGPQDLD*
*KCSQRHLGLLYQKACSAFQNVSGLEYFEKIKTFLGGASVKDLRALSQHNVSMDIATFKRLQVDSLV*
*GLSVAEVQKLLGPNIVDLKTEEDKSPVRDWLFRQHQKDLDRLGLGLQGGIPNGYLVLDFNVREAFS*
SRASLLGPGFVLIWIPALLPALRLS

Cyno MPF + MSLN

SEQ ID NO: 152

MALPMARPLSGSCGTPALGSLLFLLFSLGWVQPSRVLAGETRQEAAPLDGILTNAPDIASLSPRQLLG
FTCVEVSGLSTELVQELAVALGQKNVKLSAEQLRCLAHRLSEPPEDLDALPLDLLLFLNPDAFSGPQA
CTHFFSRVAKANVDLLPRGAPERQRLLPAALTCWGVRGSLLSEADVRALGGLACDLPGRFVAESAE

-continued

| Amino acid sequence of heavy chain of FS28m-228 mAb |
| --- |
| VVLPRLVRCLGPLDQDQQEAARAALQRGGPPYGPPSTWSISTLDDLQSLLPVLGQPVIHSIPQGILAA WRQRSSRDPSWQQPEQTVLRPRFRR***DVERTTCPPEKEVHEIDESLIFYKKRELEACVDAALLAAQ MDRVDAIPFTYEQLDVLKHKLDELYPQGYPESVIRHLGHLFLKMSPEDIRKWNVTSLETLKALLKVS KGHEMSAQVATLIDRVVVGRGQLDKDTADTLTAFCPGCLCSLSPERLSSVPPSIIGAVRPQDLDTC GPRQLDVLYPKARLAFQNMSGSEYFVKIRPFLGGAPTEDLKALSQQNVSMDLATFMKLRREAVLP LSVAEVQKLLGPHVEGLKVEEQHSPVRDWILKQRQDDLDTLGLGLQGGIPNGYLILDLSVREALS***G TPCLLGPGPVLTVLALLLASTLA |

Amino acid sequence of wild-type CH2 domain
CH2 (WT)

SEQ ID NO: 154

APELLGGPSVFLFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAK

Amino acid sequence of CH2 domain containing LALA mutation (LALA mutation in bold and underlined)
CH2 (LALA)

SEQ ID NO: 155

APEAAGGPSVFLFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAK

Amino acid sequence of CH2 domain containing LALA-PA mutation (LALA-PA mutation in bold and underlined)
CH2 (LALA-PA)

SEQ ID NO: 156

APEAAGGPSVFLFPPKPKDTLMISRTPEVTCVVVDVSHEDPEVKFNWYVDGVEVHNAKTKP REEQYNSTYRVVSVLTVLHQDWLNGKEYKCKVSNKALAAPIEKTISKAK

Amino acid and cDNA sequences of light chain of FS22-172-003-AA/FS28-256-271, FS22-172-003-AA/FS28-256-272, and FS22-172-003-AA/FS28-256-273 mAb2

Light chain AA

SEQ ID NO: 84

*EIVLTQSPGTLSLSPGERATLSCRASQSVSSSYLAWYQQKPGQAPRLLIY GASSRATGIPDRFSGSGSGTDFTLTISRLEPEDFAVYYCQQTVPYPYTFGQGTKVEIK*RTVAAPSVFIF PPSDEQLKSGTASVVCLLNNFYPREAKVQWKVDNALQSGNSQESVTEQDSKDSTYSLSSTLTLSKA DYEKHKVYACEVTHQGLSSPVTKSFNRGEC

Light chain DNA

SEQ ID NO: 91

GAAATTGTGCTGACCCAGTCTCCGGGCACGTTATCTCTGAGCCCTGG TGAGCGCGCCACTCTGTCATGCCGGGCTTCTCAAAGTGTTAGCAGTAGCTACCTGGCGTGGTAT CAGCAAAAACCGGGCCAGGCCCCGCGTCTGCTGATTTACGGTGCATCCAGCCGTGCCACCGGC ATTCCAGATCGTTTTTCCGGTAGTGGTTCTGGGACGGACTTCACTCTGACAATCTCACGCCTGGA ACCGGAGGATTTTGCGGTGTATTACTGCCAGCAAACTGTGCCGTATCCGTATACGTTCGGCCAA GGGACCAAGGTGGAAATCAAACGTACTGTGGCCGCTCCTAGCGTGTTCATTTTTCCGCCATCCG ACGAGCAGCTCAAGTCCGGCACCGCCTCCGTGGTCTGCCTGCTCAACAACTTCTACCCTCGCGA AGCTAAGGTCCAGTGGAAGGTCGACAATGCCCTGCAGTCCGGAAACTCGCAGGAAAGCGTGAC TGAACAGGACTCCAAGGACTCCACCTATTCACTGTCCTCGACTCTGACCCTGAGCAAGGCGGAT TACGAAAAGCACAAAGTGTACGCATGCGAAGTGACCCACCAGGGTCTTTCGTCCCCCGTGACCA AGAGCTTCAACAGAGGAGAGTGT

VL domain AA

SEQ ID NO: 76

*EIVLTQSPGTLSLSPGERATLSCRASQSVSSSYLAWYQQKPGQAPRLLIY GASSRATGIPDRFSGSGSGTDFTLTISRLEPEDFAVYYCQQTVPYPYTFGQGTKVEIK*

VL domain DNA

SEQ ID NO: 77

GAAATTGTGCTGACCCAGTCTCCGGGCACGTTATCTCTGAGCCCTGG TGAGCGCGCCACTCTGTCATGCCGGGCTTCTCAAAGTGTTAGCAGTAGCTACCTGGCGTGGTAT CAGCAAAAACCGGGCCAGGCCCCGCGTCTGCTGATTTACGGTGCATCCAGCCGTGCCACCGGC ATTCCAGATCGTTTTTCCGGTAGTGGTTCTGGGACGGACTTCACTCTGACAATCTCACGCCTGGA ACCGGAGGATTTTGCGGTGTATTACTGCCAGCAAACTGTGCCGTATCCGTATACGTTCGGCCAA GGGACCAAGGTGGAAATCAAA

| | | |
| --- | --- | --- |
| SEQ ID NO: 20 | LCDR1 (AA) (IMGT) | QSVSSSY |
| SEQ ID NO: 21 | LCDR1 (AA) (Kabat) | RASQSVSSSYLA |
| SEQ ID NO: 22 | LCDR2 (AA) (IMGT) | GAS |
| SEQ ID NO: 23 | LCDR2 (AA) (Kabat) | GASSRAT |
| SEQ ID NO: 80 | LCDR3 (AA) (IMGT) | QQTVPYPYT |
| SEQ ID NO: 80 | LCDR3 (AA) (Kabat) | QQTVPYPYT |

-continued

| Amino acid sequence of heavy chain of FS28m-228 mAb |
| --- |

Amino acid and cDNA sequences of heavy chain of FS22-172-003-AA/FS28-256-271 mAb[2]
Heavy chain AA (without LALA)

SEQ ID NO: 1

EVQLLESGGGLVQPGGSLRLSCAASGFTFTHTYMSWVRQAPGKGLEWV
SAISPTYSTTNYADSVKGRFTISRDNNKNTLYLQMNSLRAEDTAVYYCARYNAYHAALDYWGQGTLV
TVSSASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (without LALA)

SEQ ID NO: 2

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCGCGATTTCTCCGACTTATAGCACTACCA
ACTATGCGGATAGCGTGAAAGGCCGTTTTACCATTTCTCGCGACAACAACAAGAACACGCTGTAC
CTGCAGATGAACTCACTGCGTGCCGAAGATACGGCCGTGTATTACTGTGCGAGATACAACGCGT
ATCATGCTGCTCTGGACTACTGGGGCCAGGGAACCCTGGTCACCGTCTCGAGTGCTAGCACTAA
GGGCCCGTCGGTGTTCCCGCTGGCCCCATCGTCCAAGAGCACATCAGGGGGTACCGCCGCCCT
GGGCTGCCTTGTGAAGGATTACTTTCCCGAGCCCGTCACAGTGTCCTGGAACAGCGGAGCCCT
GACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC
GCCTTGCCCAGCCCCGGAACTGCTGGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

Heavy chain AA (with LALA)

SEQ ID NO: 3

EVQLLESGGGLVQPGGSLRLSCAASGFTFTHTYMSWVRQAPGKGLEWV
SAISPTYSTTNYADSVKGRFTISRDNNKNTLYLQMNSLRAEDTAVYYCARYNAYHAALDYWGQGTLV
TVSSASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPEAAGGPSVFLFPPKP
KDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (with LALA)

SEQ ID NO: 4

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCGCGATTTCTCCGACTTATAGCACTACCA
ACTATGCGGATAGCGTGAAAGGCCGTTTTACCATTTCTCGCGACAACAACAAGAACACGCTGTAC
CTGCAGATGAACTCACTGCGTGCCGAAGATACGGCCGTGTATTACTGTGCGAGATACAACGCGT
ATCATGCTGCTCTGGACTACTGGGGCCAGGGAACCCTGGTCACCGTCTCGAGTGCTAGCACTAA
GGGCCCGTCGGTGTTCCCGCTGGCCCCATCGTCCAAGAGCACATCAGGGGGTACCGCCGCCCT
GGGCTGCCTTGTGAAGGATTACTTTCCCGAGCCCGTCACAGTGTCCTGGAACAGCGGAGCCCT
GACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC
GCCTTGCCCAGCCCCGGAAGCTGCCGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

-continued

| Amino acid sequence of heavy chain of FS28m-228 mAb |
|---|

VH domain AA

SEQ ID NO: 177

EVQLLESGGGLVQPGGSLRLSCAASGFTFTHTYMSWVRQAPGKGLEWV
SAISPTYSTTNYADSVKGRFTISRDNNKNTLYLQMNSLRAEDTAVYYCARYNAYHAALDYWGQGTLV
TVSS

VH domain DNA

SEQ ID NO: 178

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCGCGATTTCTCCGACTTATAGCACTACCA
ACTATGCGGATAGCGTGAAAGGCCGTTTTACCATTTCTCGCGACAACAACAAGAACACGCTGTAC
CTGCAGATGAACTCACTGCGTGCCGAAGATACGGCCGTGTATTACTGTGCGAGATACAACGCGT
ATCATGCTGCTCTGGACTACTGGGGCCAGGGAACCCTGGTCACCGTCTCGAGT

| | | |
|---|---|---|
| SEQ ID NO: 42 | HCDR1 (AA) (IMGT) | GFTFTHTY |
| SEQ ID NO: 43 | HCDR1 (AA) (Kabat) | HTYMS |
| SEQ ID NO: 33 | HCDR2 (AA) (IMGT) | ISPTYSTT |
| SEQ ID NO: 5 | HCDR2 (AA) Kabat) | AISPTYSTTNYADSVKG |
| SEQ ID NO: 44 | HCDR3 (AA) (IMGT) | ARYNAYHAALDY |
| SEQ ID NO: 45 | HCDR3 (AA) (Kabat) | YNAYHAALDY |

Amino acid and cDNA sequences of heavy chain of FS22-172-003-AA/FS28-256-272 mAb[2]
Heavy chain AA (without LALA)

SEQ ID NO: 6

EVQLLESGGGLVQPGGSLRLSCAASGFTFTHTYMSWVRQAPGKGLEWV
SHISPTYSTTNYADSVKGRFTISRDNNKNTLYLQMNSLRAEDTAVYYCARYNAYHAALDYWGQGTLV
TVSSASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (without LALA)

SEQ ID NO: 7

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCCATATTTCTCCGACTTATAGCACTACCA
ACTATGCGGATAGCGTGAAAGGCCGTTTTACCATTTCTCGCGACAACAACAAGAACACGCTGTAC
CTGCAGATGAACTCACTGCGTGCCGAAGATACGGCCGTGTATTACTGTGCGAGATACAACGCGT
ATCATGCTGCTCTGGACTACTGGGGCCAGGGAACCCTGGTCACCGTCTCGAGTGCTAGCACTAA
GGGCCCGTCGGTGTTCCCGCTGGCCCCATCGTCCAAGAGCACATCAGGGGGTACCGCCGCCCT
GGGCTGCCTTGTGAAGGATTACTTTCCCGAGCCCGTCACAGTGTCCTGGAACAGCGGAGCCCT
GACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC
GCCTTGCCCAGCCCCGGAACTGCTGGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

Heavy chain AA (with LALA)

SEQ ID NO: 158

EVQLLESGGGLVQPGGSLRLSCAASGFTFTHTYMSWVRQAPGKGLEWV
SHISPTYSTTNYADSVKGRFTISRDNNKNTLYLQMNSLRAEDTAVYYCARYNAYHAALDYWGQGTLV
TVSSASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPEAAGGPSVFLFPPKP
KDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

-continued

| Amino acid sequence of heavy chain of FS28m-228 mAb |
|---|

Heavy chain DNA (with LALA)

SEQ ID NO: 159

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCCATATTTCTCCGACTTATAGCACTACCA
ACTATGCGGATAGCGTGAAAGGCCGTTTTACCATTTCTCGCGACAACAACAAGAACACGCTGTAC
CTGCAGATGAACTCACTGCGTGCCGAAGATACGGCCGTGTATTACTGTGCGAGATACAACGCGT
ATCATGCTGCTCTGGACTACTGGGGCCAGGGAACCCTGGTCACCGTCTCGAGTGCTAGCACTAA
GGGCCCGTCGGTGTTCCCGCTGGCCCCATCGTCCAAGAGCACATCAGGGGGTACCGCCGCCCT
GGGCTGCCTTGTGAAGGATTACTTTCCCGAGCCCGTCACAGTGTCCTGGAACAGCGGAGCCCT
GACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC
GCCTTGCCCAGCCCCGGAAGCTGCCGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

VH domain AA

SEQ ID NO: 70

EVQLLESGGGLVQPGGSLRLSCAASGFTFTHTYMSWVRQAPGKGLEWV
SNISPTYSTTNYADSVKGRFTISRDNNKNTLYLQMNSLRAEDTAVYYCARYNAYHAALDYWGQGTLV
TVSS

VH domain DNA

SEQ ID NO: 71

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCAATATTTCTCCGACTTATAGCACTACCAA
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAACAAGAACACGCTGTACC
TGCAGATGAACTCACTGCGTGCCGAAGATACGGCCGTGTATTACTGTGCGAGATACAACGCGTA
TCATGCTGCTCTGGACTACTGGGGCCAGGGAACCCTGGTCACCGTCTCGAGT

| | | |
|---|---|---|
| SEQ ID NO: 42 | HCDR1 (AA) (IMGT) | GFTFTHTY |
| SEQ ID NO: 43 | HCDR1 (AA) (Kabat) | HTYMS |
| SEQ ID NO: 33 | HCDR2 (AA) (IMGT) | ISPTYSTT |
| SEQ ID NO: 160 | HCDR2 (AA) Kabat) | HISPTYSTTNYADSVKG |
| SEQ ID NO: 44 | HCDR3 (AA) (IMGT) | ARYNAYHAALDY |
| SEQ ID NO: 45 | HCDR3 (AA) (Kabat) | YNAYHAALDY |

Amino acid and cDNA sequences of heavy chain of FS22-172-003-AA/FS28-256-273 mAb$^2$
Heavy chain AA (without LALA)

SEQ ID NO: 161

EVQLLESGGGLVQPGGSLRLSCAASGFTFTHTYMSWVRQAPGKGLEWV
SSISPTYSTTNYADSVKGRFTISRDNNKNTLYLQMNSLRAEDTAVYYCARYNAYHAALDYWGQGTLV
TVSSASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (without LALA)

SEQ ID NO: 162

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCTCGATTTCTCCGACTTATAGCACTACCA
ACTATGCGGATAGCGTGAAAGGCCGTTTTACCATTTCTCGCGACAACAACAAGAACACGCTGTAC
CTGCAGATGAACTCACTGCGTGCCGAAGATACGGCCGTGTATTACTGTGCGAGATACAACGCGT
ATCATGCTGCTCTGGACTACTGGGGCCAGGGAACCCTGGTCACCGTCTCGAGTGCTAGCACTAA
GGGCCCGTCGGTGTTCCCGCTGGCCCCATCGTCCAAGAGCACATCAGGGGGTACCGCCGCCCT
GGGCTGCCTTGTGAAGGATTACTTTCCCGAGCCCGTCACAGTGTCCTGGAACAGCGGAGCCCT
GACCTCCGGAGTGCATACTTTCCCGGCTGTGCTTCAGTCCTCTGGCCTGTACTCATTGTCCTCC

-continued

Amino acid sequence of heavy chain of FS28m-228 mAb

GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC
GCCTTGCCCAGCCCCGGAACTGCTGGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

Heavy chain AA (with LALA)

SEQ ID NO: 163

*EVQLLESGGGLVQPGGSLRLSCAASGFTFTHTYMSWVRQAPGKGLEWV*
*SSISPTYSTTNYADSVKGRFTISRDNNKNTLYLQMNSLRAEDTAVYYCARYNAYHAALDYWGQGTLV*
*TVSS*ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPEAAGGPSVFLFPPKP
KDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELPYIIPPYNQVSLTCLVKGFYPS
DIAVEWESNGQPENNYKTTPPVLDSDGSFFLYSKLTVGADRWLEGNVFSCSVMHEALHNHYTQKSL
SLSPG

Heavy chain DNA (with LALA)

SEQ ID NO: 164

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCTCGATTTCTCCGACTTATAGCACTACCA
ACTATGCGGATAGCGTGAAAGGCCGTTTTACCATTTCTCGCGACAACAACAAGAACACGCTGTAC
CTGCAGATGAACTCACTGCGTGCCGAAGATACGGCCGTGTATTACTGTGCGAGATACAACGCGT
ATCATGCTGCTCTGGACTACTGGGGCCAGGGAACCCTGGTCACCGTCTCGAGTGCTAGCACTAA
GGGCCCGTCGGTGTTCCCGCTGGCCCCATCGTCCAAGAGCACATCAGGGGGTACCGCCGCCCT
GGGCTGCCTTGTGAAGGATTACTTTCCCGAGCCCGTCACAGTGTCCTGGAACAGCGGAGCCCT
GACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC
GCCTTGCCCAGCCCCGGAAGCTGCCGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

VH domain AA

SEQ ID NO: 70

*EVQLLESGGGLVQPGGSLRLSCAASGFTFTHTYMSWVRQAPGKGLEWV*
*SNISPTYSTTNYADSVKGRFTISRDNNKNTLYLQMNSLRAEDTAVYYCARYNAYHAALDYWGQGTLV*
*TVSS*

VH domain DNA

SEQ ID NO: 71

GAAGTGCAACTGCTGGAGTCCGGTGGTGGTCTGGTACAGCCGGGTG
GTTCTCTGCGTCTGAGTTGCGCGGCCAGTGGCTTTACCTTCACTCATACTTATATGAGCTGGGTG
CGTCAGGCTCCGGGCAAAGGTCTGGAATGGGTTAGCAATATTTCTCCGACTTATAGCACTACCAA
CTATGCGGATAGCGTGAAAGGCCGTTTTACCATTTCTCGCGACAACAACAAGAACACGCTGTACC
TGCAGATGAACTCACTGCGTGCCGAAGATACGGCCGTGTATTACTGTGCGAGATACAACGCGTA
TCATGCTGCTCTGGACTACTGGGGCCAGGGAACCCTGGTCACCGTCTCGAGT

| | | |
|---|---|---|
| SEQ ID NO: 42 | HCDR1 (AA) (IMGT) | GFTFTHTY |
| SEQ ID NO: 43 | HCDR1 (AA) (Kabat) | HTYMS |
| SEQ ID NO: 33 | HCDR2 (AA) (IMGT) | ISPTYSTT |
| SEQ ID NO: 165 | HCDR2 (AA) Kabat) | SISPTYSTTNYADSVKG |
| SEQ ID NO: 44 | HCDR3 (AA) (IMGT) | ARYNAYHAALDY |
| SEQ ID NO: 45 | HCDR3 (AA) (Kabat) | YNAYHAALDY |

-continued

| Amino acid sequence of heavy chain of FS28m-228 mAb |
|---|

Amino acid sequence of heavy chain of FS22m-063-AA/FS28m-228-010 mAb2

SEQ ID NO: 166

Heavy chain AA (with LALA)

EVQLLESGGGLVQPGGSLRLSCAASGFTFSTYFMVWVRQAPGKGLEWV
SMISPKSSNTYYADSVKGRFTISRDNSKNTLYLQMNSLRAEDTAVYYCARYHISPRFDYWGQGTLVT
VSSASTKGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSCDKTHTCPPCPAPEAAGGPSVFLFPPKPK
DTLMISRTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSRDEPYWSYVSLTCLVKGFYPSDIAVEWE
SNGQPENNYKTTPPVLDSDGSFFLYSKLTVMNYRWELGNVFSCSVMHEALHNHYTQKSLSLSPG

Amino acid sequence of light chain of FS22m-063-AA/FS28m-228-010 mAb2
Light chain AA

SEQ ID NO: 136

EIVLTQSPGTLSLSPGERATLSCRASQSVSSSYLAWYQQKPGQAPRLLIY
GASSRATGIPDRFSGSGSGTDFTLTISRLEPEDFAVYYCQQPFPFSFTFGQGTKVEIKRTVAAPSVFIF
PPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Amino acid sequence of heavy and light chains of FS22m-063-AA/HelD1.3 mAb2
Heavy chain AA (with LALA)

SEQ ID NO: 167

QVQLQESGPGLVRPSQTLSLTCTVSGSTFSGYGVNWVRQPPGRGLEWI
GMIWGDGNTDYNSALKSRVTMLVDTSKNQFSLRLSSVTAADTAVYYCARERDYRLDYWGQGSLVTV
SSASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPEAAGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDEPYWSYVSLTCLVKGFYPSDIAVEWES
NGQPENNYKTTPPVLDSDGSFFLYSKLTVMNYRWELGNVFSCSVMHEALHNHYTQKSLSLSPG

Light chain AA

SEQ ID NO: 168

DIQMTQSPASLSASVGETVTITCRASGNIHNYLAWYQQKQGKSPQLLVY
NAKTLADGVPSRFSGSGSGTQYSLKINSLQPEDFGSYYCQHFWSTPRTFGGGTKLEIKRTVAAPSVFI
FPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Amino acid and cDNA sequences of the heavy and light chains of FS22-172-003-AA/FS28-185-002 mAb2
Heavy chain AA (with LALA)

SEQ ID NO: 169

EVQLLESGGGLVQPGGSLRLSCAASGFTFTTSAMSWVRQAPGKGLEWVSRINPYEGETNY
ADSVKGRFTISRDNSKNTLYLQMNSLRAEDTAVYYCARGWSSDTWFKSATDYWGQGTLVTVSSAS
TKGPSVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPEAAGGPSVFLFPPKPKDTLMI
SRTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSRDELPYIIPPYNQVSLTCLVKGFYPSDIAVEWE
SNGQPENNYKTTPPVLDSDGSFFLYSKLTVGADRWLEGNVFSCSVMHEALHNHYTQKSLSLSPG

Heavy chain DNA (with LALA)

SEQ ID NO: 170

GAAGTGCAACTGCTGGAGTCCGGTGGTGGTCTGGTACAGCCGGGTGGTTCTCTGCGTC
TGAGTTGCGCGGCCAGTGGCTTTACCTTCACTACATCTGCTATGAGCTGGGTGCGTCAGGCTCC
GGGCAAAGGTCTGGAATGGGTTAGCAGGATTAATCCGTATGAGGGCGAGACCAACTATGOGGAT
AGCGTGAAAGGCCGTTTTACCATTTCTCGCGACAACAGCAAGAACACGCTGTACCTGCAGATGA
ACTCACTGCGTGCCGAAGATACGGCCGTGTATTACTGTGCGAGAGGTTGGTCTAGTGATACGTG
GTTTAAATCTGCCACGGACTACTGGGGCCAGGGAACCCTGGTCACCGTCTCGAGTGCTAGCACT
AAGGGCCCGTCGGTGTTCCCGCTGGCCCCATCGTCCAAGAGCACATCAGGGGGTACCGCCGCC
CTGGGCTGCCTTGTGAAGGATTACTTTCCCGAGCCCGTCACAGTGTCCTGGAACAGCGGAGCCC
TGACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC
GCCTTGCCCAGCCCCGGAAGCTGCCGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

-continued

| Amino acid sequence of heavy chain of FS28m-228 mAb |
| --- |

Light chain AA

SEQ ID NO: 171

EIVLTQSPGTLSLSPGERATLSCRASQSVSSSYLAWYQQKPGQAPRLLIYGASSRATGIPDRFSGSG
SGTDFTLTISRLEPEDFAVYYCQQSSYSAPVTFGQGTKVEIKRTVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC

Light chain DNA

SEQ ID NO: 172

GAAATTGTGCTGACCCAGTCTCCGGGCACGTTATCTCTGAGCCCTGG
TGAGCGCGCCACTCTGTCATGCCGGGCTTCTCAAAGTGTTAGCAGTAGCTACCTGGCGTGGTAT
CAGCAAAAACCGGGCCAGGCCCCGCGTCTGCTGATTTACGGTGCATCCAGCCGTGCCACCGGC
ATTCCAGATCGTTTTTCCGGTAGTGGTTCTGGGACGGACTTCACTCTGACAATCTCACGCCTGGA
ACCGGAGGATTTTGCGGTGTATTACTGCCAGCAATCTTCTTATTCTGCTCCTGTCACGTTCGGCC
AAGGGACCAAGGTGGAAATCAAACGTACTGTGGCCGCTCCTAGCGTGTTCATTTTTCCGCCATC
CGACGAGCAGCTCAAGTCCGGCACCGCCTCCGTGGTCTGCCTGCTCAACAACTTCTACCCTCGC
GAAGCTAAGGTCCAGTGGAAGGTCGACAATGCCCTGCAGTCCGGAAACTCGCAGGAAAGCGTG
ACTGAACAGGACTCCAAGGACTCCACCTATTCACTGTCCTCGACTCTGACCCTGAGCAAGGCGG
ATTACGAAAAGCACAAAGTGTACGCATGCGAAGTGACCCACCAGGGTCTTTCGTCCCCCGTGAC
CAAGAGCTTCAACAGAGGAGAGTGT

Amino acid and cDNA sequences of the heavy and chains of FS22-172-003-AA/FS28-185-003 mAb[2]
Heavy chain AA (with LALA)

SEQ ID NO: 173

EVQLLESGGGLVQPGGSLRLSCAASGFTFTTSAMSWVRQAPGKGLEWVSRINPYEGETNYADSVK
GRFTISRDNSKNTLYLQMNSLRAEDTAVYYCARGWSATSYFKSATDYWGQGTLVTVSSASTKGPSV
FPLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPEAAGGPSVFLFPPKPKDTLMISRTPEV
TCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSRDELPYIIPPYNQVSLTCLVKGFYPSDIAVEWESNGQP
ENNYKTTPPVLDSDGSFFLYSKLTVGADRWLEGNVFSCSVMHEALHNHYTQKSLSLSPG

Heavy chain DNA (with LALA)

SEQ ID NO: 174

GAAGTGCAACTGTTGGAGTCCGGTGGTGGTCTGGTACAGCCGGGTGGTTCTCTGCGTC
TGAGTTGCGCGGCCAGTGGCTTTACCTTCACTACATCTGCTATGAGCTGGGTGCGTCAGGCTCC
GGGCAAAGGTCTGGAATGGGTTAGCAGGATTAATCCGTATGAGGGCGAGACCAACTATGCGGAT
AGCGTGAAAGGCCGTTTTACCATTTCTCGCGACAACAGCAAGAACACGCTGTACCTGCAGATGA
ACTCACTGCGTGCCGAAGATACGGCCGTGTATTACTGTGCGAGAGGTTGGTCTGCGACGAGTTA
TTTTAAATCTGCCACTGACTACTGGGGCCAGGGAACCCTGGTCACCGTCTCGAGTGCTAGCACT
AAGGGCCCGTCGGTGTTCCCGCTGGCCCCATCGTCCAAGAGCACATCAGGGGGTACCGCCGCC
CTGGGCTGCCTTGTGAAGGATTACTTTCCCGAGCCCGTCACAGTGTCCTGGAACAGCGGAGCCC
TGACCTCCGGAGTGCATACTTTCCCGGCTGTGCTTCAGTCCTCTGGCCTGTACTCATTGTCCTCC
GTGGTCACCGTCCCTTCGTCCTCCCTGGGCACCCAGACCTATATCTGTAATGTCAACCATAAGCC
CTCGAACACCAAGGTCGACAAGAAGGTCGAGCCGAAGTCGTGCGACAAGACTCACACTTGCCC
GCCTTGCCCAGCCCCGGAAGCTGCCGGTGGTCCTTCGGTGTTCCTCTTCCCGCCCAAGCCGAA
GGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAG
CCACGGGAAGAACAGTACAACTCTACCTACCGCGTGGTGTCCGTGCTCACTGTGCTGCACCAAG
ACTGGCTGAACGGGAAGGAGTACAAGTGCAAAGTGTCCAACAAGGCGCTGCCTGCCCCAATTGA
GAAAACTATCTCGAAAGCCAAGGGACAGCCTCGAGAACCACAGGTGTACACCCTGCCCCCATCC
CGGGATGAGCTGCCATACATCATCCCACCATACAACCAGGTCAGCCTGACCTGCCTGGTCAAAG
GCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGG
CGCAGATAGGTGGCTGGAAGGGAACGTCTTCTCATGCTCCGTGATGCATGAGGCGCTGCACAA
CCACTACACTCAGAAGAGCTTGTCCCTGTCGCCCGGT

Light chain AA

SEQ ID NO: 175

EIVLTQSPGTLSLSPGERATLSCRASQSVSSSYLAWYQQKPGQAPRLLIYGASSRATGIPDR
FSGSGSGTDFTLTISRLEPEDFAVYYCQQSSYSAPVTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVYAC
EVTHQGLSSPVTKSFNRGEC

Light chain DNA

SEQ ID NO: 176

GAAATTGTGCTGACCCAGTCTCCGGGCACGTTATCTCTGAGCCCTGGTGAGCGCGCCA
CTCTGTCATGCCGGGCTTCTCAAAGTGTTAGCAGTAGCTACCTGGCGTGGTATCAGCAAAAACC
GGGCCAGGCCCCGCGTCTGCTGATTTACGGTGCATCCAGCCGTGCCACCGGCATTCCAGATCG
TTTTTCCGGTAGTGGTTCTGGGACGGACTTCACTCTGACAATCTCACGCCTGGAACCGGAGGAT
TTTGCGGTGTATTACTGCCAGCAATCTTCTTATTCTGCTCCTGTCACGTTCGGCCAAGGGACCAA
GGTGGAAATCAAACGTACTGTGGCCGCTCCTAGCGTGTTCATTTTTCCGCCATCCGACGAGCAG
CTCAAGTCCGGCACCGCCTCCGTGGTCTGCCTGCTCAACAACTTCTACCCTCGCGAAGCTAAGG

-continued

| Amino acid sequence of heavy chain of FS28m-228 mAb |
|---|
| TCCAGTGGAAGGTCGACAATGCCCTGCAGTCCGGAAACTCGCAGGAAAGCGTGACTGAACAGG<br>ACTCCAAGGACTCCACCTATTCACTGTCCTCGACTCTGACCCTGAGCAAGGCGGATTACGAAAA<br>GCACAAAGTGTACGCATGCGAAGTGACCCACCAGGGTCTTTCGTCCCCCGTGACCAAGAGCTTC<br>AACAGAGGAGAGTGT |
| Amino acid sequence of WT Fcab CH3 domain<br>(SEQ ID NO: 81)<br>AB, CD and EF loops underlined<br>GQPREPQVYTLPPSRDELTKNQVSLTCLVKGFYPSDIAVEWESNGQPENNYKTTPPVLDSDGSFFLY<br>SKLTVDKSRWQQGNVFSCSVMHEALHNHYTQKSLSLSPG |
| WT CD loop sequence<br>SEQ ID NO: 157<br>WT Fcab CD loop - SNGQPENNY |

REFERENCES

All documents mentioned in this specification are incorporated herein by reference in their entirety.

Altschul S F, Gish W, Miller W, Myers E W, Lipman D J. Basic local alignment search tool. J. Mol. Biol. 215 (3), 403-10 (1990).

Altschul S F, Madden T L, Schaffer A A, Zhang J, Zhang Z, Miller W, Lipman D J. Gapped BLAST and PSI-BLAST: a new generation of protein database search programs. Nucleic Acids Res. 25 (17), 3389-402 (1997).

Bagshawe K D, Sharma S K, Springer C J, Antoniw P, Rogers G T, Burke P J, Melton R. Antibody-enzyme conjugates can generate cytotoxic drugs from inactive precursors at tumor sites. Antibody, Immunoconjugates and Radiopharmaceuticals 4, 915-922 (1991).

Bartkowiak T, Curran M A. 4-1BB Agonists: Multi-Potent Potentiators of Tumor Immunity. Front Oncol. June 8; 5, 117 (2015).

Bergman I, Burckart G J, Pohl C R, Venkataramanan R, Barmada M A, Griffin J A And Cheung N V. Pharmacokinetics of IgG and IgM Anti-Ganglioside Antibodies in Rats And Monkeys After Intrathecal Administration. The Journal of Pharmacology and Experimental Therapeutics 284 (1), 111-115 (1998)

Bitra A, Doukov T, Wang J, Picarda G, Benedict C A, Croft M, Zajonc D M. Crystal structure of murine 4-1BB and its interaction with 4-1 BBL support a role for galectin-9 in 4-1BB signaling. J Biol Chem. 293 (4): 1317-1329 (2017).

Bruhns P, Iannascoli B, England P, Mancardi D A, Fernandez N, Jorieux S and Daëron M. Specificity and affinity of human Fcγ receptors and their polymorphic variants for human IgG subclasses. Blood 113 (16), 3716-25 (2009).

Campagne O, Delmas A, Fouliard S, Chenel M, Chichili G R, Li H, Alderson R, Scherrmann J M, Mager D E. Integrated Pharmacokinetic/Pharmacodynamic Model of a Bispecific CD3×CD123 DART Molecule in Nonhuman Primates: Evaluation of Activity and Impact of Immunogenicity. Clin Cancer Res. 2018 Jun. 1; 24 (11): 2631-2641. doi: 10.1158/1078-0432.CCR-17-2265. Epub 2018 Feb. 20.

Chester C, Sanmamed M F, Wang J, Melero I. Immunotherapy targeting 4-1BB: mechanistic rationale, clinical results, and future strategies. Blood. 131 (1): 49-57 (2018).

Chester C, Ambulkar S, Kohrt H E. 4-1BB agonism: adding the accelerator to cancer immunotherapy. Cancer Immunol Immunother. 65 (10): 1243-8 (2016).

Creaney J, Dick I M and Robinson B W (2015). Discovery of new biomarkers for malignant mesothelioma. Curr Pulmonol Rep. 4:15-21.

Croft, M., 2003. Co-stimulatory members of the TNFR family: keys to effective T-cell immunity? Nat. Rev. Immunol. 3:609-620.

Cui A, Jin X0G, Zhai K, Tong Z-H and Shi H-Z (2014). Diagnostic values of soluble mesothelin-related peptides for malignant pleural mesothelioma: updated meta-analysis. BMJ Open 4: e004145.

Dubrot J, Milheiro F, Alfaro C, Palazón A, Martinez-Forero I, Perez-Gracia J L, Morales-Kastresana A, Romero-Trevejo J L, Ochoa M C, Hervás-Stubbs S, Prieto J, Jure-Kunkel M, Chen L, Melero I. Treatment with anti-CD137 mAbs causes intense accumulations of liver T cells without selective antitumor immunotherapeutic effects in this organ. Cancer Immunol Immunother. 59 (8): 1223-1233 (2010).

Fisher T S, Kamperschroer C, Oliphant T, Love V A, Lira P D, Doyonnas R, Bergqvist S, Baxi S M, Rohner A, Shen A C, Huang C, Sokolowski S A, Sharp L L. Targeting of 4-1BB by monoclonal antibody PF-05082566 enhances T-cell function and promotes anti-tumor activity. Cancer Immunol Immunother. 61 (10): 1721-33 (2012).

Grisshammer, R. and Nagai, K. (1995) Purification of over-produced proteins from *E. coli* cells In: DNA Cloning 2: Expression systems (Rickwood, D. and Hames, B. D., Eds.), The Practical Approach Series, pp. 59-92. IRL Press, Oxford University Press.

Hassan R, Kreitman R J, Pastan I and Willingham M C (2005). Localization of mesothelin in epithelial ovarian cancer. Appl Immunohistochem Mol Morphol AIMM Off Publ Soc Appl Immunohistochem 13:243-47;

Hassan R, Thomas, A, Alewine, C, Le, D T, Jaffee, E M and Pastan I (2016). Mesothelin immunotherapy for cancer: ready for prime time? J. Clin. Onc. 34:4171-4180.

Hassan R, Lerner M R, Benbrook D, Lightfoot S A, Brackett D J, Wang Q C and Pastan I (2002). Clin. Cancer Res.: 8: 3520-3526.

Hezareh M, Hessell A J, Jensen R C, van de Winkel J G and Parren P W. Effector function activities of a panel of mutants of a broadly neutralizing antibody against human immunodeficiency virus type 1. J. Virol. 75 (24), 12161-8 (2001).

Hinner M J, Aiba, R S B., Wiedenmann A, Schlosser C, Allersdorfer A, Matschiner G, Rothe C, Moebius U, Kohrt H E, Olwill S A. Costimulatory T cell engagement via a novel bispecific anti-CD137/anti-HER2 protein. J. Immunotherapy Cancer 3 (Suppl 2): P187. (2015)

Holliger P, Hudson P J. Engineered antibody fragments and the rise of single domains. Nat Biotechnol. 23 (9): 1126-36 (2005).
Hollevoet K, Reitsma J B, Creaney J, Grigoriu, B D, Robinson B W, Scherpereel A, Cristaudo A, Pass H I, Nackaerts K, Rodriques Portal J A, Schneider J, Muley, T, Di Serio F, Baas P, Tomasetti M, Rai A J and van Meerbeeck J P (2012). Serum mesothelin for diagnosing malignant pleural mesothelioma: an individual patient data meta-analysis. J Clin. Oncol. 30:1541-1549.
Hurtado J C, Kim Y J, Kwon B S. Signals through 4-1BB are costimulatory to previously activated splenic T cells and inhibit activation-induced cell death. J Immunol. 15; 158(6): 2600-9 (1997).
Hu S, Shively L, Raubitschek A, Sherman M, Williams L E, Wong J Y, Shively J E, Wu A M. Minibody: A novel engineered anti-carcinoembryonic antigen antibody fragment (single-chain Fv-CH3) which exhibits rapid, high-level targeting of xenografts. Cancer Res. 56(13):3055-61 (1996).
Kaneko O, Gong, L, Zhang, J, Hansen, J K, Hassan, R, Lee B and Ho M (2009). A binding domain on mesothelin for CA125/MUC16. J. Biol. Chem. 284:3739-3749.
Kohrt, H. E. et al., 2011. CD137 stimulation enhances the antilymphoma activity of anti-CD20 antibodies. Blood, 117 (8), pp. 2423-2432.
Kohrt, H. E. et al., 2014. Targeting CD137 enhances the efficacy of cetuximab. The Journal of clinical investigation, 124 (6), pp. 2668-2682.
Kohrt, H. E., Houot, R., Weiskopf, K., et al., 2012. Stimulation of natural killer cells with a CD137-specific antibody enhances trastuzumab efficacy in xenotransplant models of breast cancer. The Journal of clinical investigation, 122 (3), pp. 1066-1075.
Lee J-H, Kim H, Yao Z, Szajek L, Grasso L, Kim I and Paik C. H (2018). Tumour-Shed Antigen Affects Antibody Tumour Targeting: Comparison of Two $^{89}$Zr-Labeled Antibodies Directed against Shed or Nonshed Antigens. Contrast Media and Molecular Imaging. I D: 2461257.
Lefranc M P, Giudicelli V, Duroux P, Jabado-Michaloud J, Folch G, Aouinti S, Carillon E, Duvergey H, Houles A, Paysan-Lafosse T, Hadi-Saljoqi S, Sasorith S, Lefranc G, Kossida S. IMGT®, the international ImMunoGeneTics information System® 25 years on. Nucleic Acids Res. 43 (Database issue): D413-22 (2015).
Lefranc M P, Pommié C, Kaas Q, Duprat E, Bosc N, Guiraudou D, Jean C, Ruiz M, Da Piédade I, Rouard M, Foulquier E, Thouvenin V, Lefranc G. IMGT unique numbering for immunoglobulin and T cell receptor constant domains and Ig superfamily C-like domains. Dev. Comp. Immunol. 29 (3), 185-203 (2005).
Ledermann J A, Begent R H, Massof C, Kelly A M, Adam T, Bagshawe K D. A phase-I study of repeated therapy with radiolabelled antibody to carcinoembryonic antigen using intermittent or continuous administration of cyclosporin A to supress the immune response. Int. J. Cancer 47 (5), 659-64 (1991).
Link A, Hepp J, Reichen C, Schildknecht P, Tosevski I, Taylor J, Juglair L, Titz A, Matzner M, Bessey R, Zitt C, Lemaillet G, Herbst J, Dawson K, Ji H, Levitsky V, Snell D, Stumpp M T, Harsrick A, von Baur E. Preclinical pharmacology of MP0310: a 4-1BB/FAP bispecific DARPin drug candidate promoting tumor-restricted T cell co-stimulation [abstract]. In: Proceedings of the Annual Meeting of the American Association for Cancer Research; 2018 Apr. 14-18; Chicago (IL) Abstract nr 3752 (2018).
Liu et al. 2017. Tumor Antigen Expression-dependent Activation of the CD137 Costimulatory Pathway by Bispecific DART® Proteins. Annual Meeting of the American Association for Cancer Research 2017 Apr. 1-5, Washington, DC. Abstract nr 3642.
Ma J, Tang W K, Esser L, Pastan I, Xia D. (2012). Recognition of mesothelin by the therapeutic antibody MORAb-009: structural and mechanistic insights. J Biol. Chem. 287:33123-31.
Makkouk A, Chester C, Kohrt H E. Rationale for anti-CD137 cancer immunotherapy. Eur J Cancer. 54, 112-119 (2016).
Pearson W R, Lipman D J. Improved tools for biological sequence comparison. Proc. Natl. Acad. Sci. U.S.A. 85 (8), 2444-8 (1988).
Reichen C, Bessey R, DePasquale C, Imobersteg S, Behe M, Blanc A, Schibli R, Link A, Juglair L, Taylor J, Schildknecht P, Hepp J, vom Baur E, Ji H, Zitt C, Levitsky V, Dawson K, Stumpp M T, Snell D, FAP-mediated tumor accumulation of a T-cell agonistic FAP/4-1BB DARPin drug candidate analyzed by SPECT/CT and quantitative biodistribution [abstract]. In: Proceedings of the Annual Meeting of the American Association for Cancer Research; 2018 Apr. 14-18; Chicago (IL) Abstract nr 3029 (2018).
Rosenberg S. Development of Cancer Vaccines. ASCO Educational Book Spring: 60-62 (2000).
Sapede, C, Gauvrit A, Barbieux I, Padieu M, Cellerin L, Sagan C, Scherpereel A, Dabouis G, Gregoire M. Abberant splicing and protease involvement in mesothelin release from epithelioid mesothelioma cells. Canc. Sci 99 (3): 590-594 (2008)
Schropp J, Knot A, Shah D, Koch G. Target-mediated drug disposition model for bispecific antibodies: properties, approximation and optimal dosing strategy. CPT Pharmacometrics Systems Pharmacology 2019 8:177-187.
Segal N H, Logan T F, Hodi F S, McDermott D, Melero I, Hamid O, Schmidt H, Robert C, Chiarion-Sileni V, Ascierto P A, Maio M, Urba W J, Gangadhar T C, Suryawanshi S, Neely J, Jure-Kunkel M, Krishnan S, Kohrt H, Sznol M, Levy R. Results from an integrated safety analysis of urelumab, an agonist anti-CD137 monoclonal antibody. Clin Cancer Res. 23(8), 1929-1936(2017).
Simeoni M, Magni P, Cammia C, De Nicolao G, Croci V, Pesenti E, Germani M, Poggesi I, Rocchetti M. Predictive pharmacokinetic-pharmacodynamic modeling of tumor growth kinetics in xenograft models after administration of anticancer agents. Cancer Res. 2004 Feb. 1; 64 (3): 1094-101.
Smith T F, Waterman M S. Identification of common molecular subsequences. J. Mol. Biol. 147 (1), 195-7 (1981).
Shuford W W, Klussman K, Tritchler D D, Loo D T, Chalupny J, Siadak A W, Brown T J, Emswiler J, Raecho H, Larsen C P, Pearson T C, Ledbetter J A, Aruffo A, Mittler R S. 4-1BB costimulatory signals preferentially induce CD8+ T cell proliferation and lead to the amplification in vivo of cytotoxic T cell responses. J Exp Med. 186(1), 47-55(1997).
Tello, D, Goldbaum, F A, Mariuzza, R A, Ysern, X, Schwarz, F P, Poljak, R J. Three-dimensional structure and thermodynamics of antigen binding by anti-lysozyme antibodies, Biochem Soc. Trans., 21(4), 943-6 (1993)
Wen T, Bukczynski J, Watts T H. 4-1BB ligand-mediated costimulation of human T cells induces CD4 and CD8 T cell expansion, cytokine production, and the development of cytolytic effector function. J Immunol. 168(10), 4897-906 (2002).

Wesche-Soldato D E, Chung C S, Gregory S H, Salazar-Mather T P, Ayala C A, Ayala A. CD8+ T cells promote inflammation and apoptosis in the liver after sepsis: role of Fas-FasL. Am J Pathol. 2007 July; 171 (1): 87-96.

Won E Y, Cha K, Byun J S, Kim D U, Shin S, Ahn B, Kim Y H, Rice A J, Walz T, Kwon B S, Cho H S. The structure of the trimer of human 4-1BB ligand is unique among members of the tumor necrosis factor superfamily. J Biol Chem. 285 (12), 9202-10 (2010).

Wozniak-Knopp G, Bartl S, Bauer A, Mostageer M, Woisetschläger M, Antes B, Ettl K, Kainer M, Weberhofer G, Wiederkum S, Himmler G, Mudde G C, Rüker F. Introducing antigen-binding sites in structural loops of immunoglobulin constant domains: Fc fragments with engineered HER2/neu-binding sites and antibody properties. Protein Eng Des Sel. 23 (4), 289-97 (2010).

Wang X, Mathieu M, Brezski R J. IgG Fc engineering to modulate antibody effector functions. Protein Cell 9(1), 63-73 (2018).

Zhang Y, Chertov O, Zhang J, Zhang J, Hassan R, Pastan I (2011). Cytotoxic activity of immunotoxin SS1P is modulated by TACE-dependent mesothelin shedding. Cancer Res 71:5915-5922.

The invention claimed is:

1. An antibody molecule that binds to mesothelin (MSLN) and CD137, comprising (a) a complementarity determining region (CDR)-based antigen-binding site for MSLN;

wherein the CDR-based antigen-binding site comprises the VH CDR1, VH CDR2, VH CDR3, VL CDR1, VL CDR2 and VL CDR3, defined according to the ImMunoGeneTics numbering scheme, set forth in:

(i) SEQ ID NOs 42, 33, 44, 20, 22, and 80, respectively [FS28-256-271];

(ii) SEQ ID NOs 14, 16, 27, 20, 22 and 24, respectively [FS28-024-052];

(iii) SEQ ID NOs 42, 33, 44, 20, 22, and 40, respectively [FS28-256-021];

(iv) SEQ ID NOs 42, 33, 44, 20, 22, and 37, respectively [FS28-256-012];

(v) SEQ ID NOs 50, 33, 52, 20, 22 and 40, respectively [FS28-256-023];

(vi) SEQ ID NOs 42, 33, 44, 20, 22 and 41, respectively [FS28-256-024];

(vii) SEQ ID NOs 50, 33, 52, 20, 22 and 41, respectively [FS28-256-026];

(viii) SEQ ID NOs 42, 33, 44, 20, 22, and 80, respectively [FS28-256-027];

(ix) SEQ ID NOs 38, 33, 35, 20, 22, and 40, respectively [FS28-256-001];

(x) SEQ ID NOs 38, 33, 35, 20, 22, and 41 respectively [FS28-256-005];

(xi) SEQ ID NOs 46, 33, 48, 20, 22 and 37, respectively [FS28-256-014];

(xii) SEQ ID NOs 50, 33, 52, 20, 22 and 37, respectively [FS28-256-018];

(xiii) SEQ ID NOs 31, 33, 35, 20, 22 and 37, respectively [FS28-256];

(xiv) SEQ ID NOs 14, 16, 25, 20, 22 and 24, respectively [FS28-024-051];

(xv) SEQ ID NOs 14, 16, 29, 20, 22 and 24, respectively [FS28-024-053]; or (xvi) SEQ ID NOs 14, 16, 18, 20, 22 and 24, respectively [FS28-024]; and/or wherein the CDR-based antigen-binding site comprises the VH CDR1, VH CDR2, VH CDR3, VL CDR1, VL CDR2 and VL CDR3, defined according to the Kabat numbering scheme set forth in:

(i) SEQ ID NOs 43, 5, 45, 21, 23, and 80, respectively [FS28-256-271];

(ii) SEQ ID NOs 15, 17, 28, 21, 23 and 24, respectively [FS28-024-052];

(iii) SEQ ID NOs 43, 34, 45, 21, 23 and 40, respectively [FS28-256-021];

(iv) SEQ ID NOs 43, 34, 45, 21, 23 and 37, respectively [FS28-256-012];

(v) SEQ ID NOs 51, 34, 53, 21, 23 and 40, respectively [FS28-256-023];

(vi) SEQ ID NOs 43, 34, 45, 21, 23 and 41, respectively [FS28-256-024];

(vii) SEQ ID NOs 51, 34, 53, 21, 23 and 41, respectively [FS28-256-026];

(viii) SEQ ID NOs 43, 34, 45, 21, 23 and 80, respectively [FS28-256-027];

(ix) SEQ ID NOs 39, 34, 36, 21, 23 and 40, respectively [FS28-256-001];

(x) SEQ ID NOs 39, 34, 36, 21, 23 and 41, respectively [FS28-256-005];

(xi) SEQ ID NOs 47, 34, 49, 21, 23 and 37, respectively [FS28-256-014];

(xii) SEQ ID NOs 51, 34, 53, 21, 23 and 37, respectively [FS28-256-018];

(xiii) SEQ ID NOs 32, 34, 36, 21, 23 and 37, respectively [FS28-256];

(xiv) SEQ ID NOs 15, 17, 26, 21, 23 and 24, respectively [FS28-024-051];

(xv) SEQ ID NOs 15, 17, 30, 21, 23 and 24, respectively [FS28-024-053]; or (xvi) SEQ ID NOs 15, 17, 19, 21, 23 and 24, respectively [FS28-024]; and (b) a CD137 antigen-binding site located in a CH3 domain of the antibody molecule, wherein the CD137 antigen-binding site comprises a first sequence and a second sequence located in the AB and EF structural loops of the CH3 domain, respectively, wherein the first and second sequence have the sequence set forth in SEQ ID NOs 10 and 11 [FS22-172-003], respectively.

2. The antibody molecule according to claim 1, wherein the antibody molecule comprises the VH domain and the VL domain set forth in:

(i) SEQ ID NOs 177 and 76, respectively [FS28-256-271];

(ii) SEQ ID NOs 58 and 54, respectively [FS28-024-052];

(iii) SEQ ID NOs 70 and 68, respectively [FS28-256-021];

(iv) SEQ ID NOs 70 and 64, respectively [FS28-256-012];

(v) SEQ ID NOs 74 and 68, respectively [FS28-256-023];

(vi) SEQ ID NOs 70 and 78, respectively [FS28-256-024];

(vii) SEQ ID NOs 74 and 78, respectively [FS28-256-026];

(viii) SEQ ID NOs 70 and 76, respectively [FS28-256-027];

(ix) SEQ ID NOs 66 and 68, respectively [FS28-256-001];

(x) SEQ ID NOs 66 and 78, respectively [FS28-256-005];

(xi) SEQ ID NOs 72 and 64, respectively [FS28-256-014];

(xii) SEQ ID NOs 74 and 64, respectively [FS28-256-018];

(xiii) SEQ ID NOs 62 and 64, respectively [FS28-256];

(xiv) SEQ ID NOs 56 and 54, respectively [FS28-024-051];

(xv) SEQ ID NOs 60 and 54, respectively [FS28-024-053]; or (xvi) SEQ ID NOs 12 and 54, respectively [FS28-024].

3. The antibody molecule according to claim 1, wherein the antibody molecule comprises:

(i) the VH CDR1, VH CDR2, VH CDR3, VL CDR1, VL CDR2 and VL CDR3, defined according to the ImMunoGeneTics numbering scheme set forth in SEQ ID NOs 42, 33, 44, 20, 22, and 80, respectively [FS28-256-271]; and/or (ii) the VH CDR1, VH CDR2, VH CDR3, VL CDR1, VL CDR2 and VL CDR3, defined according to the Kabat numbering scheme set forth in SEQ ID NOs 43, 5, 45, 21, 23, and 80, respectively [FS28-256-271]; and/or (iii) the VH domain and VL domain set forth in SEQ ID NOs 177 and 76, respectively [FS28-256-271].

4. The antibody molecule according to claim 1, wherein the antibody molecule comprises:

(i) the VH CDR1, VH CDR2, VH CDR3, VL CDR1, VL CDR2 and VL CDR3, defined according to the ImMunoGeneTics numbering scheme set forth in SEQ ID NOS SEQ ID NOS 14, 16, 27, 20, 22 and 24, respectively [FS28-024-052]; and/or (ii) the VH CDR1, VH CDR2, VH CDR3, VL CDR1, VL CDR2 and VL CDR3, defined according to the Kabat numbering scheme set forth in SEQ ID NOs 15, 17, 28, 21, 23 and 24, respectively [FS28-024-052]; and/or (iii) the VH domain and VL domain set forth in SEQ ID NOs 58 and 54, respectively [FS28-024-052].

5. The antibody molecule according to claim 1, wherein (i) the first sequence is located between positions 14 and 17 of the CH3 domain of the antibody molecule; and/or (ii) wherein the second sequence is located between positions 91 and 99 of the CH3 domain of the antibody molecule; and wherein the amino acid residue numbering is according to the IMGT numbering scheme.

6. The antibody molecule according to claim 1, wherein the antibody molecule comprises the CH3 domain sequence set forth in SEQ ID NO: 8 [FS22-172-003].

7. The antibody molecule according to claim 1, wherein the antibody molecule comprises the heavy chain and light chain of antibody:

(i) FS22-172-003-AA/FS28-256-271 set forth in SEQ ID NOs 3 and 84, respectively;

(ii) FS22-172-003-AA/FS28-024-052 set forth in SEQ ID NOs 102 and 85, respectively;

(iii) FS22-172-003-AA/FS28-256-021 set forth in SEQ ID NOs 125 and 82, respectively;

(iv) FS22-172-003-AA/FS28-256-012 set forth in SEQ ID NOs 125 and 116, respectively;

(v) FS22-172-003-AA/FS28-256-023 set forth in SEQ ID NOs 133 and 82, (vi) FS22-172-003-AA/FS28-256-024 set forth in SEQ ID NOs 125 and 83, respectively;

(vii) FS22-172-003-AA/FS28-256-026 set forth in SEQ ID NOs 133 and 83, respectively;

(viii) FS22-172-003-AA/FS28-256-027 set forth in SEQ ID NOs 125 and 84, respectively;

(ix) FS22-172-003-AA/FS28-256-001 set forth in SEQ ID NOs 120 and 82, respectively;

(x) FS22-172-003-AA/FS28-256-005 set forth in SEQ ID NOs 120 and 83, respectively;

(xi) FS22-172-003-AA/FS28-256-014 set forth in SEQ ID NOs 129 and 116, respectively;

(xii) FS22-172-003-AA/FS28-256-018 set forth in SEQ ID NOs 133 and 116, respectively;

(xiii) FS22-172-003-AA/FS28-256 set forth in SEQ ID NOs 114 and 116, respectively;

(xiv) FS22-172-003-AA/FS28-024-051 set forth in SEQ ID NOs 98 and 85, respectively;

(xv) FS22-172-003-AA/FS28-024-053 set forth in SEQ ID NOs 106 and 85, respectively; or (xvi) FS22-172-003-AA/FS28-024 set forth in SEQ ID NOs 94 and 85, respectively.

8. The antibody molecule according to claim 7, wherein the antibody molecule comprises the heavy chain and light chain set forth in SEQ ID NOs 3 and 84, respectively [FS22-172-003-AA/FS28-256-271].

9. The antibody molecule according to claim 7, wherein the antibody molecule comprises the heavy chain and light chain set forth in SEQ ID NOs 102 and 85, respectively [FS22-172-003-AA/FS28-024-052].

10. The antibody molecule according to claim 1, wherein the antibody molecule does not bind to Fcγ receptors.

11. The antibody molecule according to claim 1, wherein the antibody molecule binds to immobilised MSLN with a higher affinity than to soluble MSLN.

12. The antibody molecule according to claim 1, wherein the antibody molecule is capable of activating CD137 on an immune cell in the presence of tumour cell-surface bound MSLN.

13. The antibody molecule according to claim 1, wherein binding of the antibody molecule to CD137 on an immune cell and to tumour cell-surface bound MSLN causes clustering of CD137 on the immune cell.

14. A nucleic acid molecule or molecules encoding the antibody molecule according to claim 1.

15. A vector or vectors comprising the nucleic acid molecule or molecules according to claim 14.

16. A recombinant host cell comprising the nucleic acid molecule(s) according to claim 14, or a vector(s) comprising the nucleic acid molecule(s) according to claim 14.

17. A method of producing an antibody molecule comprising culturing the recombinant host cell of claim 16 under conditions for production of the antibody molecule.

18. A pharmaceutical composition comprising the antibody molecule according claim 1 and a pharmaceutically acceptable excipient.

19. A method of treating cancer in an individual comprising administering to the individual a therapeutically effective amount of the antibody molecule according to claim 1, wherein the cancer expresses MSLN and comprises tumour infiltrating lymphocytes that express CD137.

20. The method according to claim 19, wherein the method further comprises administering a therapeutically effective amount of a second therapeutic to the individual.

21. A method of treating cancer in an individual comprising administering to the individual a therapeutically effective amount of the antibody molecule according to claim 1, wherein the cancer is selected from the group consisting of: ovarian cancer, pancreatic cancer, lung cancer, mesothelioma, lymphoma, head and neck cancer, colorectal cancer, breast cancer, squamous cell carcinoma, gastric cancer, endometrial cancer, and cholangiocarcinoma, wherein the cancer expresses MSLN and comprises tumour infiltrating lymphocytes that express CD137.

22. The method according to claim 21, wherein the method further comprises administering a therapeutically effective amount of a second therapeutic to the individual.

* * * * *

UNITED STATES PATENT AND TRADEMARK OFFICE
CERTIFICATE OF CORRECTION

PATENT NO. : 12,319,739 B2
APPLICATION NO. : 17/259634
DATED : June 3, 2025
INVENTOR(S) : Jose Munoz-Olaya et al.

It is certified that error appears in the above-identified patent and that said Letters Patent is hereby corrected as shown below:

In the Claims

At Column 391, Claim 4, Line 28 reads:
"NOS SEQ ID NOS 14, 16, 27, 20, 22 and 24, respec-"
Should be:
--NOs 14, 16, 27, 20, 22 and 24, respec- --

At Column 391, Claim 7, Line 59 reads:
"NOs 133 and 82,"
Should be:
--NOs 133 and 82, respectively;--

Signed and Sealed this
Twenty-second Day of July, 2025

Coke Morgan Stewart
*Acting Director of the United States Patent and Trademark Office*

SEQUENCE LISTING

```
<160> NUMBER OF SEQ ID NOS: 178

<210> SEQ ID NO 1
<211> LENGTH: 453
<212> TYPE: PRT
<213> ORGANISM: Artificial Sequence
<220> FEATURE:
<223> OTHER INFORMATION: heavy chain of FS22-172-003-AA/FS28-256-271
      mAb2 without LALA

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Ala Ile Ser Pro Thr Tyr Ser Thr Thr Asn Tyr Ala Asp Ser Val
    50                  55                  60

Lys Gly Arg Phe Thr Ile Ser Arg Asp Asn Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

-continued

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Pro Tyr Ile Ile Pro Pro Tyr Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Gly Ala Asp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 2
<211> LENGTH: 1359
<212> TYPE: DNA
<213> ORGANISM: Artificial Sequence
<220> FEATURE:
<223> OTHER INFORMATION: heavy chain of FS22-172-003-AA/FS28-256-271
      mAb2 without LALA

<400> SEQUENCE: 2

gaagtgcaac tgctggagtc cggtggtggt ctggtacagc cgggtggttc tctgcgtctg      60

agttgcgcgg ccagtggctt taccttcact catacttata tgagctgggt gcgtcaggct     120

ccgggcaaag gtctggaatg ggttagcgcg atttctccga cttatagcac taccaactat     180

gcggatagcg tgaaaggccg ttttaccatt tctcgcgaca acaacaagaa cacgctgtac     240

ctgcagatga actcactgcg tgccgaagat acggccgtgt attactgtgc gagatacaac     300

gcgtatcatg ctgctctgga ctactggggc cagggaaccc tggtcaccgt ctcgagtgct     360

agcactaagg gcccgtcggt gttcccgctg gccccatcgt ccaagagcac atcagggggt     420

accgccgccc tgggctgcct tgtgaaggat tactttcccg agcccgtcac agtgtcctgg     480

aacagcggag ccctgacctc cggagtgcat actttcccgg ctgtgcttca gtcctctggc     540

ctgtactcat tgtcctccgt ggtcaccgtc ccttcgtcct ccctgggcac ccagacctat     600

atctgtaatg tcaaccataa gccctcgaac accaaggtcg acaagaaggt cgagccgaag     660

tcgtgcgaca agactcacac ttgcccgcct tgcccagccc cggaactgct gggtggtcct     720

tcggtgttcc tcttcccgcc caagccgaag gataccctga tgatctcacg gacccccgaa     780

gtgacctgtg tggtggtgga cgtgtcccac gaggacccgg aagtgaaatt caattggtac     840

gtggatggag tggaagtgca caacgccaag accaagccac gggaagaaca gtacaactct     900
```

```
acctaccgcg tggtgtccgt gctcactgtg ctgcaccaag actggctgaa cgggaaggag    960

tacaagtgca aagtgtccaa caaggcgctg cctgccccaa ttgagaaaac tatctcgaaa   1020

gccaagggac agcctcgaga accacaggtg tacaccctgc ccccatcccg ggatgagctg   1080

ccatacatca tcccaccata caaccaggtc agcctgacct gcctggtcaa aggcttctat   1140

cccagcgaca tcgccgtgga gtgggagagc aatgggcagc cggagaacaa ctacaagacc   1200

acgcctcccg tgctggactc cgacggctcc ttcttcctct acagcaagct caccgtgggc   1260

gcagataggt ggctggaagg gaacgtcttc tcatgctccg tgatgcatga ggcgctgcac   1320

aaccactaca ctcagaagag cttgtccctg tcgcccggt                          1359


<210> SEQ ID NO 3
<211> LENGTH: 453
<212> TYPE: PRT
<213> ORGANISM: Artificial Sequence
<220> FEATURE:
<223> OTHER INFORMATION: heavy chain of FS22-172-003-AA/FS28-256-271
      mAb2 with LALA

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Ala Ile Ser Pro Thr Tyr Ser Thr Thr Asn Tyr Ala Asp Ser Val
    50                  55                  60

Lys Gly Arg Phe Thr Ile Ser Arg Asp Asn Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

-continued

```
Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Pro Tyr Ile Ile Pro Pro Tyr Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Gly Ala Asp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 4
<211> LENGTH: 1359
<212> TYPE: DNA
<213> ORGANISM: Artificial Sequence
<220> FEATURE:
<223> OTHER INFORMATION: heavy chain of FS22-172-003-AA/FS28-256-271
      mAb2 with LALA

<400> SEQUENCE: 4

gaagtgcaac tgctggagtc cggtggtggt ctggtacagc cgggtggttc tctgcgtctg      60

agttgcgcgg ccagtggctt taccttcact catacttata tgagctgggt gcgtcaggct     120

ccgggcaaag gtctggaatg ggttagcgcg atttctccga cttatagcac taccaactat     180

gcggatagcg tgaaaggccg ttttaccatt tctcgcgaca acaacaagaa cacgctgtac     240

ctgcagatga actcactgcg tgccgaagat acggccgtgt attactgtgc gagatacaac     300

gcgtatcatg ctgctctgga ctactggggc cagggaaccc tggtcaccgt ctcgagtgct     360

agcactaagg gcccgtcggt gttcccgctg gccccatcgt ccaagagcac atcagggggt     420

accgccgccc tgggctgcct tgtgaaggat tactttcccg agcccgtcac agtgtcctgg     480

aacagcggag ccctgacctc cggagtgcat actttcccgg ctgtgcttca gtcctctggc     540

ctgtactcat tgtcctccgt ggtcaccgtc ccttcgtcct ccctgggcac ccagacctat     600

atctgtaatg tcaaccataa gccctcgaac accaaggtcg acaagaaggt cgagccgaag     660

tcgtgcgaca agactcacac ttgcccgcct tgcccagccc cggaagctgc cggtggtcct     720

tcggtgttcc tcttcccgcc caagccgaag gataccctga tgatctcacg gacccccgaa     780

gtgacctgtg tggtggtgga cgtgtcccac gaggacccgg aagtgaaatt caattggtac     840

gtggatggag tggaagtgca caacgccaag accaagccac gggaagaaca gtacaactct     900

acctaccgcg tggtgtccgt gctcactgtg ctgcaccaag actggctgaa cgggaaggag     960
```

-continued

```
tacaagtgca aagtgtccaa caaggcgctg cctgccccaa ttgagaaaac tatctcgaaa   1020

gccaagggac agcctcgaga accacaggtg tacaccctgc ccccatcccg ggatgagctg   1080

ccatacatca tcccaccata caaccaggtc agcctgacct gcctggtcaa aggcttctat   1140

cccagcgaca tcgccgtgga gtgggagagc aatgggcagc cggagaacaa ctacaagacc   1200

acgcctcccg tgctggactc cgacggctcc ttcttcctct acagcaagct caccgtgggc   1260

gcagataggt ggctggaagg gaacgtcttc tcatgctccg tgatgcatga ggcgctgcac   1320

aaccactaca ctcagaagag cttgtccctg tcgcccggt                          1359


<210> SEQ ID NO 5
<211> LENGTH: 17
<212> TYPE: PRT
<213> ORGANISM: Artificial Sequence
<220> FEATURE:
<223> OTHER INFORMATION: FS22-172-003-AA/FS28-256-271 mAb2 HCDR2 (Kabat)

<400> SEQUENCE: 5

Ala Ile Ser Pro Thr Tyr Ser Thr Thr Asn Tyr Ala Asp Ser Val Lys
1               5                   10                  15

Gly


<210> SEQ ID NO 6
<211> LENGTH: 453
<212> TYPE: PRT
<213> ORGANISM: Artificial Sequence
<220> FEATURE:
<223> OTHER INFORMATION: heavy chain of FS22-172-003-AA/FS28-256-272
      mAb2 without LALA

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser His Ile Ser Pro Thr Tyr Ser Thr Thr Asn Tyr Ala Asp Ser Val
    50                  55                  60

Lys Gly Arg Phe Thr Ile Ser Arg Asp Asn Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

-continued

```
Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Pro Tyr Ile Ile Pro Pro Tyr Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Gly Ala Asp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450
```

<210> SEQ ID NO 7
<211> LENGTH: 1359
<212> TYPE: DNA
<213> ORGANISM: Artificial Sequence
<220> FEATURE:
<223> OTHER INFORMATION: heavy chain of FS22-172-003-AA/FS28-256-272 mAb2 without LALA

<400> SEQUENCE: 7

```
gaagtgcaac tgctggagtc cggtggtggt ctggtacagc cgggtggttc tctgcgtctg      60

agttgcgcgg ccagtggctt taccttcact catacttata tgagctgggt gcgtcaggct     120

ccgggcaaag gtctggaatg ggttagccat atttctccga cttatagcac taccaactat     180

gcggatagcg tgaaaggccg ttttaccatt tctcgcgaca acaacaagaa cacgctgtac     240

ctgcagatga actcactgcg tgccgaagat acggccgtgt attactgtgc gagatacaac     300

gcgtatcatg ctgctctgga ctactggggc cagggaaccc tggtcaccgt ctcgagtgct     360

agcactaagg gcccgtcggt gttcccgctg gccccatcgt ccaagagcac atcagggggt     420

accgccgccc tgggctgcct tgtgaaggat tactttcccg agcccgtcac agtgtcctgg     480

aacagcggag ccctgacctc cggagtgcat actttcccgg ctgtgcttca gtcctctggc     540

ctgtactcat tgtcctccgt ggtcaccgtc ccttcgtcct ccctgggcac ccagacctat     600
```

atctgtaatg tcaaccataa gccctcgaac accaaggtcg acaagaaggt cgagccgaag 660
tcgtgcgaca agactcacac ttgcccgcct tgcccagccc cggaactgct gggtggtcct 720
tcggtgttcc tcttcccgcc caagccgaag gataccctga tgatctcacg gacccccgaa 780
gtgacctgtg tggtggtgga cgtgtcccac gaggacccgg aagtgaaatt caattggtac 840
gtggatggag tggaagtgca caacgccaag accaagccac gggaagaaca gtacaactct 900
acctaccgcg tggtgtccgt gctcactgtg ctgcaccaag actggctgaa cgggaaggag 960
tacaagtgca aagtgtccaa caaggcgctg cctgccccaa ttgagaaaac tatctcgaaa 1020
gccaagggac agcctcgaga accacaggtg tacaccctgc ccccatcccg ggatgagctg 1080
ccatacatca tcccaccata caaccaggtc agcctgacct gcctggtcaa aggcttctat 1140
cccagcgaca tcgccgtgga gtgggagagc aatgggcagc cggagaacaa ctacaagacc 1200
acgcctcccg tgctggactc cgacggctcc ttcttcctct acagcaagct caccgtgggc 1260
gcagataggt ggctggaagg gaacgtcttc tcatgctccg tgatgcatga ggcgctgcac 1320
aaccactaca ctcagaagag cttgtccctg tcgcccggt 1359

<210> SEQ ID NO 8
<211> LENGTH: 111
<212> TYPE: PRT
<213> ORGANISM: Artificial Sequence
<220> FEATURE:
<223> OTHER INFORMATION: CH3 domain and amino acid sequence of modified regions of CH3 AB and EF structural loops of all FS22-172-003 Fcab-containing mAb2 clones and the FS22-172-003 Fcab

<400> SEQUENCE: 8

Gly Gln Pro Arg Glu Pro Gln Val Tyr Thr Leu Pro Pro Ser Arg Asp
1               5                   10                  15

Glu Leu Pro Tyr Ile Ile Pro Pro Tyr Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Gly Ala Asp
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 9
<211> LENGTH: 333
<212> TYPE: DNA
<213> ORGANISM: Artificial Sequence
<220> FEATURE:
<223> OTHER INFORMATION: CH3 domain and amino acid sequence of modified regions of CH3 AB and EF structural loops of all FS22-172-003 Fcab-containing mAb2 clones and the FS22-172-003 Fcab

<400> SEQUENCE: 9
ggacagcctc gagaaccaca ggtgtacacc ctgcccccat cccgggatga gctgccatac 60
atcatcccac catacaacca ggtcagcctg acctgcctgg tcaaaggctt ctatcccagc 120
gacatcgccg tggagtggga gagcaatggg cagccggaga acaactacaa gaccacgcct 180
cccgtgctgg actccgacgg ctccttcttc ctctacagca agctcaccgt gggcgcagat 240
aggtggctgg aagggaacgt cttctcatgc tccgtgatgc atgaggcgct gcacaaccac 300
tacactcaga agagcttgtc cctgtcgccc ggt 333

<210> SEQ ID NO 10
<211> LENGTH: 7
<212> TYPE: PRT
<213> ORGANISM: Artificial Sequence
<220> FEATURE:
<223> OTHER INFORMATION: CH3 domain and amino acid sequence of modified regions of CH3 AB and EF structural loops of all FS22-172-003 Fcab-containing mAb2 clones and the FS22-172-003 Fcab Loop AB

<400> SEQUENCE: 10

Pro Tyr Ile Ile Pro Pro Tyr
1 5

<210> SEQ ID NO 11
<211> LENGTH: 7
<212> TYPE: PRT
<213> ORGANISM: Artificial Sequence
<220> FEATURE:
<223> OTHER INFORMATION: CH3 domain and amino acid sequence of modified regions of CH3 AB and EF structural loops of all FS22-172-003 Fcab-containing mAb2 clones and the FS22-172-003 Fcab Loop EF

<400> SEQUENCE: 11

Gly Ala Asp Arg Trp Leu Glu
1 5

<210> SEQ ID NO 12
<211> LENGTH: 116
<212> TYPE: PRT
<213> ORGANISM: Artificial Sequence
<220> FEATURE:
<223> OTHER INFORMATION: heavy chain of FS22-172-003-AA/FS28-024 mAb2

<400> SEQUENCE: 12

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Leu Ser Tyr Ser
20 25 30

Ser Met Ser Trp Val Arg Gln Ala Pro Gly Lys Gly Leu Glu Trp Val
35 40 45

Ser Phe Ile Thr Pro Ser Thr Gly Tyr Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Arg Ala Leu Thr Phe Asp Tyr Trp Gly Gln Gly Thr Leu Val
100 105 110

Thr Val Ser Ser
115

<210> SEQ ID NO 13
<211> LENGTH: 348
<212> TYPE: DNA
<213> ORGANISM: Artificial Sequence
<220> FEATURE:
<223> OTHER INFORMATION: heavy chain of FS22-172-003-AA/FS28-024 mAb2

<400> SEQUENCE: 13
gaagtgcaac tgctggagtc cggtggtggt ctggtacagc cgggtggttc tctgcgtctg 60
agttgcgcgg ccagtggctt taccctcagt tattcttcta tgtcatgggt gcgtcaggct 120
ccgggcaaag gtctggaatg ggttagcttt attactccgt ctactggcta tacccactat 180
gcggatagcg tgaaaggccg ttttaccatt tctcgcgaca acagcaagaa cacgctgtac 240
ctgcagatga actcactgcg tgccgaagat acggccgtgt attactgtgc gagacgggcg 300
ctgacgttcg actactgggg ccagggaacc ttggtcaccg tctcgagt 348

<210> SEQ ID NO 14
<211> LENGTH: 8
<212> TYPE: PRT
<213> ORGANISM: Artificial Sequence
<220> FEATURE:
<223> OTHER INFORMATION: heavy chain of FS22-172-003-AA/FS28-024 mAb2
HCDR1 (IMGT)

<400> SEQUENCE: 14

Gly Phe Thr Leu Ser Tyr Ser Ser
1 5

<210> SEQ ID NO 15
<211> LENGTH: 5
<212> TYPE: PRT
<213> ORGANISM: Artificial Sequence
<220> FEATURE:
<223> OTHER INFORMATION: heavy chain of FS22-172-003-AA/FS28-024 mAb2
HCDR1 (Kabat)

<400> SEQUENCE: 15

Tyr Ser Ser Met Ser
1 5

<210> SEQ ID NO 16
<211> LENGTH: 8
<212> TYPE: PRT
<213> ORGANISM: Artificial Sequence
<220> FEATURE:
<223> OTHER INFORMATION: heavy chain of FS22-172-003-AA/FS28-024 mAb2
HCDR2 (IMGT)

<400> SEQUENCE: 16

Ile Thr Pro Ser Thr Gly Tyr Thr
1 5

<210> SEQ ID NO 17
<211> LENGTH: 17
<212> TYPE: PRT
<213> ORGANISM: Artificial Sequence
<220> FEATURE:
<223> OTHER INFORMATION: heavy chain of FS22-172-003-AA/FS28-024 mAb2
HCDR2 (Kabat)

<400> SEQUENCE: 17

Phe Ile Thr Pro Ser Thr Gly Tyr Thr His Tyr Ala Asp Ser Val Lys
1 5 10 15

Gly

<210> SEQ ID NO 18
<211> LENGTH: 9
<212> TYPE: PRT
<213> ORGANISM: Artificial Sequence
<220> FEATURE:
<223> OTHER INFORMATION: heavy chain of FS22-172-003-AA/FS28-024 mAb2
HCDR3 (IMGT)

<400> SEQUENCE: 18

Ala Arg Arg Ala Leu Thr Phe Asp Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: heavy chain of FS22-172-003-AA/FS28-024 mAb2
      HCDR3 (Kabat)

<400> SEQUENCE: 19

Arg Ala Leu Thr Phe Asp Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: light chain of FS22-172-003-AA/FS28-024 mAb2
      LCDR1 (IMGT)

<400> SEQUENCE: 20

Gln Ser Val Ser Ser Ser Tyr
1               5

<210> SEQ ID NO 21
<211> LENGTH: 12
<212> TYPE: PRT
<213> ORGANISM: Artificial Sequence
<220> FEATURE:
<223> OTHER INFORMATION: light chain of FS22-172-003-AA/FS28-024 mAb2
      LCDR1 (Kabat)

<400> SEQUENCE: 21

Arg Ala Ser Gln Ser Val Ser Ser Ser Tyr Leu Ala
1               5                   10

<210> SEQ ID NO 22
<211> LENGTH: 3
<212> TYPE: PRT
<213> ORGANISM: Artificial Sequence
<220> FEATURE:
<223> OTHER INFORMATION: light chain of FS22-172-003-AA/FS28-024 mAb2
      LCDR2 (IMGT)

<400> SEQUENCE: 22

Gly Ala Ser
1

<210> SEQ ID NO 23
<211> LENGTH: 7
<212> TYPE: PRT
<213> ORGANISM: Artificial Sequence
<220> FEATURE:
<223> OTHER INFORMATION: light chain of FS22-172-003-AA/FS28-024 mAb2
      LCDR2 (Kabat)

<400> SEQUENCE: 23

Gly Ala Ser Ser Arg Ala Thr
1               5

<210> SEQ ID NO 24
<211> LENGTH: 9
<212> TYPE: PRT
<213> ORGANISM: Artificial Sequence

```
<220> FEATURE:
<223> OTHER INFORMATION: light chain of FS22-172-003-AA/FS28-024 mAb2
      LCDR3 (IMGT) and (Kabat)

<400> SEQUENCE: 24

Gln Gln Ala Ser Ser Tyr Pro Leu Thr
1               5


<210> SEQ ID NO 25
<211> LENGTH: 9
<212> TYPE: PRT
<213> ORGANISM: Artificial Sequence
<220> FEATURE:
<223> OTHER INFORMATION: heavy chain of FS22-172-003-AA/FS28-024-051
      mAb2 HCDR3 (IMGT)

<400> SEQUENCE: 25

Ala Arg Arg Ala Leu Ile Phe Asp Tyr
1               5


<210> SEQ ID NO 26
<211> LENGTH: 7
<212> TYPE: PRT
<213> ORGANISM: Artificial Sequence
<220> FEATURE:
<223> OTHER INFORMATION: heavy chain of FS22-172-003-AA/FS28-024-051
      mAb2 HCDR3 (Kabat)

<400> SEQUENCE: 26

Arg Ala Leu Ile Phe Asp Tyr
1               5


<210> SEQ ID NO 27
<211> LENGTH: 9
<212> TYPE: PRT
<213> ORGANISM: Artificial Sequence
<220> FEATURE:
<223> OTHER INFORMATION: heavy chain of FS22-172-003-AA/FS28-024-052
      mAb2 HCDR3 (IMGT)

<400> SEQUENCE: 27

Ala Arg Arg Ala Leu Leu Phe Asp Tyr
1               5


<210> SEQ ID NO 28
<211> LENGTH: 7
<212> TYPE: PRT
<213> ORGANISM: Artificial Sequence
<220> FEATURE:
<223> OTHER INFORMATION: heavy chain of FS22-172-003-AA/FS28-024-052
      mAb2 HCDR3 (Kabat)

<400> SEQUENCE: 28

Arg Ala Leu Leu Phe Asp Tyr
1               5


<210> SEQ ID NO 29
<211> LENGTH: 9
<212> TYPE: PRT
<213> ORGANISM: Artificial Sequence
<220> FEATURE:
<223> OTHER INFORMATION: heavy chain of FS22-172-003-AA/FS28-024-053
      mAb2 HCDR3 (IMGT)

<400> SEQUENCE: 29

Ala Arg Arg Ala Leu Val Phe Asp Tyr
1               5
```

<210> SEQ ID NO 30
<211> LENGTH: 7
<212> TYPE: PRT
<213> ORGANISM: Artificial Sequence
<220> FEATURE:
<223> OTHER INFORMATION: heavy chain of FS22-172-003-AA/FS28-024-053 mAb2 HCDR3 (Kabat)

<400> SEQUENCE: 30

Arg Ala Leu Val Phe Asp Tyr
1               5

<210> SEQ ID NO 31
<211> LENGTH: 8
<212> TYPE: PRT
<213> ORGANISM: Artificial Sequence
<220> FEATURE:
<223> OTHER INFORMATION: heavy chain of FS22-172-003-AA/FS28-256 mAb2 HCDR1 (IMGT)

<400> SEQUENCE: 31

Gly Phe Thr Phe Thr Asn Thr Tyr
1               5

<210> SEQ ID NO 32
<211> LENGTH: 5
<212> TYPE: PRT
<213> ORGANISM: Artificial Sequence
<220> FEATURE:
<223> OTHER INFORMATION: heavy chain of FS22-172-003-AA/FS28-256 mAb2 HCDR1 (Kabat)

<400> SEQUENCE: 32

Asn Thr Tyr Met Ser
1               5

<210> SEQ ID NO 33
<211> LENGTH: 8
<212> TYPE: PRT
<213> ORGANISM: Artificial Sequence
<220> FEATURE:
<223> OTHER INFORMATION: heavy chain of FS22-172-003-AA/FS28-256 mAb2 HCDR2 (IMGT)

<400> SEQUENCE: 33

Ile Ser Pro Thr Tyr Ser Thr Thr
1               5

<210> SEQ ID NO 34
<211> LENGTH: 17
<212> TYPE: PRT
<213> ORGANISM: Artificial Sequence
<220> FEATURE:
<223> OTHER INFORMATION: heavy chain of FS22-172-003-AA/FS28-256 mAb2 HCDR2 (Kabat)

<400> SEQUENCE: 34

Asn Ile Ser Pro Thr Tyr Ser Thr Thr Asn Tyr Ala Asp Ser Val Lys
1               5                   10                  15

Gly

<210> SEQ ID NO 35
<211> LENGTH: 12
<212> TYPE: PRT
<213> ORGANISM: Artificial Sequence
<220> FEATURE:
<223> OTHER INFORMATION: heavy chain of FS22-172-003-AA/FS28-256 mAb2

HCDR3 (IMGT)

<400> SEQUENCE: 35

Ala Arg Tyr Asn Ser Tyr Gln Gly Gly Leu Asp Tyr
1 5 10

<210> SEQ ID NO 36
<211> LENGTH: 10
<212> TYPE: PRT
<213> ORGANISM: Artificial Sequence
<220> FEATURE:
<223> OTHER INFORMATION: heavy chain of FS22-172-003-AA/FS28-256 mAb2
HCDR3 (Kabat)

<400> SEQUENCE: 36

Tyr Asn Ser Tyr Gln Gly Gly Leu Asp Tyr
1 5 10

<210> SEQ ID NO 37
<211> LENGTH: 9
<212> TYPE: PRT
<213> ORGANISM: Artificial Sequence
<220> FEATURE:
<223> OTHER INFORMATION: light chain of FS22-172-003-AA/FS28-256 mAb2
LCDR3 (IMGT) and (Kabat)

<400> SEQUENCE: 37

Gln Gln Ser Tyr Tyr Tyr Pro Ile Thr
1 5

<210> SEQ ID NO 38
<211> LENGTH: 8
<212> TYPE: PRT
<213> ORGANISM: Artificial Sequence
<220> FEATURE:
<223> OTHER INFORMATION: heavy chain of FS22-172-003-AA/FS28-256-001
mAb2 HCDR1 (IMGT)

<400> SEQUENCE: 38

Gly Phe Thr Phe Thr Glu Thr Tyr
1 5

<210> SEQ ID NO 39
<211> LENGTH: 5
<212> TYPE: PRT
<213> ORGANISM: Artificial Sequence
<220> FEATURE:
<223> OTHER INFORMATION: heavy chain of FS22-172-003-AA/FS28-256-001
mAb2 HCDR1 (Kabat)

<400> SEQUENCE: 39

Glu Thr Tyr Met Ser
1 5

<210> SEQ ID NO 40
<211> LENGTH: 9
<212> TYPE: PRT
<213> ORGANISM: Artificial Sequence
<220> FEATURE:
<223> OTHER INFORMATION: light chain of FS22-172-003-AA/FS28-256-001
mAb2 LCDR3 (IMGT) and (Kabat)

<400> SEQUENCE: 40

Gln Gln His Asn Gln Tyr Pro Asn Thr
1 5

<210> SEQ ID NO 41

<211> LENGTH: 9
<212> TYPE: PRT
<213> ORGANISM: Artificial Sequence
<220> FEATURE:
<223> OTHER INFORMATION: light chain of FS22-172-003-AA/FS28-256-005
mAb2 LCDR3 (IMGT) and (Kabat)

<400> SEQUENCE: 41

Gln Gln Ala Leu Gly Tyr Pro His Thr
1 5

<210> SEQ ID NO 42
<211> LENGTH: 8
<212> TYPE: PRT
<213> ORGANISM: Artificial Sequence
<220> FEATURE:
<223> OTHER INFORMATION: heavy chain of FS22-172-003-AA/FS28-256-012
mAb2 HCDR1 (IMGT)

<400> SEQUENCE: 42

Gly Phe Thr Phe Thr His Thr Tyr
1 5

<210> SEQ ID NO 43
<211> LENGTH: 5
<212> TYPE: PRT
<213> ORGANISM: Artificial Sequence
<220> FEATURE:
<223> OTHER INFORMATION: heavy chain of FS22-172-003-AA/FS28-256-012
mAb2 HCDR1 (Kabat)

<400> SEQUENCE: 43

His Thr Tyr Met Ser
1 5

<210> SEQ ID NO 44
<211> LENGTH: 12
<212> TYPE: PRT
<213> ORGANISM: Artificial Sequence
<220> FEATURE:
<223> OTHER INFORMATION: heavy chain of FS22-172-003-AA/FS28-256-012
mAb2 HCDR3 (IMGT)

<400> SEQUENCE: 44

Ala Arg Tyr Asn Ala Tyr His Ala Ala Leu Asp Tyr
1 5 10

<210> SEQ ID NO 45
<211> LENGTH: 10
<212> TYPE: PRT
<213> ORGANISM: Artificial Sequence
<220> FEATURE:
<223> OTHER INFORMATION: heavy chain of FS22-172-003-AA/FS28-256-012
mAb2 HCDR3 (Kabat)

<400> SEQUENCE: 45

Tyr Asn Ala Tyr His Ala Ala Leu Asp Tyr
1 5 10

<210> SEQ ID NO 46
<211> LENGTH: 8
<212> TYPE: PRT
<213> ORGANISM: Artificial Sequence
<220> FEATURE:
<223> OTHER INFORMATION: heavy chain of FS22-172-003-AA/FS28-256-014
mAb2 HCDR1 (IMGT)

<400> SEQUENCE: 46

Gly Phe Thr Phe Thr Asp Thr Tyr
1 5

<210> SEQ ID NO 47
<211> LENGTH: 5
<212> TYPE: PRT
<213> ORGANISM: Artificial Sequence
<220> FEATURE:
<223> OTHER INFORMATION: heavy chain of FS22-172-003-AA/FS28-256-014 mAb2 HCDR1 (Kabat)

<400> SEQUENCE: 47

Asp Thr Tyr Met Ser
1 5

<210> SEQ ID NO 48
<211> LENGTH: 12
<212> TYPE: PRT
<213> ORGANISM: Artificial Sequence
<220> FEATURE:
<223> OTHER INFORMATION: heavy chain of FS22-172-003-AA/FS28-256-014 mAb2 HCDR3 (IMGT)

<400> SEQUENCE: 48

Ala Arg Tyr Asn Ala Tyr Ala Ala Gly Leu Asp Tyr
1 5 10

<210> SEQ ID NO 49
<211> LENGTH: 10
<212> TYPE: PRT
<213> ORGANISM: Artificial Sequence
<220> FEATURE:
<223> OTHER INFORMATION: heavy chain of FS22-172-003-AA/FS28-256-014 mAb2 HCDR3 (Kabat)

<400> SEQUENCE: 49

Tyr Asn Ala Tyr Ala Ala Gly Leu Asp Tyr
1 5 10

<210> SEQ ID NO 50
<211> LENGTH: 8
<212> TYPE: PRT
<213> ORGANISM: Artificial Sequence
<220> FEATURE:
<223> OTHER INFORMATION: heavy chain of FS22-172-003-AA/FS28-256-018 mAb2 HCDR1 (IMGT)

<400> SEQUENCE: 50

Gly Phe Thr Phe Thr Gln Thr Tyr
1 5

<210> SEQ ID NO 51
<211> LENGTH: 5
<212> TYPE: PRT
<213> ORGANISM: Artificial Sequence
<220> FEATURE:
<223> OTHER INFORMATION: heavy chain of FS22-172-003-AA/FS28-256-018 mAb2 HCDR1 (Kabat)

<400> SEQUENCE: 51

Gln Thr Tyr Met Ser
1 5

<210> SEQ ID NO 52
<211> LENGTH: 12
<212> TYPE: PRT
<213> ORGANISM: Artificial Sequence
<220> FEATURE:

<223> OTHER INFORMATION: heavy chain of FS22-172-003-AA/FS28-256-018
mAb2 HCDR3 (IMGT)

<400> SEQUENCE: 52

Ala Arg Tyr Asn Ala Tyr Gln Ile Gly Leu Asp Tyr
1 5 10

<210> SEQ ID NO 53
<211> LENGTH: 10
<212> TYPE: PRT
<213> ORGANISM: Artificial Sequence
<220> FEATURE:
<223> OTHER INFORMATION: heavy chain of FS22-172-003-AA/FS28-256-018
mAb2 HCDR3 (Kabat)

<400> SEQUENCE: 53

Tyr Asn Ala Tyr Gln Ile Gly Leu Asp Tyr
1 5 10

<210> SEQ ID NO 54
<211> LENGTH: 108
<212> TYPE: PRT
<213> ORGANISM: Artificial Sequence
<220> FEATURE:
<223> OTHER INFORMATION: light chain of FS22-172-003-AA/FS28-024 mAb2 VL
domain

<400> SEQUENCE: 54

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Ala Ser Ser Tyr Pro
85 90 95

Leu Thr Phe Gly Gln Gly Thr Lys Val Glu Ile Lys
100 105

<210> SEQ ID NO 55
<211> LENGTH: 324
<212> TYPE: DNA
<213> ORGANISM: Artificial Sequence
<220> FEATURE:
<223> OTHER INFORMATION: light chain of FS22-172-003-AA/FS28-024 mAb2 VL
domain

<400> SEQUENCE: 55
gaaattgtgc tgacccagtc tccgggcacg ttatctctga gccctggtga gcgcgccact 60
ctgtcatgcc gggcttctca aagtgttagc agtagctacc tggcgtggta tcagcaaaaa 120
ccgggccagg ccccgcgtct gctgatttac ggtgcatcca gccgtgccac cggcattcca 180
gatcgttttt ccggtagtgg ttctgggacg gacttcactc tgacaatctc acgcctggaa 240
ccggaggatt ttgcggtgta ttactgccag caagcttctt cttatcctct cacgttcggc 300
caagggacca aggtggaaat caaa 324

<210> SEQ ID NO 56

<211> LENGTH: 116
<212> TYPE: PRT
<213> ORGANISM: Artificial Sequence
<220> FEATURE:
<223> OTHER INFORMATION: heavy chain of FS22-172-003-AA/FS28-024-051
mAb2 VH domain

<400> SEQUENCE: 56

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Ile Phe Asp Tyr Trp Gly Gln Gly Thr Leu Val
            100                 105                 110

Thr Val Ser Ser
        115
```

<210> SEQ ID NO 57
<211> LENGTH: 348
<212> TYPE: DNA
<213> ORGANISM: Artificial Sequence
<220> FEATURE:
<223> OTHER INFORMATION: heavy chain of FS22-172-003-AA/FS28-024-051
mAb2 VH domain

<400> SEQUENCE: 57

```
gaagtgcaac tgctggagtc cggtggtggt ctggtacagc cgggtggttc tctgcgtctg     60

agttgcgcgg ccagtggctt taccctcagt tattcttcta tgtcatgggt gcgtcaggct    120

ccgggcaaag gtctggaatg ggttagcttt attactccgt ctactggcta tacccactat    180

gcggatagcg tgaaaggccg ttttaccatt tctcgcgaca acagcaagaa cacgctgtac    240

ctgcagatga actcactgcg tgccgaagat acggccgtgt attactgtgc gagacgggcg    300

ctgattttcg actactgggg ccagggaacc ctggtcaccg tctcgagt                348
```

<210> SEQ ID NO 58
<211> LENGTH: 116
<212> TYPE: PRT
<213> ORGANISM: Artificial Sequence
<220> FEATURE:
<223> OTHER INFORMATION: heavy chain of FS22-172-003-AA/FS28-024-052
mAb2 VH domain

<400> SEQUENCE: 58

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Leu Phe Asp Tyr Trp Gly Gln Gly Thr Leu Val
            100                 105                 110

Thr Val Ser Ser
        115
```

<210> SEQ ID NO 59
<211> LENGTH: 348
<212> TYPE: DNA
<213> ORGANISM: Artificial Sequence
<220> FEATURE:
<223> OTHER INFORMATION: heavy chain of FS22-172-003-AA/FS28-024-052
      mAb2 VH domain

<400> SEQUENCE: 59

```
gaagtgcaac tgctggagtc cggtggtggt ctggtacagc cgggtggttc tctgcgtctg      60

agttgcgcgg ccagtggctt taccctcagt tattcttcta tgtcatgggt gcgtcaggct     120

ccgggcaaag gtctggaatg ggttagcttt attactccgt ctactggcta tacccactat     180

gcggatagcg tgaaaggccg ttttaccatt tctcgcgaca acagcaagaa cacgctgtac     240

ctgcagatga actcactgcg tgccgaagat acggccgtgt attactgtgc gagacgggcg     300

ctgcttttcg actactgggg ccagggaacc ctggtcaccg tctcgtcg                  348
```

<210> SEQ ID NO 60
<211> LENGTH: 116
<212> TYPE: PRT
<213> ORGANISM: Artificial Sequence
<220> FEATURE:
<223> OTHER INFORMATION: heavy chain of FS22-172-003-AA/FS28-024-053
      mAb2 VH domain

<400> SEQUENCE: 60

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Val Phe Asp Tyr Trp Gly Gln Gly Thr Leu Val
            100                 105                 110

Thr Val Ser Ser
        115
```

<210> SEQ ID NO 61
<211> LENGTH: 348
<212> TYPE: DNA
<213> ORGANISM: Artificial Sequence
<220> FEATURE:
<223> OTHER INFORMATION: heavy chain of FS22-172-003-AA/FS28-024-053
      mAb2 VH domain

<400> SEQUENCE: 61
gaagtgcaac tgctggagtc cggtggtggt ctggtacagc cgggtggttc tctgcgtctg 60
agttgcgcgg ccagtggctt taccctcagt tattcttcta tgtcatgggt gcgtcaggct 120
ccgggcaaag gtctggaatg ggttagcttt attactccgt ctactggcta tacccactat 180
gcggatagcg tgaaaggccg ttttaccatt tctcgcgaca acagcaagaa cacgctgtac 240
ctgcagatga actcactgcg tgccgaagat acggccgtgt attactgtgc gagacgggcg 300
ctggtgttcg actactgggg ccagggaacc ctggtcaccg tctcgtcg 348

<210> SEQ ID NO 62
<211> LENGTH: 119
<212> TYPE: PRT
<213> ORGANISM: Artificial Sequence
<220> FEATURE:
<223> OTHER INFORMATION: heavy chain of FS22-172-003-AA/FS28-256 mAb2 VH domain

<400> SEQUENCE: 62

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Thr Asn Thr
20 25 30

Tyr Met Ser Trp Val Arg Gln Ala Pro Gly Lys Gly Leu Glu Trp Val
35 40 45

Ser Asn Ile Ser Pro Thr Tyr Ser Thr Thr Asn Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Tyr Asn Ser Tyr Gln Gly Gly Leu Asp Tyr Trp Gly Gln Gly
100 105 110

Thr Leu Val Thr Val Ser Ser
115

<210> SEQ ID NO 63
<211> LENGTH: 357
<212> TYPE: DNA
<213> ORGANISM: Artificial Sequence
<220> FEATURE:
<223> OTHER INFORMATION: heavy chain of FS22-172-003-AA/FS28-256 mAb2 VH domain

<400> SEQUENCE: 63
gaagtgcaac tgctggagtc cggtggtggt ctggtacagc cgggtggttc tctgcgtctg 60
agttgcgcgg ccagtggctt taccttcact aacacttata tgagctgggt gcgtcaggct 120
ccgggcaaag gtctggaatg ggttagcaat atttctccga cttatagcac taccaactat 180
gcggatagcg tgaaaggccg ttttaccatt tctcgcgaca acagcaagaa cacgctgtac 240
ctgcagatga actcactgcg tgccgaagat acggccgtgt attactgtgc gagatacaac 300
tcttaccagg gtggcttgga ctactggggc cagggaacct tggtcaccgt ctcgagt 357

<210> SEQ ID NO 64
<211> LENGTH: 108
<212> TYPE: PRT
<213> ORGANISM: Artificial Sequence
<220> FEATURE:
<223> OTHER INFORMATION: light chain of FS22-172-003-AA/FS28-256 mAb2 VL domain

<400> SEQUENCE: 64

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Ser Tyr Tyr Tyr Pro
85 90 95

Ile Thr Phe Gly Gln Gly Thr Lys Val Glu Ile Lys
100 105

<210> SEQ ID NO 65
<211> LENGTH: 324
<212> TYPE: DNA
<213> ORGANISM: Artificial Sequence
<220> FEATURE:
<223> OTHER INFORMATION: light chain of FS22-172-003-AA/FS28-256 mAb2 VL domain

<400> SEQUENCE: 65
gaaattgtgc tgacccagtc tccgggcacg ttatctctga gccctggtga gcgcgccact 60
ctgtcatgcc gggcttctca aagtgttagc agtagctacc tggcgtggta tcagcaaaaa 120
ccgggccagg ccccgcgtct gctgatttac ggtgcatcca gccgtgccac cggcattcca 180
gatcgttttt ccggtagtgg ttctgggacg gacttcactc tgacaatctc acgcctggaa 240
ccggaggatt ttgcggtgta ttactgccag caatcttatt attatcctat cacgttcggc 300
caagggacca aggtggaaat caaa 324

<210> SEQ ID NO 66
<211> LENGTH: 119
<212> TYPE: PRT
<213> ORGANISM: Artificial Sequence
<220> FEATURE:
<223> OTHER INFORMATION: heavy chain of FS22-172-003-AA/FS28-256-001 mAb2 VH domain

<400> SEQUENCE: 66

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Thr Glu Thr
20 25 30

Tyr Met Ser Trp Val Arg Gln Ala Pro Gly Lys Gly Leu Glu Trp Val
35 40 45

Ser Asn Ile Ser Pro Thr Tyr Ser Thr Thr Asn Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Tyr Asn Ser Tyr Gln Gly Gly Leu Asp Tyr Trp Gly Gln Gly
100 105 110

Thr Leu Val Thr Val Ser Ser
115

<210> SEQ ID NO 67
<211> LENGTH: 357
<212> TYPE: DNA
<213> ORGANISM: Artificial Sequence
<220> FEATURE:
<223> OTHER INFORMATION: heavy chain of FS22-172-003-AA/FS28-256-001
mAb2 VH domain

<400> SEQUENCE: 67
gaagtgcaac tgctggagtc cggtggtggt ctggtacagc cgggtggttc tctgcgtctg 60
agttgcgcgg ccagtggctt taccttcact gagacttata tgagctgggt gcgtcaggct 120
ccgggcaaag gtctggaatg ggttagcaat atttctccga cttatagcac taccaactat 180
gcggatagcg tgaaaggccg ttttaccatt tctcgcgaca acagcaagaa cacgctgtac 240
ctgcagatga actcactgcg tgccgaagat acggccgtgt attactgtgc gagatacaac 300
tcttaccagg gtggcttgga ctactggggc cagggaacct tggtcaccgt ctcgagt 357

<210> SEQ ID NO 68
<211> LENGTH: 108
<212> TYPE: PRT
<213> ORGANISM: Artificial Sequence
<220> FEATURE:
<223> OTHER INFORMATION: light chain of FS22-172-003-AA/FS28-256-001
mAb2 VL domain

<400> SEQUENCE: 68

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln His Asn Gln Tyr Pro
85 90 95

Asn Thr Phe Gly Gln Gly Thr Lys Val Glu Ile Lys
100 105

<210> SEQ ID NO 69
<211> LENGTH: 324
<212> TYPE: DNA
<213> ORGANISM: Artificial Sequence
<220> FEATURE:
<223> OTHER INFORMATION: light chain of FS22-172-003-AA/FS28-256-001
mAb2 VL domain

<400> SEQUENCE: 69
gaaattgtgc tgacccagtc tccgggcacg ttatctctga gccctggtga gcgcgccact 60
ctgtcatgcc gggcttctca aagtgttagc agtagctacc tggcgtggta tcagcaaaaa 120
ccgggccagg ccccgcgtct gctgatttac ggtgcatcca gccgtgccac cggcattcca 180
gatcgttttt ccggtagtgg ttctgggacg gacttcactc tgacaatctc acgcctggaa 240
ccggaggatt ttgcggtgta ttactgccag caacataatc agtatccgaa tacgttcggc 300

```
caagggacca aggtggaaat caaa                                          324


<210> SEQ ID NO 70
<211> LENGTH: 119
<212> TYPE: PRT
<213> ORGANISM: Artificial Sequence
<220> FEATURE:
<223> OTHER INFORMATION: heavy chain of FS22-172-003-AA/FS28-256-012
      mAb2 VH domain

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser
        115


<210> SEQ ID NO 71
<211> LENGTH: 357
<212> TYPE: DNA
<213> ORGANISM: Artificial Sequence
<220> FEATURE:
<223> OTHER INFORMATION: heavy chain of FS22-172-003-AA/FS28-256-012
      mAb2 VH domain

<400> SEQUENCE: 71

gaagtgcaac tgctggagtc cggtggtggt ctggtacagc cgggtggttc tctgcgtctg      60

agttgcgcgg ccagtggctt taccttcact catacttata tgagctgggt gcgtcaggct     120

ccgggcaaag gtctggaatg ggttagcaat atttctccga cttatagcac taccaactat     180

gcggatagcg tgaaaggccg ttttaccatt tctcgcgaca acaacaagaa cacgctgtac     240

ctgcagatga actcactgcg tgccgaagat acggccgtgt attactgtgc gagatacaac     300

gcgtatcatg ctgctctgga ctactggggc cagggaaccc tggtcaccgt ctcgagt        357


<210> SEQ ID NO 72
<211> LENGTH: 119
<212> TYPE: PRT
<213> ORGANISM: Artificial Sequence
<220> FEATURE:
<223> OTHER INFORMATION: heavy chain of FS22-172-003-AA/FS28-256-014
      mAb2 VH domain

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Thr
            20                  25                  30

Tyr Met Ser Trp Val Arg Gln Ala Pro Gly Lys Gly Leu Glu Trp Val
```

```
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Ala Ala Gly Leu Asp Tyr Trp Gly Gln Gly
            100                 105                 110

Thr Leu Val Thr Val Ser Ser
        115


<210> SEQ ID NO 73
<211> LENGTH: 357
<212> TYPE: DNA
<213> ORGANISM: Artificial Sequence
<220> FEATURE:
<223> OTHER INFORMATION: heavy chain of FS22-172-003-AA/FS28-256-014
      mAb2 VH domain

<400> SEQUENCE: 73

gaagtgcaac tgctggagtc cggtggtggt ctggtacagc cgggtggttc tctgcgtctg      60

agttgcgcgg ccagtggctt taccttcact gatacttata tgagctgggt gcgtcaggct     120

ccgggcaaag gtctggaatg ggttagcaat atttctccga cttatagcac taccaactat     180

gcggatagcg tgaaaggccg ttttaccatt tctcgcgaca acagcaagaa cacgctgtac     240

ctgcagatga actcactgcg tgccgaagat acggccgtgt attactgtgc gagatacaac     300

gcgtatgcgg cgggtcttga ctactggggc cagggaaccc tggtcaccgt ctcgagt        357


<210> SEQ ID NO 74
<211> LENGTH: 119
<212> TYPE: PRT
<213> ORGANISM: Artificial Sequence
<220> FEATURE:
<223> OTHER INFORMATION: heavy chain of FS22-172-003-AA/FS28-256-018
      mAb2 VH domain

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gln Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Gln Ile Gly Leu Asp Tyr Trp Gly Gln Gly
            100                 105                 110

Thr Leu Val Thr Val Ser Ser
        115


<210> SEQ ID NO 75
<211> LENGTH: 357
<212> TYPE: DNA
```

<213> ORGANISM: Artificial Sequence
<220> FEATURE:
<223> OTHER INFORMATION: heavy chain of FS22-172-003-AA/FS28-256-018
      mAb2 VH domain

<400> SEQUENCE: 75

```
gaagtgcaac tgctggagtc cggtggtggt ctggtacagc cgggtggttc tctgcgtctg      60

agttgcgcgg ccagtggctt taccttcact cagacttata tgagctgggt gcgtcaggct     120

ccgggcaaag gtctggaatg ggttagcaat atttctccga cttatagcac taccaactat     180

gcggatagcg tgaaaggccg ttttaccatt tctcgcgaca acagcaagaa cacgctgtac     240

ctgcagatga actcactgcg tgccgaagat acggccgtgt attactgtgc gagatacaac     300

gcttatcaga ttgggttgga ctactggggc cagggaaccc tggtcaccgt ctcgagt       357
```

<210> SEQ ID NO 76
<211> LENGTH: 108
<212> TYPE: PRT
<213> ORGANISM: Artificial Sequence
<220> FEATURE:
<223> OTHER INFORMATION: light chain of FS22-172-003-AA/FS28-256-027
      mAb2 VL domain

<400> SEQUENCE: 76

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Val Pro Tyr Pro
                85                  90                  95

Tyr Thr Phe Gly Gln Gly Thr Lys Val Glu Ile Lys
            100                 105
```

<210> SEQ ID NO 77
<211> LENGTH: 324
<212> TYPE: DNA
<213> ORGANISM: Artificial Sequence
<220> FEATURE:
<223> OTHER INFORMATION: light chain of FS22-172-003-AA/FS28-256-027
      mAb2 VL domain

<400> SEQUENCE: 77

```
gaaattgtgc tgacccagtc tccgggcacg ttatctctga gccctggtga gcgcgccact      60

ctgtcatgcc gggcttctca aagtgttagc agtagctacc tggcgtggta tcagcaaaaa     120

ccgggccagg ccccgcgtct gctgatttac ggtgcatcca gccgtgccac cggcattcca     180

gatcgttttt ccggtagtgg ttctgggacg gacttcactc tgacaatctc acgcctggaa     240

ccggaggatt ttgcggtgta ttactgccag caaactgtgc cgtatccgta tacgttcggc     300

caagggacca aggtggaaat caaa                                            324
```

<210> SEQ ID NO 78
<211> LENGTH: 108
<212> TYPE: PRT
<213> ORGANISM: Artificial Sequence
<220> FEATURE:
<223> OTHER INFORMATION: light chain of FS22-172-003-AA/FS28-256-005 mAb2 VL domain

<400> SEQUENCE: 78

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Leu Gly Tyr Pro
                85                  90                  95

His Thr Phe Gly Gln Gly Thr Lys Val Glu Ile Lys
            100                 105
```

<210> SEQ ID NO 79
<211> LENGTH: 324
<212> TYPE: DNA
<213> ORGANISM: Artificial Sequence
<220> FEATURE:
<223> OTHER INFORMATION: light chain of FS22-172-003-AA/FS28-256-005 mAb2 VL domain

<400> SEQUENCE: 79

```
gaaattgtgc tgacccagtc tccgggcacg ttatctctga gccctggtga gcgcgccact     60

ctgtcatgcc gggcttctca aagtgttagc agtagctacc tggcgtggta tcagcaaaaa    120

ccgggccagg ccccgcgtct gctgatttac ggtgcatcca gccgtgccac cggcattcca    180

gatcgttttt ccggtagtgg ttctgggacg gacttcactc tgacaatctc acgcctggaa    240

ccggaggatt ttgcggtgta ttactgccag caagctttgg gttatcctca tacgttcggc    300

caagggacca aggtggaaat caaa                                           324
```

<210> SEQ ID NO 80
<211> LENGTH: 9
<212> TYPE: PRT
<213> ORGANISM: Artificial Sequence
<220> FEATURE:
<223> OTHER INFORMATION: light chain of FS22-172-003-AA/FS28-256-027 mAb2 LCDR3 (IMGT) and (Kabat)

<400> SEQUENCE: 80

```
Gln Gln Thr Val Pro Tyr Pro Tyr Thr
1               5
```

<210> SEQ ID NO 81
<211> LENGTH: 106
<212> TYPE: PRT
<213> ORGANISM: Artificial Sequence
<220> FEATURE:
<223> OTHER INFORMATION: WT Fcab CH3 domain

<400> SEQUENCE: 81

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30
```

-continued

Tyr Pro Ser Asp Ile Ala Val Glu Trp Glu Ser Asn Gly Gln Pro Glu
35 40 45

Asn Asn Tyr Lys Thr Thr Pro Pro Val Leu Asp Ser Asp Gly Ser Phe
50 55 60

Phe Leu Tyr Ser Lys Leu Thr Val Asp Lys Ser Arg Trp Gln Gln Gly
65 70 75 80

Asn Val Phe Ser Cys Ser Val Met His Glu Ala Leu His Asn His Tyr
85 90 95

Thr Gln Lys Ser Leu Ser Leu Ser Pro Gly
100 105

<210> SEQ ID NO 82
<211> LENGTH: 215
<212> TYPE: PRT
<213> ORGANISM: Artificial Sequence
<220> FEATURE:
<223> OTHER INFORMATION: light chain of FS22-172-003-AA/FS28-256-001 mAb2

<400> SEQUENCE: 82

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln His Asn Gln Tyr Pro
85 90 95

Asn Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 83
<211> LENGTH: 215
<212> TYPE: PRT
<213> ORGANISM: Artificial Sequence
<220> FEATURE:
<223> OTHER INFORMATION: light chain of FS22-172-003-AA/FS28-256-005 mAb2

<400> SEQUENCE: 83

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Leu Gly Tyr Pro
                85                  90                  95

His Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 84
<211> LENGTH: 215
<212> TYPE: PRT
<213> ORGANISM: Artificial Sequence
<220> FEATURE:
<223> OTHER INFORMATION: light chain of FS22-172-003-AA/FS28-256-027 mAb2

<400> SEQUENCE: 84

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Val Pro Tyr Pro
                85                  90                  95

Tyr Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
```

```
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 85
<211> LENGTH: 215
<212> TYPE: PRT
<213> ORGANISM: Artificial Sequence
<220> FEATURE:
<223> OTHER INFORMATION: light chain of FS22-172-003-AA/FS28-024 mAb2

<400> SEQUENCE: 85

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ser Ser Tyr Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 86
<211> LENGTH: 645
<212> TYPE: DNA
<213> ORGANISM: Artificial Sequence
<220> FEATURE:
<223> OTHER INFORMATION: light chain of FS22-172-003-AA/FS28-024 mAb2

<400> SEQUENCE: 86
```

-continued

```
gaaattgtgc tgacccagtc tccgggcacg ttatctctga gccctggtga gcgcgccact      60

ctgtcatgcc gggcttctca aagtgttagc agtagctacc tggcgtggta tcagcaaaaa     120

ccgggccagg ccccgcgtct gctgatttac ggtgcatcca gccgtgccac cggcattcca     180

gatcgttttt ccggtagtgg ttctgggacg gacttcactc tgacaatctc acgcctggaa     240

ccggaggatt ttgcggtgta ttactgccag caagcttctt cttatcctct cacgttcggc     300

caagggacca aggtggaaat caaacgtact gtggccgctc ctagcgtgtt catttttccg     360

ccatccgacg agcagctcaa gtccggcacc gcctccgtgg tctgcctgct caacaacttc     420

taccctcgcg aagctaaggt ccagtggaag gtcgacaatg ccctgcagtc cggaaactcg     480

caggaaagcg tgactgaaca ggactccaag gactccacct attcactgtc ctcgactctg     540

accctgagca aggcggatta cgaaaagcac aaagtgtacg catgcgaagt gacccaccag     600

ggtctttcgt cccccgtgac caagagcttc aacagaggag agtgt                     645


<210> SEQ ID NO 87
<211> LENGTH: 215
<212> TYPE: PRT
<213> ORGANISM: Artificial Sequence
<220> FEATURE:
<223> OTHER INFORMATION: light chain of FS22-172-003-AA/FS28-026 mAb2

<400> SEQUENCE: 87

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Tyr Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 88
<211> LENGTH: 215
<212> TYPE: PRT
<213> ORGANISM: Artificial Sequence
```

<220> FEATURE:
<223> OTHER INFORMATION: light chain of FS22-172-003-AA/FS28-091 mAb2

<400> SEQUENCE: 88

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 89
<211> LENGTH: 216
<212> TYPE: PRT
<213> ORGANISM: Artificial Sequence
<220> FEATURE:
<223> OTHER INFORMATION: light chain of FS22-172-003-AA/FS28-185 mAb2

<400> SEQUENCE: 89

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Tyr Ser Ala
                85                  90                  95

Pro Val Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
```

```
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 90
<211> LENGTH: 645
<212> TYPE: DNA
<213> ORGANISM: Artificial Sequence
<220> FEATURE:
<223> OTHER INFORMATION: light chain of FS22-172-003-AA/FS28-256-005
      mAb2

<400> SEQUENCE: 90

gaaattgtgc tgacccagtc tccgggcacg ttatctctga gccctggtga gcgcgccact     60

ctgtcatgcc gggcttctca aagtgttagc agtagctacc tggcgtggta tcagcaaaaa    120

ccgggccagg ccccgcgtct gctgatttac ggtgcatcca gccgtgccac cggcattcca    180

gatcgttttt ccggtagtgg ttctgggacg gacttcactc tgacaatctc acgcctggaa    240

ccggaggatt ttgcggtgta ttactgccag caagctttgg gttatcctca tacgttcggc    300

caagggacca aggtggaaat caaacgtact gtagcagctc cttccgtgtt catctttccg    360

cccagtgatg agcagctgaa gtcaggtact gcttccgtgg tttgcctgct caacaacttt    420

taccccagag aagccaaagt ccagtggaaa gtggacaatg cgttgcaaag cgggaactct    480

caggaatccg tcacagagca ggactctaag gactccacct atagcctctc tagtacgctg    540

acactgagca aagccgatta cgagaagcac aaggtgtatg cctgtgaggt tacccatcaa    600

ggccttagct caccagtgac caagagcttc aataggggag aatgc                    645


<210> SEQ ID NO 91
<211> LENGTH: 645
<212> TYPE: DNA
<213> ORGANISM: Artificial Sequence
<220> FEATURE:
<223> OTHER INFORMATION: light chain of FS22-172-003-AA/FS28-256-027
      mAb2

<400> SEQUENCE: 91

gaaattgtgc tgacccagtc tccgggcacg ttatctctga gccctggtga gcgcgccact     60

ctgtcatgcc gggcttctca aagtgttagc agtagctacc tggcgtggta tcagcaaaaa    120

ccgggccagg ccccgcgtct gctgatttac ggtgcatcca gccgtgccac cggcattcca    180

gatcgttttt ccggtagtgg ttctgggacg gacttcactc tgacaatctc acgcctggaa    240

ccggaggatt ttgcggtgta ttactgccag caaactgtgc cgtatccgta tacgttcggc    300

caagggacca aggtggaaat caaacgtact gtggccgctc ctagcgtgtt catttttccg    360

ccatccgacg agcagctcaa gtccggcacc gcctccgtgg tctgcctgct caacaacttc    420

taccctcgcg aagctaaggt ccagtggaag gtcgacaatg ccctgcagtc cggaaactcg    480
```

caggaaagcg tgactgaaca ggactccaag gactccacct attcactgtc ctcgactctg 540
accctgagca aggcggatta cgaaaagcac aaagtgtacg catgcgaagt gacccaccag 600
ggtctttcgt cccccgtgac caagagcttc aacagaggag agtgt 645

<210> SEQ ID NO 92
<211> LENGTH: 450
<212> TYPE: PRT
<213> ORGANISM: Artificial Sequence
<220> FEATURE:
<223> OTHER INFORMATION: heavy chain of FS22-172-003-AA/FS28-024 mAb2 without LALA

<400> SEQUENCE: 92

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Leu Ser Tyr Ser
20 25 30

Ser Met Ser Trp Val Arg Gln Ala Pro Gly Lys Gly Leu Glu Trp Val
35 40 45

Ser Phe Ile Thr Pro Ser Thr Gly Tyr Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Arg Ala Leu Thr Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser

-continued

```
                325                 330                 335

Lys Ala Lys Gly Gln Pro Arg Glu Pro Gln Val Tyr Thr Leu Pro Pro
            340                 345                 350

Ser Arg Asp Glu Leu Pro Tyr Ile Ile Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 93
<211> LENGTH: 1350
<212> TYPE: DNA
<213> ORGANISM: Artificial Sequence
<220> FEATURE:
<223> OTHER INFORMATION: heavy chain of FS22-172-003-AA/FS28-024 mAb2 without LALA

<400> SEQUENCE: 93

```
gaagtgcaac tgctggagtc cggtggtggt ctggtacagc cgggtggttc tctgcgtctg     60

agttgcgcgg ccagtggctt taccctcagt tattcttcta tgtcatgggt gcgtcaggct    120

ccgggcaaag gtctggaatg ggttagcttt attactccgt ctactggcta tacccactat    180

gcggatagcg tgaaaggccg ttttaccatt tctcgcgaca acagcaagaa cacgctgtac    240

ctgcagatga actcactgcg tgccgaagat acggccgtgt attactgtgc gagacgggcg    300

ctgacgttcg actactgggg ccagggaacc ttggtcaccg tctcgagtgc tagcactaag    360

ggcccgtcgg tgttcccgct ggccccatcg tccaagagca catcaggggg taccgccgcc    420

ctgggctgcc ttgtgaagga ttactttccc gagcccgtca cagtgtcctg gaacagcgga    480

gccctgacct ccggagtgca tactttcccg gctgtgcttc agtcctctgg cctgtactca    540

ttgtcctccg tggtcaccgt cccttcgtcc tccctgggca cccagaccta tatctgtaat    600

gtcaaccata agccctcgaa caccaaggtc gacaagaagg tcgagccgaa gtcgtgcgac    660

aagactcaca cttgcccgcc ttgcccagcc ccggaactgc tgggtggtcc ttcggtgttc    720

ctcttcccgc ccaagccgaa ggataccctg atgatctcac ggacccccga agtgacctgt    780

gtggtggtgg acgtgtccca cgaggacccg gaagtgaaat tcaattggta cgtggatgga    840

gtggaagtgc acaacgccaa gaccaagcca cgggaagaac agtacaactc tacctaccgc    900

gtggtgtccg tgctcactgt gctgcaccaa gactggctga acgggaagga gtacaagtgc    960

aaagtgtcca acaaggcgct gcctgcccca attgagaaaa ctatctcgaa agccaaggga   1020

cagcctcgag aaccacaggt gtacaccctg cccccatccc gggatgagct gccatacatc   1080

atcccaccat acaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtggg cgcagatagg   1260
```

```
tggctggaag ggaacgtctt ctcatgctcc gtgatgcatg aggcgctgca caaccactac   1320

actcagaaga gcttgtccct gtcgcccggt                                    1350


<210> SEQ ID NO 94
<211> LENGTH: 450
<212> TYPE: PRT
<213> ORGANISM: Artificial Sequence
<220> FEATURE:
<223> OTHER INFORMATION: heavy chain of FS22-172-003-AA/FS28-024 mAb2
      with LALA

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Thr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
```

```
            340                 345                 350

Ser Arg Asp Glu Leu Pro Tyr Ile Ile Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 95
<211> LENGTH: 1350
<212> TYPE: DNA
<213> ORGANISM: Artificial Sequence
<220> FEATURE:
<223> OTHER INFORMATION: heavy chain of FS22-172-003-AA/FS28-024 mAb2
      with LALA

<400> SEQUENCE: 95

gaagtgcaac tgctggagtc cggtggtggt ctggtacagc cgggtggttc tctgcgtctg     60

agttgcgcgg ccagtggctt taccctcagt tattcttcta tgtcatgggt gcgtcaggct    120

ccgggcaaag gtctggaatg ggttagcttt attactccgt ctactggcta tacccactat    180

gcggatagcg tgaaaggccg ttttaccatt tctcgcgaca acagcaagaa cacgctgtac    240

ctgcagatga actcactgcg tgccgaagat acggccgtgt attactgtgc gagacgggcg    300

ctgacgttcg actactgggg ccagggaacc ttggtcaccg tctcgagtgc tagcactaag    360

ggcccgtcgg tgttcccgct ggccccatcg tccaagagca catcaggggg taccgccgcc    420

ctgggctgcc ttgtgaagga ttactttccc gagcccgtca cagtgtcctg gaacagcgga    480

gccctgacct ccggagtgca tactttcccg gctgtgcttc agtcctctgg cctgtactca    540

ttgtcctccg tggtcaccgt cccttcgtcc tccctgggca cccagaccta tatctgtaat    600

gtcaaccata agccctcgaa caccaaggtc gacaagaagg tcgagccgaa gtcgtgcgac    660

aagactcaca cttgcccgcc ttgcccagcc ccggaagctg ccggtggtcc ttcggtgttc    720

ctcttcccgc ccaagccgaa ggataccctg atgatctcac ggacccccga agtgacctgt    780

gtggtggtgg acgtgtccca cgaggacccg gaagtgaaat tcaattggta cgtggatgga    840

gtggaagtgc acaacgccaa gaccaagcca cgggaagaac agtacaactc tacctaccgc    900

gtggtgtccg tgctcactgt gctgcaccaa gactggctga acgggaagga gtacaagtgc    960

aaagtgtcca acaaggcgct gcctgcccca attgagaaaa ctatctcgaa agccaaggga   1020

cagcctcgag aaccacaggt gtacaccctg cccccatccc gggatgagct gccatacatc   1080

atcccaccat acaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtggg cgcagatagg   1260

tggctggaag ggaacgtctt ctcatgctcc gtgatgcatg aggcgctgca caaccactac   1320

actcagaaga gcttgtccct gtcgcccggt                                    1350
```

<210> SEQ ID NO 96
<211> LENGTH: 450
<212> TYPE: PRT
<213> ORGANISM: Artificial Sequence
<220> FEATURE:
<223> OTHER INFORMATION: heavy chain of FS22-172-003-AA/FS28-024-051
mAb2 without LALA

<400> SEQUENCE: 96

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Leu Ser Tyr Ser
20 25 30

Ser Met Ser Trp Val Arg Gln Ala Pro Gly Lys Gly Leu Glu Trp Val
35 40 45

Ser Phe Ile Thr Pro Ser Thr Gly Tyr Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Arg Ala Leu Ile Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Asp Glu Leu Pro Tyr Ile Ile Pro Pro Tyr Asn Gln Val Ser 355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 97
<211> LENGTH: 1350
<212> TYPE: DNA
<213> ORGANISM: Artificial Sequence
<220> FEATURE:
<223> OTHER INFORMATION: heavy chain of FS22-172-003-AA/FS28-024-051
      mAb2 without LALA

<400> SEQUENCE: 97
gaagtgcaac tgctggagtc cggtggtggt ctggtacagc cgggtggttc tctgcgtctg 60
agttgcgcgg ccagtggctt taccctcagt tattcttcta tgtcatgggt gcgtcaggct 120
ccgggcaaag gtctggaatg ggttagcttt attactccgt ctactggcta tacccactat 180
gcggatagcg tgaaaggccg ttttaccatt tctcgcgaca acagcaagaa cacgctgtac 240
ctgcagatga actcactgcg tgccgaagat acggccgtgt attactgtgc gagacgggcg 300
ctgattttcg actactgggg ccagggaacc ctggtcaccg tctcgagtgc tagcactaag 360
ggcccgtcgg tgttcccgct ggccccatcg tccaagagca catcaggggg taccgccgcc 420
ctgggctgcc ttgtgaagga ttactttccc gagcccgtca cagtgtcctg gaacagcgga 480
gccctgacct ccggagtgca tactttcccg gctgtgcttc agtcctctgg cctgtactca 540
ttgtcctccg tggtcaccgt cccttcgtcc tccctgggca cccagaccta tatctgtaat 600
gtcaaccata agccctcgaa caccaaggtc gacaagaagg tcgagccgaa gtcgtgcgac 660
aagactcaca cttgcccgcc ttgcccagcc ccggaactgc tgggtggtcc ttcggtgttc 720
ctcttcccgc ccaagccgaa ggataccctg atgatctcac ggacccccga agtgacctgt 780
gtggtggtgg acgtgtccca cgaggacccg gaagtgaaat tcaattggta cgtggatgga 840
gtggaagtgc acaacgccaa gaccaagcca cgggaagaac agtacaactc tacctaccgc 900
gtggtgtccg tgctcactgt gctgcaccaa gactggctga acgggaagga gtacaagtgc 960
aaagtgtcca acaaggcgct gcctgcccca attgagaaaa ctatctcgaa agccaaggga 1020
cagcctcgag aaccacaggt gtacaccctg cccccatccc gggatgagct gccatacatc 1080
atcccaccat acaaccaggt cagcctgacc tgcctggtca aaggcttcta tcccagcgac 1140
atcgccgtgg agtgggagag caatgggcag ccggagaaca actacaagac cacgcctccc 1200
gtgctggact ccgacggctc cttcttcctc tacagcaagc tcaccgtggg cgcagatagg 1260
tggctggaag ggaacgtctt ctcatgctcc gtgatgcatg aggcgctgca caaccactac 1320
actcagaaga gcttgtccct gtcgcccggt 1350

<210> SEQ ID NO 98

```
<211> LENGTH: 450
<212> TYPE: PRT
<213> ORGANISM: Artificial Sequence
<220> FEATURE:
<223> OTHER INFORMATION: heavy chain of FS22-172-003-AA/FS28-024-051
      mAb2 with LALA

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Pro Tyr Ile Ile Pro Pro Tyr Asn Gln Val Ser
        355                 360                 365

Leu Thr Cys Leu Val Lys Gly Phe Tyr Pro Ser Asp Ile Ala Val Glu
```

```
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 99
<211> LENGTH: 1350
<212> TYPE: DNA
<213> ORGANISM: Artificial Sequence
<220> FEATURE:
<223> OTHER INFORMATION: heavy chain of FS22-172-003-AA/FS28-024-051
      mAb2 with LALA

<400> SEQUENCE: 99

gaagtgcaac tgctggagtc cggtggtggt ctggtacagc cgggtggttc tctgcgtctg     60

agttgcgcgg ccagtggctt taccctcagt tattcttcta tgtcatgggt gcgtcaggct    120

ccgggcaaag gtctggaatg ggttagcttt attactccgt ctactggcta tacccactat    180

gcggatagcg tgaaaggccg ttttaccatt tctcgcgaca acagcaagaa cacgctgtac    240

ctgcagatga actcactgcg tgccgaagat acggccgtgt attactgtgc gagacgggcg    300

ctgattttcg actactgggg ccagggaacc ctggtcaccg tctcgagtgc tagcactaag    360

ggcccgtcgg tgttcccgct ggccccatcg tccaagagca catcaggggg taccgccgcc    420

ctgggctgcc ttgtgaagga ttactttccc gagcccgtca cagtgtcctg gaacagcgga    480

gccctgacct ccggagtgca tactttcccg gctgtgcttc agtcctctgg cctgtactca    540

ttgtcctccg tggtcaccgt cccttcgtcc tccctgggca cccagaccta tatctgtaat    600

gtcaaccata agccctcgaa caccaaggtc gacaagaagg tcgagccgaa gtcgtgcgac    660

aagactcaca cttgcccgcc ttgcccagcc ccggaagctg ccggtggtcc ttcggtgttc    720

ctcttcccgc ccaagccgaa ggataccctg atgatctcac ggacccccga agtgacctgt    780

gtggtggtgg acgtgtccca cgaggacccg gaagtgaaat tcaattggta cgtggatgga    840

gtggaagtgc acaacgccaa gaccaagcca cgggaagaac agtacaactc tacctaccgc    900

gtggtgtccg tgctcactgt gctgcaccaa gactggctga acgggaagga gtacaagtgc    960

aaagtgtcca acaaggcgct gcctgcccca attgagaaaa ctatctcgaa agccaaggga   1020

cagcctcgag aaccacaggt gtacaccctg cccccatccc gggatgagct gccatacatc   1080

atcccaccat acaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtggg cgcagatagg   1260

tggctggaag ggaacgtctt ctcatgctcc gtgatgcatg aggcgctgca caaccactac   1320

actcagaaga gcttgtccct gtcgcccggt                                    1350


<210> SEQ ID NO 100
<211> LENGTH: 450
<212> TYPE: PRT
<213> ORGANISM: Artificial Sequence
```

<220> FEATURE:
<223> OTHER INFORMATION: heavy chain of FS22-172-003-AA/FS28-024-052
mAb2 without LALA

<400> SEQUENCE: 100

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Leu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Pro Tyr Ile Ile Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
```

-continued

```
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 101
<211> LENGTH: 1350
<212> TYPE: DNA
<213> ORGANISM: Artificial Sequence
<220> FEATURE:
<223> OTHER INFORMATION: heavy chain of FS22-172-003-AA/FS28-024-052
      mAb2 without LALA

<400> SEQUENCE: 101

gaagtgcaac tgctggagtc cggtggtggt ctggtacagc cgggtggttc tctgcgtctg     60

agttgcgcgg ccagtggctt taccctcagt tattcttcta tgtcatgggt gcgtcaggct    120

ccgggcaaag gtctggaatg ggttagcttt attactccgt ctactggcta tacccactat    180

gcggatagcg tgaaaggccg ttttaccatt tctcgcgaca acagcaagaa cacgctgtac    240

ctgcagatga actcactgcg tgccgaagat acggccgtgt attactgtgc gagacgggcg    300

ctgcttttcg actactgggg ccagggaacc ctggtcaccg tctcgtcggc tagcactaag    360

ggcccgtcgg tgttcccgct ggccccatcg tccaagagca catcaggggg taccgccgcc    420

ctgggctgcc ttgtgaagga ttactttccc gagcccgtca cagtgtcctg gaacagcgga    480

gccctgacct ccggagtgca tactttcccg gctgtgcttc agtcctctgg cctgtactca    540

ttgtcctccg tggtcaccgt cccttcgtcc tccctgggca cccagaccta tatctgtaat    600

gtcaaccata agccctcgaa caccaaggtc gacaagaagg tcgagccgaa gtcgtgcgac    660

aagactcaca cttgcccgcc ttgcccagcc ccggaactgc tgggtggtcc ttcggtgttc    720

ctcttcccgc ccaagccgaa ggataccctg atgatctcac ggacccccga agtgacctgt    780

gtggtggtgg acgtgtccca cgaggacccg gaagtgaaat tcaattggta cgtggatgga    840

gtggaagtgc acaacgccaa gaccaagcca cgggaagaac agtacaactc tacctaccgc    900

gtggtgtccg tgctcactgt gctgcaccaa gactggctga acgggaagga gtacaagtgc    960

aaagtgtcca acaaggcgct gcctgcccca attgagaaaa ctatctcgaa agccaaggga   1020

cagcctcgag aaccacaggt gtacaccctg cccccatccc gggatgagct gccatacatc   1080

atcccaccat acaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtggg cgcagatagg   1260

tggctggaag ggaacgtctt ctcatgctcc gtgatgcatg aggcgctgca caaccactac   1320

actcagaaga gcttgtccct gtcgcccggt                                    1350


<210> SEQ ID NO 102
<211> LENGTH: 450
<212> TYPE: PRT
<213> ORGANISM: Artificial Sequence
<220> FEATURE:
<223> OTHER INFORMATION: heavy chain of FS22-172-003-AA/FS28-024-052
      mAb2 with LALA
```

-continued

<400> SEQUENCE: 102

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Leu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Pro Tyr Ile Ile Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
```

-continued

```
            405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 103
<211> LENGTH: 1350
<212> TYPE: DNA
<213> ORGANISM: Artificial Sequence
<220> FEATURE:
<223> OTHER INFORMATION: heavy chain of FS22-172-003-AA/FS28-024-052
      mAb2 with LALA

<400> SEQUENCE: 103

```
gaagtgcaac tgctggagtc cggtggtggt ctggtacagc cgggtggttc tctgcgtctg     60

agttgcgcgg ccagtggctt taccctcagt tattcttcta tgtcatgggt gcgtcaggct    120

ccgggcaaag gtctggaatg ggttagcttt attactccgt ctactggcta tacccactat    180

gcggatagcg tgaaaggccg ttttaccatt tctcgcgaca acagcaagaa cacgctgtac    240

ctgcagatga actcactgcg tgccgaagat acggccgtgt attactgtgc gagacgggcg    300

ctgcttttcg actactgggg ccagggaacc ctggtcaccg tctcgtcggc tagcactaag    360

ggcccgtcgg tgttcccgct ggccccatcg tccaagagca catcaggggg taccgccgcc    420

ctgggctgcc ttgtgaagga ttactttccc gagcccgtca cagtgtcctg gaacagcgga    480

gccctgacct ccggagtgca tactttcccg gctgtgcttc agtcctctgg cctgtactca    540

ttgtcctccg tggtcaccgt cccttcgtcc tccctgggca cccagaccta tatctgtaat    600

gtcaaccata agccctcgaa caccaaggtc gacaagaagg tcgagccgaa gtcgtgcgac    660

aagactcaca cttgcccgcc ttgcccagcc ccggaagctg ccggtggtcc ttcggtgttc    720

ctcttcccgc ccaagccgaa ggatacccctg atgatctcac ggacccccga agtgacctgt    780

gtggtggtgg acgtgtccca cgaggacccg gaagtgaaat tcaattggta cgtggatgga    840

gtggaagtgc acaacgccaa gaccaagcca cgggaagaac agtacaactc tacctaccgc    900

gtggtgtccg tgctcactgt gctgcaccaa gactggctga acgggaagga gtacaagtgc    960

aaagtgtcca acaaggcgct gcctgcccca attgagaaaa ctatctcgaa agccaaggga   1020

cagcctcgag aaccacaggt gtacaccctg cccccatccc gggatgagct gccatacatc   1080

atcccaccat acaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtggg cgcagatagg   1260

tggctggaag ggaacgtctt ctcatgctcc gtgatgcatg aggcgctgca caaccactac   1320

actcagaaga gcttgtccct gtcgcccggt                                    1350
```

<210> SEQ ID NO 104
<211> LENGTH: 450
<212> TYPE: PRT
<213> ORGANISM: Artificial Sequence
<220> FEATURE:
<223> OTHER INFORMATION: heavy chain of FS22-172-003-AA/FS28-024-053
      mAb2 without LALA

<400> SEQUENCE: 104

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Pro Tyr Ile Ile Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
```

```
            420                 425                 430

His Glu Ala Leu His Asn His Tyr Thr Gln Lys Ser Leu Ser Leu Ser
        435                 440                 445

Pro Gly
    450


<210> SEQ ID NO 105
<211> LENGTH: 1350
<212> TYPE: DNA
<213> ORGANISM: Artificial Sequence
<220> FEATURE:
<223> OTHER INFORMATION: heavy chain of FS22-172-003-AA/FS28-024-053
      mAb2 without LALA

<400> SEQUENCE: 105

gaagtgcaac tgctggagtc cggtggtggt ctggtacagc cgggtggttc tctgcgtctg      60

agttgcgcgg ccagtggctt taccctcagt tattcttcta tgtcatgggt gcgtcaggct     120

ccgggcaaag gtctggaatg ggttagcttt attactccgt ctactggcta tacccactat     180

gcggatagcg tgaaaggccg ttttaccatt tctcgcgaca acagcaagaa cacgctgtac     240

ctgcagatga actcactgcg tgccgaagat acggccgtgt attactgtgc gagacgggcg     300

ctggtgttcg actactgggg ccagggaacc ctggtcaccg tctcgtcggc tagcactaag     360

ggcccgtcgg tgttcccgct ggccccatcg tccaagagca catcaggggg taccgccgcc     420

ctgggctgcc ttgtgaagga ttactttccc gagcccgtca cagtgtcctg gaacagcgga     480

gccctgacct ccggagtgca tactttcccg gctgtgcttc agtcctctgg cctgtactca     540

ttgtcctccg tggtcaccgt cccttcgtcc tccctgggca cccagaccta tatctgtaat     600

gtcaaccata agccctcgaa caccaaggtc gacaagaagg tcgagccgaa gtcgtgcgac     660

aagactcaca cttgcccgcc ttgcccagcc ccggaactgc tgggtggtcc ttcggtgttc     720

ctcttcccgc ccaagccgaa ggataccctg atgatctcac ggacccccga agtgacctgt     780

gtggtggtgg acgtgtccca cgaggacccg gaagtgaaat tcaattggta cgtggatgga     840

gtggaagtgc acaacgccaa gaccaagcca cgggaagaac agtacaactc tacctaccgc     900

gtggtgtccg tgctcactgt gctgcaccaa gactggctga acgggaagga gtacaagtgc     960

aaagtgtcca acaaggcgct gcctgcccca attgagaaaa ctatctcgaa agccaaggga    1020

cagcctcgag aaccacaggt gtacaccctg cccccatccc gggatgagct gccatacatc    1080

atcccaccat acaaccaggt cagcctgacc tgcctggtca aaggcttcta tcccagcgac    1140

atcgccgtgg agtgggagag caatgggcag ccggagaaca actacaagac cacgcctccc    1200

gtgctggact ccgacggctc cttcttcctc tacagcaagc tcaccgtggg cgcagatagg    1260

tggctggaag ggaacgtctt ctcatgctcc gtgatgcatg aggcgctgca caaccactac    1320

actcagaaga gcttgtccct gtcgcccggt                                     1350


<210> SEQ ID NO 106
<211> LENGTH: 450
<212> TYPE: PRT
<213> ORGANISM: Artificial Sequence
<220> FEATURE:
<223> OTHER INFORMATION: heavy chain of FS22-172-003-AA/FS28-024-053
      mAb2 with LALA

<400> SEQUENCE: 106

Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Phe Thr Leu Ser Tyr Ser
            20                  25                  30

Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Pro Tyr Ile Ile Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
```

435 440 445

Pro Gly
450

<210> SEQ ID NO 107
<211> LENGTH: 1350
<212> TYPE: DNA
<213> ORGANISM: Artificial Sequence
<220> FEATURE:
<223> OTHER INFORMATION: heavy chain of FS22-172-003-AA/FS28-024-053
mAb2 with LALA

<400> SEQUENCE: 107
gaagtgcaac tgctggagtc cggtggtggt ctggtacagc cgggtggttc tctgcgtctg 60
agttgcgcgg ccagtggctt taccctcagt tattcttcta tgtcatgggt gcgtcaggct 120
ccgggcaaag gtctggaatg ggttagcttt attactccgt ctactggcta tacccactat 180
gcggatagcg tgaaaggccg ttttaccatt tctcgcgaca acagcaagaa cacgctgtac 240
ctgcagatga actcactgcg tgccgaagat acggccgtgt attactgtgc gagacgggcg 300
ctggtgttcg actactgggg ccagggaacc ctggtcaccg tctcgtcggc tagcactaag 360
ggcccgtcgg tgttcccgct ggccccatcg tccaagagca catcaggggg taccgccgcc 420
ctgggctgcc ttgtgaagga ttactttccc gagcccgtca cagtgtcctg gaacagcgga 480
gccctgacct ccggagtgca tactttcccg gctgtgcttc agtcctctgg cctgtactca 540
ttgtcctccg tggtcaccgt cccttcgtcc tccctgggca cccagaccta tatctgtaat 600
gtcaaccata agccctcgaa caccaaggtc gacaagaagg tcgagccgaa gtcgtgcgac 660
aagactcaca cttgcccgcc ttgcccagcc ccggaagctg ccggtggtcc ttcggtgttc 720
ctcttcccgc ccaagccgaa ggataccctg atgatctcac ggacccccga agtgacctgt 780
gtggtggtgg acgtgtccca cgaggacccg gaagtgaaat tcaattggta cgtggatgga 840
gtggaagtgc acaacgccaa gaccaagcca cgggaagaac agtacaactc tacctaccgc 900
gtggtgtccg tgctcactgt gctgcaccaa gactggctga acgggaagga gtacaagtgc 960
aaagtgtcca acaaggcgct gcctgcccca attgagaaaa ctatctcgaa agccaaggga 1020
cagcctcgag aaccacaggt gtacaccctg cccccatccc gggatgagct gccatacatc 1080
atcccaccat acaaccaggt cagcctgacc tgcctggtca aaggcttcta tcccagcgac 1140
atcgccgtgg agtgggagag caatgggcag ccggagaaca actacaagac cacgcctccc 1200
gtgctggact ccgacggctc cttcttcctc tacagcaagc tcaccgtggg cgcagatagg 1260
tggctggaag ggaacgtctt ctcatgctcc gtgatgcatg aggcgctgca caaccactac 1320
actcagaaga gcttgtccct gtcgcccggt 1350

<210> SEQ ID NO 108
<211> LENGTH: 450
<212> TYPE: PRT
<213> ORGANISM: Artificial Sequence
<220> FEATURE:
<223> OTHER INFORMATION: heavy chain of FS22-172-003-AA/FS28-024-060
mAb2 with LALA

<400> SEQUENCE: 108

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Leu Ser Tyr Ser
20 25 30

```
Ser Met Ser Trp Val Arg Gln Ala Pro Gly Lys Gly Leu Glu Trp Val
        35                  40                  45

Ser Phe Ile Thr Pro Ser Thr Gly Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Leu Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Pro Tyr Ile Ile Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
```

450

<210> SEQ ID NO 109
<211> LENGTH: 450
<212> TYPE: PRT
<213> ORGANISM: Artificial Sequence
<220> FEATURE:
<223> OTHER INFORMATION: heavy chain of FS22-172-003-AA/FS28-026 mAb2

<400> SEQUENCE: 109

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Thr Trp Val Arg Gln Ala Pro Gly Lys Gly Leu Glu Trp Val
35 40 45

Ser Ser Ile Thr Pro Tyr Tyr Ser Lys Thr Asp Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asn Trp Tyr Arg Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Ala Ala Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Asp Glu Leu Pro Tyr Ile Ile Pro Pro Tyr Asn Gln Val Ser

```
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 110
<211> LENGTH: 450
<212> TYPE: PRT
<213> ORGANISM: Artificial Sequence
<220> FEATURE:
<223> OTHER INFORMATION: heavy chain of FS22-172-003-AA/FS28-091 mAb2

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Lys Gly Leu Glu Trp Val
        35                  40                  45

Ser Ser Ile Lys Pro Tyr Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Arg Trp Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
```

```
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Pro Tyr Ile Ile Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 111
<211> LENGTH: 457
<212> TYPE: PRT
<213> ORGANISM: Artificial Sequence
<220> FEATURE:
<223> OTHER INFORMATION: heavy chain of FS22-172-003-AA/FS28-185 mAb2

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Thr Ser
            20                  25                  30

Ala Met Ser Trp Val Arg Gln Ala Pro Gly Lys Gly Leu Glu Trp Val
        35                  40                  45

Ser Arg Ile Asn Pro Tyr Glu Gly Glu Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Ser Ile Ala Thr Tyr Tyr Lys Ser Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
```

```
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Pro Tyr Ile Ile
        355                 360                 365

Pro Pro Tyr Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Gly Ala Asp Arg Trp Leu Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
    450                 455


<210> SEQ ID NO 112
<211> LENGTH: 453
<212> TYPE: PRT
<213> ORGANISM: Artificial Sequence
<220> FEATURE:
<223> OTHER INFORMATION: heavy chain of FS22-172-003-AA/FS28-256 mAb2
      without LALA

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ser Tyr Gln Gly Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Pro Tyr Ile Ile Pro Pro Tyr Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Gly Ala Asp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450
```

<210> SEQ ID NO 113
<211> LENGTH: 1359
<212> TYPE: DNA

<213> ORGANISM: Artificial Sequence
<220> FEATURE:
<223> OTHER INFORMATION: heavy chain of FS22-172-003-AA/FS28-256 mAb2 without LALA

<400> SEQUENCE: 113

```
gaagtgcaac tgctggagtc cggtggtggt ctggtacagc cgggtggttc tctgcgtctg     60

agttgcgcgg ccagtggctt taccttcact aacacttata tgagctgggt gcgtcaggct    120

ccgggcaaag gtctggaatg ggttagcaat atttctccga cttatagcac taccaactat    180

gcggatagcg tgaaaggccg ttttaccatt tctcgcgaca acagcaagaa cacgctgtac    240

ctgcagatga actcactgcg tgccgaagat acggccgtgt attactgtgc gagatacaac    300

tcttaccagg gtggcttgga ctactggggc cagggaacct tggtcaccgt ctcgagtgct    360

agcactaagg gcccgtcggt gttcccgctg gccccatcgt ccaagagcac atcagggggt    420

accgccgccc tgggctgcct tgtgaaggat tactttcccg agcccgtcac agtgtcctgg    480

aacagcggag ccctgacctc cggagtgcat actttcccgg ctgtgcttca gtcctctggc    540

ctgtactcat tgtcctccgt ggtcaccgtc ccttcgtcct ccctgggcac ccagacctat    600

atctgtaatg tcaaccataa gccctcgaac accaaggtcg acaagaaggt cgagccgaag    660

tcgtgcgaca agactcacac ttgcccgcct tgcccagccc cggaactgct gggtggtcct    720

tcggtgttcc tcttcccgcc caagccgaag gataccctga tgatctcacg gacccccgaa    780

gtgacctgtg tggtggtgga cgtgtcccac gaggacccgg aagtgaaatt caattggtac    840

gtggatggag tggaagtgca caacgccaag accaagccac gggaagaaca gtacaactct    900

acctaccgcg tggtgtccgt gctcactgtg ctgcaccaag actggctgaa cgggaaggag    960

tacaagtgca aagtgtccaa caaggcgctg cctgccccaa ttgagaaaac tatctcgaaa   1020

gccaagggac agcctcgaga accacaggtg tacaccctgc ccccatcccg ggatgagctg   1080

ccatacatca tcccaccata caaccaggtc agcctgacct gcctggtcaa aggcttctat   1140

cccagcgaca tcgccgtgga gtgggagagc aatgggcagc cggagaacaa ctacaagacc   1200

acgcctcccg tgctggactc cgacggctcc ttcttcctct acagcaagct caccgtgggc   1260

gcagataggt ggctggaagg gaacgtcttc tcatgctccg tgatgcatga ggcgctgcac   1320

aaccactaca ctcagaagag cttgtccctg tcgcccggt                          1359
```

<210> SEQ ID NO 114
<211> LENGTH: 453
<212> TYPE: PRT
<213> ORGANISM: Artificial Sequence
<220> FEATURE:
<223> OTHER INFORMATION: heavy chain of FS22-172-003-AA/FS28-256 mAb2 with LALA

<400> SEQUENCE: 114

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Tyr Asn Ser Tyr Gln Gly Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Pro Tyr Ile Ile Pro Pro Tyr Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Gly Ala Asp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450
```

<210> SEQ ID NO 115
<211> LENGTH: 1359
<212> TYPE: DNA
<213> ORGANISM: Artificial Sequence
<220> FEATURE:
<223> OTHER INFORMATION: heavy chain of FS22-172-003-AA/FS28-256 mAb2 with LALA

<400> SEQUENCE: 115

```
gaagtgcaac tgctggagtc cggtggtggt ctggtacagc cgggtggttc tctgcgtctg      60
agttgcgcgg ccagtggctt taccttcact aacacttata tgagctgggt gcgtcaggct     120
ccgggcaaag gtctggaatg ggttagcaat atttctccga cttatagcac taccaactat     180
gcggatagcg tgaaaggccg ttttaccatt tctcgcgaca acagcaagaa cacgctgtac     240
ctgcagatga actcactgcg tgccgaagat acggccgtgt attactgtgc gagatacaac     300
tcttaccagg gtggcttgga ctactggggc cagggaacct tggtcaccgt ctcgagtgct     360
agcactaagg gcccgtcggt gttcccgctg gccccatcgt ccaagagcac atcagggggt     420
accgccgccc tgggctgcct tgtgaaggat tactttcccg agcccgtcac agtgtcctgg     480
aacagcggag ccctgacctc cggagtgcat actttcccgg ctgtgcttca gtcctctggc     540
ctgtactcat tgtcctccgt ggtcaccgtc ccttcgtcct ccctgggcac ccagacctat     600
atctgtaatg tcaaccataa gccctcgaac accaaggtcg acaagaaggt cgagccgaag     660
tcgtgcgaca agactcacac ttgcccgcct tgcccagccc cggaagctgc cggtggtcct     720
tcggtgttcc tcttcccgcc caagccgaag gataccctga tgatctcacg gacccccgaa     780
gtgacctgtg tggtggtgga cgtgtcccac gaggacccgg aagtgaaatt caattggtac     840
gtggatggag tggaagtgca caacgccaag accaagccac gggaagaaca gtacaactct     900
acctaccgcg tggtgtccgt gctcactgtg ctgcaccaag actggctgaa cgggaaggag     960
tacaagtgca aagtgtccaa caaggcgctg cctgccccaa ttgagaaaac tatctcgaaa    1020
gccaagggac agcctcgaga accacaggtg tacaccctgc ccccatcccg ggatgagctg    1080
ccatacatca tcccaccata caaccaggtc agcctgacct gcctggtcaa aggcttctat    1140
cccagcgaca tcgccgtgga gtgggagagc aatgggcagc cggagaacaa ctacaagacc    1200
acgcctcccg tgctggactc cgacggctcc ttcttcctct acagcaagct caccgtgggc    1260
gcagataggt ggctggaagg gaacgtcttc tcatgctccg tgatgcatga ggcgctgcac    1320
aaccactaca ctcagaagag cttgtccctg tcgcccggt                           1359
```

<210> SEQ ID NO 116
<211> LENGTH: 215
<212> TYPE: PRT
<213> ORGANISM: Artificial Sequence
<220> FEATURE:
<223> OTHER INFORMATION: light chain of FS22-172-003-AA/FS28-256 mAb2

<400> SEQUENCE: 116

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Tyr Tyr Pro
                85                  90                  95

Ile Thr Phe Gly Gln Gly Thr Lys Val Glu Ile Lys Arg Thr Val Ala
```

```
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 117
<211> LENGTH: 645
<212> TYPE: DNA
<213> ORGANISM: Artificial Sequence
<220> FEATURE:
<223> OTHER INFORMATION: light chain of FS22-172-003-AA/FS28-256 mAb2

<400> SEQUENCE: 117

gaaattgtgc tgacccagtc tccgggcacg ttatctctga gccctggtga gcgcgccact     60

ctgtcatgcc gggcttctca aagtgttagc agtagctacc tggcgtggta tcagcaaaaa    120

ccgggccagg ccccgcgtct gctgatttac ggtgcatcca gccgtgccac cggcattcca    180

gatcgttttt ccggtagtgg ttctgggacg gacttcactc tgacaatctc acgcctggaa    240

ccggaggatt ttgcggtgta ttactgccag caatcttatt attatcctat cacgttcggc    300

caagggacca aggtggaaat caaacgtact gtggccgctc ctagcgtgtt catttttccg    360

ccatccgacg agcagctcaa gtccggcacc gcctccgtgg tctgcctgct caacaacttc    420

taccctcgcg aagctaaggt ccagtggaag gtcgacaatg ccctgcagtc cggaaactcg    480

caggaaagcg tgactgaaca ggactccaag gactccacct attcactgtc ctcgactctg    540

accctgagca aggcggatta cgaaaagcac aaagtgtacg catgcgaagt gacccaccag    600

ggtctttcgt cccccgtgac caagagcttc aacagaggag agtgt                    645


<210> SEQ ID NO 118
<211> LENGTH: 453
<212> TYPE: PRT
<213> ORGANISM: Artificial Sequence
<220> FEATURE:
<223> OTHER INFORMATION: heavy chain of FS22-172-003-AA/FS28-256-001
      mAb2 without LALA

<400> SEQUENCE: 118

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Glu Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
```

```
65                  70                  75                  80

Leu Gln Met Asn Ser Leu Arg Ala Glu Asp Thr Ala Val Tyr Tyr Cys
                85                  90                  95

Ala Arg Tyr Asn Ser Tyr Gln Gly Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Pro Tyr Ile Ile Pro Pro Tyr Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Gly Ala Asp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450
```

<210> SEQ ID NO 119
<211> LENGTH: 1359
<212> TYPE: DNA
<213> ORGANISM: Artificial Sequence -continued
<220> FEATURE:
<223> OTHER INFORMATION: heavy chain of FS22-172-003-AA/FS28-256-001
      mAb2 without LALA

<400> SEQUENCE: 119
gaagtgcaac tgctggagtc cggtggtggt ctggtacagc cgggtggttc tctgcgtctg     60
agttgcgcgg ccagtggctt taccttcact gagacttata tgagctgggt gcgtcaggct    120
ccgggcaaag gtctggaatg ggttagcaat atttctccga cttatagcac taccaactat    180
gcggatagcg tgaaaggccg ttttaccatt tctcgcgaca acagcaagaa cacgctgtac    240
ctgcagatga actcactgcg tgccgaagat acggccgtgt attactgtgc gagatacaac    300
tcttaccagg gtggcttgga ctactggggc cagggaacct tggtcaccgt ctcgagtgct    360
agcactaagg gcccgtcggt gttcccgctg gccccatcgt ccaagagcac atcagggggt    420
accgccgccc tgggctgcct tgtgaaggat tactttcccg agcccgtcac agtgtcctgg    480
aacagcggag ccctgacctc cggagtgcat actttcccgg ctgtgcttca gtcctctggc    540
ctgtactcat tgtcctccgt ggtcaccgtc ccttcgtcct ccctgggcac ccagacctat    600
atctgtaatg tcaaccataa gccctcgaac accaaggtcg acaagaaggt cgagccgaag    660
tcgtgcgaca agactcacac ttgcccgcct tgcccagccc cggaactgct gggtggtcct    720
tcggtgttcc tcttcccgcc caagccgaag gataccctga tgatctcacg gacccccgaa    780
gtgacctgtg tggtggtgga cgtgtcccac gaggacccgg aagtgaaatt caattggtac    840
gtggatggag tggaagtgca caacgccaag accaagccac gggaagaaca gtacaactct    900
acctaccgcg tggtgtccgt gctcactgtg ctgcaccaag actggctgaa cgggaaggag    960
tacaagtgca aagtgtccaa caaggcgctg cctgccccaa ttgagaaaac tatctcgaaa   1020
gccaagggac agcctcgaga accacaggtg tacaccctgc ccccatcccg ggatgagctg   1080
ccatacatca tcccaccata caaccaggtc agcctgacct gcctggtcaa aggcttctat   1140
cccagcgaca tcgccgtgga gtgggagagc aatgggcagc cggagaacaa ctacaagacc   1200
acgcctcccg tgctggactc cgacggctcc ttcttcctct acagcaagct caccgtgggc   1260
gcagataggt ggctggaagg gaacgtcttc tcatgctccg tgatgcatga ggcgctgcac   1320
aaccactaca ctcagaagag cttgtccctg tcgcccggt                          1359

<210> SEQ ID NO 120
<211> LENGTH: 453
<212> TYPE: PRT
<213> ORGANISM: Artificial Sequence
<220> FEATURE:
<223> OTHER INFORMATION: heavy chain of FS22-172-003-AA/FS28-256-001
      mAb2 with LALA

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Glu Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

-continued

```
                85                  90                  95

Ala Arg Tyr Asn Ser Tyr Gln Gly Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Pro Tyr Ile Ile Pro Pro Tyr Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Gly Ala Asp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450
```

<210> SEQ ID NO 121
<211> LENGTH: 1359
<212> TYPE: DNA
<213> ORGANISM: Artificial Sequence
<220> FEATURE:
<223> OTHER INFORMATION: heavy chain of FS22-172-003-AA/FS28-256-001
mAb2 with LALA

<400> SEQUENCE: 121
gaagtgcaac tgctggagtc cggtggtggt ctggtacagc cgggtggttc tctgcgtctg 60
agttgcgcgg ccagtggctt taccttcact gagacttata tgagctgggt gcgtcaggct 120
ccgggcaaag gtctggaatg ggttagcaat atttctccga cttatagcac taccaactat 180
gcggatagcg tgaaaggccg ttttaccatt tctcgcgaca acagcaagaa cacgctgtac 240
ctgcagatga actcactgcg tgccgaagat acggccgtgt attactgtgc gagatacaac 300
tcttaccagg gtggcttgga ctactggggc cagggaacct tggtcaccgt ctcgagtgct 360
agcactaagg gcccgtcggt gttcccgctg gccccatcgt ccaagagcac atcagggggt 420
accgccgccc tgggctgcct tgtgaaggat tactttcccg agcccgtcac agtgtcctgg 480
aacagcggag ccctgacctc cggagtgcat actttcccgg ctgtgcttca gtcctctggc 540
ctgtactcat tgtcctccgt ggtcaccgtc ccttcgtcct ccctgggcac ccagacctat 600
atctgtaatg tcaaccataa gccctcgaac accaaggtcg acaagaaggt cgagccgaag 660
tcgtgcgaca agactcacac ttgcccgcct tgcccagccc cggaagctgc cggtggtcct 720
tcggtgttcc tcttcccgcc caagccgaag gataccctga tgatctcacg gaccccccgaa 780
gtgacctgtg tggtggtgga cgtgtcccac gaggacccgg aagtgaaatt caattggtac 840
gtggatggag tggaagtgca caacgccaag accaagccac gggaagaaca gtacaactct 900
acctaccgcg tggtgtccgt gctcactgtg ctgcaccaag actggctgaa cgggaaggag 960
tacaagtgca aagtgtccaa caaggcgctg cctgccccaa ttgagaaaac tatctcgaaa 1020
gccaagggac agcctcgaga accacaggtg tacaccctgc ccccatcccg ggatgagctg 1080
ccatacatca tcccaccata caaccaggtc agcctgacct gcctggtcaa aggcttctat 1140
cccagcgaca tcgccgtgga gtgggagagc aatgggcagc cggagaacaa ctacaagacc 1200
acgcctcccg tgctggactc cgacggctcc ttcttcctct acagcaagct caccgtgggc 1260
gcagataggt ggctggaagg gaacgtcttc tcatgctccg tgatgcatga ggcgctgcac 1320
aaccactaca ctcagaagag cttgtccctg tcgcccggt 1359

<210> SEQ ID NO 122
<211> LENGTH: 645
<212> TYPE: DNA
<213> ORGANISM: Artificial Sequence
<220> FEATURE:
<223> OTHER INFORMATION: light chain of FS22-172-003-AA/FS28-256-001
mAb2

<400> SEQUENCE: 122
gaaattgtgc tgacccagtc tccgggcacg ttatctctga gccctggtga gcgcgccact 60
ctgtcatgcc gggcttctca aagtgttagc agtagctacc tggcgtggta tcagcaaaaa 120
ccgggccagg ccccgcgtct gctgatttac ggtgcatcca gccgtgccac cggcattcca 180
gatcgttttt ccggtagtgg ttctgggacg gacttcactc tgacaatctc acgcctggaa 240
ccggaggatt ttgcggtgta ttactgccag caacataatc agtatccgaa tacgttcggc 300
caagggacca aggtggaaat caaacgtact gtagcagctc cttccgtgtt catctttccg 360
cccagtgatg agcagctgaa gtcaggtact gcttccgtgg tttgcctgct caacaacttt 420
taccccagag aagccaaagt ccagtggaaa gtggacaatg cgttgcaaag cgggaactct 480
caggaatccg tcacagagca ggactctaag gactccacct atagcctctc tagtacgctg 540
acactgagca aagccgatta cgagaagcac aaggtgtatg cctgtgaggt tacccatcaa 600
ggccttagct caccagtgac caagagcttc aataggggag aatgc 645

<210> SEQ ID NO 123
<211> LENGTH: 453
<212> TYPE: PRT
<213> ORGANISM: Artificial Sequence
<220> FEATURE:
<223> OTHER INFORMATION: heavy chain of FS22-172-003-AA/FS28-256-012 mAb2 without LALA

<400> SEQUENCE: 123

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Thr His Thr
20 25 30

Tyr Met Ser Trp Val Arg Gln Ala Pro Gly Lys Gly Leu Glu Trp Val
35 40 45

Ser Asn Ile Ser Pro Thr Tyr Ser Thr Thr Asn Tyr Ala Asp Ser Val
50 55 60

Lys Gly Arg Phe Thr Ile Ser Arg Asp Asn Asn Lys Asn Thr Leu Tyr
65 70 75 80

Leu Gln Met Asn Ser Leu Arg Ala Glu Asp Thr Ala Val Tyr Tyr Cys
85 90 95

Ala Arg Tyr Asn Ala Tyr His Ala Ala Leu Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

```
Leu Pro Pro Ser Arg Asp Glu Leu Pro Tyr Ile Ile Pro Pro Tyr Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Gly Ala Asp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 124
<211> LENGTH: 1359
<212> TYPE: DNA
<213> ORGANISM: Artificial Sequence
<220> FEATURE:
<223> OTHER INFORMATION: heavy chain of FS22-172-003-AA/FS28-256-012
      mAb2 without LALA

<400> SEQUENCE: 124

gaagtgcaac tgctggagtc cggtggtggt ctggtacagc cgggtggttc tctgcgtctg      60

agttgcgcgg ccagtggctt taccttcact catacttata tgagctgggt gcgtcaggct     120

ccgggcaaag gtctggaatg ggttagcaat atttctccga cttatagcac taccaactat     180

gcggatagcg tgaaaggccg ttttaccatt tctcgcgaca acaacaagaa cacgctgtac     240

ctgcagatga actcactgcg tgccgaagat acggccgtgt attactgtgc gagatacaac     300

gcgtatcatg ctgctctgga ctactggggc cagggaaccc tggtcaccgt ctcgagtgct     360

agcactaagg gcccgtcggt gttcccgctg gccccatcgt ccaagagcac atcagggggt     420

accgccgccc tgggctgcct tgtgaaggat tactttcccg agcccgtcac agtgtcctgg     480

aacagcggag ccctgacctc cggagtgcat actttcccgg ctgtgcttca gtcctctggc     540

ctgtactcat tgtcctccgt ggtcaccgtc ccttcgtcct ccctgggcac ccagacctat     600

atctgtaatg tcaaccataa gccctcgaac accaaggtcg acaagaaggt cgagccgaag     660

tcgtgcgaca agactcacac ttgcccgcct tgcccagccc cggaactgct gggtggtcct     720

tcggtgttcc tcttcccgcc caagccgaag gataccctga tgatctcacg gacccccgaa     780

gtgacctgtg tggtggtgga cgtgtcccac gaggacccgg aagtgaaatt caattggtac     840

gtggatggag tggaagtgca caacgccaag accaagccac gggaagaaca gtacaactct     900

acctaccgcg tggtgtccgt gctcactgtg ctgcaccaag actggctgaa cgggaaggag     960

tacaagtgca aagtgtccaa caaggcgctg cctgccccaa ttgagaaaac tatctcgaaa    1020

gccaagggac agcctcgaga accacaggtg tacaccctgc ccccatcccg ggatgagctg    1080

ccatacatca tcccaccata caaccaggtc agcctgacct gcctggtcaa aggcttctat    1140

cccagcgaca tcgccgtgga gtgggagagc aatgggcagc cggagaacaa ctacaagacc    1200

acgcctcccg tgctggactc cgacggctcc ttcttcctct acagcaagct caccgtgggc    1260

gcagataggt ggctggaagg gaacgtcttc tcatgctccg tgatgcatga ggcgctgcac    1320

aaccactaca ctcagaagag cttgtccctg tcgcccggt                           1359
```

<210> SEQ ID NO 125
<211> LENGTH: 453
<212> TYPE: PRT
<213> ORGANISM: Artificial Sequence
<220> FEATURE:
<223> OTHER INFORMATION: heavy chain of FS22-172-003-AA/FS28-256-012
mAb2 with LALA

<400> SEQUENCE: 125

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Pro Tyr Ile Ile Pro Pro Tyr Asn
        355                 360                 365
```

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Gly Ala Asp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 126
<211> LENGTH: 1359
<212> TYPE: DNA
<213> ORGANISM: Artificial Sequence
<220> FEATURE:
<223> OTHER INFORMATION: heavy chain of FS22-172-003-AA/FS28-256-012
      mAb2 with LALA

<400> SEQUENCE: 126
gaagtgcaac tgctggagtc cggtggtggt ctggtacagc cgggtggttc tctgcgtctg 60
agttgcgcgg ccagtggctt taccttcact catacttata tgagctgggt gcgtcaggct 120
ccgggcaaag gtctggaatg ggttagcaat atttctccga cttatagcac taccaactat 180
gcggatagcg tgaaaggccg ttttaccatt tctcgcgaca acaacaagaa cacgctgtac 240
ctgcagatga actcactgcg tgccgaagat acggccgtgt attactgtgc gagatacaac 300
gcgtatcatg ctgctctgga ctactggggc cagggaaccc tggtcaccgt ctcgagtgct 360
agcactaagg gcccgtcggt gttcccgctg gccccatcgt ccaagagcac atcagggggt 420
accgccgccc tgggctgcct tgtgaaggat tactttcccg agcccgtcac agtgtcctgg 480
aacagcggag ccctgacctc cggagtgcat actttcccgg ctgtgcttca gtcctctggc 540
ctgtactcat tgtcctccgt ggtcaccgtc ccttcgtcct ccctgggcac ccagacctat 600
atctgtaatg tcaaccataa gccctcgaac accaaggtcg acaagaaggt cgagccgaag 660
tcgtgcgaca agactcacac ttgcccgcct tgcccagccc cggaagctgc cggtggtcct 720
tcggtgttcc tcttcccgcc caagccgaag gataccctga tgatctcacg gaccccccgaa 780 gtgacctgtg tggtggtgga cgtgtcccac gaggacccgg aagtgaaatt caattggtac 840
gtggatggag tggaagtgca caacgccaag accaagccac gggaagaaca gtacaactct 900
acctaccgcg tggtgtccgt gctcactgtg ctgcaccaag actggctgaa cgggaaggag 960
tacaagtgca aagtgtccaa caaggcgctg cctgccccaa ttgagaaaac tatctcgaaa 1020
gccaagggac agcctcgaga accacaggtg tacaccctgc ccccatcccg ggatgagctg 1080
ccatacatca tcccaccata caaccaggtc agcctgacct gcctggtcaa aggcttctat 1140
cccagcgaca tcgccgtgga gtgggagagc aatgggcagc cggagaacaa ctacaagacc 1200
acgcctcccg tgctggactc cgacggctcc ttcttcctct acagcaagct caccgtgggc 1260
gcagataggt ggctggaagg gaacgtcttc tcatgctccg tgatgcatga ggcgctgcac 1320
aaccactaca ctcagaagag cttgtccctg tcgcccggt 1359

<210> SEQ ID NO 127
<211> LENGTH: 453

<212> TYPE: PRT
<213> ORGANISM: Artificial Sequence
<220> FEATURE:
<223> OTHER INFORMATION: heavy chain of FS22-172-003-AA/FS28-256-014
      mAb2 without LALA

<400> SEQUENCE: 127

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Ala Ala Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Pro Tyr Ile Ile Pro Pro Tyr Asn
        355                 360                 365

Gln Val Ser Leu Thr Cys Leu Val Lys Gly Phe Tyr Pro Ser Asp Ile
    370                 375                 380
```

```
Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Gly Ala Asp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 128
<211> LENGTH: 1359
<212> TYPE: DNA
<213> ORGANISM: Artificial Sequence
<220> FEATURE:
<223> OTHER INFORMATION: heavy chain of FS22-172-003-AA/FS28-256-014
      mAb2 without LALA

<400> SEQUENCE: 128

gaagtgcaac tgctggagtc cggtggtggt ctggtacagc cgggtggttc tctgcgtctg     60

agttgcgcgg ccagtggctt taccttcact gatacttata tgagctgggt gcgtcaggct    120

ccgggcaaag gtctggaatg ggttagcaat atttctccga cttatagcac taccaactat    180

gcggatagcg tgaaaggccg ttttaccatt tctcgcgaca acagcaagaa cacgctgtac    240

ctgcagatga actcactgcg tgccgaagat acggccgtgt attactgtgc gagatacaac    300

gcgtatgcgg cgggtcttga ctactggggc cagggaaccc tggtcaccgt ctcgagtgct    360

agcactaagg gcccgtcggt gttcccgctg gccccatcgt ccaagagcac atcagggggt    420

accgccgccc tgggctgcct tgtgaaggat tactttcccg agcccgtcac agtgtcctgg    480

aacagcggag ccctgacctc cggagtgcat actttcccgg ctgtgcttca gtcctctggc    540

ctgtactcat tgtcctccgt ggtcaccgtc ccttcgtcct ccctgggcac ccagacctat    600

atctgtaatg tcaaccataa gccctcgaac accaaggtcg acaagaaggt cgagccgaag    660

tcgtgcgaca agactcacac ttgcccgcct tgcccagccc cggaactgct gggtggtcct    720

tcggtgttcc tcttcccgcc caagccgaag gataccctga tgatctcacg gaccccccgaa    780

gtgacctgtg tggtggtgga cgtgtcccac gaggacccgg aagtgaaatt caattggtac    840

gtggatggag tggaagtgca caacgccaag accaagccac gggaagaaca gtacaactct    900

acctaccgcg tggtgtccgt gctcactgtg ctgcaccaag actggctgaa cgggaaggag    960

tacaagtgca aagtgtccaa caaggcgctg cctgccccaa ttgagaaaac tatctcgaaa   1020

gccaagggac agcctcgaga accacaggtg tacaccctgc ccccatcccg ggatgagctg   1080

ccatacatca tcccaccata caaccaggtc agcctgacct gcctggtcaa aggcttctat   1140

cccagcgaca tcgccgtgga gtgggagagc aatgggcagc cggagaacaa ctacaagacc   1200

acgcctcccg tgctggactc cgacggctcc ttcttcctct acagcaagct caccgtgggc   1260

gcagataggt ggctggaagg gaacgtcttc tcatgctccg tgatgcatga ggcgctgcac   1320

aaccactaca ctcagaagag cttgtccctg tcgcccggt                           1359


<210> SEQ ID NO 129
<211> LENGTH: 453
<212> TYPE: PRT
<213> ORGANISM: Artificial Sequence
<220> FEATURE:
```

-continued

<223> OTHER INFORMATION: heavy chain of FS22-172-003-AA/FS28-256-014
mAb2 with LALA

<400> SEQUENCE: 129

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Ala Ala Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Pro Tyr Ile Ile Pro Pro Tyr Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400
```

Thr Pro Pro Val Leu Asp Ser Asp Gly Ser Phe Phe Leu Tyr Ser Lys
405 410 415

Leu Thr Val Gly Ala Asp Arg Trp Leu Glu Gly Asn Val Phe Ser Cys
420 425 430

Ser Val Met His Glu Ala Leu His Asn His Tyr Thr Gln Lys Ser Leu
435 440 445

Ser Leu Ser Pro Gly
450

<210> SEQ ID NO 130
<211> LENGTH: 1359
<212> TYPE: DNA
<213> ORGANISM: Artificial Sequence
<220> FEATURE:
<223> OTHER INFORMATION: heavy chain of FS22-172-003-AA/FS28-256-014
mAb2 with LALA

<400> SEQUENCE: 130
gaagtgcaac tgctggagtc cggtggtggt ctggtacagc cgggtggttc tctgcgtctg 60
agttgcgcgg ccagtggctt taccttcact gatacttata tgagctgggt gcgtcaggct 120
ccgggcaaag gtctggaatg ggttagcaat atttctccga cttatagcac taccaactat 180
gcggatagcg tgaaaggccg ttttaccatt tctcgcgaca acagcaagaa cacgctgtac 240
ctgcagatga actcactgcg tgccgaagat acggccgtgt attactgtgc gagatacaac 300
gcgtatgcgg cgggtcttga ctactggggc cagggaaccc tggtcaccgt ctcgagtgct 360
agcactaagg gcccgtcggt gttcccgctg gccccatcgt ccaagagcac atcaggggt 420 accgccgccc tgggctgcct tgtgaaggat tactttcccg agcccgtcac agtgtcctgg 480
aacagcggag ccctgacctc cggagtgcat actttcccgg ctgtgcttca gtcctctggc 540
ctgtactcat tgtcctccgt ggtcaccgtc ccttcgtcct ccctgggcac ccagacctat 600
atctgtaatg tcaaccataa gccctcgaac accaaggtcg acaagaaggt cgagccgaag 660
tcgtgcgaca agactcacac ttgcccgcct tgcccagccc cggaagctgc cggtggtcct 720
tcggtgttcc tcttcccgcc caagccgaag gataccctga tgatctcacg gacccccgaa 780
gtgacctgtg tggtggtgga cgtgtcccac gaggacccgg aagtgaaatt caattggtac 840
gtggatggag tggaagtgca caacgccaag accaagccac gggaagaaca gtacaactct 900
acctaccgcg tggtgtccgt gctcactgtg ctgcaccaag actggctgaa cgggaaggag 960
tacaagtgca aagtgtccaa caaggcgctg cctgccccaa ttgagaaaac tatctcgaaa 1020
gccaagggac agcctcgaga accacaggtg tacaccctgc ccccatcccg ggatgagctg 1080
ccatacatca tcccaccata caaccaggtc agcctgacct gcctggtcaa aggcttctat 1140
cccagcgaca tcgccgtgga gtgggagagc aatgggcagc cggagaacaa ctacaagacc 1200
acgcctcccg tgctggactc cgacggctcc ttcttcctct acagcaagct caccgtgggc 1260
gcagataggt ggctggaagg gaacgtcttc tcatgctccg tgatgcatga ggcgctgcac 1320
aaccactaca ctcagaagag cttgtccctg tcgcccggt 1359

<210> SEQ ID NO 131
<211> LENGTH: 453
<212> TYPE: PRT
<213> ORGANISM: Artificial Sequence
<220> FEATURE:
<223> OTHER INFORMATION: heavy chain of FS22-172-003-AA/FS28-256-018
mAb2 without LALA -continued

<400> SEQUENCE: 131

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Thr Gln Thr
20 25 30

Tyr Met Ser Trp Val Arg Gln Ala Pro Gly Lys Gly Leu Glu Trp Val
35 40 45

Ser Asn Ile Ser Pro Thr Tyr Ser Thr Thr Asn Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Tyr Asn Ala Tyr Gln Ile Gly Leu Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Pro Tyr Ile Ile Pro Pro Tyr Asn
355 360 365

Gln Val Ser Leu Thr Cys Leu Val Lys Gly Phe Tyr Pro Ser Asp Ile
370 375 380

Ala Val Glu Trp Glu Ser Asn Gly Gln Pro Glu Asn Asn Tyr Lys Thr
385 390 395 400

Thr Pro Pro Val Leu Asp Ser Asp Gly Ser Phe Phe Leu Tyr Ser Lys
405 410 415

```
Leu Thr Val Gly Ala Asp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450
```

<210> SEQ ID NO 132
<211> LENGTH: 1359
<212> TYPE: DNA
<213> ORGANISM: Artificial Sequence
<220> FEATURE:
<223> OTHER INFORMATION: heavy chain of FS22-172-003-AA/FS28-256-018 mAb2 without LALA

<400> SEQUENCE: 132

```
gaagtgcaac tgctggagtc cggtggtggt ctggtacagc cgggtggttc tctgcgtctg     60

agttgcgcgg ccagtggctt taccttcact cagacttata tgagctgggt gcgtcaggct    120

ccgggcaaag gtctggaatg ggttagcaat atttctccga cttatagcac taccaactat    180

gcggatagcg tgaaaggccg ttttaccatt tctcgcgaca acagcaagaa cacgctgtac    240

ctgcagatga actcactgcg tgccgaagat acggccgtgt attactgtgc gagatacaac    300

gcttatcaga ttgggttgga ctactggggc cagggaaccc tggtcaccgt ctcgagtgct    360

agcactaagg gcccgtcggt gttcccgctg gccccatcgt ccaagagcac atcagggggt    420

accgccgccc tgggctgcct tgtgaaggat tactttcccg agcccgtcac agtgtcctgg    480

aacagcggag ccctgacctc cggagtgcat actttcccgg ctgtgcttca gtcctctggc    540

ctgtactcat tgtcctccgt ggtcaccgtc ccttcgtcct ccctgggcac ccagacctat    600

atctgtaatg tcaaccataa gccctcgaac accaaggtcg acaagaaggt cgagccgaag    660

tcgtgcgaca agactcacac ttgcccgcct tgcccagccc cggaactgct gggtggtcct    720

tcggtgttcc tcttcccgcc caagccgaag gataccctga tgatctcacg gacccccgaa    780

gtgacctgtg tggtggtgga cgtgtcccac gaggacccgg aagtgaaatt caattggtac    840

gtggatggag tggaagtgca caacgccaag accaagccac gggaagaaca gtacaactct    900

acctaccgcg tggtgtccgt gctcactgtg ctgcaccaag actggctgaa cgggaaggag    960

tacaagtgca aagtgtccaa caaggcgctg cctgccccaa ttgagaaaac tatctcgaaa   1020

gccaagggac agcctcgaga accacaggtg tacaccctgc ccccatcccg ggatgagctg   1080

ccatacatca tcccaccata caaccaggtc agcctgacct gcctggtcaa aggcttctat   1140

cccagcgaca tcgccgtgga gtgggagagc aatgggcagc cggagaacaa ctacaagacc   1200

acgcctcccg tgctggactc cgacggctcc ttcttcctct acagcaagct caccgtgggc   1260

gcagataggt ggctggaagg gaacgtcttc tcatgctccg tgatgcatga ggcgctgcac   1320

aaccactaca ctcagaagag cttgtccctg tcgcccggt                          1359
```

<210> SEQ ID NO 133
<211> LENGTH: 453
<212> TYPE: PRT
<213> ORGANISM: Artificial Sequence
<220> FEATURE:
<223> OTHER INFORMATION: heavy chain of FS22-172-003-AA/FS28-256-018 mAb2 with LALA

<400> SEQUENCE: 133

```
Glu Val Gln Leu Leu Glu Ser Gly Gly Gly Leu Val Gln Pro Gly Gly
```

-continued

```
1               5                   10                  15

Ser Leu Arg Leu Ser Cys Ala Ala Ser Gly Phe Thr Phe Thr Gln Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr Gln Ile Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Pro Tyr Ile Ile Pro Pro Tyr Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Gly Ala Asp Arg Trp Leu Glu Gly Asn Val Phe Ser Cys
            420                 425                 430
```

```
Ser Val Met His Glu Ala Leu His Asn His Tyr Thr Gln Lys Ser Leu
        435                 440                 445

Ser Leu Ser Pro Gly
    450


<210> SEQ ID NO 134
<211> LENGTH: 1359
<212> TYPE: DNA
<213> ORGANISM: Artificial Sequence
<220> FEATURE:
<223> OTHER INFORMATION: heavy chain of FS22-172-003-AA/FS28-256-018
      mAb2 with LALA

<400> SEQUENCE: 134

gaagtgcaac tgctggagtc cggtggtggt ctggtacagc cgggtggttc tctgcgtctg      60

agttgcgcgg ccagtggctt taccttcact cagacttata tgagctgggt gcgtcaggct     120

ccgggcaaag gtctggaatg ggttagcaat atttctccga cttatagcac taccaactat     180

gcggatagcg tgaaaggccg ttttaccatt tctcgcgaca acagcaagaa cacgctgtac     240

ctgcagatga actcactgcg tgccgaagat acggccgtgt attactgtgc gagatacaac     300

gcttatcaga ttgggttgga ctactggggc cagggaaccc tggtcaccgt ctcgagtgct     360

agcactaagg gcccgtcggt gttcccgctg gccccatcgt ccaagagcac atcagggggt     420

accgccgccc tgggctgcct tgtgaaggat tactttcccg agcccgtcac agtgtcctgg     480

aacagcggag ccctgacctc cggagtgcat actttcccgg ctgtgcttca gtcctctggc     540

ctgtactcat tgtcctccgt ggtcaccgtc ccttcgtcct ccctgggcac ccagacctat     600

atctgtaatg tcaaccataa gccctcgaac accaaggtcg acaagaaggt cgagccgaag     660

tcgtgcgaca agactcacac ttgcccgcct tgcccagccc cggaagctgc cggtggtcct     720

tcggtgttcc tcttcccgcc caagccgaag gataccctga tgatctcacg gacccccgaa     780

gtgacctgtg tggtggtgga cgtgtcccac gaggacccgg aagtgaaatt caattggtac     840

gtggatggag tggaagtgca caacgccaag accaagccac gggaagaaca gtacaactct     900

acctaccgcg tggtgtccgt gctcactgtg ctgcaccaag actggctgaa cgggaaggag     960

tacaagtgca aagtgtccaa caaggcgctg cctgccccaa ttgagaaaac tatctcgaaa    1020

gccaagggac agcctcgaga accacaggtg tacaccctgc ccccatcccg ggatgagctg    1080

ccatacatca tcccaccata caaccaggtc agcctgacct gcctggtcaa aggcttctat    1140

cccagcgaca tcgccgtgga gtgggagagc aatgggcagc cggagaacaa ctacaagacc    1200

acgcctcccg tgctggactc cgacggctcc ttcttcctct acagcaagct caccgtgggc    1260

gcagataggt ggctggaagg gaacgtcttc tcatgctccg tgatgcatga ggcgctgcac    1320

aaccactaca ctcagaagag cttgtccctg tcgcccggt                           1359


<210> SEQ ID NO 135
<211> LENGTH: 446
<212> TYPE: PRT
<213> ORGANISM: Artificial Sequence
<220> FEATURE:
<223> OTHER INFORMATION: heavy chain of FS28m-228 mAb

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

-continued

```
Phe Met Val Trp Val Arg Gln Ala Pro Gly Lys Gly Leu Glu Trp Val
        35                  40                  45

Ser Met Ile Ser Pro Lys Ser Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Phe Thr Pro Ala Arg Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445
```

<210> SEQ ID NO 136
<211> LENGTH: 215
<212> TYPE: PRT
<213> ORGANISM: Artificial Sequence
<220> FEATURE:
<223> OTHER INFORMATION: light chain of FS28m-228 mAb

<400> SEQUENCE: 136

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Pro Phe Pro Phe Ser
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 137
<211> LENGTH: 447
<212> TYPE: PRT
<213> ORGANISM: Artificial Sequence
<220> FEATURE:
<223> OTHER INFORMATION: heavy chain of FS22m-063-AA/FS28m-228 mAb2

<400> SEQUENCE: 137

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Phe Met Val Trp Val Arg Gln Ala Pro Gly Lys Gly Leu Glu Trp Val
        35                  40                  45

Ser Met Ile Ser Pro Lys Ser Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Trp Phe Thr Pro Ala Arg Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Pro Tyr Trp Ser Tyr Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Met Asn Tyr
                405                 410                 415

Arg Trp Glu Leu Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 138
<211> LENGTH: 445
<212> TYPE: PRT
<213> ORGANISM: Artificial Sequence
<220> FEATURE:
<223> OTHER INFORMATION: heavy chain of G1AA/HelD1.3 mAb

<400> SEQUENCE: 138

```
Gln Val Gln Leu Gln Glu Ser Gly Pro Gly Leu Val Arg Pro Ser Gln
1               5                   10                  15
```

-continued

```
Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430
```

```
Asn His Tyr Thr Gln Lys Ser Leu Ser Leu Ser Pro Gly
        435                 440                 445


<210> SEQ ID NO 139
<211> LENGTH: 214
<212> TYPE: PRT
<213> ORGANISM: Artificial Sequence
<220> FEATURE:
<223> OTHER INFORMATION: light chain of G1AA/HelD1.3 mAb

<400> SEQUENCE: 139

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 140
<211> LENGTH: 448
<212> TYPE: PRT
<213> ORGANISM: Artificial Sequence
<220> FEATURE:
<223> OTHER INFORMATION: G1AA/SS1 mAb heavy chain with LALA

<400> SEQUENCE: 140

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80
```

```
Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Ser Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 141
<211> LENGTH: 213
<212> TYPE: PRT
<213> ORGANISM: Artificial Sequence
<220> FEATURE:
<223> OTHER INFORMATION: G1AA/SS1 mAb light chain

<400> SEQUENCE: 141

```
Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Ser Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 142
<211> LENGTH: 303
<212> TYPE: PRT
<213> ORGANISM: Artificial Sequence
<220> FEATURE:
<223> OTHER INFORMATION: Synthetic-Human MSLN (without MPF and C terminus)

<400> SEQUENCE: 142

```
Glu Val Glu Lys Thr Ala Cys Pro Ser Gly Lys Lys Ala Arg Glu Ile
1               5                   10                  15

Asp Glu Ser Leu Ile Phe Tyr Lys Lys Trp Glu Leu Glu Ala Cys Val
            20                  25                  30

Asp Ala Ala Leu Leu Ala Thr Gln Met Asp Arg Val Asn Ala Ile Pro
        35                  40                  45

Phe Thr Tyr Glu Gln Leu Asp Val Leu Lys His Lys Leu Asp Glu Leu
    50                  55                  60

Tyr Pro Gln Gly Tyr Pro Glu Ser Val Ile Gln His Leu Gly Tyr Leu
65                  70                  75                  80

Phe Leu Lys Met Ser Pro Glu Asp Ile Arg Lys Trp Asn Val Thr Ser
                85                  90                  95

Leu Glu Thr Leu Lys Ala Leu Leu Glu Val Asn Lys Gly His Glu Met
            100                 105                 110

Ser Pro Gln Val Ala Thr Leu Ile Asp Arg Phe Val Lys Gly Arg Gly
        115                 120                 125

Gln Leu Asp Lys Asp Thr Leu Asp Thr Leu Thr Ala Phe Tyr Pro Gly
```

```
    130                 135                 140

Tyr Leu Cys Ser Leu Ser Pro Glu Glu Leu Ser Ser Val Pro Pro Ser
145                 150                 155                 160

Ser Ile Trp Ala Val Arg Pro Gln Asp Leu Asp Thr Cys Asp Pro Arg
                165                 170                 175

Gln Leu Asp Val Leu Tyr Pro Lys Ala Arg Leu Ala Phe Gln Asn Met
            180                 185                 190

Asn Gly Ser Glu Tyr Phe Val Lys Ile Gln Ser Phe Leu Gly Gly Ala
        195                 200                 205

Pro Thr Glu Asp Leu Lys Ala Leu Ser Gln Gln Asn Val Ser Met Asp
    210                 215                 220

Leu Ala Thr Phe Met Lys Leu Arg Thr Asp Ala Val Leu Pro Leu Thr
225                 230                 235                 240

Val Ala Glu Val Gln Lys Leu Leu Gly Pro His Val Glu Gly Leu Lys
                245                 250                 255

Ala Glu Glu Arg His Arg Pro Val Arg Asp Trp Ile Leu Arg Gln Arg
            260                 265                 270

Gln Asp Asp Leu Asp Thr Leu Gly Leu Gly Leu Gln Gly Gly Ile Pro
        275                 280                 285

Asn Gly Tyr Leu Val Leu Asp Leu Ser Met Gln Glu Ala Leu Ser
    290                 295                 300


<210> SEQ ID NO 143
<211> LENGTH: 303
<212> TYPE: PRT
<213> ORGANISM: Artificial Sequence
<220> FEATURE:
<223> OTHER INFORMATION: Synthetic-Cynomolgus MSLN (without MPF and C
      terminus)

<400> SEQUENCE: 143

Asp Val Glu Arg Thr Thr Cys Pro Pro Glu Lys Glu Val His Glu Ile
1               5                   10                  15

Asp Glu Ser Leu Ile Phe Tyr Lys Lys Arg Glu Leu Glu Ala Cys Val
            20                  25                  30

Asp Ala Ala Leu Leu Ala Ala Gln Met Asp Arg Val Asp Ala Ile Pro
        35                  40                  45

Phe Thr Tyr Glu Gln Leu Asp Val Leu Lys His Lys Leu Asp Glu Leu
    50                  55                  60

Tyr Pro Gln Gly Tyr Pro Glu Ser Val Ile Arg His Leu Gly His Leu
65                  70                  75                  80

Phe Leu Lys Met Ser Pro Glu Asp Ile Arg Lys Trp Asn Val Thr Ser
                85                  90                  95

Leu Glu Thr Leu Lys Ala Leu Leu Lys Val Ser Lys Gly His Glu Met
            100                 105                 110

Ser Ala Gln Val Ala Thr Leu Ile Asp Arg Val Val Val Gly Arg Gly
        115                 120                 125

Gln Leu Asp Lys Asp Thr Ala Asp Thr Leu Thr Ala Phe Cys Pro Gly
    130                 135                 140

Cys Leu Cys Ser Leu Ser Pro Glu Arg Leu Ser Ser Val Pro Pro Ser
145                 150                 155                 160

Ile Ile Gly Ala Val Arg Pro Gln Asp Leu Asp Thr Cys Gly Pro Arg
                165                 170                 175

Gln Leu Asp Val Leu Tyr Pro Lys Ala Arg Leu Ala Phe Gln Asn Met
            180                 185                 190
```

```
Ser Gly Ser Glu Tyr Phe Val Lys Ile Arg Pro Phe Leu Gly Gly Ala
        195                 200                 205

Pro Thr Glu Asp Leu Lys Ala Leu Ser Gln Gln Asn Val Ser Met Asp
    210                 215                 220

Leu Ala Thr Phe Met Lys Leu Arg Arg Glu Ala Val Leu Pro Leu Ser
225                 230                 235                 240

Val Ala Glu Val Gln Lys Leu Leu Gly Pro His Val Glu Gly Leu Lys
                245                 250                 255

Val Glu Glu Gln His Ser Pro Val Arg Asp Trp Ile Leu Lys Gln Arg
            260                 265                 270

Gln Asp Asp Leu Asp Thr Leu Gly Leu Gly Leu Gln Gly Gly Ile Pro
        275                 280                 285

Asn Gly Tyr Leu Ile Leu Asp Leu Ser Val Arg Glu Ala Leu Ser
    290                 295                 300


<210> SEQ ID NO 144
<211> LENGTH: 303
<212> TYPE: PRT
<213> ORGANISM: Artificial Sequence
<220> FEATURE:
<223> OTHER INFORMATION: Synthetic-Mouse MSLN (without MPF and C
      terminus)

<400> SEQUENCE: 144

Asp Ala Glu Gln Lys Ala Cys Pro Pro Gly Lys Glu Pro Tyr Lys Val
1               5                   10                  15

Asp Glu Asp Leu Ile Phe Tyr Gln Asn Trp Glu Leu Glu Ala Cys Val
            20                  25                  30

Asp Gly Thr Met Leu Ala Arg Gln Met Asp Leu Val Asn Glu Ile Pro
        35                  40                  45

Phe Thr Tyr Glu Gln Leu Ser Ile Phe Lys His Lys Leu Asp Lys Thr
    50                  55                  60

Tyr Pro Gln Gly Tyr Pro Glu Ser Leu Ile Gln Gln Leu Gly His Phe
65                  70                  75                  80

Phe Arg Tyr Val Ser Pro Glu Asp Ile His Gln Trp Asn Val Thr Ser
                85                  90                  95

Pro Asp Thr Val Lys Thr Leu Leu Lys Val Ser Lys Gly Gln Lys Met
            100                 105                 110

Asn Ala Gln Ala Ile Ala Leu Val Ala Cys Tyr Leu Arg Gly Gly Gly
        115                 120                 125

Gln Leu Asp Glu Asp Met Val Lys Ala Leu Gly Asp Ile Pro Leu Ser
    130                 135                 140

Tyr Leu Cys Asp Phe Ser Pro Gln Asp Leu His Ser Val Pro Ser Ser
145                 150                 155                 160

Val Met Trp Leu Val Gly Pro Gln Asp Leu Asp Lys Cys Ser Gln Arg
                165                 170                 175

His Leu Gly Leu Leu Tyr Gln Lys Ala Cys Ser Ala Phe Gln Asn Val
            180                 185                 190

Ser Gly Leu Glu Tyr Phe Glu Lys Ile Lys Thr Phe Leu Gly Gly Ala
        195                 200                 205

Ser Val Lys Asp Leu Arg Ala Leu Ser Gln His Asn Val Ser Met Asp
    210                 215                 220

Ile Ala Thr Phe Lys Arg Leu Gln Val Asp Ser Leu Val Gly Leu Ser
225                 230                 235                 240

Val Ala Glu Val Gln Lys Leu Leu Gly Pro Asn Ile Val Asp Leu Lys
                245                 250                 255
```

```
Thr Glu Glu Asp Lys Ser Pro Val Arg Asp Trp Leu Phe Arg Gln His
            260                 265                 270

Gln Lys Asp Leu Asp Arg Leu Gly Leu Gly Leu Gln Gly Gly Ile Pro
        275                 280                 285

Asn Gly Tyr Leu Val Leu Asp Phe Asn Val Arg Glu Ala Phe Ser
    290                 295                 300


<210> SEQ ID NO 145
<211> LENGTH: 625
<212> TYPE: PRT
<213> ORGANISM: Mus musculus

<400> SEQUENCE: 145

Met Ala Leu Pro Thr Ala Arg Pro Leu Leu Gly Ser Cys Gly Ser Pro
1               5                   10                  15

Ile Cys Ser Arg Ser Phe Leu Leu Leu Leu Leu Ser Leu Gly Trp Ile
            20                  25                  30

Pro Arg Leu Gln Thr Gln Thr Thr Lys Thr Ser Gln Glu Ala Thr Leu
        35                  40                  45

Leu His Ala Val Asn Gly Ala Ala Asp Phe Ala Ser Leu Pro Thr Gly
    50                  55                  60

Leu Phe Leu Gly Leu Thr Cys Glu Glu Val Ser Asp Leu Ser Met Glu
65                  70                  75                  80

Gln Ala Lys Gly Leu Ala Met Ala Val Arg Gln Lys Asn Ile Thr Leu
                85                  90                  95

Arg Gly His Gln Leu Arg Cys Leu Ala Arg Arg Leu Pro Arg His Leu
            100                 105                 110

Thr Asp Glu Glu Leu Asn Ala Leu Pro Leu Asp Leu Leu Leu Phe Leu
        115                 120                 125

Asn Pro Ala Met Phe Pro Gly Gln Gln Ala Cys Ala His Phe Phe Ser
    130                 135                 140

Leu Ile Ser Lys Ala Asn Val Asp Val Leu Pro Arg Arg Ser Leu Glu
145                 150                 155                 160

Arg Gln Arg Leu Leu Met Glu Ala Leu Lys Cys Gln Gly Val Tyr Gly
                165                 170                 175

Phe Gln Val Ser Glu Ala Asp Val Arg Ala Leu Gly Gly Leu Ala Cys
            180                 185                 190

Asp Leu Pro Gly Lys Phe Val Ala Arg Ser Ser Glu Val Leu Leu Pro
        195                 200                 205

Trp Leu Ala Gly Cys Gln Gly Pro Leu Asp Gln Ser Gln Glu Lys Ala
    210                 215                 220

Val Arg Glu Val Leu Arg Ser Gly Arg Thr Gln Tyr Gly Pro Pro Ser
225                 230                 235                 240

Lys Trp Ser Val Ser Thr Leu Asp Ala Leu Gln Ser Leu Val Ala Val
                245                 250                 255

Leu Asp Glu Ser Ile Val Gln Ser Ile Pro Lys Asp Val Lys Ala Glu
            260                 265                 270

Trp Leu Gln His Ile Ser Arg Asp Pro Ser Arg Leu Gly Ser Lys Leu
        275                 280                 285

Thr Val Ile His Pro Arg Phe Arg Arg Asp Ala Glu Gln Lys Ala Cys
    290                 295                 300

Pro Pro Gly Lys Glu Pro Tyr Lys Val Asp Glu Asp Leu Ile Phe Tyr
305                 310                 315                 320

Gln Asn Trp Glu Leu Glu Ala Cys Val Asp Gly Thr Met Leu Ala Arg
```

```
                325                 330                 335

Gln Met Asp Leu Val Asn Glu Ile Pro Phe Thr Tyr Glu Gln Leu Ser
            340                 345                 350

Ile Phe Lys His Lys Leu Asp Lys Thr Tyr Pro Gln Gly Tyr Pro Glu
        355                 360                 365

Ser Leu Ile Gln Gln Leu Gly His Phe Phe Arg Tyr Val Ser Pro Glu
    370                 375                 380

Asp Ile His Gln Trp Asn Val Thr Ser Pro Asp Thr Val Lys Thr Leu
385                 390                 395                 400

Leu Lys Val Ser Lys Gly Gln Lys Met Asn Ala Gln Ala Ile Ala Leu
                405                 410                 415

Val Ala Cys Tyr Leu Arg Gly Gly Gly Gln Leu Asp Glu Asp Met Val
            420                 425                 430

Lys Ala Leu Gly Asp Ile Pro Leu Ser Tyr Leu Cys Asp Phe Ser Pro
        435                 440                 445

Gln Asp Leu His Ser Val Pro Ser Ser Val Met Trp Leu Val Gly Pro
    450                 455                 460

Gln Asp Leu Asp Lys Cys Ser Gln Arg His Leu Gly Leu Leu Tyr Gln
465                 470                 475                 480

Lys Ala Cys Ser Ala Phe Gln Asn Val Ser Gly Leu Glu Tyr Phe Glu
                485                 490                 495

Lys Ile Lys Thr Phe Leu Gly Gly Ala Ser Val Lys Asp Leu Arg Ala
            500                 505                 510

Leu Ser Gln His Asn Val Ser Met Asp Ile Ala Thr Phe Lys Arg Leu
        515                 520                 525

Gln Val Asp Ser Leu Val Gly Leu Ser Val Ala Glu Val Gln Lys Leu
    530                 535                 540

Leu Gly Pro Asn Ile Val Asp Leu Lys Thr Glu Glu Asp Lys Ser Pro
545                 550                 555                 560

Val Arg Asp Trp Leu Phe Arg Gln His Gln Lys Asp Leu Asp Arg Leu
                565                 570                 575

Gly Leu Gly Leu Gln Gly Gly Ile Pro Asn Gly Tyr Leu Val Leu Asp
            580                 585                 590

Phe Asn Val Arg Glu Ala Phe Ser Ser Arg Ala Ser Leu Leu Gly Pro
        595                 600                 605

Gly Phe Val Leu Ile Trp Ile Pro Ala Leu Leu Pro Ala Leu Arg Leu
    610                 615                 620

Ser
625


<210> SEQ ID NO 146
<211> LENGTH: 164
<212> TYPE: PRT
<213> ORGANISM: Artificial Sequence
<220> FEATURE:
<223> OTHER INFORMATION: Synthetic-Extracellular domain of human CD137

<400> SEQUENCE: 146

Ser Leu Gln Asp Pro Cys Ser Asn Cys Pro Ala Gly Thr Phe Cys Asp
1               5                   10                  15

Asn Asn Arg Asn Gln Ile Cys Ser Pro Cys Pro Pro Asn Ser Phe Ser
            20                  25                  30

Ser Ala Gly Gly Gln Arg Thr Cys Asp Ile Cys Arg Gln Cys Lys Gly
        35                  40                  45

Val Phe Arg Thr Arg Lys Glu Cys Ser Ser Thr Ser Asn Ala Glu Cys
```

```
    50                  55                  60

Asp Cys Thr Pro Gly Phe His Cys Leu Gly Ala Gly Cys Ser Met Cys
65                  70                  75                  80

Glu Gln Asp Cys Lys Gln Gly Gln Glu Leu Thr Lys Lys Gly Cys Lys
                85                  90                  95

Asp Cys Cys Phe Gly Thr Phe Asn Asp Gln Lys Arg Gly Ile Cys Arg
            100                 105                 110

Pro Trp Thr Asn Cys Ser Leu Asp Gly Lys Ser Val Leu Val Asn Gly
        115                 120                 125

Thr Lys Glu Arg Asp Val Val Cys Gly Pro Ser Pro Ala Asp Leu Ser
    130                 135                 140

Pro Gly Ala Ser Ser Val Thr Pro Pro Ala Pro Ala Arg Glu Pro Gly
145                 150                 155                 160

His Ser Pro Gln


<210> SEQ ID NO 147
<211> LENGTH: 164
<212> TYPE: PRT
<213> ORGANISM: Artificial Sequence
<220> FEATURE:
<223> OTHER INFORMATION: Synthetic-Extracellular domain of cynomolgus
      CD137

<400> SEQUENCE: 147

Ser Leu Gln Asp Leu Cys Ser Asn Cys Pro Ala Gly Thr Phe Cys Asp
1               5                   10                  15

Asn Asn Arg Ser Gln Ile Cys Ser Pro Cys Pro Pro Asn Ser Phe Ser
            20                  25                  30

Ser Ala Gly Gly Gln Arg Thr Cys Asp Ile Cys Arg Gln Cys Lys Gly
        35                  40                  45

Val Phe Lys Thr Arg Lys Glu Cys Ser Ser Thr Ser Asn Ala Glu Cys
    50                  55                  60

Asp Cys Ile Ser Gly Tyr His Cys Leu Gly Ala Glu Cys Ser Met Cys
65                  70                  75                  80

Glu Gln Asp Cys Lys Gln Gly Gln Glu Leu Thr Lys Lys Gly Cys Lys
                85                  90                  95

Asp Cys Cys Phe Gly Thr Phe Asn Asp Gln Lys Arg Gly Ile Cys Arg
            100                 105                 110

Pro Trp Thr Asn Cys Ser Leu Asp Gly Lys Ser Val Leu Val Asn Gly
        115                 120                 125

Thr Lys Glu Arg Asp Val Val Cys Gly Pro Ser Pro Ala Asp Leu Ser
    130                 135                 140

Pro Gly Ala Ser Ser Ala Thr Pro Pro Ala Pro Ala Arg Glu Pro Gly
145                 150                 155                 160

His Ser Pro Gln


<210> SEQ ID NO 148
<211> LENGTH: 165
<212> TYPE: PRT
<213> ORGANISM: Artificial Sequence
<220> FEATURE:
<223> OTHER INFORMATION: Synthetic-Extracellular domain of mouse CD137

<400> SEQUENCE: 148

Ala Val Gln Asn Ser Cys Asp Asn Cys Gln Pro Gly Thr Phe Cys Arg
1               5                   10                  15

Lys Tyr Asn Pro Val Cys Lys Ser Cys Pro Pro Ser Thr Phe Ser Ser
```

```
            20                  25                  30

Ile Gly Gly Gln Pro Asn Cys Asn Ile Cys Arg Val Cys Ala Gly Tyr
        35                  40                  45

Phe Arg Phe Lys Lys Phe Cys Ser Ser Thr His Asn Ala Glu Cys Glu
    50                  55                  60

Cys Ile Glu Gly Phe His Cys Leu Gly Pro Gln Cys Thr Arg Cys Glu
65                  70                  75                  80

Lys Asp Cys Arg Pro Gly Gln Glu Leu Thr Lys Gln Gly Cys Lys Thr
                85                  90                  95

Cys Ser Leu Gly Thr Phe Asn Asp Gln Asn Gly Thr Gly Val Cys Arg
            100                 105                 110

Pro Trp Thr Asn Cys Ser Leu Asp Gly Arg Ser Val Leu Lys Thr Gly
        115                 120                 125

Thr Thr Glu Lys Asp Val Val Cys Gly Pro Pro Val Val Ser Phe Ser
    130                 135                 140

Pro Ser Thr Thr Ile Ser Val Thr Pro Glu Gly Gly Pro Gly Gly His
145                 150                 155                 160

Ser Leu Gln Val Leu
                165


<210> SEQ ID NO 149
<211> LENGTH: 232
<212> TYPE: PRT
<213> ORGANISM: Artificial Sequence
<220> FEATURE:
<223> OTHER INFORMATION: Synthetic-Human CD137

<400> SEQUENCE: 149

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln Ile Ile Ser Phe Phe Leu Ala Leu Thr Ser Thr Ala Leu
                165                 170                 175

Leu Phe Leu Leu Phe Phe Leu Thr Leu Arg Phe Ser Val Val Lys Arg
            180                 185                 190

Gly Arg Lys Lys Leu Leu Tyr Ile Phe Lys Gln Pro Phe Met Arg Pro
        195                 200                 205

Val Gln Thr Thr Gln Glu Glu Asp Gly Cys Ser Cys Arg Phe Pro Glu
```

```
    210                 215                 220

Glu Glu Glu Gly Gly Cys Glu Leu
225                 230


<210> SEQ ID NO 150
<211> LENGTH: 233
<212> TYPE: PRT
<213> ORGANISM: Artificial Sequence
<220> FEATURE:
<223> OTHER INFORMATION: Synthetic-Mouse CD137

<400> SEQUENCE: 150

Val Gln Asn Ser Cys Asp Asn Cys Gln Pro Gly Thr Phe Cys Arg Lys
1               5                   10                  15

Tyr Asn Pro Val Cys Lys Ser Cys Pro Pro Ser Thr Phe Ser Ser Ile
            20                  25                  30

Gly Gly Gln Pro Asn Cys Asn Ile Cys Arg Val Cys Ala Gly Tyr Phe
        35                  40                  45

Arg Phe Lys Lys Phe Cys Ser Ser Thr His Asn Ala Glu Cys Glu Cys
    50                  55                  60

Ile Glu Gly Phe His Cys Leu Gly Pro Gln Cys Thr Arg Cys Glu Lys
65                  70                  75                  80

Asp Cys Arg Pro Gly Gln Glu Leu Thr Lys Gln Gly Cys Lys Thr Cys
                85                  90                  95

Ser Leu Gly Thr Phe Asn Asp Gln Asn Gly Thr Gly Val Cys Arg Pro
            100                 105                 110

Trp Thr Asn Cys Ser Leu Asp Gly Arg Ser Val Leu Lys Thr Gly Thr
        115                 120                 125

Thr Glu Lys Asp Val Val Cys Gly Pro Pro Val Val Ser Phe Ser Pro
    130                 135                 140

Ser Thr Thr Ile Ser Val Thr Pro Glu Gly Gly Pro Gly Gly His Ser
145                 150                 155                 160

Leu Gln Val Leu Thr Leu Phe Leu Ala Leu Thr Ser Ala Leu Leu Leu
                165                 170                 175

Ala Leu Ile Phe Ile Thr Leu Leu Phe Ser Val Leu Lys Trp Ile Arg
            180                 185                 190

Lys Lys Phe Pro His Ile Phe Lys Gln Pro Phe Lys Lys Thr Thr Gly
        195                 200                 205

Ala Ala Gln Glu Glu Asp Ala Cys Ser Cys Arg Cys Pro Gln Glu Glu
    210                 215                 220

Glu Gly Gly Gly Gly Gly Tyr Glu Leu
225                 230


<210> SEQ ID NO 151
<211> LENGTH: 622
<212> TYPE: PRT
<213> ORGANISM: Artificial Sequence
<220> FEATURE:
<223> OTHER INFORMATION: Synthetic-Human MPF + MSLN

<400> SEQUENCE: 151

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45
```

-continued

```
Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
```

-continued

```
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
    610                 615                 620


<210> SEQ ID NO 152
<211> LENGTH: 622
<212> TYPE: PRT
<213> ORGANISM: Artificial Sequence
<220> FEATURE:
<223> OTHER INFORMATION: Synthetic-Cynomolgus MPF + MSLN

<400> SEQUENCE: 152

Met Ala Leu Pro Met Ala Arg Pro Leu Ser Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Val Leu Ala Gly Glu Thr Arg Gln Glu Ala Ala Pro Leu
        35                  40                  45

Asp Gly Ile Leu Thr Asn Ala Pro Asp Ile Ala Ser Leu Ser Pro Arg
    50                  55                  60

Gln Leu Leu Gly Phe Thr Cys Val Glu Val Ser Gly Leu Ser Thr Glu
65                  70                  75                  80

Leu Val Gln Glu Leu Ala Val Ala Leu Gly Gln Lys Asn Val Lys Leu
                85                  90                  95

Ser Ala Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr His Phe Phe Ser Arg Val
    130                 135                 140

Ala Lys Ala Asn Val Asp Leu Leu Pro Arg Gly Ala Pro Glu Arg Gln
145                 150                 155                 160

Arg Leu Leu Pro Ala Ala Leu Thr Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Val Leu Pro Arg Leu
        195                 200                 205

Val Arg Cys Leu Gly Pro Leu Asp Gln Asp Gln Gln Glu Ala Ala Arg
```

```
    210                 215                 220

Ala Ala Leu Gln Arg Gly Gly Pro Pro Tyr Gly Pro Pro Ser Thr Trp
225                 230                 235                 240

Ser Ile Ser Thr Leu Asp Asp Leu Gln Ser Leu Leu Pro Val Leu Gly
                245                 250                 255

Gln Pro Val Ile His Ser Ile Pro Gln Gly Ile Leu Ala Ala Trp Arg
            260                 265                 270

Gln Arg Ser Ser Arg Asp Pro Ser Trp Gln Gln Pro Glu Gln Thr Val
        275                 280                 285

Leu Arg Pro Arg Phe Arg Arg Asp Val Glu Arg Thr Thr Cys Pro Pro
    290                 295                 300

Glu Lys Glu Val His Glu Ile Asp Glu Ser Leu Ile Phe Tyr Lys Lys
305                 310                 315                 320

Arg Glu Leu Glu Ala Cys Val Asp Ala Ala Leu Leu Ala Ala Gln Met
                325                 330                 335

Asp Arg Val Asp Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Arg His Leu Gly His Leu Phe Leu Lys Met Ser Pro Glu Asp Ile
    370                 375                 380

Arg Lys Trp Asn Val Thr Ser Leu Glu Thr Leu Lys Ala Leu Leu Lys
385                 390                 395                 400

Val Ser Lys Gly His Glu Met Ser Ala Gln Val Ala Thr Leu Ile Asp
                405                 410                 415

Arg Val Val Val Gly Arg Gly Gln Leu Asp Lys Asp Thr Ala Asp Thr
            420                 425                 430

Leu Thr Ala Phe Cys Pro Gly Cys Leu Cys Ser Leu Ser Pro Glu Arg
        435                 440                 445

Leu Ser Ser Val Pro Pro Ser Ile Ile Gly Ala Val Arg Pro Gln Asp
    450                 455                 460

Leu Asp Thr Cys Gly Pro Arg Gln Leu Asp Val Leu Tyr Pro Lys Ala
465                 470                 475                 480

Arg Leu Ala Phe Gln Asn Met Ser Gly Ser Glu Tyr Phe Val Lys Ile
                485                 490                 495

Arg Pro Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Arg
        515                 520                 525

Glu Ala Val Leu Pro Leu Ser Val Ala Glu Val Gln Lys Leu Leu Gly
    530                 535                 540

Pro His Val Glu Gly Leu Lys Val Glu Glu Gln His Ser Pro Val Arg
545                 550                 555                 560

Asp Trp Ile Leu Lys Gln Arg Gln Asp Asp Leu Asp Thr Leu Gly Leu
                565                 570                 575

Gly Leu Gln Gly Gly Ile Pro Asn Gly Tyr Leu Ile Leu Asp Leu Ser
            580                 585                 590

Val Arg Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
    610                 615                 620
```

<210> SEQ ID NO 153

<211> LENGTH: 231
<212> TYPE: PRT
<213> ORGANISM: Artificial Sequence
<220> FEATURE:
<223> OTHER INFORMATION: Synthetic-Cynomolgus CD137

<400> SEQUENCE: 153

```
Leu Gln Asp Leu Cys Ser Asn Cys Pro Ala Gly Thr Phe Cys Asp Asn
1               5                   10                  15

Asn Arg Ser Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Lys Thr Arg Lys Glu Cys Ser Ser Thr Ser Asn Ala Glu Cys Asp
    50                  55                  60

Cys Ile Ser Gly Tyr His Cys Leu Gly Ala Glu Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Ala Thr Pro Pro Ala Pro Ala Arg Glu Pro Gly His
145                 150                 155                 160

Ser Pro Gln Ile Ile Phe Phe Leu Ala Leu Thr Ser Thr Val Val Leu
                165                 170                 175

Phe Leu Leu Phe Phe Leu Val Leu Arg Phe Ser Val Val Lys Arg Ser
            180                 185                 190

Arg Lys Lys Leu Leu Tyr Ile Phe Lys Gln Pro Phe Met Arg Pro Val
        195                 200                 205

Gln Thr Thr Gln Glu Glu Asp Gly Cys Ser Cys Arg Phe Pro Glu Glu
    210                 215                 220

Glu Glu Gly Gly Cys Glu Leu
225                 230
```

<210> SEQ ID NO 154
<211> LENGTH: 110
<212> TYPE: PRT
<213> ORGANISM: Artificial Sequence
<220> FEATURE:
<223> OTHER INFORMATION: wild-type CH2 domain

<400> SEQUENCE: 154

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
```

```
                85                  90                  95

Ala Leu Pro Ala Pro Ile Glu Lys Thr Ile Ser Lys Ala Lys
            100                 105                 110


<210> SEQ ID NO 155
<211> LENGTH: 110
<212> TYPE: PRT
<213> ORGANISM: Artificial Sequence
<220> FEATURE:
<223> OTHER INFORMATION: CH2 domain containing LALA mutation

<400> SEQUENCE: 155

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110


<210> SEQ ID NO 156
<211> LENGTH: 110
<212> TYPE: PRT
<213> ORGANISM: Artificial Sequence
<220> FEATURE:
<223> OTHER INFORMATION: CH2 domain containing LALA-PA mutation

<400> SEQUENCE: 156

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Ala Ala Pro Ile Glu Lys Thr Ile Ser Lys Ala Lys
            100                 105                 110


<210> SEQ ID NO 157
<211> LENGTH: 9
<212> TYPE: PRT
<213> ORGANISM: Artificial Sequence
<220> FEATURE:
<223> OTHER INFORMATION: WT Fcab CD loop

<400> SEQUENCE: 157

Ser Asn Gly Gln Pro Glu Asn Asn Tyr
1               5
```

<210> SEQ ID NO 158
<211> LENGTH: 453
<212> TYPE: PRT
<213> ORGANISM: Artificial Sequence
<220> FEATURE:
<223> OTHER INFORMATION: heavy chain of FS22-172-003-AA/FS28-256-272
      mAb2 with LALA

<400> SEQUENCE: 158

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser His Ile Ser Pro Thr Tyr Ser Thr Thr Asn Tyr Ala Asp Ser Val
    50                  55                  60

Lys Gly Arg Phe Thr Ile Ser Arg Asp Asn Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Pro Tyr Ile Ile Pro Pro Tyr Asn
```

```
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Gly Ala Asp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450
```

<210> SEQ ID NO 159
<211> LENGTH: 1359
<212> TYPE: DNA
<213> ORGANISM: Artificial Sequence
<220> FEATURE:
<223> OTHER INFORMATION: heavy chain of FS22-172-003-AA/FS28-256-272 mAb2 with LALA

<400> SEQUENCE: 159

```
gaagtgcaac tgctggagtc cggtggtggt ctggtacagc cgggtggttc tctgcgtctg     60

agttgcgcgg ccagtggctt taccttcact catacttata tgagctgggt gcgtcaggct    120

ccgggcaaag gtctggaatg ggttagccat atttctccga cttatagcac taccaactat    180

gcggatagcg tgaaaggccg ttttaccatt tctcgcgaca acaacaagaa cacgctgtac    240

ctgcagatga actcactgcg tgccgaagat acggccgtgt attactgtgc gagatacaac    300

gcgtatcatg ctgctctgga ctactggggc cagggaaccc tggtcaccgt ctcgagtgct    360

agcactaagg gcccgtcggt gttcccgctg gccccatcgt ccaagagcac atcagggggt    420

accgccgccc tgggctgcct tgtgaaggat tactttcccg agcccgtcac agtgtcctgg    480

aacagcggag ccctgacctc cggagtgcat actttcccgg ctgtgcttca gtcctctggc    540

ctgtactcat tgtcctccgt ggtcaccgtc ccttcgtcct ccctgggcac ccagacctat    600

atctgtaatg tcaaccataa gccctcgaac accaaggtcg acaagaaggt cgagccgaag    660

tcgtgcgaca agactcacac ttgcccgcct tgcccagccc cggaagctgc cggtggtcct    720

tcggtgttcc tcttcccgcc caagccgaag gataccctga tgatctcacg gacccccgaa    780

gtgacctgtg tggtggtgga cgtgtcccac gaggacccgg aagtgaaatt caattggtac    840

gtggatggag tggaagtgca caacgccaag accaagccac gggaagaaca gtacaactct    900

acctaccgcg tggtgtccgt gctcactgtg ctgcaccaag actggctgaa cgggaaggag    960

tacaagtgca aagtgtccaa caaggcgctg cctgccccaa ttgagaaaac tatctcgaaa   1020

gccaagggac agcctcgaga accacaggtg tacaccctgc ccccatcccg ggatgagctg   1080

ccatacatca tcccaccata caaccaggtc agcctgacct gcctggtcaa aggcttctat   1140

cccagcgaca tcgccgtgga gtgggagagc aatgggcagc cggagaacaa ctacaagacc   1200

acgcctcccg tgctggactc cgacggctcc ttcttcctct acagcaagct caccgtgggc   1260

gcagataggt ggctggaagg gaacgtcttc tcatgctccg tgatgcatga ggcgctgcac   1320

aaccactaca ctcagaagag cttgtccctg tcgcccggt                          1359
```

<210> SEQ ID NO 160

<211> LENGTH: 17
<212> TYPE: PRT
<213> ORGANISM: Artificial Sequence
<220> FEATURE:
<223> OTHER INFORMATION: heavy chain of FS22-172-003-AA/FS28-256-272
mAb2 HCDR2 (Kabat)

<400> SEQUENCE: 160

His Ile Ser Pro Thr Tyr Ser Thr Thr Asn Tyr Ala Asp Ser Val Lys
1 5 10 15

Gly

<210> SEQ ID NO 161
<211> LENGTH: 453
<212> TYPE: PRT
<213> ORGANISM: Artificial Sequence
<220> FEATURE:
<223> OTHER INFORMATION: heavy chain of FS22-172-003-AA/FS28-256-273
mAb2 without LALA

<400> SEQUENCE: 161

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Thr His Thr
20 25 30

Tyr Met Ser Trp Val Arg Gln Ala Pro Gly Lys Gly Leu Glu Trp Val
35 40 45

Ser Ser Ile Ser Pro Thr Tyr Ser Thr Thr Asn Tyr Ala Asp Ser Val
50 55 60

Lys Gly Arg Phe Thr Ile Ser Arg Asp Asn Asn Lys Asn Thr Leu Tyr
65 70 75 80

Leu Gln Met Asn Ser Leu Arg Ala Glu Asp Thr Ala Val Tyr Tyr Cys
85 90 95

Ala Arg Tyr Asn Ala Tyr His Ala Ala Leu Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Pro Tyr Ile Ile Pro Pro Tyr Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Gly Ala Asp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 162
<211> LENGTH: 1359
<212> TYPE: DNA
<213> ORGANISM: Artificial Sequence
<220> FEATURE:
<223> OTHER INFORMATION: heavy chain of FS22-172-003-AA/FS28-256-273
      mAb2 without LALA

<400> SEQUENCE: 162

gaagtgcaac tgctggagtc cggtggtggt ctggtacagc cgggtggttc tctgcgtctg     60

agttgcgcgg ccagtggctt taccttcact catacttata tgagctgggt gcgtcaggct    120

ccgggcaaag gtctggaatg ggttagctcg atttctccga cttatagcac taccaactat    180

gcggatagcg tgaaaggccg ttttaccatt tctcgcgaca acaacaagaa cacgctgtac    240

ctgcagatga actcactgcg tgccgaagat acggccgtgt attactgtgc gagatacaac    300

gcgtatcatg ctgctctgga ctactggggc cagggaaccc tggtcaccgt ctcgagtgct    360

agcactaagg gcccgtcggt gttcccgctg gccccatcgt ccaagagcac atcagggggt    420

accgccgccc tgggctgcct tgtgaaggat tactttcccg agcccgtcac agtgtcctgg    480

aacagcggag ccctgacctc cggagtgcat actttcccgg ctgtgcttca gtcctctggc    540

ctgtactcat tgtcctccgt ggtcaccgtc ccttcgtcct ccctgggcac ccagacctat    600

atctgtaatg tcaaccataa gccctcgaac accaaggtcg acaagaaggt cgagccgaag    660

tcgtgcgaca agactcacac ttgcccgcct tgcccagccc cggaactgct gggtggtcct    720

tcggtgttcc tcttcccgcc caagccgaag gataccctga tgatctcacg gacccccgaa    780

gtgacctgtg tggtggtgga cgtgtcccac gaggacccgg aagtgaaatt caattggtac    840

gtggatggag tggaagtgca caacgccaag accaagccac gggaagaaca gtacaactct    900

acctaccgcg tggtgtccgt gctcactgtg ctgcaccaag actggctgaa cgggaaggag    960

tacaagtgca aagtgtccaa caaggcgctg cctgccccaa ttgagaaaac tatctcgaaa   1020

gccaagggac agcctcgaga accacaggtg tacaccctgc ccccatcccg ggatgagctg   1080
```

```
ccatacatca tcccaccata caaccaggtc agcctgacct gcctggtcaa aggcttctat   1140

cccagcgaca tcgccgtgga gtgggagagc aatgggcagc cggagaacaa ctacaagacc   1200

acgcctcccg tgctggactc cgacggctcc ttcttcctct acagcaagct caccgtgggc   1260

gcagataggt ggctggaagg gaacgtcttc tcatgctccg tgatgcatga ggcgctgcac   1320

aaccactaca ctcagaagag cttgtccctg tcgcccggt                          1359
```

<210> SEQ ID NO 163
<211> LENGTH: 453
<212> TYPE: PRT
<213> ORGANISM: Artificial Sequence
<220> FEATURE:
<223> OTHER INFORMATION: heavy chain of FS22-172-003-AA/FS28-256-273 mAb2 with LALA

<400> SEQUENCE: 163

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Ser Ile Ser Pro Thr Tyr Ser Thr Thr Asn Tyr Ala Asp Ser Val
    50                  55                  60

Lys Gly Arg Phe Thr Ile Ser Arg Asp Asn Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

-continued

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Pro Tyr Ile Ile Pro Pro Tyr Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Gly Ala Asp Arg Trp Leu Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450
```

<210> SEQ ID NO 164
<211> LENGTH: 1359
<212> TYPE: DNA
<213> ORGANISM: Artificial Sequence
<220> FEATURE:
<223> OTHER INFORMATION: heavy chain of FS22-172-003-AA/FS28-256-273
      mAb2 with LALA

<400> SEQUENCE: 164

```
gaagtgcaac tgctggagtc cggtggtggt ctggtacagc cgggtggttc tctgcgtctg      60

agttgcgcgg ccagtggctt taccttcact catacttata tgagctgggt gcgtcaggct     120

ccgggcaaag gtctggaatg ggttagctcg atttctccga cttatagcac taccaactat     180

gcggatagcg tgaaaggccg ttttaccatt tctcgcgaca acaacaagaa cacgctgtac     240

ctgcagatga actcactgcg tgccgaagat acggccgtgt attactgtgc gagatacaac     300

gcgtatcatg ctgctctgga ctactggggc cagggaaccc tggtcaccgt ctcgagtgct     360

agcactaagg gcccgtcggt gttcccgctg gccccatcgt ccaagagcac atcagggggt     420

accgccgccc tgggctgcct tgtgaaggat tactttcccg agcccgtcac agtgtcctgg     480

aacagcggag ccctgacctc cggagtgcat actttcccgg ctgtgcttca gtcctctggc     540

ctgtactcat tgtcctccgt ggtcaccgtc ccttcgtcct ccctgggcac ccagacctat     600

atctgtaatg tcaaccataa gccctcgaac accaaggtcg acaagaaggt cgagccgaag     660

tcgtgcgaca agactcacac ttgcccgcct tgcccagccc cggaagctgc cggtggtcct     720

tcggtgttcc tcttcccgcc caagccgaag gataccctga tgatctcacg gaccccccgaa     780

gtgacctgtg tggtggtgga cgtgtcccac gaggacccgg aagtgaaatt caattggtac     840

gtggatggag tggaagtgca caacgccaag accaagccac gggaagaaca gtacaactct     900

acctaccgcg tggtgtccgt gctcactgtg ctgcaccaag actggctgaa cgggaaggag     960

tacaagtgca aagtgtccaa caaggcgctg cctgccccaa ttgagaaaac tatctcgaaa    1020

gccaagggac agcctcgaga accacaggtg tacaccctgc ccccatcccg ggatgagctg    1080

ccatacatca tcccaccata caaccaggtc agcctgacct gcctggtcaa aggcttctat    1140
```

```
cccagcgaca tcgccgtgga gtgggagagc aatgggcagc cggagaacaa ctacaagacc   1200

acgcctcccg tgctggactc cgacggctcc ttcttcctct acagcaagct caccgtgggc   1260

gcagataggt ggctggaagg gaacgtcttc tcatgctccg tgatgcatga ggcgctgcac   1320

aaccactaca ctcagaagag cttgtccctg tcgcccggt                          1359


<210> SEQ ID NO 165
<211> LENGTH: 17
<212> TYPE: PRT
<213> ORGANISM: Artificial Sequence
<220> FEATURE:
<223> OTHER INFORMATION: heavy chain of FS22-172-003-AA/FS28-256-273
      mAb2 HCDR2 (Kabat)

<400> SEQUENCE: 165

Ser Ile Ser Pro Thr Tyr Ser Thr Thr Asn Tyr Ala Asp Ser Val Lys
1               5                   10                  15

Gly


<210> SEQ ID NO 166
<211> LENGTH: 447
<212> TYPE: PRT
<213> ORGANISM: Artificial Sequence
<220> FEATURE:
<223> OTHER INFORMATION: heavy chain of FS22m-063-AA/FS28m-228-010 mAb2
      with LALA

<400> SEQUENCE: 166

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Phe Met Val Trp Val Arg Gln Ala Pro Gly Lys Gly Leu Glu Trp Val
        35                  40                  45

Ser Met Ile Ser Pro Lys Ser Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr His Ile Ser Pro Arg Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Pro Tyr Trp Ser Tyr Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Met Asn Tyr
                405                 410                 415

Arg Trp Glu Leu Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 167
<211> LENGTH: 445
<212> TYPE: PRT
<213> ORGANISM: Artificial Sequence
<220> FEATURE:
<223> OTHER INFORMATION: heavy chain of FS22m-063-AA/HelD1.3 mAb2

<400> SEQUENCE: 167

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Pro Tyr Trp Ser Tyr Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Met Asn Tyr Arg Trp
                405                 410                 415

Glu Leu Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 168
<211> LENGTH: 214
<212> TYPE: PRT
<213> ORGANISM: Artificial Sequence
<220> FEATURE:
<223> OTHER INFORMATION: light chain of FS22m-063-AA/HelD1.3 mAb2

<400> SEQUENCE: 168

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80
```

```
Glu Asp Phe Gly Ser Tyr Tyr Cys Gln His Phe Trp Ser Thr Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 169
<211> LENGTH: 457
<212> TYPE: PRT
<213> ORGANISM: Artificial Sequence
<220> FEATURE:
<223> OTHER INFORMATION: FS22-172-003-AA/FS28-185-002 mAb2 heavy chain
      with LALA

<400> SEQUENCE: 169

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Thr Ser
            20                  25                  30

Ala Met Ser Trp Val Arg Gln Ala Pro Gly Lys Gly Leu Glu Trp Val
        35                  40                  45

Ser Arg Ile Asn Pro Tyr Glu Gly Glu Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Ser Ser Asp Thr Trp Phe Lys Ser Ala Thr Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
```

```
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Pro Tyr Ile Ile
        355                 360                 365

Pro Pro Tyr Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Gly Ala Asp Arg Trp Leu Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
    450                 455
```

<210> SEQ ID NO 170
<211> LENGTH: 1371
<212> TYPE: DNA
<213> ORGANISM: Artificial Sequence
<220> FEATURE:
<223> OTHER INFORMATION: FS22-172-003-AA/FS28-185-002 mAb2 heavy chain with LALA

<400> SEQUENCE: 170

```
gaagtgcaac tgctggagtc cggtggtggt ctggtacagc cgggtggttc tctgcgtctg     60

agttgcgcgg ccagtggctt taccttcact acatctgcta tgagctgggt gcgtcaggct    120

ccgggcaaag gtctggaatg ggttagcagg attaatccgt atgagggcga gaccaactat    180

gcggatagcg tgaaaggccg ttttaccatt tctcgcgaca acagcaagaa cacgctgtac    240

ctgcagatga actcactgcg tgccgaagat acggccgtgt attactgtgc gagaggttgg    300

tctagtgata cgtggtttaa atctgccacg gactactggg gccagggaac cctggtcacc    360

gtctcgagtg ctagcactaa gggcccgtcg gtgttcccgc tggccccatc gtccaagagc    420

acatcagggg gtaccgccgc cctgggctgc cttgtgaagg attactttcc cgagcccgtc    480

acagtgtcct ggaacagcgg agccctgacc tccggagtgc atactttccc ggctgtgctt    540

cagtcctctg gcctgtactc attgtcctcc gtggtcaccg tcccttcgtc ctccctgggc    600

acccagacct atatctgtaa tgtcaaccat aagccctcga acaccaaggt cgacaagaag    660
```

gtcgagccga agtcgtgcga caagactcac acttgcccgc cttgcccagc cccggaagct 720
gccggtggtc cttcggtgtt cctcttcccg cccaagccga aggataccct gatgatctca 780
cggacccccg aagtgacctg tgtggtggtg gacgtgtccc acgaggaccc ggaagtgaaa 840
ttcaattggt acgtggatgg agtggaagtg cacaacgcca agaccaagcc acgggaagaa 900
cagtacaact ctacctaccg cgtggtgtcc gtgctcactg tgctgcacca agactggctg 960
aacgggaagg agtacaagtg caaagtgtcc aacaaggcgc tgcctgcccc aattgagaaa 1020
actatctcga aagccaaggg acagcctcga gaaccacagg tgtacaccct gcccccatcc 1080
cgggatgagc tgccatacat catcccacca tacaaccagg tcagcctgac ctgcctggtc 1140
aaaggcttct atcccagcga catcgccgtg gagtgggaga gcaatgggca gccggagaac 1200
aactacaaga ccacgcctcc cgtgctggac tccgacggct ccttcttcct ctacagcaag 1260
ctcaccgtgg gcgcagatag gtggctggaa gggaacgtct tctcatgctc cgtgatgcat 1320
gaggcgctgc acaaccacta cactcagaag agcttgtccc tgtcgcccgg t 1371

<210> SEQ ID NO 171
<211> LENGTH: 216
<212> TYPE: PRT
<213> ORGANISM: Artificial Sequence
<220> FEATURE:
<223> OTHER INFORMATION: FS22-172-003-AA/FS28-185-002 mAb2 light chain

<400> SEQUENCE: 171

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Ser Ser Tyr Ser Ala
85 90 95

Pro Val Thr Phe Gly Gln Gly Thr Lys Val Glu Ile Lys Arg Thr Val
100 105 110

Ala Ala Pro Ser Val Phe Ile Phe Pro Pro Ser Asp Glu Gln Leu Lys
115 120 125

Ser Gly Thr Ala Ser Val Val Cys Leu Leu Asn Asn Phe Tyr Pro Arg
130 135 140

Glu Ala Lys Val Gln Trp Lys Val Asp Asn Ala Leu Gln Ser Gly Asn
145 150 155 160

Ser Gln Glu Ser Val Thr Glu Gln Asp Ser Lys Asp Ser Thr Tyr Ser
165 170 175

Leu Ser Ser Thr Leu Thr Leu Ser Lys Ala Asp Tyr Glu Lys His Lys
180 185 190

Val Tyr Ala Cys Glu Val Thr His Gln Gly Leu Ser Ser Pro Val Thr
195 200 205

Lys Ser Phe Asn Arg Gly Glu Cys
210 215

<210> SEQ ID NO 172

<211> LENGTH: 648
<212> TYPE: DNA
<213> ORGANISM: Artificial Sequence
<220> FEATURE:
<223> OTHER INFORMATION: FS22-172-003-AA/FS28-185-002 mAb2 light chain

<400> SEQUENCE: 172
gaaattgtgc tgacccagtc tccgggcacg ttatctctga gccctggtga gcgcgccact 60
ctgtcatgcc gggcttctca aagtgttagc agtagctacc tggcgtggta tcagcaaaaa 120
ccgggccagg ccccgcgtct gctgatttac ggtgcatcca gccgtgccac cggcattcca 180
gatcgttttt ccggtagtgg ttctgggacg gacttcactc tgacaatctc acgcctggaa 240
ccggaggatt ttgcggtgta ttactgccag caatcttctt attctgctcc tgtcacgttc 300
ggccaaggga ccaaggtgga aatcaaacgt actgtggccg ctcctagcgt gttcattttt 360
ccgccatccg acgagcagct caagtccggc accgcctccg tggtctgcct gctcaacaac 420
ttctaccctc gcgaagctaa ggtccagtgg aaggtcgaca atgccctgca gtccggaaac 480
tcgcaggaaa gcgtgactga acaggactcc aaggactcca cctattcact gtcctcgact 540
ctgaccctga gcaaggcgga ttacgaaaag cacaaagtgt acgcatgcga agtgacccac 600
cagggtcttt cgtcccccgt gaccaagagc ttcaacagag gagagtgt 648

<210> SEQ ID NO 173
<211> LENGTH: 457
<212> TYPE: PRT
<213> ORGANISM: Artificial Sequence
<220> FEATURE:
<223> OTHER INFORMATION: FS22-172-003-AA/FS28-185-003 mAb2 heavy chain
with LALA

<400> SEQUENCE: 173

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Thr Thr Ser
20 25 30

Ala Met Ser Trp Val Arg Gln Ala Pro Gly Lys Gly Leu Glu Trp Val
35 40 45

Ser Arg Ile Asn Pro Tyr Glu Gly Glu Thr Asn Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Trp Ser Ala Thr Ser Tyr Phe Lys Ser Ala Thr Asp Tyr
100 105 110

Trp Gly Gln Gly Thr Leu Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

```
Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Pro Tyr Ile Ile
        355                 360                 365

Pro Pro Tyr Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Gly Ala Asp Arg Trp Leu Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
    450                 455
```

<210> SEQ ID NO 174
<211> LENGTH: 1371
<212> TYPE: DNA
<213> ORGANISM: Artificial Sequence
<220> FEATURE:
<223> OTHER INFORMATION: FS22-172-003-AA/FS28-185-003 mAb2 heavy chain
with LALA

<400> SEQUENCE: 174

```
gaagtgcaac tgttggagtc cggtggtggt ctggtacagc cgggtggttc tctgcgtctg      60

agttgcgcgg ccagtggctt taccttcact acatctgcta tgagctgggt gcgtcaggct     120

ccgggcaaag gtctggaatg ggttagcagg attaatccgt atgagggcga gaccaactat     180

gcggatagcg tgaaaggccg ttttaccatt tctcgcgaca acagcaagaa cacgctgtac     240

ctgcagatga actcactgcg tgccgaagat acggccgtgt attactgtgc gagaggttgg     300

tctgcgacga gttattttaa atctgccact gactactggg gccagggaac cctggtcacc     360

gtctcgagtg ctagcactaa gggcccgtcg gtgttcccgc tggccccatc gtccaagagc     420

acatcagggg gtaccgccgc cctgggctgc cttgtgaagg attactttcc cgagcccgtc     480

acagtgtcct ggaacagcgg agccctgacc tccggagtgc atactttccc ggctgtgctt     540

cagtcctctg gcctgtactc attgtcctcc gtggtcaccg tcccttcgtc ctccctgggc     600
```

```
acccagacct atatctgtaa tgtcaaccat aagccctcga acaccaaggt cgacaagaag    660

gtcgagccga agtcgtgcga caagactcac acttgcccgc cttgcccagc cccggaagct    720

gccggtggtc cttcggtgtt cctcttcccg cccaagccga aggataccct gatgatctca    780

cggacccccg aagtgacctg tgtggtggtg gacgtgtccc acgaggaccc ggaagtgaaa    840

ttcaattggt acgtggatgg agtggaagtg cacaacgcca agaccaagcc acgggaagaa    900

cagtacaact ctacctaccg cgtggtgtcc gtgctcactg tgctgcacca agactggctg    960

aacgggaagg agtacaagtg caaagtgtcc aacaaggcgc tgcctgcccc aattgagaaa   1020

actatctcga aagccaaggg acagcctcga gaaccacagg tgtacaccct gcccccatcc   1080

cgggatgagc tgccatacat catcccacca tacaaccagg tcagcctgac ctgcctggtc   1140

aaaggcttct atcccagcga catcgccgtg gagtgggaga gcaatgggca gccggagaac   1200

aactacaaga ccacgcctcc cgtgctggac tccgacggct ccttcttcct ctacagcaag   1260

ctcaccgtgg gcgcagatag gtggctggaa gggaacgtct tctcatgctc cgtgatgcat   1320

gaggcgctgc acaaccacta cactcagaag agcttgtccc tgtcgcccgg t            1371
```

<210> SEQ ID NO 175
<211> LENGTH: 216
<212> TYPE: PRT
<213> ORGANISM: Artificial Sequence
<220> FEATURE:
<223> OTHER INFORMATION: FS22-172-003-AA/FS28-185-003 mAb2 light chain

<400> SEQUENCE: 175

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Tyr Ser Ala
                85                  90                  95

Pro Val Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 176
<211> LENGTH: 648
<212> TYPE: DNA
<213> ORGANISM: Artificial Sequence
<220> FEATURE:
<223> OTHER INFORMATION: FS22-172-003-AA/FS28-185-003 mAb2 light chain

<400> SEQUENCE: 176
gaaattgtgc tgacccagtc tccgggcacg ttatctctga gccctggtga gcgcgccact 60
ctgtcatgcc gggcttctca aagtgttagc agtagctacc tggcgtggta tcagcaaaaa 120
ccgggccagg ccccgcgtct gctgatttac ggtgcatcca gccgtgccac cggcattcca 180
gatcgttttt ccggtagtgg ttctgggacg gacttcactc tgacaatctc acgcctggaa 240
ccggaggatt ttgcggtgta ttactgccag caatcttctt attctgctcc tgtcacgttc 300
ggccaaggga ccaaggtgga aatcaaacgt actgtggccg ctcctagcgt gttcattttt 360
ccgccatccg acgagcagct caagtccggc accgcctccg tggtctgcct gctcaacaac 420
ttctaccctc gcgaagctaa ggtccagtgg aaggtcgaca atgccctgca gtccggaaac 480
tcgcaggaaa gcgtgactga acaggactcc aaggactcca cctattcact gtcctcgact 540
ctgaccctga gcaaggcgga ttacgaaaag cacaaagtgt acgcatgcga agtgacccac 600
cagggtcttt cgtcccccgt gaccaagagc ttcaacagag gagagtgt 648

<210> SEQ ID NO 177
<211> LENGTH: 119
<212> TYPE: PRT
<213> ORGANISM: Artificial Sequence
<220> FEATURE:
<223> OTHER INFORMATION: heavy chain of FS22-172-003-AA/FS28-256-271
mAb2 VH domain

<400> SEQUENCE: 177

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Thr His Thr
20 25 30

Tyr Met Ser Trp Val Arg Gln Ala Pro Gly Lys Gly Leu Glu Trp Val
35 40 45

Ser Ala Ile Ser Pro Thr Tyr Ser Thr Thr Asn Tyr Ala Asp Ser Val
50 55 60

Lys Gly Arg Phe Thr Ile Ser Arg Asp Asn Asn Lys Asn Thr Leu Tyr
65 70 75 80

Leu Gln Met Asn Ser Leu Arg Ala Glu Asp Thr Ala Val Tyr Tyr Cys
85 90 95

Ala Arg Tyr Asn Ala Tyr His Ala Ala Leu Asp Tyr Trp Gly Gln Gly
100 105 110

Thr Leu Val Thr Val Ser Ser
115

<210> SEQ ID NO 178
<211> LENGTH: 357
<212> TYPE: DNA
<213> ORGANISM: Artificial Sequence
<220> FEATURE:
<223> OTHER INFORMATION: heavy chain of FS22-172-003-AA/FS28-256-271
mAb2 VH domain

<400> SEQUENCE: 178
gaagtgcaac tgctggagtc cggtggtggt ctggtacagc cgggtggttc tctgcgtctg 60

-continued

```
agttgcgcgg ccagtggctt taccttcact catacttata tgagctgggt gcgtcaggct    120

ccgggcaaag gtctggaatg ggttagcgcg atttctccga cttatagcac taccaactat    180

gcggatagcg tgaaaggccg ttttaccatt tctcgcgaca acaacaagaa cacgctgtac    240

ctgcagatga actcactgcg tgccgaagat acggccgtgt attactgtgc gagatacaac    300

gcgtatcatg ctgctctgga ctactggggc cagggaaccc tggtcaccgt ctcgagt       357
```